US012331301B2

(12) United States Patent
Bidard-Michelot et al.

(10) Patent No.: US 12,331,301 B2
(45) Date of Patent: Jun. 17, 2025

(54) **MUTANT STRAINS OF *TRICHODERMA* reesei**

(71) Applicant: IFP Energies Nouvelles, Rueil Malmaison (FR)

(72) Inventors: Frédérique Bidard-Michelot, L'Etang la Ville (FR); Antoine Margeot, Paris (FR)

(73) Assignee: IFP Energies Nouvelles, Rueil Malmaison (FR)

( * ) Notice: Subject to any disclaimer, the term of this patent is extended or adjusted under 35 U.S.C. 154(b) by 310 days.

(21) Appl. No.: 16/063,954

(22) PCT Filed: Dec. 21, 2016

(86) PCT No.: PCT/FR2016/053601
§ 371 (c)(1),
(2) Date: Jun. 19, 2018

(87) PCT Pub. No.: WO2017/115033
PCT Pub. Date: Jul. 6, 2017

(65) Prior Publication Data
US 2020/0270619 A1     Aug. 27, 2020

(30) Foreign Application Priority Data

Dec. 28, 2015   (FR) ...................... 1563382

(51) Int. Cl.
| | |
|---|---|
| *C12N 15/80* | (2006.01) |
| *C07K 14/37* | (2006.01) |
| *C12N 1/14* | (2006.01) |
| *C12N 9/42* | (2006.01) |
| *C12N 15/67* | (2006.01) |
| *C12R 1/885* | (2006.01) |

(52) U.S. Cl.
CPC .............. *C12N 15/80* (2013.01); *C07K 14/37* (2013.01); *C12N 15/67* (2013.01); *C12N 1/145* (2021.05); *C12N 9/2437* (2013.01); *C12R 2001/885* (2021.05)

(58) Field of Classification Search
None
See application file for complete search history.

(56) References Cited

U.S. PATENT DOCUMENTS

| | | | |
|---|---|---|---|
| 2014/0302587 A1 | 10/2014 | Ben Chaabane et al. | |
| 2017/0152498 A1 | 6/2017 | Persillon et al. | |
| 2018/0215797 A1* | 8/2018 | Landowski | ............ C07K 14/37 |

FOREIGN PATENT DOCUMENTS

| | | |
|---|---|---|
| CN | 104862237 A | 8/2015 |
| FR | 2979111 A1 | 2/2013 |

(Continued)

OTHER PUBLICATIONS

Hakkinen et al., Screening of candidate regulators for cellulase and hemicellulase production in Trichoderma reesei and identification of a factor essential for cellulase production, Biotechnol. Biofuels, 2014, 7, 14. (Year: 2014).*

(Continued)

*Primary Examiner* — Todd M Epstein
(74) *Attorney, Agent, or Firm* — Morgan, Lewis & Bockius LLP

(57) ABSTRACT

The invention relates to a method for producing a protein in a filamentous fungus cell, comprising the overexpression of the TrAZF1 gene or of one of the variants thereof in said cell.

Figure 1:
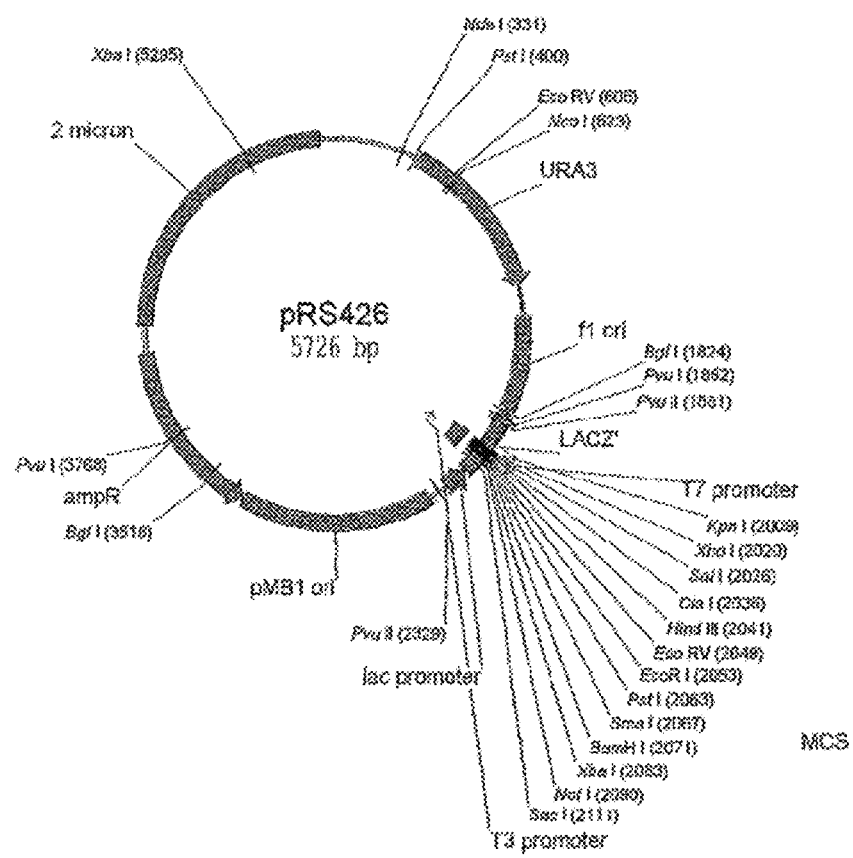

5 Claims, 3 Drawing Sheets
Specification includes a Sequence Listing.

(56) References Cited

FOREIGN PATENT DOCUMENTS

| FR | 3018522 A1 | 9/2015 | | |
|---|---|---|---|---|
| FR | 3022558 A1 | 12/2015 | | |
| WO | 92/03541 A1 | 3/1992 | | |
| WO | WO-0020596 A1 * | 4/2000 | ............. | C07K 14/38 |
| WO | 2008/156605 A1 | 12/2008 | | |
| WO | 2011/151515 A2 | 12/2011 | | |
| WO | 2015/140455 A1 | 9/2015 | | |

OTHER PUBLICATIONS

Deane et al., Transformation of Trichoderma reesei with a constitutively expressed heterologous fungal chitinase gene, Enz. Microbial Technol., 1999, 24, 419-24. (Year: 1999).*

Peterson et al., Trichoderma reesei RUT-C30—thirty years of strain improvement, Microbiology 158, 2012, 58-68. (Year: 2012).*

Seidl et al., Sexual development in the industrial workhorse Trichoderma reesei, Proc. Natl. Acad. Sci. USA 106, 2009, 13909-14. ( Year: 2009).*

Martinez et al., Genome sequencing and analysis of the biomass-degrading fungus Trichoderma reesei, Nature Biotechnol. 26, 2008, 553-60. (Year: 2008).*

Genbank, Accession No. AAIL00000000.2, 2014, www.ncbi.nlm.gov. (Year: 2014).*

Genbank, Accession No. CP016235, 2017, www.ncbi.nlm.gov. (Year: 2017).*

Dienes et al. (Identification of a trypsin-like serine protease from Trichoderma reesei QM9414, Enz. Microbial. Technol. 40, 2007, 1087-94. (Year: 2007).*

Zambare et al., Strain Improvement of Alkaline Protease From Trichoderma Reesei MTCC-3929 By Physical and Chemical Mutagen, IIOAB J 1, 2010, 25-28. (Year: 2010).*

European patent application 15180972.0 filed Aug. 13, 2015. (Year: 2015).*

Koonin, Orthologs, paralogs, and evolutionary genomics, Annu. Rev. Genet. 39, 2005, 309-38. (Year: 2005).*

Druzhinia et al., Novel traits of Trichoderma predicted through the analysis of its secretome, FEMS Microbiol. Lett 337, 2012, 1-9. ( Year: 2012).*

International Search Report issued in corresponding International Patent Application No. PCT/FR2016/053601 dated Apr. 3, 2017.

Anderson et al., "Activity-based protein profiling of secreted cellulolytic enzyme activity dynamics in Trichoderma reesei QM6a, NG14, and RUT-C30," Molecular Biosystems, 9: 2992-3000 (2013).

Slattery et al., "The Function and Properties of the Azf1 Transcriptional Regulator Change with Growth Conditions in *Saccharomyces cerevisiae*," Eukaryotic Cell, 5: 313-320 (2006).

Wang et al., "Enhancing cellulase production in Trichoderma reesei Rut C30 through combined manipulation of activating and repressing genes," Journal of Industrial Microbiology & Biotechnology, 40: 633-641 (2013).

Li et al., "Achieving efficient protein expression in Trichoderma reesei by using strong constitutive promoters," Microbial Cell Factories, 11: 84 (2012).

Newcomb et al., "AZF1 Is a Glucose-Dependent Positive Regulator of CLN3 Transcription in *Saccharomyces cerevisiae*," Molecular and Cellular Biology, 22: 1607-1614 (2002).

* cited by examiner

MUTANT STRAINS OF *TRICHODERMA reesei*

SEQUENCE LISTING SUBMISSION VIA EFS-WEB

A computer readable text file, entitled "SequenceListing.txt," created on or about Jul. 20, 2018 with a file size of about 566 kb contains the sequence listing for this application and is hereby incorporated by reference in its entirety.

The present invention relates to a method for producing a protein in a filamentous fungus cell, comprising the overexpression of the TrAZF1 gene or of a variant thereof, in said cell.

The possibility of producing ethanol from cellulose has received a lot of attention because of the availability of large amounts of raw material and also of the advantage of ethanol as a fuel. Cellulose-based natural raw materials for such a process are denoted "biomass". Many types of biomass, for example wood, agricultural residues, herbaceous crops and municipal solid waste, have been considered as potential raw materials for biofuel production. These materials consist mainly of cellulose, hemicellulose and lignin.

Cellulose is a polymer consisting of glucose molecules linked by beta-1,4 bonds, which are very resistant to degradation or to depolymerization. Once cellulose has been converted into glucose, the latter is easily fermented into biofuel, for example ethanol, using a yeast.

The oldest methods studied for converting cellulose to glucose are based on acid hydrolysis. This process can be carried out in the presence of concentrated or dilute acids. However, several drawbacks, such as poor recovery of the acid when concentrated acids are used and low glucose production in the context of the use of dilute acids, are detrimental to the cost-effectiveness of the acid hydrolysis process.

In order to overcome the drawbacks of the acid hydrolysis process, cellulose conversion processes have more recently related to enzymatic hydrolysis, using enzymes of cellulase type. The microorganisms comprising enzymes which hydrolyze cellulose are, for example, the fungi *Trichoderma, Aspergillus, Humicola* and *Fusarium*. This enzymatic hydrolysis of the lignocellulosic biomass (for example, cellulose), on an industrial scale, has however the drawback of being expensive.

In order to reduce the cost associated with enzymatic hydrolysis of lignocellulose, the industry is constantly searching for methods which are more productive or which give a better yield.

There is therefore a need to optimize the production of enzymes in the industrial process. In particular, there is an unsatisfied and long-anticipated need to develop a method for producing enzymes that is improved and economically advantageous.

The inventors have thus developed an improved method for producing a protein of interest in a filamentous fungus, in which the protein is in particular a cellulolytic enzyme.

Thus, the invention relates to a method for producing a protein in a filamentous fungus cell, comprising the overexpression of the TrAZF1 gene or of a variant thereof, in said cell.

The invention also relates to a filamentous fungus strain, preferably a *Trichoderma reesei* strain, overexpressing the TrAZF1 gene or a variant thereof. The expression "overexpressing the TrAZF1 gene or a variant thereof" is intended to mean that said strain possesses at least the TrAZF1 gene or a variant thereof, said gene or the variants thereof being expressed constitutively.

According to one embodiment, the filamentous fungus strain according to the invention, preferably *Trichoderma reesei* strain, comprises the endogenous TrAZF1 gene, said gene being under the control of a constitutive promoter. In this case, the endogenous TrAZF1 gene is present in the native genome of the strain, and the promoter has been modified, mutated or replaced, so as to be constitutive. According to another embodiment, the filamentous fungus strain according to the invention, preferably *Trichoderma reesei* strain, comprises, in addition to the TrAZF1 gene present in its genome, an additional copy of the TrAZF1 gene, said copy being expressed constitutively. It therefore comprises, in this case, at least two copies of the TrAZF1 gene, one of these copies being expressed constitutively.

This mutated strain according to the invention is characterized by an improvement in the production of cellulolytic enzymes compared with the same *T. reesei* strain which has not been modified, or compared with a reference *T. reesei* strain.

*Trichoderma reesei* is a cellulolytic filamentous fungus. Given the capacity of *T. reesei* to secrete large amounts of cellulases and hemicellulases, this strain is highly advantageous for the production of enzymes for converting plant biomass materials into bioproducts that are of industrial use, such as bioethanol.

The expression "*T. reesei* reference strain" is intended to mean a *Trichoderma reesei* strain chosen from the strains QM6a, NG14, RutC30 and QM9414. These strains are available to the public and have in particular been the subject of deposits made respectively under the numbers:

ATCC 13631 (strain QM6a);
ATCC 56767 (strain NG14);
ATCC 56765 (strain RutC30); and
ATCC 26921 (strain QM9414).

In one particular embodiment, the strain is the CL847 strain. This strain is a hyperproductive strain.

Among the filamentous fungi that can be used according to the invention, mention may be made of certain fungi of the phyla of the Ascomycetes (*Ascomycota*), of the Basidiomycetes (*Basidiomycota*) and of the Zygomycetes (*Zygomycota*). Typically, the fungi are chosen from the classes of the orbiliomycetes, of the pezizomycetes, of the dothideomycetes, of the eurotiomycetes, of the lecanoromycetes, of the leotiomycetes, of the sordariomycetes and of the saccharomycetes.

In particular, mention may be made of *Trichoderma reesei, Arthrobotrys oligospora, Tuber melanosporum, Alternaria brassicicola, Baudoinia compniacensis, Cochliobolus heterostrophus, Cochliobolus sativus, Hysterium pulicare, Leptosphaeria maculans, Mycosphaerella pini, Mycosphaerella populorum, Phaeosphaeria nodorum, Pseudocercospora fijiensis, Pyrenophora teres, Pyrenophora tritici-repentis, Rhytidhysteron rufulum, Setosphaeria turcica, Zymoseptoria tritici, Ajellomyces capsulatus, Ajellomyces dermatitides, Arthroderma benhamiae, Arthroderma gypseum, Arthroderma otae, Aspergillus aculeatus, Aspergillus carbonarius, Aspergillus clavatus, Aspergillus flavus, Aspergillus fumigatus, Aspergillus niger, Aspergillus oryzae, Aspergillus terreus, Coccidioides immitis, Coccidioides posadasii, Emericella nidulans, Neosartorya fischeri, Paracoccidioides brasiliensis, Paracoccidioides sp. lutzii, Penicillium chrysogenum, Penicillium marneffei, Talaromyces stipitatus, Trichophyton equinum, Trichophyton rubrum, Trichophyton tonsurans, Trichophyton verrucosum, Uncinocarpus reesei, Cladonia grayi, Botryotinia fuceliana, Geomyces destructans, Sclerotinia sclerotiorum, Acremonium alcalophilum, Chaetomium globosum, Colletotrichum* higginsianum, *Cryphonectria parasitica, Epichloe festucae, Fusarium oxysporum, Gaeumannomyces graminis, Gibberella moniliformis, Gibberella zeae, Glomerella graminicola, Magnaporthe grisea, Magnaporthe poae, Myceliophthora thermophila, Nectria haematococca, Neurospora crassa, Neurospora discreta, Neurospora tetrasperma, Podospora anserina, Sordaria macrospora, Thielavia terrestris, Trichoderma atroviride, Trichoderma vixens, Verticillium alboatrum, Verticillium dahliae, Clavispora lusitaniae, Pichia membranifaciens, Scheffersomyces stipitis, Wickerhamomyces anomalus, Ceriporiopsis subvermispora, Fomitopsis pinicola, Phlebiopsis gigantea, Wallemia sebi, Melampsora larici-populina* or *Rhizopus oryzae*. Preferably, the filamentous fungus that can be used according to the invention is *Trichoderma reesei*.

In the context of the present invention, the term "TrAZF1 gene" is intended to mean the gene of sequence SEQ ID NO:1 or SEQ ID NO:3. This gene encodes a transcription factor of which the native protein sequence is represented in SEQ ID NO:2. This sequence is available online under the GenBank accession number: XM_006961831.1 (*T.reesei* strain QM6a) and on the site dedicated to the *T. reesei* genome, under number ID103275 at the following address (genome.jgi.doe.gov/cgi-bin/dispGeneModel?db=Trire2&id=103275).

The sequence SEQ ID NO:1 is the nucleotide sequence of the TrAZF1 gene without intron. It is therefore the cDNA sequence.

The sequence SEQ ID NO:3 is the genomic nucleotide sequence of the TrAZF1 gene. It consists of four exons and three introns. It is reproduced below, and the three introns are highlighted:

```
                                         (SEQ ID NO: 3)
ATGGCCCTCGCAGCTCAACAGCATACTCAGGCCGATTGGGGCCGCTGG

TCTCACCAGATTCCACAGAGTTTTCCCATGATGGGCTCTCCAGGATTCA

TGTCATACGATCCCAGAGCTCAGGACGGCAGTCAGATGCAGCGTCAG

GTGTCTGCTCAGTACCTGGTGAACTCGAACTACAACCAGCCCCCGATG

CCCACTGCTTCGTCTCCCCAGTATCAACACGCAGGGCCATTTTCCTATG

TGCCTTACCACAGCCCGCCGCCGTCCACTCCTCTTGGTTCCCCATTCAA

GAGCGAATTTCCCGAGCACCCTCTTACGCGCATGACACACTCTACGGT

CGATCGACACCATTCTCAGGCCATGAGGGACTACCAACCTTATTCTCC

TGTATCGAGGAGGGATCGATTTCTTCAGTCGCCACCAAGCCCTCAGC

AGCTCCCGTCACACCAGGTCCAACTACTCCTGGCTCTTTCACTTCAAGT

TCCGACGCCCAGAGCCCCAGCACTCCAAACCCCCAGACTGCGTCTCAG

CCTGTCAGCTCCAAGACTCTCACTTACAATGAGACCGTTCATCCGGGC

GATAGGATCAGCTTCAGAACCGATGTTGATGAACTCATGAAGGCCATC

CAGAAGACACAGACGACCGACGAGTGTCAGCAAACACTCACACCTGC

GCGAACACCAAAGAACTGTACCACAAGTACTCCCGTACTTCGTACACA

AAGCGGGAAGCCGAGAAAACAGTGGGTTTGCGATGGCCCCAACTGCG

GCAAGGCCTTTGTCAGAAGACGCATCGCGACATTCACCGACGCACTC

ACACCGGCCATCGACCATACGTACGCGCCCAGCTCCTCTTCACTGCAA

CGCCGGCTAATTAAATGTTGATAGGTCTGCACCATGGAAAATTGCGGT

CTTACGTTCTCGCAGCGAGGAAACCTCAAGGTAAGCTTCAGCTGCTAA
```

```
                             -continued
GAATCTCCTTTGAGAATGCGTATACTGACCAGATGGTGTGTGGACAGA

CTCACATACGACGCCACACAGGTGAAAAGCCGTTCTCTTGCGCTGCTT

GTGGCAAGTGCTTCGCTCAGCGTGGGAATCTTCGATCCCACGAGGAGA

CACACAAAGGCCTGAAGCCCTTCGTCTGCCGGCTCGATGATTGCAACA

AGTCGTTTTCTCAGCTGGGCAATATGAAGGTATGCAACATCTAGCACA

TGAAAGCAGTATGAGAACGCTCTAACGCTGAGGGAACTGCAGACTCA

TCAGAACAACTTTCACAAAGAAACGCTCCAGAAACTCACACACATGTT

TGTGCAATTCTCGGAGAACGGCGAGGTGCCCAGAGACTATCAGGATCT

TTTCGAATACTTCCAGAAGCACTACAAGAATAGCAACAAGGGAGTCA

AGGGCCGAGGAAAGACTCGCGCTGTGGCAGCTCGTGGGCCTCAAGAT

TCCGCGTTTCGGCAGGCTGCCTCCCCAGTGCCCGCGTTACTGAAGACG

CCGGCTACGACTCATTTGCCCCAGATGACAATGCCAGCCCATGATCCC

CATGGCAGAATCTCACCATACGCCATGACCCAGGGAGCTGCGAACAC

TCTGAGCAATGTCCTGCGCAACCCCAACCCCTCTTACGGCCTTTATGG

ACCCACGTTTGCCCCGGGCCCTGTACGAGATGGCGTCTTTCACATGGG

CATTGCGAGCCACCTATCCTGA
```

Thus, the sequence SEQ ID NO:1 corresponds to the sequence SEQ ID NO:3 without the introns.

A strain according to the invention therefore preferably comprises either at least two copies of the sequence SEQ ID NO:3 or at least one copy of the sequence SEQ ID NO:1.

The term "variant" of the TrAZF1 gene is intended to mean a gene encoding a protein having the same function as that of sequence SEQ ID NO:2, namely a transcription factor. Preferably, the variant of the TrAZF1 gene is an ortholog. Preferably, the variant of the TrAZF1 gene encodes a protein having the same function as that of sequence SEQ ID NO:2. Preferably, the variant of the TrAZF1 gene encodes a protein chosen from the sequences SEQ ID NO:6 to SEQ ID NO:140.

The inventors have now shown, for the first time, that the overexpression of the TrAZF1 gene results in a significant increase in the production of cellulolytic proteins.

In particular, the inventors have demonstrated that *T. reesei* strains RutC30 and CL847 mutated according to the invention, i.e. comprising two copies of the TrAZF1 gene, one of which is constitutively expressed, exhibit an improvement in the production of extracellular proteins, in particular of cellulolytic enzymes.

The proteins produced according to the invention are preferably cellulolytic enzymes, more preferentially cellulases or hemicellulases, even more preferentially they are cellulases.

The method according to the invention relates to the production of a protein in a filamentous fungus cell, comprising the overexpression of the TrAZF1 gene or of a variant thereof, in said cell.

This overexpression of the TrAZF1 gene is preferably carried out by introducing a cassette comprising said gene into the genome of the cell. The knowledge of such methods is part of the knowledge of those skilled in the art.

Preferably, this cassette comprises:
a) at least one constitutive promoter;
b) the gene of sequence SEQ ID NO:1 or SEQ ID NO:3, or a variant thereof; and
c) optionally, a terminator.

The constitutive promoter a) is a strong promoter. The term "constitutive promoter" is intended to mean a promoter which is not inducible. This constitutive promoter expresses the gene all the time; thus, a constant and strong production of proteins takes place.

This promoter can in particular originate from *Trichoderma reesei*, but also from *Aspergillus nidulans*.

Preferably, the constitutive promoter a) is chosen from:
the gpd promoter of *Trichoderma reesei* (Li J. et al (2012), *Achieving efficient protein expression in Trichoderma reesei by using strong constitutive promoters*, Microbial cell factories, 11(1), 84. doi:10.1186/1475-2859-11-84). This promoter has the sequence SEQ ID NO:4, the gpd promoter of *Aspergillus nidulans* (Penttilä M. et al (1987), *A versatile transformation system for the cellulolytic filamentous fungus Trichoderma reesei*, Gene, 61(2), 155-64; ncbi.nlm.nih.gov/pubmed/3127274), and the tef1 promoter of *Trichoderma reesei* (Nakari-Setälä T, Penttilä M., *Production of Trichoderma reesei cellulases on glucose-containing media*, Applied and Environmental Microbiology. 1995;61(10):3650-3655).

Preferably, the constitutive promoter a) is the gpd promoter of sequence SEQ ID NO:4.

The cassette used in the method of the invention also comprises the element b), i.e. the gene of sequence SEQ ID NO:1 or SEQ ID NO:3 or a variant thereof. The variant is as described above.

Finally, the cassette used in the method of the invention can optionally comprise a terminator c).

The terminator is preferably the gpd terminator of *Trichoderma reesei*, of sequence SEQ ID NO:5.

The present invention also relates to the use of a cassette as described above, for the production of proteins, in particular of cellulolytic enzymes.

The overexpression of the TrAZF1 gene is preferably carried out by introducing a DNA fragment comprising the TrAZF1 gene with a constitutive promoter, a terminator and a selectable marker. This cassette can also be introduced into the cell by a vector, such as plasmid, comprising the cassette. According to the invention, the term "vector" is intended to mean any DNA sequence into which it is possible to insert fragments of foreign nucleic acid, the vectors making it possible to introduce foreign DNA into a host cell. Examples of vectors are plasmids, cosmids, yeast artificial chromosomes (YACs), bacterial artificial chromosomes (BACs) and bacteriophage P1-derived artificial chromosomes (PACs), and virus-derived vectors.

The vector according to the invention may also carry a selectable marker. The term "selectable marker" is intended to mean a gene of which the expression confers on the cells that contain it a characteristic which makes it possible to select them. It is for example an antibiotic-resistance gene.

Preferentially, said vector is a plasmid. More preferentially, the plasmid is a plasmid of pRS426 type, as described in the examples and in FIG. 1.

The cassette according to the invention, once inserted into the genome, allows the translation of the TrAZF1 gene of interest, which gives the corresponding protein.

The invention also relates to the use of the strain according to the invention for the production of cellulolytic enzymes. Thus, in one particular embodiment, the invention relates to the use of a *Trichoderma reesei* strain, for the production of cellulolytic enzymes, said strain overexpressing the TrAZF1 gene or a variant thereof.

The invention also relates to the use of the strain according to the invention, for the hydrolysis of cellulose and degradation products thereof, including cellobiose, to glucose.

A subject of the invention is also the use of the strain according to the invention, for the production of biofuel. According to the invention, the term "biofuel" can be defined as any product which results from the conversion of biomass and which can be used for energy purposes. Furthermore, and without wishing to be limited thereto, mention may be made, by way of example, of biogases, products which can be incorporated (optionally after subsequent conversion) into a fuel or which can be a fuel in their own right, such as alcohols, (ethanol, butanol and/or isopropanol depending on the type of fermented organism used), solvents (acetone), acids (butyric acid), lipids and derivatives thereof (short-chain or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol. In another embodiment, the biofuel is biogas.

The invention also relates to the use of the strain according to the invention, for the hydrolysis of beta-oligosaccharides.

The following examples illustrate the invention without limiting the scope thereof.

FIGURES

Figure 2:
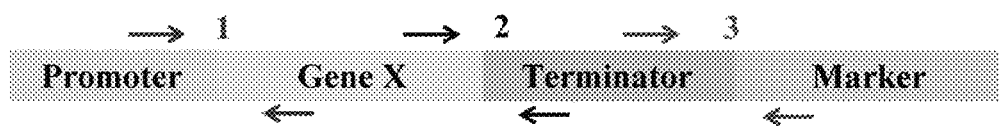
Figure 3:
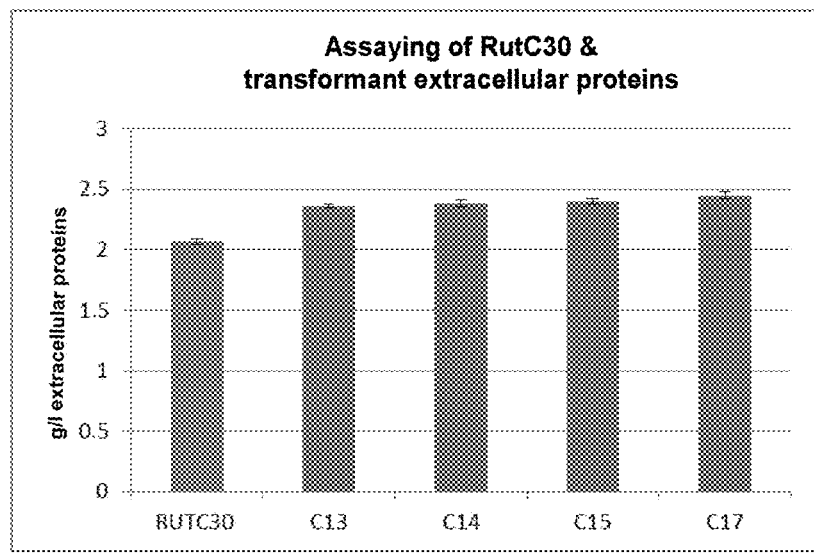
Figure 4:
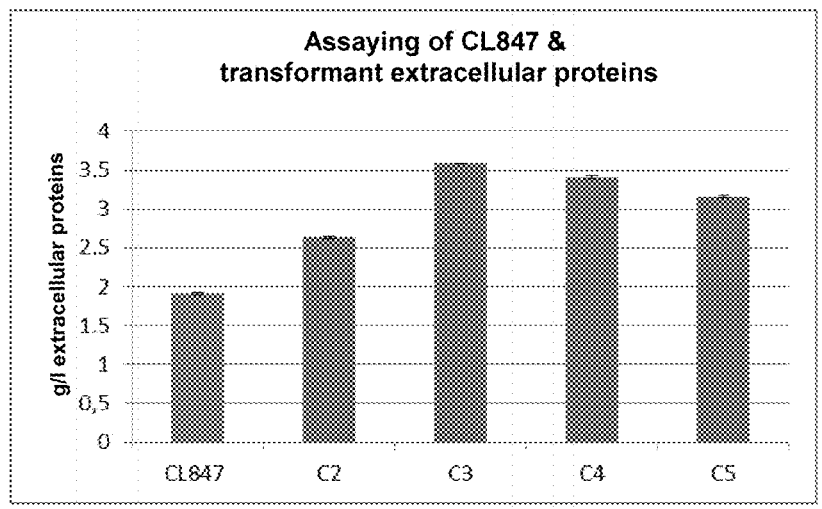
Figure 5:
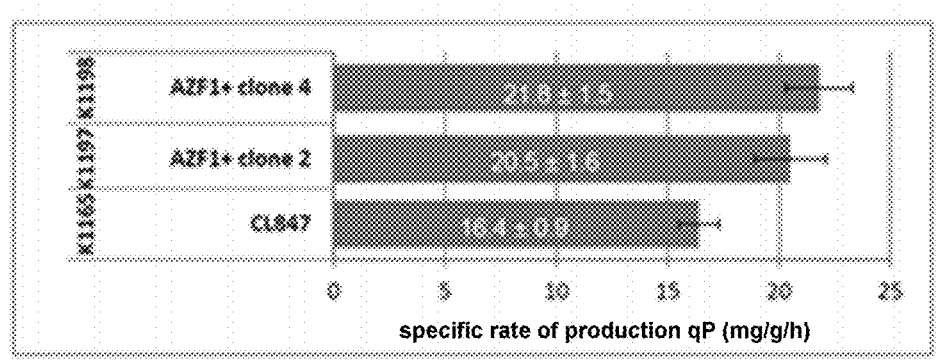

FIG. 1: Representation of the pRS426 plasmid.
FIG. 2: Position of the primers used to verify the presence of the cassette for overexpression of the transformed strains.
FIG. 3: Production of extracellular proteins by the RutC30 strains transformed according to the invention and a RutC30 strain of *T. reesei* which has not been modified, after 7 days of culture.
FIG. 4: Production of extracellular proteins by the Cl847 strains transformed according to the invention and a Cl847 strain of *T. reesei* which has not been modified, after 7 days of culture.
FIG. 5: Specific production rate of the Cl847 strain and two transformants under fed flask culture conditions.

EXAMPLES

Example 1: Lactose-Induction Transcriptomic Studies of the *Trichoderma reesei* Strains ATCC 56767 and ATCC 56765

In this study, the inventors used the following *Trichoderma reesei* strains:
ATCC 56767 (NG14), and
ATCC 56765 (RUTC30).
The RutC30 strain is derived by mutagenesis of the NG14 strain and has an increased cellulase production.

The TrAZF1 gene (ID 103275) is a transcription factor (protein involved in the regulation of other genes) identified as differentially expressed during kinetics of induction on lactose (Poggi-Parodi et al. 2014). More specifically, the transcriptomic study shows that the expression of TrAZF1 decreases during induction in the NG14 strain, whereas, in RutC30, its expression does not vary.

Example 2: Construction of an Overexpression Cassette for the TrAZF1 Gene

The overexpression cassette is made up of three DNA fragments:
the promoter region of the glyceraldehyde-3-phosphate dehydrogenase gene (GPDp) of *T. reesei*. The size of the promoter region was defined in the article by Li et al. 2012 (SEQ ID NO: 141);

the coding region of the gene of interest (TrAZF1) (SEQ ID NO: 3);

the terminator region of the glyceraldehyde-3-phosphate dehydrogenase gene (GPDt) of *T. reesei*. The size of the promoter region was defined in the article by Li et al. 2012 (SEQ ID NO: 142).

In order to be able to select the transformants, a cassette called HygroR (SEQ ID NO: 143) containing the Hph gene is fused with the overexpression cassette. The Hph gene encodes hygromycin B phosphotransferase responsible for resistance to hygromycin B. It was isolated from *Escherichia coli*. For the expression of the gene in *Trichoderma reesei*, the Hph gene is placed under the control of the promoter of the cpc-1 gene of *Neurospora crassa* (NCU04050) and the terminator of the trpC gene of *Aspergillus nidulans* (ANID_00648).

The pRS426 plasmid (ATCC 77107) was used as vector for the construction of the deletion cassette via in vivo recombination in *S. cerevisiae* according to a method based on the literature (Schuster et al. 2012). To do this, the plasmid was digested with EcoRI and XhoI (New England Biolabs) and purified by gel electrophoresis using the QIAquick Gel Extraction Kit (Qiagen). The pRS426 plasmid is represented in FIG. 1.

The parts of primers specific for the TrAZF1 gene of interest were designed on the basis of the ORF prediction in the version v2.0 of the genome (genome.jgi-psf.org/Trire2/Trire2.home.html).

Amplification of the Promoter Region of the Glyceraldehyde-3-Phosphate Dehydrogenase Gene of *T. reesei* GPDp The primers used for the amplification of the promoter region GPDp from the DNA of the RutC30 strain are described below:

The forward primer consists of two parts: a part of 20 nucleotides (nt) which is a homolog of the pRS426 vector sequence (FIG. 1) in the vicinity of the XhoI restriction site and a part of 20 nt which is homologous to the 5' end of GPDp (SEQ ID NO: 141), the whole forming the sequence SEQ ID NO: 144 (ATGGGTACCGGGCCCCCCGACGCAGAAGAAGGAAATCG).

The reverse primer consists of two parts: a part of 10 nt homologous to the 5' end of the coding region of the TrAZF1 gene (SEQ ID NO: 3) and a part of 20 nt homologous to the 3' end of GPDp (SEQ ID NO: 141), the whole forming the sequence SEQ ID NO: 145 (CGAGGGCCATTTTGTATCTGCGAATTGAGC).

Amplification of the Coding Region of the TrAZF1 Gene of Interest

The primers used for the amplification of the TrAZF1 gene of interest from the DNA of the RutC30 strain are described below:

The forward primer consists of two parts: a part of 10 nt which is a homolog of the 3' end of GPDp (SEQ ID NO: 141) and a part of 20 nt homologous to the 5' coding region of the TrAZF1 gene (SEQ ID NO: 3), the whole forming the sequence SEQ ID NO: 146 (CAGATACAAAATGGCCCTCGCAGCTCAACA).

The reverse primer consists of two parts: a part of 10 nt homologous to the 5' end of the GPDt region (SEQ ID NO: 142) and a part of 20 nt homologous to the 3' coding region of the TrAZF1 gene (SEQ ID NO: 3), the whole forming the sequence SEQ ID NO: 147 (AACACAGCACTCAGGATAGGTGGCTCGCAATG).

Amplification of the Terminator Region of the Glyceraldehyde-3-Phosphate Dehydrogenase Gene of *T. reesei* GPDt The primers used for the amplification of the terminator region GPDp from the DNA of the RutC30 strain are described below:

The forward primer consists of two parts: a part of 10 nt homologous to the 3' end of the coding region of the TrAZF1 gene (SEQ ID NO: 3) and a part of 20 nt homologous to the 5' end of GPDt (SEQ ID NO: 142), the whole forming the sequence SEQ ID NO: 148 (CCTATCCTGAGTGCTGTGTTCCTCAGAATG).

The reverse primer consists of two parts: a part of 10 nt homologous to the 5' end of the HygroR cassette (SEQ ID NO: 143) and a part of 20 nt homologous to the 3' end of GPDt (SEQ ID NO: 142), the whole forming the sequence SEQ ID NO: 149 (GGTACACTTGTTACGGATCTGATCACTCGG).

Amplification of the HygroR Cassette

The primers used for the amplification of the HygroR cassette are described below:

The forward primer consists of two parts: a part of 10 nt homologous to the 3' end of GPDt (SEQ ID NO: 142) and a part of 20 nt homologous to the 5' end of the HygroR cassette (SEQ ID NO: 143), the whole forming the sequence SEQ ID NO: 150 (AGATCCGTAACAAGTGTACCTGTGCATTCTG).

The reverse primer consists of two parts: a part of 20 nt homologous to the pRS426 vector sequence in the vicinity of the EcoRI restriction site and a part of 20 nt homologous to the 3' end of the HygroR cassette (SEQ ID NO: 143), the whole forming the sequence SEQ ID NO: 151 (TGGATCCCCCGGGCTGCAGGGGCAGTGCTAGTGTGTGTAC).

The PCRs carried out using the above primers gave rise to DNA fragments with homologous ends. A competent *Saccharomyces cerevisiae* strain W303 was transformed with these DNA fragments and also the digested pRS426 plasmid. The pRS426 plasmids containing the overexpression cassette for the TrAZF1 gene and the HygroR cassette were extracted from *S. cerevisiae* and used as template for PCR amplification of the overexpression cassette fused to the HygroR cassette (SEQ ID NO: 154) using the forward primer (SEQ ID NO: 152) and the reverse primer (SEQ ID NO: 153).

Example 3: Transformation of the *T. reesei* Strains RutC30 and Cl1847 with the TrAZF1 Overexpression Cassette The *T. reesei* RutC30 (ATCC 56765) and Cl847 strains were then transformed with the PCR product (SEQ ID NO 154) (Durand et al., 1988). The transformants were selected on the basis of the Hph selectable marker gene function. The transformants were purified from the colonies resulting from individual spores. The ectopic integration of the cassette was confirmed by three PCR amplifications. The position of the primers used and also the fragments amplified are indicated in FIG. 2. The primers used for the PCRs are described below:

```
Primers for verification amplification 1:
A forward primer in the GPDp promoter
(SEQ ID NO: 155):
GTCAGAAACGACCAAGCTAAG.
```

```
A reverse primer in the TrAZF1 gene
(SEQ ID NO: 156):
GCCTGAGAATGGTGTCGATC.

Primers for verification amplification 2:
A forward primer in the TrAZF1 gene
(SEQ ID NO: 157):
TCGTGGGCCTCAAGATTC.

A reverse primer in the GPDt terminator
(SEQ ID NO: 158):
GACGCCTGAGAGGTCCTA.

Primers for verification amplification 3:
A forward primer in the GPDt terminator
(SEQ ID NO: 159):
CCTTCTTAGAGAGCTCTCGG.

A reverse primer in the HygroR cassette
(SEQ ID NO: 160):
CGGGTTTACCTCTTCCAGAT.
```

The amplifications were carried out from the genomic DNA of the purified transformants: four transformants were selected for each strain.

Example 4: Culture of the *T. reesei* Strain RutC30 with the TrAZF1 Overexpression Cassette and Analysis of the Cultures for Protein Production The spores originating from four transformants of the RutC30 strain which exhibit ectopic integration of the TrAZF1 overexpression cassette were used to inoculate a 24-well culture plate containing 2 ml of culture medium per well.

The medium was composed of $K_2HPO_4$ 8.7 g.l$^{-1}$; $(NH_4)_2SO_4$ 4.2 g.l$^{-1}$; $MgSO_4.7H_2O$ 0.3 g.l$^{-1}$; cornsteep 1.5 g.l$^{-1}$; lactose 10 g.l$^{-1}$; cellulose 10 g.l$^{-1}$; maleic acid 11.6 g.l$^{-1}$; $CaCl_2$ 0.3 g.l$^{-1}$; $FeSO_4.7H_2O$ 5.0 mg.l$^{-1}$; $MnSO_4.H_2O$ 1.6 mg.l$^{-1}$; $ZnSO_4.7H_2O$ 1.4 mg.l$^{-1}$; $CoCl_2.6H_2O$ 2.0 mg.l$^{-1}$; pH 6.

The culture was carried out at 30° C. with shaking at 150 rpm, in duplicate.

After 7 days of culture, the supernatant was collected in order to measure the protein concentration in the medium (Folin method). The extracellular-protein production of the cultures is presented in FIG. 3. This figure shows an increase in the protein production for the transformants compared with the unmodified *T. reesei* strain.

Example 5: Culture of the *T. reesei* Strain Cl847 with the TrAZF1 Overexpression Cassette and Analysis of the Cultures for Protein Production The spores originating from four transformants of the Cl847 strain which exhibit an ectopic integration of the TrAZF1 overexpression cassette were used to inoculate a 24-well culture plate containing 2 ml of culture medium per well.

The medium was composed of $K_2HPO_4$ 8.7 g.l$^{-1}$; $(NH_4)_2SO_4$ 4.2 g.l$^{-1}$; $MgSO_4.7H_2O$ 0.3 g.l$^{-1}$; cornsteep 1.5 g.l$^{-1}$; lactose 10 g.l$^{-1}$; cellulose 10 g.l$^{-1}$; maleic acid 11.6 g.l$^{-1}$; $CaCl_2$ 0.3 g.l$^{-1}$; $FeSO_4.7H_2O$ 5.0 mg.l$^{-1}$; $MnSO_4.H_2O$ 1.6 mg.l$^{-1}$; $ZnSO_4.7H_2O$ 1.4 mg.l$^{-1}$; $CoCl_2.6H_2O$ 2.0 mg.l$^{-1}$; pH 6.

The culture was carried out at 30° C. with shaking at 150 rpm, in duplicate.

After 7 days of culture, the supernatant was collected in order to measure the protein concentration in the medium (Folin method). The extracellular-protein production of the cultures is presented in FIG. 4. This figure shows an increase in the protein production for the transformants compared with the unmodified *T. reesei* strain.

Example 6: Culture of the *T. reesei* Strain Cl847 with Overexpressed AZF1 in Fed Flasks and Analysis of the Cultures for Protein Production and Growth A culture of two transformants of the *T. reesei* strain Cl847 and also of the non-transformed strain using the cellulase production method described in patent WO 2013/026964 A1. The extracellular-protein production and also the biomass were measured over time in order to obtain a measurement of the specific rate of protein production (protein production per mg of fungal biomass per unit of time, or qP) at the end of the culture. These values are presented in FIG. 5.

The data show improved qP values in the mutants compared with the unmodified *T. reesei* strain.

LITERATURE

Durand, H., Clanet, M., & Tiraby, G. (1988). Genetic Improvement of *Trichoderma reesei* for large scale cellulase production. Enzyme and Microbial Technology, 10, 341-346.

Li, Junxin; Wang, Juan; Wang, Shaowen; Xing, Miao; Yu, Shaowen; Liu, Gang (2012) Achieving efficient protein expression in *Trichoderma reesei* by using strong constitutive promoters. In: Microbial cell factories, vol. 11, p. 84. DOI: 10.1186/1475-2859-11-84.

Poggi-Parodi, Dante; Bidard, Frédérique; Pirayre, Aurélie; Portnoy, Thomas; Blugeon, Corinne; Seiboth, Bernhard et al. (2014) Kinetic transcriptome analysis reveals an essentially intact induction system in a cellulase hyper-producer *Trichoderma reesei* strain. In: Biotechnology for biofuels, vol. 7, n° 1, p. 173. DOI: 10.1186/s13068-014-0173-z.

Schuster, André; Bruno, Kenneth S.; Collett, James R.; Baker, Scott E.; Seiboth, Bernhard; Kubicek, Christian P.; Schmoll, Monika (2012) A versatile toolkit for high throughput functional genomics with *Trichoderma reesei*. In: Biotechnology for biofuels, vol. 5, no° 1, p. 1. DOI: 10.1186/1754-6834-5-1. WO09026716 (A1)—METHOD FOR CELLULASE PRODUCTION.

The invention claimed is:

1. A method of increasing the expression of a cellulase enzyme in a strain of a filamentous fungus, comprising
culturing a strain overexpressing a TrAZF1 gene, and collecting supernatant containing the cellulase enzyme from the strain culture;
wherein the strain genome contains a cassette comprising:
(a) at least one constitutive promoter which induces overexpression of SEQ ID NO:1 or SEQ ID NO:3 during strain culture;
(b) a nucleotide sequence of SED ID NO:1 or SEQ ID NO:3; and
(c) optionally, a terminator.

2. The method as claimed in claim 1, wherein the cellulase enzyme is chosen from the group consisting of cellulases and hemicellulases.

3. The method as claimed in claim 1, wherein the filamentous fungus is chosen from the group consisting of orbiliomycetes, pezizomycetes, dothideomycetes, eurotiomycetes, lecanoromycetes, leotiomycetes, sordariomycetes and saccharomyces.

4. A strain of *Trichoderma reesei*, transformed with a cassette comprising:
(a) at least one constitutive promoter;
(b) a nucleotide sequence of SED ID NO:1 or SEQ ID NO:3; and
(c) optionally, a terminator.

5. The strain of claim 4, wherein said strain expresses a cellulolytic enzyme.

* * * * *

SEQUENCE LISTING

```
<160> NUMBER OF SEQ ID NOS: 160

<210> SEQ ID NO 1
<211> LENGTH: 1521
<212> TYPE: DNA
<213> ORGANISM: Artificial Sequence
```

```
<220> FEATURE:
<223> OTHER INFORMATION: Nucleotidic sequence of TrAZF1 gene of T.reesei

<400> SEQUENCE: 1
atggccctcg cagctcaaca gcatactcag gccgattggg gccgctggtc tcaccagatt      60
ccacagagtt tcccatgat gggctctcca ggattcatgt catacgatcc cagagctcag     120
gacggcagtc agatgcagcg tcaggtgtct gctcagtacc tggtgaactc gaactacaac     180
cagccccccga tgcccactgc ttcgtctccc cagtatcaac acgcagggcc attttcctat     240
gtgccttacc acagcccgcc gccgtccact cctcttggtt ccccattcaa gagcgaattt     300
cccgagcacc ctcttacgcg catgacacac tctacggtcg atcgacacca ttctcaggcc     360
atgagggact accaacctta ttctcctgta tcgaggaggg gatcgatttc ttcagtcgcc     420
accaagccct cagcagctcc cgtcacacca ggtccaacta ctcctggctc tttcacttca     480
agttccgacg cccagagccc cagcactcca accccccaga ctgcgtctca gcctgtcagc     540
tccaagactc tcacttacaa tgagaccgtt catccgggcg ataggatcag cttcagaacc     600
gatgttgatg aactcatgaa ggccatccag aagacacaga cgaccgacga gtgtcagcaa     660
acactcacac ctgcgcgaac accaaagaac tgtaccacaa gtactcccgt acttcgtaca     720
caaagcggga agccgagaaa acagtggggtt tgcgatggcc ccaactgcgg caaggccttt     780
gtccagaaga cgcatcgcga cattcaccga cgcactcaca ccggccatcg accatacgtc     840
tgcaccatgg aaaattgcgg tcttacgttc tcgcagcgag aaacctcaa gactcacata     900
cgacgccaca caggtgaaaa gccgttctct tgcgctgctt gtggcaagtg cttcgctcag     960
cgtgggaatc ttcgatccca cgaggagaca cacaaaggcc tgaagccctt cgtctgccgg    1020
ctcgatgatt gcaacaagtc gttttctcag ctgggcaata tgaagactca tcagaacaac    1080
tttcacaaag aaacgctcca gaaactcaca cacatgttg tgcaattctc ggagaacggc    1140
gaggtgccca gagactatca ggatctttc gaatacttcc agaagcacta caagaatagc    1200
aacaagggag tcaagggccg aggaaagact cgcgctgtgg cagctcgtgg gcctcaagat    1260
tccgcgtttc ggcaggctgc ctccccagtg cccgcgttac tgaagacgcc ggctacgact    1320
catttgcccc agatgacaat gccagcccat gatcccatg gcagaatctc accatacgcc    1380
atgacccagg gagctgcgaa cactctgagc aatgtcctgc gcaacccaa ccctcttac     1440
ggcctttatg gacccacgtt tgccccgggc cctgtacgag atggcgtctt tcacatgggc    1500
attgcgagcc acctatcctg a                                              1521

<210> SEQ ID NO 2
<211> LENGTH: 506
<212> TYPE: PRT
<213> ORGANISM: Artificial Sequence
<220> FEATURE:
<223> OTHER INFORMATION: TrAZF1 protein of T.reesei

<400> SEQUENCE: 2

Met Ala Leu Ala Ala Gln Gln His Thr Gln Ala Asp Trp Gly Arg Trp
1               5                   10                  15

Ser His Gln Ile Pro Gln Ser Phe Pro Met Met Gly Ser Pro Gly Phe
            20                  25                  30

Met Ser Tyr Asp Pro Arg Ala Gln Asp Gly Ser Gln Met Gln Arg Gln
        35                  40                  45

Val Ser Ala Gln Tyr Leu Val Asn Ser Asn Tyr Asn Gln Pro Pro Met
    50                  55                  60
```

-continued

```
Pro Thr Ala Ser Ser Pro Gln Tyr Gln His Ala Gly Pro Phe Ser Tyr
 65                  70                  75                  80

Val Pro Tyr His Ser Pro Pro Ser Thr Pro Leu Gly Ser Pro Phe
                 85                  90                  95

Lys Ser Glu Phe Pro Glu His Pro Leu Thr Arg Met Thr His Ser Thr
            100                 105                 110

Val Asp Arg His His Ser Gln Ala Met Arg Asp Tyr Gln Pro Tyr Ser
            115                 120                 125

Pro Val Ser Arg Arg Gly Ser Ile Ser Ser Val Ala Thr Lys Pro Ser
        130                 135                 140

Ala Ala Pro Val Thr Pro Gly Pro Thr Thr Pro Gly Ser Phe Thr Ser
145                 150                 155                 160

Ser Ser Asp Ala Gln Ser Pro Ser Thr Pro Asn Pro Gln Thr Ala Ser
                165                 170                 175

Gln Pro Val Ser Ser Lys Thr Leu Thr Tyr Asn Glu Thr Val His Pro
            180                 185                 190

Gly Asp Arg Ile Ser Phe Arg Thr Asp Val Asp Glu Leu Met Lys Ala
        195                 200                 205

Ile Gln Lys Thr Gln Thr Thr Asp Glu Cys Gln Gln Thr Leu Thr Pro
210                 215                 220

Ala Arg Thr Pro Lys Asn Cys Thr Thr Ser Thr Pro Val Leu Arg Thr
225                 230                 235                 240

Gln Ser Gly Lys Pro Arg Lys Gln Trp Val Cys Asp Gly Pro Asn Cys
                245                 250                 255

Gly Lys Ala Phe Val Gln Lys Thr His Arg Asp Ile His Arg Arg Thr
            260                 265                 270

His Thr Gly His Arg Pro Tyr Val Cys Thr Met Glu Asn Cys Gly Leu
        275                 280                 285

Thr Phe Ser Gln Arg Gly Asn Leu Lys Thr His Ile Arg Arg His Thr
290                 295                 300

Gly Glu Lys Pro Phe Ser Cys Ala Ala Cys Gly Lys Cys Phe Ala Gln
305                 310                 315                 320

Arg Gly Asn Leu Arg Ser His Glu Glu Thr His Lys Gly Leu Lys Pro
                325                 330                 335

Phe Val Cys Arg Leu Asp Asp Cys Asn Lys Ser Phe Ser Gln Leu Gly
            340                 345                 350

Asn Met Lys Thr His Gln Asn Asn Phe His Lys Glu Thr Leu Gln Lys
        355                 360                 365

Leu Thr His Met Phe Val Gln Phe Ser Glu Asn Gly Glu Val Pro Arg
370                 375                 380

Asp Tyr Gln Asp Leu Phe Glu Tyr Phe Gln Lys His Tyr Lys Asn Ser
385                 390                 395                 400

Asn Lys Gly Val Lys Gly Arg Gly Lys Thr Arg Ala Val Ala Ala Arg
                405                 410                 415

Gly Pro Gln Asp Ser Ala Phe Arg Gln Ala Ala Ser Pro Val Pro Ala
            420                 425                 430

Leu Leu Lys Thr Pro Ala Thr Thr His Leu Pro Gln Met Thr Met Pro
        435                 440                 445

Ala His Asp Pro His Gly Arg Ile Ser Pro Tyr Ala Met Thr Gln Gly
450                 455                 460

Ala Ala Asn Thr Leu Ser Asn Val Leu Arg Asn Pro Asn Pro Ser Tyr
465                 470                 475                 480

Gly Leu Tyr Gly Pro Thr Phe Ala Pro Gly Pro Val Arg Asp Gly Val
```

```
                485                 490                 495
Phe His Met Gly Ile Ala Ser His Leu Ser
            500                 505

<210> SEQ ID NO 3
<211> LENGTH: 1699
<212> TYPE: DNA
<213> ORGANISM: Artificial Sequence
<220> FEATURE:
<223> OTHER INFORMATION: Genomic nucleotidic sequence of TrAZF1 gene

<400> SEQUENCE: 3
atggccctcg cagctcaaca gcatactcag gccgattggg gccgctggtc tcaccagatt      60
ccacagagtt ttcccatgat gggctctcca ggattcatgt catacgatcc cagagctcag     120
gacggcagtc agatgcagcg tcaggtgtct gctcagtacc tggtgaactc gaactacaac     180
cagcccccga tgcccactgc ttcgtctccc cagtatcaac acgcagggcc attttcctat     240
gtgccttacc acagcccgcc gccgtccact cctcttggtt ccccattcaa gagcgaattt     300
cccgagcacc ctcttacgcg catgacacac tctacggtcg atcgacacca ttctcaggcc     360
atgagggact accaacctta ttctcctgta tcgaggaggg gatcgatttc ttcagtcgcc     420
accaagccct cagcagctcc cgtcacacca ggtccaacta ctcctggctc tttcacttca     480
agttccgacg cccagagccc cagcactcca aaccccagac tgcgtctcag gcctgtcagc     540
tccaagactc tcacttacaa tgagaccgtt catccgggcg ataggatcag cttcagaacc     600
gatgttgatg aactcatgaa ggccatccag aagacacaga cgaccgacga gtgtcagcaa     660
acactcacac ctgcgcgaac accaaagaac tgtaccacaa gtactcccgt acttcgtaca     720
caaagcggga agccgagaaa acagtggggtt tgcgatggcc ccaactgcgg caaggccttt     780
gtccagaaga cgcatcgcga cattcaccga cgcactcaca ccggccatcg accatacgta     840
cgcgcccagc tcctcttcac tgcaacgccg gctaattaaa tgttgatagg tctgcaccat     900
ggaaaattgc ggtcttacgt tctcgcagcg aggaaacctc aaggtaagct tcagctgcta     960
agaatctcct ttgagaatgc gtatactgac cagatggtgt gtggacagac tcacatacga    1020
cgccacacag gtgaaaagcc gttctcttgc gctgcttgtg gcaagtgctt cgctcagcgt    1080
gggaatcttc gatcccacga ggagacacac aaaggcctga gcccttcgt ctgccggctc    1140
gatgattgca caagtcgtt ttctcagctg gcaatatga aggtatgcaa catctagcac    1200
atgaaagcag tatgagaacg ctctaacgct gagggaactg cagactcatc agaacaactt    1260
tcacaaagaa acgctccaga aactcacaca catgtttgtg caattctcgg agaacggcga    1320
ggtgcccaga gactatcagg atcttttcga atacttccag aagcactaca agaatagcaa    1380
caagggagtc aagggccgag aaagactcg cgctgtggca gctcgtgggc tcaagattc     1440
cgcgtttcgg caggctgcct ccccagtgcc cgcgttactg aagacgccgg ctacgactca    1500
tttgccccag atgacaatgc cagcccatga tccccatggc agaatctcac catacgccat    1560
gacccaggga gctgcgaaca ctctgagcaa tgtcctgcgc aaccccaacc cctcttacgg    1620
cctttatgga cccacgtttg ccccgggccc tgtacgagat ggcgtctttc acatgggcat    1680
tgcgagccac ctatcctga                                                 1699

<210> SEQ ID NO 4
<211> LENGTH: 1437
<212> TYPE: DNA
<213> ORGANISM: Artificial Sequence
<220> FEATURE:
```

<223> OTHER INFORMATION: gpd promoter

<400> SEQUENCE: 4

```
gacgcagaag aaggaaatcg ccccgccggt tccgtaaaaa aaatatgagc gcagggacaa        60
gcacagcctt ggccctgggc ctagccttgc gccttgtttg atgcaatcgg cgacatgtcg       120
aatgctgtaa tttttttttgt ttaggttccc cttttccttt tgtgttaata ataattctcg      180
aagggcgctg attttgaaat tgtcggtga gagccaaacg gatatacagg cgcggctgat        240
gaataatgat gaatcgagct gacttgatgc tgtatgtaca atattgactg cgaggaccat       300
caggtgttgt atggatggaa tcattctgta accaccaagg tgcatgcatc ataaggtatt       360
ctcctcagct caccaacaac gaacgatggc catgttagta aaggcaccgt gatggcaaga       420
tagaaccact attgcatctg cgcttcccac gcacagtacg tcaatgtaac gtcaaagccg       480
ccctcccgta acctcgcccg ttgttgctcc ccccgattgc ctcaatcaca tagtacctac       540
ctatgcatta tggcgcctca acccacccccc ccagattgag agctacctta catcaatatg      600
gccagcacct cttcggcgat acatactcgc caccccagcc ggggcgattg tgtgtactag       660
gtaggctcgt actataccag caggagaggt gctgcttggc aatcgtgctc agctgttagg       720
ttgtacttgt atggtacttg taaggtggtc atgcagttgc taaggtacct agggagggat       780
tcaacgagcc ctgcttccaa tgtccatctg gataggatgg cggctggcgg ggccgaagct       840
gggaactcgc caacagtcat atgtaatagc tcaagttgat gataccgttt gccaggatt       900
aggatgcgag aagcagcatg aatgtcgctc atccgatgcc gcatcaccgt tgtgtcagaa       960
acgaccaagc taagcaacta aggtaccttta ccgtccacta tctcaggtaa ccaggtacta      1020
ccagctaccc tacctgccgt gcctacctgc tttagtatta atctttccac ctccctcctc      1080
aatcttcttt tccctcctct cctctttttt ttttcttcct cctcttcttc tccataacca      1140
ttcctaacaa catcgacatt ctctcctaat caccagcctc gcaaatcctc aggttagtat      1200
tactactact acaatcatca ccacgatgct ccgcccgacg atgcggcttc tgttcgcctg      1260
cccctcctct cactcgtgcc cttgacgagc taccccgcca gactctcctg cgtcaccaat      1320
tttttttccct atttaccccct cctccctctc tccctctcgt ttcttcctaa caaacaacca   1380
ccaccaaaat ctctttggaa gctcacgact cacgcaagct caattcgcag atacaaa        1437
```

<210> SEQ ID NO 5
<211> LENGTH: 645
<212> TYPE: DNA
<213> ORGANISM: Artificial Sequence
<220> FEATURE:
<223> OTHER INFORMATION: gpd terminator

<400> SEQUENCE: 5

```
tctagaaaga aggattacct ctaaacaagt gtacctgtgc attctgggta aacgactcat        60
aggagagttg taaaaaagtt tcggccggcg tattgggtgt tacggagcat tcactaggca       120
accatgcatc cttactattg tataccatct tagtaggaat gatttcgagg tttataccta       180
cgatgaatgt gtgtcctgta ggcttgagag ttcaaggaag aaacatgcaa ttatctttgc       240
gaacccaggg ctggtgacgg aattttcata gtcaagctat cagagtaaag aagaggagca       300
tgtcaaagta caattagaga caaatatata gtcgcgtgga gccaagagcg gattcctcag       360
tctcgtaggt ctcttgacga ccgttgatct gcttgatctc gtctcccgaa aatgaaaata       420
gctctgctaa gctattcttc tcttcgccgg agcctgaagg cgttactagg ttgcagtcaa       480
tgcattaatg cattgcagat gagctgtatc tggaagaggt aaacccgaaa acgcgtttta       540
```

```
ttcttgttga catggagcta ttaaatcact agaaggcact ctttgctgct tggacaaatg    600
aacgtatctt atcgagatcc tgaacaccat ttgtctcaac tccgg                    645
```

<210> SEQ ID NO 6
<211> LENGTH: 475
<212> TYPE: PRT
<213> ORGANISM: Artificial Sequence
<220> FEATURE:
<223> OTHER INFORMATION: synthesized

<400> SEQUENCE: 6

```
Met Glu Thr Ala Val Pro Val Ala Tyr Asn Val Thr Asn His Asp Met
1               5                   10                  15

Asn Ala Val Ala His Arg Arg Met Met Ala Pro His Gln Gln His His
            20                  25                  30

His His His His His Asp Gln Asn Ile Ala Tyr Phe Ser Asn Pro
        35                  40                  45

Pro Ile Pro Tyr Ser Thr Pro Leu Gln Pro Pro Ser Phe Gly Gly Phe
    50                  55                  60

Gly His Ile Leu Asn Asn His Pro His His Thr Ser Tyr Gln Gly Tyr
65                  70                  75                  80

Phe Asn Ser Asn Pro Asn Pro Asn Pro Gln Val Asn Ser His His His
                85                  90                  95

Arg Leu Ala Thr Glu Thr Asn Pro Val His Gln Val Ser Asp Ile Arg
            100                 105                 110

His Val Lys Asn Pro Asn Gln Arg Leu Ile Arg Pro Ser Pro Pro Lys
        115                 120                 125

Glu Asp Thr Leu Pro Pro Ala Pro Ala Pro Ala Pro Ala Val Ala Pro
    130                 135                 140

Pro Pro Pro Arg Leu Pro Pro Gln Arg Val Ser Val Ala Pro Val
145                 150                 155                 160

Arg Asn Thr Thr Gln His Glu Asp Ser Lys Pro Met Pro Lys Pro Gly
                165                 170                 175

Val Glu Phe Gly Thr Glu Val Asp Thr Leu Met Lys Ala Ile Gln Ser
            180                 185                 190

Lys Pro Gln Pro Ala Ser Pro Gln Val Glu His Gln Leu Pro Pro Leu
        195                 200                 205

His Gln Lys Phe Asn Asn Gly Val Ala Asn Trp Ile His Pro Ala Tyr
    210                 215                 220

Ala Asn Gln Met Ala Gly Asn Gln Ala Ile Phe Pro Asn Ala Pro Gln
225                 230                 235                 240

Asp Arg Val Pro Pro Asn Gln Lys Ala Lys Arg Lys Tyr Glu Cys
                245                 250                 255

Thr Leu Pro His Cys Arg Lys Ser Phe Phe Gln Lys Thr His Leu Asp
            260                 265                 270

Ile His Met Arg Ala His Thr Gly Asp Lys Pro Phe Thr Cys Lys Glu
        275                 280                 285

Pro Ser Cys Gly Gln Arg Phe Ser Gln Leu Gly Asn Leu Lys Thr His
    290                 295                 300

Glu Arg Arg His Thr Gly Glu Lys Pro Tyr Ser Cys Glu Ile Cys His
305                 310                 315                 320

Lys Lys Phe Ala Gln Arg Gly Asn Val Arg Ala His Lys Ile Thr His
                325                 330                 335

Glu Gln Ala Lys Pro Phe Lys Cys Gln Leu Asp Asp Cys Gly Lys Gln
```

```
                     340             345             350
Phe Thr Gln Leu Gly Asn Leu Lys Ser His Gln Asn Lys Phe His Ala
            355                 360                 365

Gln Thr Leu Arg Asn Leu Thr Leu Arg Phe Ala Ser Ile Gly Asp Ile
    370                 375                 380

Asp Arg Met Ser Pro Gln Asp Lys Glu Leu Trp Ser Tyr Phe Ser Thr
385                 390                 395                 400

Leu Tyr Arg Asn Ser Asn Lys Gly Ile Lys Gly Arg Gly Lys Asp Arg
                405                 410                 415

Arg Val Ser Thr Ala Lys Thr Ser Thr Ser Ala Tyr Asp Gly Ser His
            420                 425                 430

Ser Glu Ser Glu Gly Glu Ala Lys Gly Arg Ser Arg Ser Tyr Asp Arg
            435                 440                 445

Ala Ser Ala Val Met Thr Ser Ser Asp Glu Pro Asp Tyr Arg Glu
            450                 455                 460

Gln Leu Tyr His His Arg Asn Gly Ala His His
465                 470                 475

<210> SEQ ID NO 7
<211> LENGTH: 389
<212> TYPE: PRT
<213> ORGANISM: Artificial Sequence
<220> FEATURE:
<223> OTHER INFORMATION: synthesized

<400> SEQUENCE: 7

Met Asp Ile Val Asn Ile Leu Asn Lys Lys Glu Ala Ser Ala Ser Ser
1               5                   10                  15

Asp Asn Ala Val Ser Pro Thr Ser Arg Gln Pro Glu Thr Gly Gln Ala
            20                  25                  30

Arg Phe Glu Lys Gln Asp Ala Val Arg Leu Pro Ser Met Ala Pro Asn
        35                  40                  45

Ser Phe Ser Thr Tyr Pro His Ala Thr Phe Ala Pro Arg Tyr Ser Tyr
    50                  55                  60

Glu Thr Gln His Ser Pro Pro Ala Ala Ser Pro Ser Asn Pro Phe
65                  70                  75                  80

Ala Thr Ser Pro Gly Pro Ser Ser Glu Gly Pro His Ser Asn Asn Gly
                85                  90                  95

Asn Asp Asp Pro Thr Lys Pro Tyr His Cys Lys Thr Cys Ser Lys Gly
            100                 105                 110

Phe Ala Arg Arg Ser Asp Leu Ser Arg His Glu Arg Ile His Ser Gly
        115                 120                 125

Ile Arg Pro His Ile Cys Asp Phe Glu Gly Cys Gly Lys Gln Phe Ile
    130                 135                 140

Gln Arg Ser Ala Leu Thr Val His Ala Arg Val His Thr Gly Glu Lys
145                 150                 155                 160

Pro His Met Cys Glu Ala Cys Gly Lys Pro Phe Ser Asp Ser Ser Ser
                165                 170                 175

Leu Ala Arg His Arg Arg Ile His Ser Gly Lys Arg Pro Tyr Lys Cys
            180                 185                 190

Pro Tyr Ala Asp Cys Gln Lys Thr Phe Thr Arg Arg Thr Thr Leu Thr
        195                 200                 205

Arg His Gln Asn His His Thr Gly Thr Ile Ser Glu Ala Ala Ala
    210                 215                 220

Thr Ala Ala Ala Leu Ala Ser Arg Arg Ser Ser Ser Lys Ser Ser Val
```

```
            225                 230                 235                 240
        Gln Ser Leu Ser Leu Thr Gly Asn Ser Pro Arg Glu Asp Asn Met Glu
                        245                 250                 255

Ser Val Ser Gln Ser Arg Thr Gly Ser Asn Ser Ser Leu Arg Leu Ser
                        260                 265                 270

Gln Gly Ser Ser Pro Ala Ala Asp Leu Asp Lys Gln Val Ile Leu Ala
                        275                 280                 285

Trp Arg Glu Ser Pro Pro Tyr Gln Ala Val Thr Ser Leu Pro Thr Pro
                290                 295                 300

Val Ser Thr Pro Thr Ile Pro Ala Asn Leu Val Thr Gly Thr Ala Ala
        305                 310                 315                 320

Leu Gln Ile Ser Asp Ser Arg Gln Asn Leu Arg Gly Leu Pro Pro Leu
                        325                 330                 335

Gly Ser Gly Ser Gln Pro Arg Ser Leu Ser Pro Leu His Arg Ser Pro
                        340                 345                 350

Ser Ser Gly Ile Ser His His Ile Trp Gln His His Thr His Asn Gly
                        355                 360                 365

Ser Pro Thr Ser Leu Leu Pro Ile His Thr Ala Ile Ser Leu Ser Pro
                370                 375                 380

Gln Pro Ala Tyr Arg
        385

<210> SEQ ID NO 8
        <211> LENGTH: 482
        <212> TYPE: PRT
        <213> ORGANISM: Artificial Sequence
        <220> FEATURE:
        <223> OTHER INFORMATION: synthesized

<400> SEQUENCE: 8

Met Ala Ala Arg Pro Phe Gln Cys Glu Trp Pro Glu Gly Cys Ser Lys
        1               5                   10                  15

Ser Phe Asn Arg Lys Ser Asp Leu Gln Arg His Tyr Arg Ile His Thr
                        20                  25                  30

Asn Glu Arg Pro Tyr Ala Cys Asp Tyr Lys Pro Cys Thr Lys Thr Phe
                        35                  40                  45

Ile Gln Arg Ser Ala Leu Thr Val His Arg Arg Thr His Thr Gly Asp
                50                  55                  60

Lys Pro His Lys Cys Pro Phe Leu Gly Cys Gly Lys Cys Phe Ser Asp
        65                  70                  75                  80

Ser Ser Ser Leu Ala Arg His Arg Arg Ile His Thr Asn Asp Lys Pro
                        85                  90                  95

Tyr Ile Cys Arg Asn Gln Arg Cys Lys Lys Ala Phe Cys Arg Lys Thr
                        100                 105                 110

Thr Met Thr Lys His Ile Arg Lys Glu His Pro Ala Glu Pro Ile Gln
                    115                 120                 125

Glu Asp Gln Asp Ala Glu Tyr Ser Asp Val Asp Pro Ser Asp Asp Glu
                130                 135                 140

Val Leu Glu Asp Asp Ile Asp Glu Ile Lys Glu Glu Ala Gly Ser Pro
        145                 150                 155                 160

Tyr Gln Glu Asp Pro Lys Asp Ser Arg Leu Thr Arg Pro Leu Ser Asn
                        165                 170                 175

Tyr His Ala Asn Leu Trp Pro Leu Pro Ala Gln Thr Ala Gln Arg Pro
                        180                 185                 190

Thr Leu His Arg Ser Glu Ser Ser Ser His Asp Ile Lys Leu Glu Arg
```

```
                195                 200                 205
Thr Ser Ser Gly Thr Pro Gln Arg Ser Leu Thr Asp Pro Tyr Pro Asp
    210                 215                 220

Ser Ser Ile His Ser Ala Gly Leu Asn Gly Val Thr Ile His Ser Val
225                 230                 235                 240

Met Pro His Gly Leu Asn Thr Ser Asn Met Pro Gln Gln Phe Gln Tyr
                245                 250                 255

Arg Ser His Asp Asn Asn Val Gly Leu Trp Ser Pro Gly His Asp Ser
            260                 265                 270

Pro Thr Ser Ile Thr Asn Ser Ser Pro Ser Val Ser Ala Gln Thr
        275                 280                 285

His Pro Ile Tyr Thr Ser Gln Pro Tyr Gln Leu Gln Pro Asn Ser Leu
    290                 295                 300

Pro Thr His Ala Gln Ile Gln Tyr Ser His Asp Gly Met Val Ser Asn
305                 310                 315                 320

Ile Gln Gln Pro Met Asn Asp Leu Ala Val His Asp Ile His Leu Asp
                325                 330                 335

Gln Pro Gln Gln His Gln Tyr His Asp Met Ala Ser Thr Pro Ile Gln
            340                 345                 350

Gln Gln Gln Gln Tyr Glu Gly Val Pro Gln Val Ser Pro Gln Asp
        355                 360                 365

His Tyr Ile Glu Met Ser Arg Asp Pro Pro Gln His Pro Ala Tyr Ala
    370                 375                 380

Glu Gly Pro Pro Gln Ala Ala Val His His Phe Gln Ser Glu Val Pro
385                 390                 395                 400

Pro Thr Pro Ala Thr Asn Arg Asp Leu Ser Arg Tyr Ala Thr Ser Ile
                405                 410                 415

Pro Gln Glu Gln Thr Tyr Gln Gln Pro Gln Leu Leu Pro Ile Glu Glu
            420                 425                 430

Thr Phe Ser Ile Gly His Gln Tyr Phe Leu Pro Asn His Gly Ser Tyr
        435                 440                 445

Gln Ile Asn Gln Pro Ser Tyr Phe Phe Asp Glu Leu Lys Asp Lys Pro
    450                 455                 460

Asp Thr Met Trp Ala Gly Pro Leu Pro Asp Gln Arg Leu Lys Asp Glu
465                 470                 475                 480

Trp Pro

<210> SEQ ID NO 9
<211> LENGTH: 397
<212> TYPE: PRT
<213> ORGANISM: Artificial Sequence
<220> FEATURE:
<223> OTHER INFORMATION: synthesized

<400> SEQUENCE: 9

Met Ala Gly Val Met Ser Ser Phe Asn Met Ala Phe Gln Pro Asp Thr
1               5                   10                  15

Ser Ala Ile Leu Pro Tyr Met Gln Met Gln Glu Gln Glu Arg His Thr
            20                  25                  30

Met His Ala Pro Ser Ile Ile Pro Ser Asp Leu Met Asn Thr Gln Ile
        35                  40                  45

Asn Ala Asp Leu Ser Val Gly Leu Gly Met Asp Ala Ser Phe Ala Asn
    50                  55                  60

Ala His Ala Met Asn Val Asp Tyr Asn Asn Ala Thr Phe Gly Asn Leu
65                  70                  75                  80
```

```
Ala Ala Trp Pro Ala Pro Ile Asn Thr Asn Phe Asn Ala Met Pro Arg
                85                  90                  95

Pro Val Met Met Gln Ala Glu Ser Tyr Ser Ser Thr Asp Ser Ser Glu
            100                 105                 110

Pro Tyr Ile Lys Thr Glu Asp Asp Ser Pro Val His Ala Ser Gln Val
        115                 120                 125

Phe Tyr Asn Ala Asn Ala Tyr Ala Ser Ser Pro Glu Ser Gln Thr Gly
    130                 135                 140

Thr Asp Glu Pro Glu Glu Thr Lys Pro Thr Val Phe Ala Thr Asp Ile
145                 150                 155                 160

Asp Thr Leu Met Arg Ala Ile Gln Thr Lys Thr Gly Ser Ala Ala Glu
                165                 170                 175

Gln Arg Gln Lys Asp Gln Thr Glu Val Thr Ile Thr Glu Ile Ser Pro
            180                 185                 190

Val Lys Pro Lys Lys Arg Tyr Glu Cys Asn Val Pro Asp Cys Gly Lys
        195                 200                 205

Ala Phe Tyr Gln Lys Thr His Leu Glu Ile His Thr Arg Ala His Thr
    210                 215                 220

Gly Ile Lys Pro Phe Leu Cys Arg Glu Pro Ser Cys Gly Gln Arg Phe
225                 230                 235                 240

Ser Gln Leu Gly Asn Leu Lys Thr His Glu Arg Arg His Thr Gly Glu
                245                 250                 255

Arg Pro Tyr His Cys Asp Ile Cys Gly Lys Thr Phe Ala Gln His Gly
            260                 265                 270

Asn Val Arg Ala His Lys Ile Val His Thr Ala Ala Lys Pro Phe Thr
        275                 280                 285

Cys Lys Leu Asp Ser Cys Asn Lys Gln Phe Thr Gln Leu Gly Asn Leu
    290                 295                 300

Lys Ser His Gln Asn Lys Phe His Ile Glu Thr Ile Arg Arg Leu Lys
305                 310                 315                 320

Ser Arg Phe Glu Ser Phe Arg Glu Gly Asp Val Val Asp Thr Trp Glu
                325                 330                 335

Lys Glu Met Trp Glu Tyr Phe Ala Ser Leu Tyr Lys Asn Cys Asn Lys
            340                 345                 350

Gly Ile Lys Gly Arg Gly Lys Asp Arg Arg Ile Ser Asn Thr Ala Ala
        355                 360                 365

Ala Gln Arg Arg Asn Ser Ile Val Ser Ser Val Gly Ser Ser Ser Gly
    370                 375                 380

Ser Met Ser Ala Gly His Ser Val Pro Gln Arg Thr Tyr
385                 390                 395

<210> SEQ ID NO 10
<211> LENGTH: 434
<212> TYPE: PRT
<213> ORGANISM: Artificial Sequence
<220> FEATURE:
<223> OTHER INFORMATION: synthesized

<400> SEQUENCE: 10

Met Glu Leu Met Glu Leu Val Glu Asn Glu Pro Thr Val Arg Pro Phe
1               5                   10                  15

Gln Cys Glu Trp Pro Ser Cys Gln Lys Asn Phe Asn Arg Lys Ser Asp
            20                  25                  30

Leu Gln Arg His Phe Arg Ile His Thr Asn Glu Arg Pro Tyr Ser Cys
        35                  40                  45
```

Leu Thr Pro Gly Cys Asn Lys Ser Phe Ile Gln Arg Ser Ala Leu Thr
 50                  55                  60

Val His Ile Arg Thr His Thr Gly Glu Lys Pro His Gln Cys Gln Gln
 65                  70                  75                  80

Leu Glu Cys Gly Lys Arg Phe Ser Asp Ser Ser Leu Ala Arg His
                 85                  90                  95

Arg Arg Ile His Thr Gly Lys Arg Pro Tyr Lys Cys Ala His Glu Gly
                100                 105                 110

Cys Leu Lys Ser Phe Cys Arg Lys Thr Thr Met Val Lys His Gln Arg
             115                 120                 125

Arg Ser His Gln Arg Gly Gly Val Asn Ser Ser Glu Leu Glu Asp
         130                 135                 140

Gly Asp Thr Ser Asp Ser Asp Met Gly Glu Ser Pro Ser Thr Pro Gln
145                 150                 155                 160

Leu Val Met Gln Ala His Trp Pro Gln Asp Leu Asn Thr Val Ile Thr
                165                 170                 175

His Ser Val Met Gln Ser His His Gln Ala Thr His Arg Ser Gln Ser
            180                 185                 190

Phe Ala Asp Phe Gly His Tyr His Asn Ala Asn Ser Gln Pro Tyr Val
            195                 200                 205

Thr Thr Asp Val Tyr Pro Pro Arg His Ser Leu Ser Glu Ser Pro Gln
210                 215                 220

His Tyr Gln His Arg Ser Leu Ser Leu Gln Asp Gln Arg His Pro Gln
225                 230                 235                 240

Asp Leu Ile Gln Gln Gln Arg Gln His Gln His Pro Tyr Phe Ile
            245                 250                 255

Pro Glu Gln Asn Asn Pro Gly Val Ala Thr Met Asn Thr Asn Pro Asn
            260                 265                 270

Ser His Ile Gln Thr Tyr Ile Ala Arg Gln Ile Pro Asp Leu Gln Ile
            275                 280                 285

Pro Asp Leu Gln Ile Pro Tyr Thr Thr Gln Pro Leu Pro Ala Ser Val
    290                 295                 300

Tyr Ala Gly Ser Asp Thr Tyr Ser Ala Leu Ser Ala Arg Thr Pro Pro
305                 310                 315                 320

Pro Pro Glu Leu Tyr Tyr Ala His Gln Gln Pro Ile Gln Lys Phe Glu
                325                 330                 335

Tyr Pro Ala His Gln Pro Ser Pro Ile Asp Gln Gln Gln Gln His Gln
            340                 345                 350

Gln Val Pro Val Val Gln Tyr Gln Arg Leu Gln Val Gln Gln Val Val
            355                 360                 365

Pro Thr Pro Gln Gln Gln Gln Tyr Gln Thr Pro Gln Glu Gln Trp
    370                 375                 380

Tyr Ala Gln Ala Pro Phe Gln Glu Pro Val Glu Leu Ala Ser Ala Ile
385                 390                 395                 400

Asn Ser Tyr Thr Ser Ala Gly Leu Asn Asp Pro Trp Gln Leu Lys Met
                405                 410                 415

Glu Ala Phe Glu Asp Pro Ser Met Gln Leu Pro Ser Ala Arg Cys Glu
            420                 425                 430

Asn Leu

<210> SEQ ID NO 11
<211> LENGTH: 471
<212> TYPE: PRT

<213> ORGANISM: Artificial Sequence
<220> FEATURE:
<223> OTHER INFORMATION: synthesized

<400> SEQUENCE: 11

```
Met Met Ala Ser Pro His Met Leu Pro Phe Asp Ser Arg Ala Thr Thr
1               5                   10                  15

Thr Gly Pro Leu Gln Arg Pro Val Met Ala Pro Tyr Met Val His Pro
            20                  25                  30

Pro Tyr Ser Ser Gly Pro Val Asn Ser Leu Thr Ala Pro His Tyr Gln
        35                  40                  45

Val Pro Asn Pro Tyr Gln Phe Gly Gly Tyr Gln Gly Pro Pro Thr Pro
50                  55                  60

Pro His His Ser Thr Pro Phe Lys Met Glu Tyr Asn Asp Arg Arg Pro
65                  70                  75                  80

Met Gly His Asp Asn Asp His Gly Arg Met Pro Ser Tyr Ser Arg Glu
                85                  90                  95

Met Lys Tyr Thr Tyr Ala Glu Gln Ala Pro Ser Pro Ala Arg Ser Asp
            100                 105                 110

Ser Gln Ala Ser Thr Val Arg Ser Ser Gly Thr Asn Pro Ser Met Gly
        115                 120                 125

Ser Lys Thr Ile Thr Ser Asn Glu Thr Leu Asn Pro Gly Asp Gln Ile
    130                 135                 140

Asn Phe Glu Thr Glu Val Asp Glu Leu Met Lys Ala Ile Gln Arg Lys
145                 150                 155                 160

Val Asp Leu Gln Val Asp Thr Val Gln Gln Pro Leu Thr Pro Gly Met
                165                 170                 175

Ser Pro Val Ser Glu Ala Ser Phe Glu Ser Gln Gly Thr Pro Gly Pro
            180                 185                 190

Met Asp Ser Lys Thr Ala Arg Lys Arg Tyr Arg Cys Asp Gly Pro Asn
        195                 200                 205

Cys Gln Lys Ser Phe Thr Gln Lys Thr His Leu Asp Ile His Arg Arg
    210                 215                 220

Thr His Thr Gly Ile Lys Pro Tyr Asn Cys Asp Phe Pro Gly Cys Asp
225                 230                 235                 240

Leu Thr Phe Ser Gln Leu Gly Asn Leu Lys Thr His Arg Arg Arg His
                245                 250                 255

Thr Gly Glu Arg Pro Phe Ala Cys Asp Lys Cys Asp Arg His Phe Ala
            260                 265                 270

Gln Arg Gly Asn Leu Arg Ala His Leu Gln Thr His Gln Gly Leu Lys
        275                 280                 285

Pro Phe Ile Cys Ile Leu Asp Asp Cys Asn Lys Thr Phe Ser Gln Leu
    290                 295                 300

Gly Asn Met Lys Thr His Gln Asn Asn Phe His Lys Lys Thr Leu Lys
305                 310                 315                 320

Lys Leu Thr Met Lys Phe Ala Asn Ile Ile Ala Ser Gly Glu Glu Val
                325                 330                 335

Ser Glu Ala Asp Arg Glu Leu Phe Glu Tyr Phe Ala Ala His Tyr Lys
            340                 345                 350

Asn Ser Asn Lys Gly Ile Lys Gly Arg Gly Lys Ala Arg Thr Val Ala
        355                 360                 365

Asp Arg Lys Ala Lys Thr Ser Gln Ser Pro Ala Asn Thr Met Thr
    370                 375                 380

Ala Val Pro Gln Tyr Pro Leu Pro Gln Ile Ala Pro Thr Pro Val Thr
```

```
                385                 390                 395                 400
        Pro His Gly Leu Pro Val Ser Gly Ser Leu Ala Ser Tyr Ser Val Thr
                        405                 410                 415

Arg Gly Gln Pro Gly Pro Ile Asn His Met Ser Arg Gln Thr His Thr
                        420                 425                 430

Gly Gly Tyr Glu Val Tyr Asp Ile Gln Gly His His Ile Gln Pro
                        435                 440                 445

Pro Asn Asn Gly Met Leu Tyr Glu Thr Gly Ser Thr Arg Glu Met
        450                 455                 460

Gly Tyr His Gly Arg Met Tyr
        465                 470

<210> SEQ ID NO 12
<211> LENGTH: 413
<212> TYPE: PRT
<213> ORGANISM: Artificial Sequence
<220> FEATURE:
<223> OTHER INFORMATION: synthesized

<400> SEQUENCE: 12

Met Asp Val Ser Ala Ile Thr Asn His Asp Thr Ala Asn Thr Glu Pro
        1               5                   10                  15

Gly Ala Ala Lys Glu Thr Glu Leu Lys Gln Ser Gln Asp His Ala Phe
                        20                  25                  30

Ser Ile Ser Ser Met Met Asn Asn Asp Glu Glu Arg Thr Val Ser Pro
                        35                  40                  45

Asp Pro Ile Gln Thr Glu Glu Arg Gln Glu Asn Gly Lys Glu Glu
                50                  55                  60

Asn Gly Ile His His Ser Asp Ser Gln Asn Asp Leu Val Pro Lys Asp
        65                  70                  75                  80

Val Asp Ala Gly Ser Glu Ser Thr Leu Ser Asp Val Glu Ser Thr Lys
                        85                  90                  95

Ala Gln Ser Glu Asp Glu Phe Thr Asp Leu Glu Leu Ser Asp Asp Asn
                        100                 105                 110

Ala Glu Glu Ile Glu Ser Lys Arg Ile Glu Ala Asp Cys His Trp Ser
                        115                 120                 125

Gly Cys Gln Asp Lys Phe Leu Asn Ile Asp Asp Leu Val Gln His Leu
        130                 135                 140

Asn Ser Lys His Ile Thr Asn Val Asp Ser Val Tyr Arg Cys Glu Trp
        145                 150                 155                 160

Asp Asn Cys Phe Arg Lys Gly Val Thr Gln Pro Ser Arg Phe Ala Leu
                        165                 170                 175

Ile Ser His Leu Arg Thr His Thr Gly Glu Lys Pro Phe Phe Cys Ile
                        180                 185                 190

Ile Pro Glu Cys Ser Lys His Phe Thr Arg Ala Asp Ala Leu Ser Gln
                        195                 200                 205

His Ile Arg Thr Val His Gln Thr Ser Asn Leu Ser Val Glu Tyr Pro
                        210                 215                 220

Phe Trp Tyr Ser Tyr Leu Asn Gly Leu Lys Asn Asp Glu Thr Phe Ala
        225                 230                 235                 240

Lys Arg Phe Arg Leu Met Pro Glu Met His Ser Leu Glu Arg Tyr Ser
                        245                 250                 255

Lys Leu Asp Ser Gly Asp Gln Phe Gln Lys Glu Leu Ala Asn Lys Lys
                        260                 265                 270

Ile Gln Phe Asp Asn Ile His Asn Ile Glu Leu Thr Asp Leu Thr Glu
```

```
                275                 280                 285
Pro Thr Ser Lys Arg Gln Lys Thr Ser Leu Lys Asp Ile Asn Ala Gly
    290                 295                 300

Leu Lys Ala Ser Phe Glu Lys Glu Asp Ala Asp Phe Lys His His Ile
305                 310                 315                 320

Ala Ala Ala Ala Lys Asp Thr Phe Lys Ser Leu Glu Gly Val Glu Ser
                325                 330                 335

Leu Pro Thr Asp Ala Ser Ile Glu Ser Val Gln Ser Leu Glu Glu Leu
                340                 345                 350

Gln Ala Leu His Glu Ser Leu Arg Arg Lys Tyr Val Trp Gly Leu Glu
                355                 360                 365

Val Glu Lys Leu Ile Thr Lys Glu Leu Lys Gln Leu Arg Thr Glu Lys
        370                 375                 380

Thr Gln Leu Trp Leu Lys Lys Glu Thr Leu Leu Asp Ala His Ile Glu
385                 390                 395                 400

Leu Glu Ile Ser Glu Asn Arg Asp Leu Tyr Ser Leu Lys
                405                 410

<210> SEQ ID NO 13
<211> LENGTH: 373
<212> TYPE: PRT
<213> ORGANISM: Artificial Sequence
<220> FEATURE:
<223> OTHER INFORMATION: synthesized

<400> SEQUENCE: 13

Met Arg Tyr Pro Pro His Gly Gln Pro Ser Gly Met Arg Ile Leu
1               5                   10                  15

Gln Asn Pro Tyr Val Pro Gly Ala Tyr Thr Gly Ser Ala Gln Ile Pro
                20                  25                  30

Gly Gly Ala Thr Pro Gln Arg Ala Asp Pro Pro Lys Thr Phe His
                35                  40                  45

Cys Ser Thr Cys Gly Lys Gly Phe Ala Arg Arg Ser Asp Leu Ala Arg
        50                  55                  60

His Glu Arg Ile His Thr Gly Ile Arg Pro His Ala Cys Asp Trp Pro
65                  70                  75                  80

Gly Cys Gly Lys Gln Phe Ile Gln Arg Ser Ala Leu Thr Val His Ser
                85                  90                  95

Arg Val His Thr Gly Glu Lys Pro His Met Cys Glu Arg Cys Gly Lys
                100                 105                 110

Pro Phe Ser Asp Ser Ser Ser Leu Ala Arg His Arg Arg Ile His Ser
            115                 120                 125

Gly Lys Arg Pro Tyr Lys Cys Pro Tyr Ala Asn Cys Gln Lys Thr Phe
        130                 135                 140

Thr Arg Arg Thr Thr Leu Thr Arg His Gln Asn His His Thr Gly Thr
145                 150                 155                 160

Ile Glu Glu Ala Ala Ala Glu Thr Glu Ala Asn Leu Arg Gln Asn Lys
                165                 170                 175

Glu Arg Val Arg Ala Pro Gly Asp Gly Gly Phe Ser Glu His Ala Ser
                180                 185                 190

Val His Ser Thr Pro Ser Pro Ala His His Pro Val Ser Ile Pro Pro
            195                 200                 205

Pro Gly Asp Leu Pro Pro Leu Asn Met Pro Arg Ser Ala Gly Asp Tyr
        210                 215                 220

Tyr Met Gly Asn Gly Ser Ile Pro Pro His Val Arg Gly Asp Phe Ser
```

```
            225                 230                 235                 240
        Gln Ala Ser Pro Arg Ser Ser Pro Thr Ala Thr Ser Pro Ser Leu Ser
                        245                 250                 255

Ser Phe Ser Gly Ala Pro His Gln Arg Pro Ser Met Thr Ser His Pro
                        260                 265                 270

Ser Gly Tyr Ala Pro Pro Gln Pro Leu Glu Pro Pro Ala Asn Ser Asp
                        275                 280                 285

His Arg Pro Asn Ser Val Ser Gly Ser Pro His Met Thr Ser Leu Gly
                        290                 295                 300

Trp Ala Ser Pro Ser His Gly Ser Ile Pro Ser Pro Gly Ser Val Asn
        305                 310                 315                 320

Asp Phe Asn Tyr Pro Glu Pro Ser Gly Pro Ala Tyr Pro Ser Ser Met
                        325                 330                 335

Pro Pro His Met Tyr Phe Pro Asn Ser Thr Ile Arg Arg Pro Thr Ser
                        340                 345                 350

Thr Glu Pro Glu Asn Tyr Glu Leu Lys Pro Arg Leu Gly Asp Asn Gly
                        355                 360                 365

Trp Ser Thr Pro Val
                        370

<210> SEQ ID NO 14
<211> LENGTH: 435
<212> TYPE: PRT
<213> ORGANISM: Artificial Sequence
<220> FEATURE:
<223> OTHER INFORMATION: synthesized

<400> SEQUENCE: 14

Met Asp Ile Thr Thr Ile Leu Asn Lys Lys Ala Ser Val Ser Val Val
1               5                   10                  15

Ala Ala Glu Val Gln Gln Leu Gln Gln His Leu Ala Gln Ala Gln Ala
                20                  25                  30

Ala Asp Asp Ala Lys Ser Arg Ser Pro Ser Glu Met Gly Ser Glu His
            35                  40                  45

Gly Ser Ala Ser Ala Pro Pro Ser Glu His Gln Gln Thr Tyr Pro Ser
        50                  55                  60

Ser Thr Gln Ser Leu Pro Gln Met Ala His Leu Ala Gln Tyr His Val
65                  70                  75                  80

Gln Ala Gln Ala Thr His Asn Asn Tyr Ala His Ser Ala His Gly Ser
                85                  90                  95

Asp Tyr Gly Arg Asn Gly Ser Gly Asn Met Arg Pro Ser Gly Leu Pro
            100                 105                 110

Ala Leu Lys Thr Phe His Cys Gln Thr Cys Ser Lys Gly Phe Ala Arg
        115                 120                 125

Arg Ser Asp Leu Ala Arg His Glu Arg Ile His Ser Gly Ile Arg Pro
130                 135                 140

His Ala Cys Asp Trp Pro Gly Cys Gly Lys Gln Phe Ile Gln Arg Ser
145                 150                 155                 160

Ala Leu Thr Val His Thr Arg Val His Thr Gly Glu Lys Pro His Met
                165                 170                 175

Cys Asp Arg Cys Gly Lys Pro Phe Ser Asp Ser Ser Ser Leu Ala Arg
            180                 185                 190

His Arg Arg Ile His Ser Gly Lys Arg Pro Tyr Lys Cys Pro Tyr Ala
        195                 200                 205

Asn Cys Gln Lys Thr Phe Thr Arg Arg Thr Thr Leu Thr Arg His Gln
```

```
               210                 215                 220
Asn His His Thr Gly Thr Ile Glu Glu Ala Ala Ala Glu Thr Glu Ala
225                 230                 235                 240

Asn Leu Arg His Ser Lys Asp Arg Val Ser Arg Pro Ser Asp Tyr Ser
                245                 250                 255

Glu Ala Gly Ser Ala His Ser Thr Pro Ser Pro Ala Gln Arg Pro Ser
                260                 265                 270

Leu Ser Pro Gly Asn Glu Leu Pro Pro Leu Asn Leu Ser Arg Pro Ser
                275                 280                 285

Gly Asp Tyr Tyr Thr Ser Leu Pro Pro His Leu Arg Thr Asp Phe Gln
                290                 295                 300

Gln Ser Ser Pro Arg Ala Ser Pro Thr Ser Pro Ser Pro Thr Leu Thr
305                 310                 315                 320

Ser Leu Ser Gly Pro Ala Ser Tyr His Asn Arg Pro Ser Leu Thr Ser
                325                 330                 335

His Pro Ser Gly Tyr Gly Pro Pro Gln Pro Leu Glu Pro Pro Ala Asn
                340                 345                 350

Ser Asp Pro Arg Pro Asn Ser Val Ala Gly Ser Pro His Leu Ser Ser
                355                 360                 365

Val Gly Trp Ala Ser Pro Thr Leu Ser Ser Met Pro Ser Pro Ser Ser
                370                 375                 380

Ala Ser Ala Pro Glu Tyr Ser Tyr Pro Glu Pro Ser Ser His Gln Tyr
385                 390                 395                 400

Pro Gly Gly Ile Thr Pro His Met Phe Phe Ser Gly Gln Gly Leu Arg
                405                 410                 415

Arg Pro Gln Ser Ser Glu Pro Glu Asn Tyr Glu Met Lys Pro Lys Leu
                420                 425                 430

Glu Met Ser
        435

<210> SEQ ID NO 15
<211> LENGTH: 436
<212> TYPE: PRT
<213> ORGANISM: Artificial Sequence
<220> FEATURE:
<223> OTHER INFORMATION: synthesized

<400> SEQUENCE: 15

Met Ser Gly Met Arg Ser Pro Ala Pro Thr Glu Val Met Asp Ile Thr
1               5                   10                  15

Asn Met Leu Asn Lys Lys Gly Gln Met Gln Gln Leu Thr Ser Gly Leu
                20                  25                  30

Leu Asp His Gln Gln Tyr Gln His Ala Phe Val Lys His Glu Pro Gly
                35                  40                  45

Met Glu Arg Ser Ala Ser Pro His Gly Ser Glu His Ser Gln Tyr Ser
        50                  55                  60

Asn Pro His Ser Ile Ala Arg Ala Tyr Pro Ser Pro Ser Thr Met Gln
65                  70                  75                  80

Ala Pro Met His Met Pro Asn Pro Met Ser Ala Ala Met Thr Ile Gln
                85                  90                  95

Gly Tyr Pro Glu Met Pro Asn Met Gly Gly Met Pro His Met His Met
                100                 105                 110

Gln Gln Met Pro Gln Gln Pro Pro Pro Gln Gln Pro Ile Lys
                115                 120                 125

Ala Tyr Pro Cys Ser Thr Cys Gly Lys Gly Phe Ala Arg Arg Ser Asp
```

```
                130               135               140
Leu Ala Arg His Glu Arg Ile His Ser Gly Val Arg Pro His Val Cys
145                 150                 155                 160

Asp Trp Pro Gln Cys Gly Lys Gln Phe Ile Gln Arg Ser Ala Leu Thr
                165                 170                 175

Val His Gln Arg Val His Thr Gly Glu Lys Pro His His Cys Glu Thr
                180                 185                 190

Cys Ala Lys Pro Phe Ser Asp Ser Ser Leu Ala Arg His Arg Arg
                195                 200                 205

Thr His Ser Gly Lys Arg Pro Tyr Lys Cys Pro Tyr Ala Asp Cys Gln
                210                 215                 220

Lys Thr Phe Thr Arg Thr Thr Leu Thr Arg His Gln Asn His His
225                 230                 235                 240

Ser Gly Thr Ile Glu Glu Ala Ala Ala Thr Ala Ala Ala Leu Ala
                245                 250                 255

Ala Ser Lys Ser Lys Gly Leu Ser Gln Ala Arg Ser Glu Ser Asp His
                260                 265                 270

Met Ser Asn His Gly Ser Pro Leu Thr Thr Pro Ser Pro Ser Gln Arg
                275                 280                 285

Thr Met Ser Met Ser Pro Ser Val Asp Leu Ser Gly Asn Asn Ser Ile
                290                 295                 300

Pro Arg His Pro Gly Asp Phe Gln Tyr Leu Ser Gln Asn Gly Ser Leu
305                 310                 315                 320

Pro Met His Met Arg Val Gly Ser Pro Thr Ser Thr Ser Gly Gly
                325                 330                 335

Tyr Asn Met Met Arg Pro Thr Ser His Pro Thr Ser Tyr Gly Pro Pro
                340                 345                 350

Pro Thr Leu Glu Pro Asn Leu Asp Asn Ser Gln Gly Thr Pro Ser Ser
                355                 360                 365

Asn Gly Gly Ser Pro His Met Ala Asn Val Gly Trp Gln Ser Pro Ser
370                 375                 380

His Met Ala Ser Pro Ser Gln Asn Asn Ala Ser Tyr Val Tyr Pro Asp
385                 390                 395                 400

Pro Ala Asp Ala Tyr Pro Ala Asn Gln Ala Met Asn Gln Met Tyr Tyr
                405                 410                 415

Ser Ala Ala Thr His Met Arg Arg Pro Gln Ser Thr Glu Pro Gly Leu
                420                 425                 430

Val His Met Ala
        435

<210> SEQ ID NO 16
<211> LENGTH: 445
<212> TYPE: PRT
<213> ORGANISM: Artificial Sequence
<220> FEATURE:
<223> OTHER INFORMATION: synthesized

<400> SEQUENCE: 16

Met Asp Ile Thr Thr Ile Leu Asn Lys Lys Ala Ser Val Ser Ile Val
1               5                   10                  15

Ala Ala Asp Val His Gln Leu Gln Gln His Leu Ala Gln Ala Pro Val
                20                  25                  30

Thr Val Thr Val Ala Val Thr Ser Arg Ser Pro Ser Glu Leu Gly Ala
                35                  40                  45

Ser Glu His His Arg Ser Ala Ser Ala Pro Pro Ser Glu His His His
```

```
            50                  55                  60
His His His His His Gln Pro Thr Ser Ser Phe Pro Ser Ser Thr Gln
 65                  70                  75                  80

Ser Leu Pro Gln Met Ala His Leu Ala Gln Tyr His Val Gln Ala Gln
                    85                  90                  95

Ala Asn His Ala Gly Thr Ser Gln Gly Tyr Ala His Ser Ala His Gly
                100                 105                 110

Ser Asp Tyr Gly Arg Ser Thr Thr Ser Met Arg Pro Thr Gly Leu Pro
                115                 120                 125

Ala Leu Lys Thr Phe His Cys Gln Thr Cys Ser Lys Gly Phe Ala Arg
                130                 135                 140

Arg Ser Asp Leu Ala Arg His Glu Arg Ile His Ser Gly Ile Arg Pro
145                 150                 155                 160

His Ala Cys Asp Trp Pro Gly Cys Gly Lys Gln Phe Ile Gln Arg Ser
                165                 170                 175

Ala Leu Thr Val His Thr Arg Val His Thr Gly Glu Lys Pro His Met
                180                 185                 190

Cys Asp Arg Cys Gly Lys Pro Phe Ser Glu Ser Ser Leu Ala Arg
                195                 200                 205

His Cys Arg Ile His Ser Gly Lys Arg Pro Tyr Lys Cys Pro Tyr Ala
210                 215                 220

Asn Cys Gln Lys Thr Phe Thr Arg Arg Thr Thr Leu Thr Arg His Gln
225                 230                 235                 240

Asn His His Thr Gly Thr Ile Glu Glu Ala Ala Ala Glu Thr Glu Ala
                245                 250                 255

Asn Leu Arg His Ser Lys Asp Arg Ser Thr Thr Ser Arg Pro Ser Asp
                260                 265                 270

Ala Leu Leu Ser Pro Leu Asn Leu Ser Ser Arg Pro Thr Ser Gly Trp
                275                 280                 285

Arg Pro Leu Leu Ser Ala Gly Gly Ala Ala Asp Tyr Tyr Thr Ser Leu
290                 295                 300

Arg Pro Ile Ser Glu Arg Thr Phe Ala Lys Leu Gln Ser Leu Ala Pro
305                 310                 315                 320

Arg Leu Leu Pro Leu Arg Gln Pro Ser Pro Ala Ser Pro Gly Pro Ala
                325                 330                 335

Ser Phe His His His Asn His Asn Arg Pro Ser Leu Thr Ser His
                340                 345                 350

Pro Ser Gly Tyr Ala Pro Pro Gln Pro Leu Glu Pro Pro Ala Asn Ser
                355                 360                 365

Asp Pro Arg Pro Asn Ser Val Ala Gly Ser Pro His Leu Ser Ser Val
370                 375                 380

Gly Trp Ala Ser Pro Thr Leu Ser Ser Met Pro Ser Pro Ser Ser Ala
385                 390                 395                 400

Ser Ala Pro Glu Tyr Pro Tyr Pro Glu Pro Ser Asn His Gln Tyr Pro
                405                 410                 415

Gly Ser Ile Thr Pro His Met Phe Phe Pro Arg Arg Pro Gln Ser Ser
                420                 425                 430

Glu Pro Glu Asn Tyr Glu Leu Lys Pro Lys Leu Glu Leu
                435                 440                 445

<210> SEQ ID NO 17
<211> LENGTH: 230
<212> TYPE: PRT
<213> ORGANISM: Artificial Sequence
```

<220> FEATURE:
<223> OTHER INFORMATION: synthesized

<400> SEQUENCE: 17

Met Gln Pro Leu Ser Lys Thr Glu Lys Pro Lys Asp Pro Ala Asn
1               5                   10                  15

Thr Asn Thr Ala Ser Pro Leu Ala Ala Ser Val Ser Gln Thr Ser
            20                  25                  30

Gln Thr Thr Gln Pro Leu Gln Thr Ser Gln Val Ser Ala Pro Ser Gln
        35                  40                  45

Ala Pro Gln Thr Ser Gln Ser Thr Ser Pro Asn Ser Ser Thr Thr Gln
    50                  55                  60

Ser Ser Pro Gln Ser Thr Ser Gln Thr Ser Ser Ser Phe Ser Arg Glu
65                  70                  75                  80

Pro Lys Asp Ala Pro Gln Lys Glu Ser Ser Asn Glu Ala Ser Asn Glu
                85                  90                  95

Ala Ser Asp Ser Asp Lys Ser Leu Ser Thr Ser Lys Ser Ala Pro Glu
            100                 105                 110

Ser Ala Gly Ser Ala Glu Asn Gln Ala Asp His Asp Ala Lys Glu
        115                 120                 125

Lys Lys Leu Glu Lys His Phe Phe Cys Arg Ile Cys Lys Gln Gly Phe
130                 135                 140

Thr Arg Lys His Asn Met Val Ser His Glu Leu Ile His Ser Ser Asn
145                 150                 155                 160

Lys Pro His Val Cys Ser Val Cys Asp Ala Thr Phe Arg Arg Ile His
                165                 170                 175

Asp Leu Arg Arg His Glu Lys Leu His Ser Gly Lys Pro Phe His
            180                 185                 190

Cys Gln His Cys Asn Arg Gly Phe Ala Arg Thr Asp Ala Leu Thr Arg
        195                 200                 205

His Ile Asn Ser Ser Asn Ala Cys Leu Val Lys Gln Arg Gln Thr Arg
    210                 215                 220

Lys Arg Thr Asn Leu Ile
225                 230

<210> SEQ ID NO 18
<211> LENGTH: 259
<212> TYPE: PRT
<213> ORGANISM: Artificial Sequence
<220> FEATURE:
<223> OTHER INFORMATION: synthesized

<400> SEQUENCE: 18

Met Asp Ile Arg Asn Leu Leu Asn Glu Thr Glu Asn Ile Glu Lys Pro
1               5                   10                  15

Phe Arg Cys Thr Trp Asn Asp Cys Asp Lys Lys Phe Ser Arg Lys Ser
            20                  25                  30

Asp Leu Ser Arg His Ile Arg Ile His Thr Gly Glu Arg Pro Tyr His
        35                  40                  45

Cys Gly Trp Pro Ser Cys Gly Lys Gln Phe Ile Gln Arg Ser Ala Leu
    50                  55                  60

Thr Val His Tyr Arg Thr His Thr Gly Glu Arg Pro His Val Cys Glu
65                  70                  75                  80

Tyr Asp Ser Cys Gly Lys Ala Phe Ser Asp Ser Ser Ser Leu Ala Arg
                85                  90                  95

His Arg Arg Thr His Thr Gly Lys Arg Pro Tyr Ser Cys Leu His Pro

-continued

```
                100                 105                 110
Gly Cys Gly Lys Ser Phe Thr Arg Lys Thr Thr Leu Ser Arg His Gln
            115                 120                 125

Arg Cys His Asp Pro Lys Trp Glu Ser Tyr Asn Leu Lys Asn His Lys
        130                 135                 140

Ile Thr Phe Asn Lys His Glu Glu Ser Asn Glu Cys Leu Ile Val Asp
145                 150                 155                 160

Gln Gln Pro Phe His Gln Thr Ser Ala Ala Ser Pro Ile Ser Ser Ser
                165                 170                 175

Ser Asp Ser Glu Leu Asp Ser Pro Leu Asn Ser Pro Val Glu Tyr Phe
            180                 185                 190

Asn Leu Tyr His Gln Arg Gln Gln Leu Pro Phe Ile Lys His His His
        195                 200                 205

Pro Met Val Glu Met Pro Gln Arg Ile Lys His Val His Thr Tyr Arg
    210                 215                 220

Ile Leu Asp Tyr Asn Ser Phe Gly Asn Pro Ser Ile Ala Pro Leu
225                 230                 235                 240

Gln Gln Gln Pro Ser Phe Ile His Gln Lys Thr Arg Met Ser Tyr Tyr
                245                 250                 255

Asn Phe Pro
```

<210> SEQ ID NO 19
<211> LENGTH: 436
<212> TYPE: PRT
<213> ORGANISM: Artificial Sequence
<220> FEATURE:
<223> OTHER INFORMATION: synthesized

<400> SEQUENCE: 19

```
Met Gln Gln His Ala Ser Leu His Asn Gly Ser Thr Pro Glu Arg Gln
1               5                   10                  15

Met His Gln Leu Pro Gln Leu Thr Ala Arg Asn Met Pro Glu Pro Pro
            20                  25                  30

Met Asp Arg Ala Gly Ser Pro His Gly Ser Glu His Ser Gln Tyr Ser
        35                  40                  45

Arg His Thr Met Glu Gly Val Pro Arg Ser Tyr Pro Ser Pro Ser Ala
    50                  55                  60

Met Val Gly Ala Pro Met Gln Met Gln Val Pro Val Ser His Met Gly
65                  70                  75                  80

Pro Gly Pro Val Ile Leu Pro Gly Ile Pro Gln His Asp Met Ser Gln
                85                  90                  95

Gly Met Pro Gln Tyr Lys Val Pro Asp Gln Gln Ala Pro Gln Gln Pro
            100                 105                 110

Thr Lys Ala Tyr Pro Cys Ser Thr Cys Gly Lys Gly Phe Ala Arg Arg
        115                 120                 125

Ser Asp Leu Ala Arg His Glu Arg Ile His Ser Gly Ile Arg Pro His
    130                 135                 140

Val Cys Asp Phe Pro Asn Cys Gly Lys Gln Phe Ile Gln Arg Ser Ala
145                 150                 155                 160

Leu Thr Val His Gln Arg Val His Thr Gly Glu Lys Pro His Met Cys
                165                 170                 175

Glu Arg Cys Gly Lys Pro Phe Ser Asp Ser Ser Ser Leu Ala Arg His
            180                 185                 190

Arg Arg Ile His Ser Gly Lys Arg Pro Tyr Lys Cys Pro Tyr Ala Asp
        195                 200                 205
```

```
Cys Gln Lys Thr Phe Thr Arg Arg Thr Thr Leu Thr Arg His Gln Asn
    210                 215                 220

His His Thr Gly Thr Val Glu Glu Ala Ala Ala Thr Ala Ala Ala
225                 230                 235                 240

Leu Ala Ala Arg Gly Ala Thr Ala Lys Pro Asn Ala Thr Arg Ser Asp
                245                 250                 255

Gly Asp Ala Val Ser Asn Arg Gly Ser Pro Leu Thr Thr Pro Ser Pro
                260                 265                 270

Gly Gln Arg Thr Leu Ser Met Ser Pro Ser Ala Asp Gly Met His Arg
            275                 280                 285

Thr Asn Ser Glu Phe Gln Tyr Met Gly Asn Ser Ser Leu Pro Val His
            290                 295                 300

Leu Gln Arg Asp Met His Val Gly Ser Pro Ala Ser Thr Thr Ser Gly
305                 310                 315                 320

Gly Tyr Asn Thr Gly Met Arg Pro Thr Ser His Pro Thr Ser Tyr Gly
                325                 330                 335

Pro Pro Pro Thr Leu Glu Pro Ser Val Glu Gln His Ser Gly Pro Gly
                340                 345                 350

Ser Ala Gly Gly Ser Pro His Met Ser Asn Val Gly Trp Gln Ser Pro
            355                 360                 365

Ser His Val Ala Ser Pro Ser His Ser Ser Asn Gly Gly Gly Tyr Thr
    370                 375                 380

Tyr Pro Asp Pro Asp Ala Tyr Pro Ala Ala Pro Ser Leu Ser Gly Gln
385                 390                 395                 400

Met Phe Tyr Gly Asn Pro Gly Gln Val Arg Arg Pro Gln Ser Thr Glu
                405                 410                 415

Pro Pro Ala Gly Ala Tyr Asp Ile Lys Gly Arg Gln Ser Glu Leu Trp
            420                 425                 430

Ala Gly Ala His
        435

<210> SEQ ID NO 20
<211> LENGTH: 470
<212> TYPE: PRT
<213> ORGANISM: Artificial Sequence
<220> FEATURE:
<223> OTHER INFORMATION: synthesized

<400> SEQUENCE: 20

Met Met Glu Ser Pro His Met Ile Pro Phe Asp Ser Arg Ala Thr Thr
1               5                   10                  15

Thr Gly Pro Leu Gln Arg Pro Val Met Ala Pro Tyr Ile Val Gln Pro
            20                  25                  30

Pro Tyr Ser Ser Gly Pro Val Asn Ser Leu Thr Ala Pro His Tyr Gln
        35                  40                  45

Val Pro Asn Pro Tyr Gln Phe Gly Gly Tyr Gln Gly Pro Pro Thr Pro
    50                  55                  60

Pro His His Ser Thr Pro Phe Lys Ile Glu Tyr Asn Asp Arg Arg Pro
65                  70                  75                  80

Met Gly His Asp Asn Asp His Gly Arg Val Pro Ser Tyr Ser Arg Glu
                85                  90                  95

Met Lys Cys Thr Tyr Ala Glu Gln Ala Pro Ser Pro Ala Arg Ser Asp
            100                 105                 110

Ser Gln Ala Ser Thr Val Arg Ser Ser Gly Thr Asn Pro Ser Met Cys
        115                 120                 125
```

```
Ser Lys Thr Ile Thr Ser Asn Glu Thr Leu Asn Pro Gly Asp Gln Ile
    130                 135                 140

Asn Phe Glu Thr Glu Val Asp Glu Leu Met Lys Ala Ile Gln Arg Lys
145                 150                 155                 160

Ala Asp Leu Gln Val Asp Thr Val Gln Gln Pro Leu Thr Pro Gly Met
                165                 170                 175

Ser Pro Val Ser Glu Ala Ser Phe Glu Ser Gln Gly Thr Pro Gly Pro
            180                 185                 190

Met Asp Asn Lys Thr Ala Arg Lys Arg Tyr Arg Cys Asp Gly Pro Asn
        195                 200                 205

Cys Gln Lys Ser Phe Thr Gln Lys Thr His Leu Asp Ile His Arg Arg
    210                 215                 220

Thr His Thr Gly Ile Lys Pro Tyr Asn Cys Asp Phe Pro Gly Cys Asp
225                 230                 235                 240

Leu Thr Phe Ser Gln Leu Gly Asn Leu Lys Thr His Arg Arg Arg His
                245                 250                 255

Thr Gly Glu Arg Pro Phe Ala Cys Asp Lys Cys Asp Arg His Phe Ala
            260                 265                 270

Gln Arg Gly Asn Leu Arg Ala His Leu Gln Thr His Gln Gly Leu Lys
        275                 280                 285

Pro Phe Val Cys Ile Leu Asp Asp Cys Asn Lys Thr Phe Ser Gln Leu
    290                 295                 300

Gly Asn Met Lys Thr His Gln Asn Asn Phe His Lys Lys Thr Leu Lys
305                 310                 315                 320

Lys Leu Thr Met Lys Phe Ala Lys Ile Ile Ala Ser Gly Glu Glu Val
                325                 330                 335

Thr Glu Ala Asp Arg Glu Leu Phe Glu Tyr Phe Ala Thr His Tyr Lys
            340                 345                 350

Asn Ser Asn Lys Gly Ile Lys Gly Arg Gly Lys Ala Arg Thr Val Ala
        355                 360                 365

Glu Arg Lys Thr Lys Ala Ser Gln Ser Pro Ala Asn Thr Met Thr Ala
    370                 375                 380

Val Pro Gln Tyr Pro Leu Pro Gln Ile Ala Ser Thr Pro Val Thr Pro
385                 390                 395                 400

His Gly Leu Pro Val Ser Gly Ser Leu Ala Ser Tyr Ser Val Thr Arg
                405                 410                 415

Gly Gln Pro Ala Pro Ile Asn His Met Ser Arg Gln Thr His Asn Gly
            420                 425                 430

Gly Tyr Glu Val Tyr Asp Met His Gly His His Val Gln Pro Pro
        435                 440                 445

Asn Asn Asn Gly Met Leu Tyr Glu Thr Gly Ser Thr Arg Glu Met Gly
    450                 455                 460

Tyr His Gly Arg Met Tyr
465                 470

<210> SEQ ID NO 21
<211> LENGTH: 445
<212> TYPE: PRT
<213> ORGANISM: Artificial Sequence
<220> FEATURE:
<223> OTHER INFORMATION: synthesized

<400> SEQUENCE: 21

Met Glu Thr Ala Glu Pro Val Ser Tyr Glu Phe Thr Gly His Ala Met
1               5                   10                  15
```

Gly Ser Met Ala Pro Arg Arg Leu Leu His Ala Gly Leu Gly Ser Asn
            20                  25                  30

Phe Ser Tyr Tyr Asn Asn Pro Ala Thr Ser Phe Pro Leu Pro Tyr His
        35                  40                  45

Gln Ser Ser Ser Thr Pro Tyr Gly Phe Ser His Thr Ile Asn Gln His
    50                  55                  60

Pro His Gln Leu Pro Gly Tyr Gln His Phe Tyr Leu Thr Gly His Pro
65                  70                  75                  80

Ser Leu Asn Leu Gln Pro Val Arg Leu Ser Ser Glu Pro Pro Thr Val
                85                  90                  95

Gln Gln Ile Pro Asp Ile Arg Pro Ala Lys Asn Ala Ile Ser Arg Ile
            100                 105                 110

Val Gly Lys Pro Leu Ala Lys Ser Glu Gln Ser Val Ser Ser Gln Pro
        115                 120                 125

Ile Ala Ala Ala Gln Pro Pro Ala Thr Gly Ala Thr Gln Glu Lys Gly
    130                 135                 140

Pro Gly Ser Thr Glu Ile Glu Phe Ser Thr Glu Val Asp Ile Leu Met
145                 150                 155                 160

Lys Ala Ile Gln Ala Lys Ala Val Pro Gln Gln Ser Ala Leu Gln Ser
                165                 170                 175

Leu Pro Pro Leu Gln Gln Leu Thr His Ser Gly Glu Asn Gly Phe Ser
            180                 185                 190

Gln Thr Ser Tyr Ala Met Ala Ser Ser Thr Pro Arg Cys Asn Met Ala
        195                 200                 205

Val Glu Glu Leu Ala Ser Arg Pro Gly Lys Lys Arg Lys Tyr Ile Cys
    210                 215                 220

Arg Leu Ser Asn Cys Gly Lys Ser Phe Ala Gln Lys Thr His Leu Asp
225                 230                 235                 240

Ile His Met Arg Ala His Thr Gly Asp Lys Pro Phe Val Cys Lys Glu
                245                 250                 255

Pro Ser Cys Gly Gln Arg Phe Ser Gln Leu Gly Asn Leu Lys Thr His
            260                 265                 270

Gln Arg Arg His Thr Gly Glu Lys Pro Phe Ser Cys Asp Ile Cys Gln
        275                 280                 285

Lys Arg Phe Ala Gln Arg Gly Asn Val Arg Ala His Lys Ile Thr His
    290                 295                 300

Gln His Ala Lys Pro Phe Thr Cys Leu Leu Asp Asp Cys Gly Lys Gln
305                 310                 315                 320

Phe Thr Gln Leu Gly Asn Leu Lys Ser His Gln Asn Lys Phe His Ala
                325                 330                 335

Ala Thr Leu Arg Thr Leu Thr Leu Lys Phe Ser Gln Met Ser Glu Ala
            340                 345                 350

Gln Leu Met Asn Pro Gln Asp Arg Gln Leu Trp Glu Tyr Phe Ala Thr
        355                 360                 365

Leu Tyr Lys Asn Ser Asn Lys Gly Ile Lys Gly Arg Gly Lys Asp Arg
    370                 375                 380

Arg Ile Ser Pro Thr Ser Lys Ser Ser Asp Ser Ser Ala Ser Cys Thr
385                 390                 395                 400

Arg Met Gln Ser Phe Glu Ser Asp Glu Asp Ile Lys Ala Ser Arg Asp
                405                 410                 415

Ser Arg Glu Ala Ser Ser Ala Tyr Thr Gly Ser Ser Ser Gly Glu Glu
            420                 425                 430

```
Glu Asp Pro Glu Ile Tyr Tyr Thr Asp Arg Arg Gly His
            435                 440                 445

<210> SEQ ID NO 22
<211> LENGTH: 441
<212> TYPE: PRT
<213> ORGANISM: Artificial Sequence
<220> FEATURE:
<223> OTHER INFORMATION: synthesized

<400> SEQUENCE: 22

Met Asp Ile Thr Thr Ile Leu Asn Lys Asn Arg Ser Ala Val Ala Ala
1               5                   10                  15

Ala Ala Glu Ala Gln Leu Gln His Gln Leu Ala Gln Thr Ala Gln Ile
                20                  25                  30

Lys Ser Arg Ser Pro Ser Glu Leu Gly Ser Glu His Asp Ala Gln Gln
                35                  40                  45

Pro Gly Arg His Ser Glu Pro Tyr His Pro Ala His Gln Pro Ile Gln
    50                  55                  60

Leu Pro Thr Ile Ser Gln Tyr His Ser Pro Ile Gln Thr Asn His His
65              70                  75                  80

Ala Ser Met Leu Arg Gly Asp Tyr Ala Gln Asn Gly His Glu Asn Met
                85                  90                  95

Phe Arg Asn Met Pro Thr Ser Asn Ser Ser Pro Gly Arg Gly Thr Gly
            100                 105                 110

Glu Pro Ala Pro Lys Ser Phe His Cys Gln Thr Cys Ser Lys Gly Phe
        115                 120                 125

Ala Arg Arg Ser Asp Leu Ala Arg His Glu Arg Ile His Ser Gly Ile
    130                 135                 140

Arg Pro His Val Cys Asp Trp Pro Gly Cys Gly Lys Gln Phe Ile Gln
145                 150                 155                 160

Arg Ser Ala Leu Thr Val His Thr Arg Val His Thr Gly Glu Lys Pro
                165                 170                 175

His Met Cys Asp Arg Cys Gly Lys Pro Phe Ser Asp Ser Ser Ser Leu
            180                 185                 190

Ala Arg His Arg Arg Ile His Ser Gly Lys Arg Pro Tyr Lys Cys Pro
        195                 200                 205

Tyr Ala Asn Cys Gln Lys Thr Phe Thr Arg Arg Thr Thr Leu Thr Arg
    210                 215                 220

His Gln Asn His His Thr Gly Thr Ile Glu Glu Ala Ala Ala Glu Thr
225                 230                 235                 240

Glu Ala Asn Leu Arg Gln Gly Lys Val Val Arg Pro Asp Gly Val Tyr
                245                 250                 255

Ser Glu Thr Ala Ser Pro His Gly Thr Ala Ser Pro Ala Gln Arg Ser
            260                 265                 270

Ser Val Ser Pro Arg His Glu Leu Pro Pro Leu His Ser His Arg Gln
        275                 280                 285

Met Gly Asp Tyr Phe Met Ala Ser Ser Leu Pro His Leu Arg
    290                 295                 300

Asp Phe Gln Gln Ala Ser Pro Arg Ala Ser Pro Ser Thr Pro Ser Pro
305                 310                 315                 320

Thr Leu Ser Thr Phe Ser Ala Ala His His Pro Arg Pro Ser Leu Thr
                325                 330                 335

Ser His Pro Thr Ser Tyr Gly Pro Pro Gln Pro Leu Glu Pro Pro Pro
            340                 345                 350
```

Asn Ser Gly Ser Arg Pro Gly Ser Val Thr Gly Ser Pro His Met Thr
            355                 360                 365

Thr Val Gly Trp Ala Ser Pro Ser Leu Asn Ser Val Pro Ser Pro Gly
370                 375                 380

Ser Val Ser Ala Pro Glu Tyr Thr Tyr Pro Glu Pro Ser Gly Pro Pro
385                 390                 395                 400

Phe Ala Gly Gly Met Pro Ala His Met Tyr Tyr Pro Asn Ser Thr Ile
            405                 410                 415

Arg Arg Pro Gln Ser Thr Glu Pro Glu Asn Tyr Glu Leu Lys Pro Lys
            420                 425                 430

Val Glu Glu Pro Trp Ala Thr His Ala
            435                 440

<210> SEQ ID NO 23
<211> LENGTH: 395
<212> TYPE: PRT
<213> ORGANISM: Artificial Sequence
<220> FEATURE:
<223> OTHER INFORMATION: synthesized

<400> SEQUENCE: 23

Met Glu Leu Leu Glu Leu Val Glu Tyr Glu Ser Thr Thr Arg Pro Phe
1               5                   10                  15

Gln Cys Asp Trp Glu Ser Cys Asn Lys Ser Phe Asn Arg Lys Ser Asp
            20                  25                  30

Leu Gln Arg His Tyr Arg Ile His Thr Asn Glu Arg Pro Tyr Thr Cys
        35                  40                  45

Thr Thr Pro Gly Cys Gly Lys Ser Phe Ile Gln Arg Ser Ala Leu Thr
    50                  55                  60

Val His Ile Arg Thr His Thr Gly Glu Lys Pro His Gln Cys Gln His
65                  70                  75                  80

Val Gly Cys Gly Lys Arg Phe Ser Asp Ser Ser Ser Leu Ala Arg His
                85                  90                  95

Arg Arg Ile His Thr Gly Lys Arg Pro Tyr Lys Cys Ala His Asp Gly
            100                 105                 110

Cys Leu Lys Ser Phe Cys Arg Lys Thr Thr Met Val Lys His Gln Arg
        115                 120                 125

Arg Ser His Gln Arg Gly Met Asn Pro Asn Asp Ile Leu Asp Asp Cys
    130                 135                 140

Thr Ser Glu Ser Asp Met Gly Glu Ser Pro Ser Thr Pro Gly Gln Thr
145                 150                 155                 160

Ala Met Ser Trp Ser Met Pro Gly Thr Ile Ile His Pro Ala Met Ala
                165                 170                 175

His Ser His Pro Met His Arg Ser Ala Thr Phe Gly Asp Phe Gly Gln
            180                 185                 190

Gln Met Thr Pro Tyr Gly Met Asp His Gln Ile Ala Gln Arg Gln Ser
        195                 200                 205

Val Pro Ala Glu Val His Glu Phe His Gly Gln Asp Pro Asn Met His
    210                 215                 220

Met Ile Gln Arg Thr Ala Asn Ile Pro His Gln Pro Tyr Tyr Val Ile
225                 230                 235                 240

Asp Gln Asn Asn Pro Gly Ile Ala Thr Met Asn Thr Asn Val Pro Ala
                245                 250                 255

Ala Tyr His Ile Pro Arg Gln His Val Glu Arg Ser Leu Glu Met Ala
            260                 265                 270

```
Tyr Asn Ser Gly Ser Met Pro Ser Leu Ser Ser Ser Pro Ala Ser Phe
            275                 280                 285

Ser Pro Ala Ser Gly His Ser Ser Ser Met His Asp Gly Leu Tyr Thr
    290                 295                 300

His Gln Pro Pro Ala Ser Ala Thr Tyr Gly Leu Gln Glu Ala His Ala
305                 310                 315                 320

Val Glu Pro Ser Asn Asn Met Val Ser Tyr Thr Gln Met His Gln
                325                 330                 335

Thr Arg Ser Ser Gln Pro Glu Ala Glu Trp Val Tyr Gln Tyr Gln Ser
                340                 345                 350

Pro Val Glu Val Ala Thr Ile Gly Gln Ile Pro Ala Phe Gly Thr Gly
            355                 360                 365

Val Tyr Asp Met Tyr Ser Gly Pro Lys Ile Asp Phe Asp Asp Pro Thr
    370                 375                 380

Met Gln Leu Pro Ser Ser Arg Val Glu Thr Leu
385                 390                 395

<210> SEQ ID NO 24
<211> LENGTH: 447
<212> TYPE: PRT
<213> ORGANISM: Artificial Sequence
<220> FEATURE:
<223> OTHER INFORMATION: synthesized

<400> SEQUENCE: 24

Met Asp Ile Thr Thr Ile Leu Asn Lys Lys Gly Thr Ala Ala Val Ala
1               5                   10                  15

Ala Ala Glu Ala His Leu Gln Gln His Leu Val His Ala Thr His Met
            20                  25                  30

Lys Ser Lys Thr Pro Ser Glu Ile Ser Ser Glu His Gly Thr Pro Gln
        35                  40                  45

Asn Gly Asp Gln Ser Asn Ile Tyr His Pro Thr Ser Gln Pro Asn Pro
    50                  55                  60

Gln Leu Val Gly Ser Ser Lys Tyr His His Ser Gln Ser Gln Gly His
65              70                  75                  80

Ala Gly Ile Pro Pro Val Arg Ser Asn Tyr Val Gln Asp Gly Gln Gly
                85                  90                  95

Ile Val Lys Tyr Leu Gln Asn Gly Asn Gly Asn Gly Arg Ser Ser
            100                 105                 110

Gly Glu Pro Val Pro Lys Thr Phe His Cys Ser Thr Cys Ser Lys Gly
        115                 120                 125

Phe Ala Arg Arg Ser Asp Leu Ala Arg His Glu Arg Ile His Ser Gly
    130                 135                 140

Ile Arg Pro His Val Cys Asp Trp Pro Gly Cys Gly Lys Gln Phe Ile
145                 150                 155                 160

Gln Arg Ser Ala Leu Thr Val His Thr Arg Val His Thr Gly Glu Lys
                165                 170                 175

Pro His Met Cys Asp Arg Cys Gly Lys Pro Phe Ser Asp Ser Ser Ser
            180                 185                 190

Leu Ala Arg His Arg Arg Ile His Ser Gly Lys Arg Pro Tyr Lys Cys
        195                 200                 205

Pro Tyr Ala Asn Cys Gln Lys Thr Phe Thr Arg Thr Thr Leu Thr
    210                 215                 220

Arg His Gln Asn His His Thr Gly Thr Ile Glu Glu Ala Ala Ala Glu
225                 230                 235                 240
```

```
Thr Glu Ala Asn Leu Arg Gln Asn Lys Glu Arg Ala Val Arg Pro Pro
                245                 250                 255

Asp Gly Met Tyr Ser Glu Ala Gly Ser Thr Gln Ser Thr Pro Ser Pro
            260                 265                 270

Gly Gln Arg His Ser Leu Ser Pro Gly Asn Glu Leu Pro Pro Met Tyr
        275                 280                 285

Leu Pro Arg Gln Met Ser Asp Tyr Tyr Met Gly Asn Thr Pro Ile Pro
    290                 295                 300

Ala His Leu Arg Gly Asp Phe Gln Gln Ala Ser Pro Arg Ala Ser Pro
305                 310                 315                 320

Ser Thr Ser Ser Pro Pro Leu Ser Thr Tyr Ser Ser Val Pro His Ala
                325                 330                 335

Arg Pro Ser Met Thr Ser His Pro Ser Gly Tyr Gly Pro Pro Gln Pro
            340                 345                 350

Val Glu Pro Pro Ala Asn Ser Asp Pro Arg Pro Asn Ser Val Ala Gly
        355                 360                 365

Ser Pro His Ile Thr Ser Met Gly Trp Ala Ser Pro Thr Leu His Ser
    370                 375                 380

Ile Gly Ser Pro Asp Ser Ala Ser Ala Thr Glu Tyr Ser Tyr Pro Glu
385                 390                 395                 400

Pro Ser Ala Pro Ser Tyr Pro Ser Gln Ile Pro Pro His Met Tyr Phe
                405                 410                 415

Pro Asn Ser Thr Ile Arg Arg Pro Gln Ser Thr Glu Pro Glu Asn Tyr
            420                 425                 430

Glu Pro Lys Pro Lys Leu Asn Gly Asp Ser Trp Thr Thr Pro Val
        435                 440                 445

<210> SEQ ID NO 25
<211> LENGTH: 368
<212> TYPE: PRT
<213> ORGANISM: Artificial Sequence
<220> FEATURE:
<223> OTHER INFORMATION: synthesized

<400> SEQUENCE: 25

Met Gln Gln Thr Ser Tyr Tyr Ser Pro Asn Met Pro His Pro Val Ser
1               5                   10                  15

Tyr Ala Gln Ser His Asp Ile Gln Gln Leu Pro Thr Leu Pro Asp Val
                20                  25                  30

Arg His Val Phe Asn Pro Asn Val Lys Ser Glu Gly Thr Ser Pro Ala
            35                  40                  45

Gln Ser Asn Gln Met Tyr Ala Asn Gln Ser Tyr Gly Thr Glu Leu Lys
        50                  55                  60

Arg Ser Thr Ser Glu Pro Thr Glu Gly Ser Ser Thr Asn Phe Ala Thr
65                  70                  75                  80

Asp Val Asp Thr Leu Met Arg Ala Ile Gln Ala Lys Gln Thr Asn Leu
                85                  90                  95

Pro Gln Glu Asn Asp Gln Lys Asp Ala Ala Lys Thr Ala Gln Lys
            100                 105                 110

Pro Arg Lys Arg Tyr Gln Cys Thr Val Pro Asn Cys Asn Lys Ser Phe
        115                 120                 125

Tyr Gln Lys Thr His Leu Glu Ile His Ile Arg Ala His Thr Gly Asp
130                 135                 140

Lys Pro Phe Pro Cys Lys Ala Pro Gly Cys Gly Gln Ser Phe Ser Gln
145                 150                 155                 160
```

-continued

Leu Gly Asn Leu Lys Thr His Glu Arg Arg His Thr Gly Glu Arg Pro
            165                 170                 175

Tyr Ser Cys Asp Ile Cys Gly Lys Thr Phe Ala Gln Arg Gly Asn Val
        180                 185                 190

Arg Ala His Lys Ile Val His Gln Gln Ile Lys Pro Phe Ser Cys Lys
    195                 200                 205

Leu Asp Asp Cys Gly Lys Gln Phe Thr Gln Leu Gly Asn Leu Lys Ser
210                 215                 220

His Gln Asn Lys Phe His Ala Ala Thr Leu Arg Tyr Leu Thr Thr Lys
225                 230                 235                 240

Phe Ala Thr Ile Asn Gln Gly Asp Tyr Val Ser Gln Glu Asp Lys Glu
                245                 250                 255

Leu Trp Glu Tyr Phe Ala Ser Leu Tyr Lys Asn Ser Asn Lys Gly Ile
            260                 265                 270

Lys Gly Arg Gly Lys Asp Arg Arg Ile Ser Ala Met Ser Ser Ser Ala
        275                 280                 285

Ser Ser Tyr Pro Ser Ser Tyr Ala Ala Met Pro Met Ala Ser Met Ser
    290                 295                 300

Arg Gly Tyr Ala Ser Ser Phe His Gln His Ser Ser Asp Arg Ser Ser
305                 310                 315                 320

Arg Cys Ser Ser Met Ser Ser Asp Thr Ile Pro Ile Gln Arg Ala Asp
                325                 330                 335

Ser Ala Tyr Asp Phe Ser Ala Pro Met His Asn Gly Tyr His Gln Pro
            340                 345                 350

Gln Gly Asn Gly Tyr Asp Asp Met Val Phe Pro Glu Arg Lys Met Tyr
        355                 360                 365

<210> SEQ ID NO 26
<211> LENGTH: 467
<212> TYPE: PRT
<213> ORGANISM: Artificial Sequence
<220> FEATURE:
<223> OTHER INFORMATION: synthesized

<400> SEQUENCE: 26

Met Asp Ile Thr Thr Ile Leu Asn Lys Lys Ala Ser Val Ser Ile Val
1               5                   10                  15

Ala Ala Asp Val His Gln Leu Gln Gln His Leu Ala Gln Ala Gln Ser
                20                  25                  30

Gln Ser Gln Thr Asp Asp Ala Val Lys Ser Arg Ser Pro Ser Glu Leu
            35                  40                  45

Gly Ala Ser Glu His His Arg Ser Ala Ser Ala Pro Pro Ser Glu His
        50                  55                  60

His His His His His His His Gln Pro Thr Ser Ser Phe Pro Ser
65                  70                  75                  80

Ser Thr Gln Ser Leu Pro Gln Met Ala His Leu Ala Gln Tyr His Val
                85                  90                  95

Gln Ala Gln Ala Asn His Ala Gly Thr Ser Pro Gly Tyr Ala His Ser
            100                 105                 110

Ala His Gly Ser Asp Tyr Gly Arg Ser Ser Thr Ser Met Arg Pro Thr
        115                 120                 125

Gly Leu Pro Ala Leu Lys Thr Phe His Cys Gln Thr Cys Ser Lys Gly
    130                 135                 140

Phe Ala Arg Arg Ser Asp Leu Ala Arg His Glu Arg Ile His Ser Gly
145                 150                 155                 160

```
Ile Arg Pro His Ala Cys Asp Trp Pro Gly Cys Gly Lys Gln Phe Ile
            165                 170                 175

Gln Arg Ser Ala Leu Thr Val His Thr Arg Val His Thr Gly Glu Lys
        180                 185                 190

Pro His Met Cys Asp Arg Cys Gly Lys Pro Phe Ser Asp Ser Ser Ser
    195                 200                 205

Leu Ala Arg His Arg Arg Ile His Ser Gly Lys Arg Pro Tyr Lys Cys
210                 215                 220

Pro Tyr Ala Asn Cys Gln Lys Thr Phe Thr Arg Arg Thr Thr Leu Thr
225                 230                 235                 240

Arg His Gln Asn His His Thr Gly Thr Ile Glu Glu Ala Ala Ala Glu
            245                 250                 255

Thr Glu Ala Asn Leu Arg His Ser Lys Asp Arg Ser Thr Ala Ser Arg
        260                 265                 270

Pro Ser Glu Tyr Ser Glu Pro Gly Ser Ala His Ser Thr Pro Ser Pro
    275                 280                 285

Ala Gln Arg Pro Ser Leu Ser Pro Gly Asn Glu Leu Pro Pro Leu Asn
290                 295                 300

Leu Ser Ser Arg Pro Ser Ala Ala Gly Gly Pro Thr Ser Ala Gly Gly
305                 310                 315                 320

Ser Ala Asp Tyr Tyr Thr Ser Leu Pro Pro His Leu Arg Thr Asp Phe
            325                 330                 335

Ala Asn Ser Ser Pro Arg Ala Ser Pro Thr Ser Pro Ser Pro Thr Leu
        340                 345                 350

Thr Ser Leu Ser Gly Pro Ala Ser Phe His His Asn His Asn Arg
    355                 360                 365

Pro Ser Leu Thr Ser His Pro Ser Gly Tyr Ala Pro Pro Gln Pro Leu
370                 375                 380

Glu Pro Pro Ala Asn Ser Asp Pro Arg Pro Asn Ser Val Ala Gly Ser
385                 390                 395                 400

Pro His Leu Ser Ser Val Gly Trp Ala Ser Pro Thr Leu Ser Ser Met
            405                 410                 415

Pro Ser Pro Ser Ser Ala Ser Ala Pro Glu Tyr Pro Tyr Pro Glu Pro
        420                 425                 430

Ser Ser His Gln Tyr Pro Gly Ser Ile Thr Pro His Met Phe Phe Pro
    435                 440                 445

Arg Arg Pro Gln Ser Ser Glu Pro Glu Asn Tyr Glu Leu Lys Pro Lys
450                 455                 460

Leu Glu Leu
465

<210> SEQ ID NO 27
<211> LENGTH: 475
<212> TYPE: PRT
<213> ORGANISM: Artificial Sequence
<220> FEATURE:
<223> OTHER INFORMATION: synthesized

<400> SEQUENCE: 27

Met Gln Tyr Glu Val Pro Met Pro Leu Ser Met Asn His Asp Met His
1               5                   10                  15

Thr Pro Asn Gly Asn Tyr Leu Gly Gln Asn Leu Tyr Val Pro Thr Ala
            20                  25                  30

Asn Arg Ile Lys Ser Glu Asn Gly Ser Asp Arg Gly Val Ser Pro His
        35                  40                  45
```

```
Ser Ser Glu His Ser Ser Arg Tyr Ser Ser Thr Ala Pro Gln Asn Ser
     50                  55                  60

Val Ala Tyr Gln Gln Ile Ala Ala Gln Leu Thr Asn Gly Met Arg Tyr
 65                  70                  75                  80

Pro Ser Pro Ser Met Pro Gln Ser Asn Ser Met Pro Met Leu Gln Gln
                 85                  90                  95

His Tyr Gln Pro Thr Gly Thr Pro Asp Ser Asn Tyr Pro Gln His Thr
            100                 105                 110

Pro Thr Leu Gly Ala Thr Gln Ser Thr Pro Gln Glu Pro Ser Pro
            115                 120                 125

Met Glu Gly Ala Arg Thr Ser Thr Gly Ser Ser Gly Leu Pro Lys Ala
130                 135                 140

Phe Ala Cys Ser Thr Cys Asn Lys Gly Phe Ala Arg Arg Ser Asp Leu
145                 150                 155                 160

Ala Arg His Glu Arg Ile His Ser Gly Val Arg Pro His Val Cys Asp
                165                 170                 175

Tyr Ala Gly Cys Gly Lys Gln Phe Ile Gln Arg Ser Ala Leu Thr Val
            180                 185                 190

His Ser Arg Val His Thr Gly Glu Lys Pro His Met Cys Glu Arg Cys
            195                 200                 205

Gly Lys Pro Phe Ser Asp Ser Ser Leu Ala Arg His Arg Arg Ile
210                 215                 220

His Ser Gly Lys Arg Pro Tyr Lys Cys Pro Tyr Ala Asp Cys Gln Lys
225                 230                 235                 240

Thr Phe Thr Arg Arg Thr Thr Leu Thr Arg His Gln Asn His His Thr
                245                 250                 255

Gly Thr Ile Glu Glu Ser Glu Ala Ala Thr Ala Ala Leu Ala Ser
            260                 265                 270

Arg Val Ser Met Gln Gly Gln Arg Ser Arg Gly Ser Asp Asp Glu Asn
            275                 280                 285

Asp Phe Ser Asp Asn Gly Lys Ser Pro Leu Pro Gln Pro Asp Arg Gln
290                 295                 300

Ser Thr Asn Ser Pro Ala Ala Gly Met Asn Asn Met Pro Thr Leu Gln
305                 310                 315                 320

Arg Gln Thr Ser Glu Phe Tyr Met Asn Ala Ile Ser Gly Gly Met Ala
                325                 330                 335

Ala Val Pro Pro His Met Arg Ser Gln Val Gln Ala Ser Pro Arg Ala
            340                 345                 350

Gln Ser Pro Gln Gln Tyr Ser Met Pro Gly Asn Asn Gly Thr Pro Gln
            355                 360                 365

Pro Arg Ile Thr Ser Ile Ser Ala Ala Gly Tyr Asn Gly Pro Pro Gln
            370                 375                 380

Ile Met Glu Pro Pro Thr Thr Asn Gly His Gln Gln Thr Gly Ser Gly
385                 390                 395                 400

His Asn Ser Pro His Leu Asn Gly Trp Gln Ser Pro His Asn Gly Met
                405                 410                 415

Gly Pro Gly Gln His Gln Thr Thr Asp Tyr Ser Tyr Gln Asp Ala Ser
            420                 425                 430

Gly Tyr Pro Ser His Ser Val Asn Ala Met His Ala Tyr Tyr Gln Ala
            435                 440                 445

Pro Asn Val Ser Arg Pro His Ser Thr Gly Pro Val Asp Tyr Ser Ser
450                 455                 460

Gly Leu Arg Gln Asp Val Trp Thr Gln Gln Pro
```

465         470         475

<210> SEQ ID NO 28
<211> LENGTH: 482
<212> TYPE: PRT
<213> ORGANISM: Artificial Sequence
<220> FEATURE:
<223> OTHER INFORMATION: synthesized

<400> SEQUENCE: 28

Met Ser Gln Ser Pro Ser Ser Gly Gly Ala Met Gly Ile Gly Ser Val
1               5                   10                  15

Leu Asn Ile Lys Ala Glu Ser Gly Met Leu Gln Pro Gln Gln Gly Leu
            20                  25                  30

Ala Pro Glu Gln Gln Gln Gln Gln Gln Gln Glu Gln Gln Gln Gln
        35                  40                  45

Gln Gln Gln Gln Pro Gln Pro Gln Pro Gln Gln Gln Gln Gln Gln
    50                  55                  60

Gln Gln Gln Pro Ser Arg Pro Ala Gln Thr His Gln Ile Gln Gly Asp
65                  70                  75                  80

Gln Pro Asp Ala Ser His Gly Ser Glu Gln Ser Arg Tyr Ser Gly Pro
                85                  90                  95

Met Asn Ala Ser Tyr Pro Ser Pro Thr Ala Met Ala Ala Pro Leu
            100                 105                 110

Pro Pro Val Pro Ser Ala Asn Met Ala Pro Ala Pro Met Asn Ser Ala
        115                 120                 125

Met Leu His Pro Asp Leu Pro Pro Glu Leu Val Ala Gly Ile Pro Pro
    130                 135                 140

Gly Gly Tyr Ala Pro Ala Glu Ala Arg Ala Gln Pro Ala Lys Ser Phe
145                 150                 155                 160

Pro Cys Gly Thr Cys Gly Lys Pro Phe Thr Arg Arg Ser Asp Leu Ala
                165                 170                 175

Arg His Glu Arg Ile His Ser Gly Ile Arg Pro His Ala Cys Asp Tyr
            180                 185                 190

Pro Gly Cys Asp Lys Arg Phe Ile Gln Arg Ser Ala Leu Thr Val His
        195                 200                 205

Ser Arg Val His Thr Gly Glu Lys Pro His Gln Cys Glu Arg Cys Gly
    210                 215                 220

Lys Pro Phe Ser Asp Ser Ser Leu Ala Arg His Arg Arg Ile His
225                 230                 235                 240

Ser Gly Lys Arg Pro Tyr Lys Cys Pro Tyr Glu Asp Cys Gln Lys Thr
                245                 250                 255

Phe Thr Arg Arg Thr Thr Leu Thr Arg His Gln Asn His His Val Gly
            260                 265                 270

Thr Val Glu Asp Ser Ala Arg Ala Arg Ala Glu Ala Leu Ala Gln Gly
        275                 280                 285

Ala Ser Ala Ala Ala Ala Ala Ala Arg Asn Lys Ser Arg Ser
    290                 295                 300

Ser Glu Gln Ala Ser Asn His Glu Ser Pro Leu Thr Thr Pro Ser Pro
305                 310                 315                 320

Ala Gln Gly Ala Met Ser Met Ser Pro Ala Asp Leu Ala Asn Met
                325                 330                 335

Asn Ser Met Gln Tyr Leu Ala Asn Asn Ser Leu Pro Pro His Leu Arg
            340                 345                 350

Gly Asp Val His Val Gly Ser Pro Ser Pro Thr Ala Ser Thr Gly Tyr

```
                355                 360                 365
Asn Asn Gly Met Arg Pro Thr Ser His Pro Thr Gly Tyr Ala Pro Pro
    370                 375                 380
Gln Thr Met Glu Pro Ser Ile Glu His Gln Gln Gly Pro Gly Ser Val
385                 390                 395                 400
Ala Gly Ser Pro His Val Ala Ser Val Gly Trp Pro Ser Pro Gly Pro
                405                 410                 415
Val Gly Ser Pro Thr Gln Ser Pro Asn Gly Asn Gly Tyr Thr Tyr Pro
            420                 425                 430
Asp Pro Ser Asp Val Tyr Gln Ser Gly Thr Pro Ile Ala Gln Met Phe
            435                 440                 445
Tyr Asn Ser Ala Pro Ala Thr Arg Arg Pro Gly Ser Ala Glu Pro Gly
            450                 455                 460
Asn Pro Ala Tyr Asp Ala Lys Gly Arg Gln Ala Glu Leu Trp Thr Asn
465                 470                 475                 480
Ala Gln

<210> SEQ ID NO 29
<211> LENGTH: 388
<212> TYPE: PRT
<213> ORGANISM: Artificial Sequence
<220> FEATURE:
<223> OTHER INFORMATION: synthesized

<400> SEQUENCE: 29

Met Ser Pro Ser Pro Thr Pro Gln Pro Trp Asp Gln Trp Ser Gln Gln
1               5                   10                  15
Gln Gln Gln Gln Gln Gln Gln Gln Pro Gln His His Ser Gly
                20                  25                  30
Tyr Pro Leu Met Asp Gln Ser Val Phe Pro Gln Tyr Ala Ser Gln Pro
            35                  40                  45
Thr Gln Tyr Asp Pro Arg Thr Ser Gln Tyr Asp Pro Arg Thr Val Val
        50                  55                  60
Thr Ser Gly Pro Leu Val Ala Pro His Met Ala Thr His Tyr Val Thr
65                  70                  75                  80
Ala Pro Ala Tyr Gly Ala Ser Pro Ile Ser Asn Met Lys Pro His Phe
                85                  90                  95
Pro Ala Gln Thr His Tyr Ser Tyr Gly Gln Tyr Asp Gln Pro Ala Gly
                100                 105                 110
His Leu Ala Met Ala Tyr Ser His Pro Ala Ser Pro Met Thr Pro
            115                 120                 125
Gly Pro Met Asn Thr Lys Asp Ile Thr Tyr Asn Lys Pro Ala Leu Gln
        130                 135                 140
Lys Arg Lys Asp Lys Glu Leu Ala Ser Ser Asn Ser Ser Glu Ala
145                 150                 155                 160
Gly Ala Gly Ser Val Lys Ser Glu Pro Ser Ser Pro His Pro Ser Ser
                165                 170                 175
Thr Asp Gly Ser Gln Glu Thr Thr Asp Lys Val Lys Lys Tyr Arg Cys
            180                 185                 190
Pro Tyr Asp Gly Cys Pro Lys Ser Phe Gln Ser Thr His Leu Glu
        195                 200                 205
Thr His Lys Arg Ala His Thr Gly Asp Lys Pro Tyr Lys Cys Glu Trp
        210                 215                 220
His Gly Cys Gly Arg Arg Phe Ser Gln Pro Gly Asn Leu Lys Thr His
225                 230                 235                 240
```

```
Thr Arg Leu His Thr Gly Glu Arg Pro Phe Glu Cys Glu Met Cys Gly
                245                 250                 255

Thr Cys Phe Ala Gln Arg Gly Asn Leu Thr Ala His Lys Ala Thr His
            260                 265                 270

Ser Lys Thr Lys Pro Phe Val Cys Lys Leu Asp Thr Cys Asn Lys Cys
        275                 280                 285

Phe Thr Thr Arg Gly Asn Leu Lys Asn His Gln Asn Lys Tyr His Lys
    290                 295                 300

Glu Thr Ile Ala Gln Leu Val Asp Trp Ile Ile Ser Leu Thr Asp Val
305                 310                 315                 320

Asp Ala Leu Ser Pro Lys Asp Arg Asp Leu Leu Trp Tyr Phe Ser Asn
                325                 330                 335

Ile Tyr Lys Asn Ser Asn Lys Gly Ile Lys Gly Arg Gly Arg Asp Arg
            340                 345                 350

Arg Val Ser Glu Val Arg Met Gly Lys Thr Lys Leu Asn Ser Pro Gly
        355                 360                 365

Met Gly Leu Pro Arg Ser Lys Met Leu Asp Ser Ser Phe Ser Arg Leu
    370                 375                 380

Gly Leu Gly Phe
385

<210> SEQ ID NO 30
<211> LENGTH: 335
<212> TYPE: PRT
<213> ORGANISM: Artificial Sequence
<220> FEATURE:
<223> OTHER INFORMATION: synthesized

<400> SEQUENCE: 30

Met Arg Pro Ser Lys Leu Lys Arg Pro Ile Leu Leu Lys Cys Ala Phe
1               5                   10                  15

Cys Ile Leu Glu Asn Pro Cys Glu Pro Val Lys Thr Trp Gly Arg Arg
            20                  25                  30

Gly Asp Leu Asn Arg His Met Arg Lys His Gly Asp Val Lys Pro Tyr
        35                  40                  45

Tyr Cys Thr Arg Cys Val Lys Gly Phe Val Gln Lys Ser Ala Met Glu
    50                  55                  60

Thr His Met Asn Thr His Thr Gly Ala Lys Pro His Ala Cys Pro Val
65                  70                  75                  80

Ser Gly Cys Gly Lys Lys Phe Gly Asp Pro Ser Ser Arg Thr Arg His
                85                  90                  95

Lys Asn Glu Ala His Ser Ser Ile Ala Ala Phe Arg Cys Pro Glu Val
            100                 105                 110

Gly Cys Pro Thr Arg Ile Lys Arg Lys Gly Thr Phe Ile Lys His Leu
        115                 120                 125

Thr Val His His Asn Trp Leu Thr Arg Pro Thr Glu Gln Gln Leu Met
    130                 135                 140

Asp Met Ile Val Tyr His Ala Lys Gly Glu Ser Ala Lys Gln Glu Ser
145                 150                 155                 160

Glu Gly Ala Lys Gln Glu Gly Gln Gly Ala Lys Gln Glu Val Gln Ser
                165                 170                 175

Ala Lys Gln Glu Ser Gln Val Val Lys Gln Glu Thr Gln Val Val Lys
            180                 185                 190

Gln Glu Thr Gln Val Val Lys Gln Glu Ser Pro Ser Ala Lys Gln Glu
        195                 200                 205
```

Ser Val Glu Pro Ser Val Leu Asp Ala Leu Val Ser Arg Ser Ser Pro
210                 215                 220

Ser Pro Thr Thr Arg Arg Leu Ser Ser Ser Leu Leu Pro Leu Asn Ala
225                 230                 235                 240

Pro Tyr Ser Phe Asp Lys Tyr Thr Lys Leu Tyr Pro Glu Pro Pro Ser
                245                 250                 255

Tyr Asp Ser Tyr His Thr Gly Thr Thr Val Tyr Ser Gln Pro Val Asp
            260                 265                 270

Pro Trp Gln Glu Leu Ser Ser Tyr Ala Asp Gly Leu Leu Leu Ser Ser
        275                 280                 285

Thr Ser Ser Ser Ser Leu Pro Val Ser Thr Ser Met Ile Ser Trp Asp
    290                 295                 300

Ser Asp Pro Asp Met Met Val Tyr Pro Thr Tyr Arg Ser Gly Tyr Thr
305                 310                 315                 320

Ser His Pro Pro Leu Ser Tyr Asp Trp Ser Leu Gly Leu Leu Gly
                325                 330                 335

<210> SEQ ID NO 31
<211> LENGTH: 456
<212> TYPE: PRT
<213> ORGANISM: Artificial Sequence
<220> FEATURE:
<223> OTHER INFORMATION: synthesized

<400> SEQUENCE: 31

Met Glu Thr Ala Glu Pro Val Ser Tyr Glu Phe Pro Gly His Thr Ile
1               5                   10                  15

Gly Ala Val Ala Pro Arg Arg Met Met Thr Ser Asn Leu Gly His Asn
                20                  25                  30

Phe Pro Phe Tyr Ala Thr Pro Ala Ala Ser Phe Pro Leu Pro Phe His
            35                  40                  45

Gln Ser Ser Ser Thr Ala Tyr Gly Phe Gly His Ala Leu Asn His His
50                  55                  60

His His Asn His His Gln Pro Ser Tyr Pro Gln Phe Phe Val Ala Ser
65                  70                  75                  80

His Glu Ser Ile Asn Ser Gln Pro Met Arg Leu Ser Ser Glu Pro Pro
                85                  90                  95

Pro Val Gln Ser Ile Pro Asp Ile Arg Pro Ala Lys Asn Ala Val Asn
            100                 105                 110

Arg Val Ser Arg Asp Pro Leu Val Lys Asn Asp Pro Ser Ser Asn Thr
            115                 120                 125

Gln Gln Thr Pro Met Ala Arg Ser Ser Thr His Gly Ala Ala Ala Gln
130                 135                 140

Ser Lys Ser Pro Ser Val Ser Glu Ile Glu Phe Thr Thr Glu Val Asp
145                 150                 155                 160

Ile Leu Met Lys Ala Ile Gln Ser Arg Asn Ser Val Gln Pro Pro Asn
                165                 170                 175

Thr Gln Ser Leu Pro Pro Leu Gln Gln Leu Thr His Arg Gly Cys His
            180                 185                 190

Gly Tyr Pro Gln Thr Phe Ser Leu His Pro Ser Gly Asn Thr Arg Cys
            195                 200                 205

Asn Met Met Ala Glu Glu Val Gln Ser Arg Ser Gly Lys Lys Arg Lys
210                 215                 220

Tyr Val Cys Thr Leu Pro His Cys Gly Lys Ser Phe Ala Gln Lys Thr
225                 230                 235                 240

```
His Leu Asp Ile His Thr Arg Ala His Thr Gly Asp Lys Pro Phe Ile
            245                 250                 255

Cys Lys Glu Pro Ser Cys Gly Gln Arg Phe Ser Gln Leu Gly Asn Leu
        260                 265                 270

Lys Arg Glu Lys Thr Asp Ser Asn Pro Gly Ala His Lys Gln Thr His
    275                 280                 285

Gln Arg Arg His Thr Gly Glu Lys Pro Phe Ser Cys Asp Ile Cys Gln
290                 295                 300

Lys Arg Phe Ala Gln Arg Gly Asn Val Arg Ala His Lys Ile Thr His
305                 310                 315                 320

Gln His Ala Lys Pro Phe Thr Cys Leu Leu Asp Asp Cys Gly Lys Gln
                325                 330                 335

Phe Thr Gln Leu Gly Asn Leu Lys Ser His Gln Asn Lys Phe His Ala
            340                 345                 350

Thr Thr Leu Arg Asp Leu Thr Leu Lys Phe Ser Gln Val Thr Ile Gly
        355                 360                 365

Asp Pro Met Ser Pro Gln Asp Arg Lys Leu Trp Glu Tyr Phe Ala Thr
    370                 375                 380

Leu Tyr Lys Asn Ser Asn Lys Gly Ile Lys Gly Arg Gly Lys Asp Arg
385                 390                 395                 400

Arg Ile Ser Pro Thr Ser Arg Ser Gly Pro Gly Lys Arg His Gln Thr
                405                 410                 415

Leu Gly Asn Asn Asp Asp Lys Leu Gln Arg Pro Ile Tyr Glu Glu Ser
            420                 425                 430

Ser Val Tyr Thr Gly Gly Ser Ser Asp Glu Asp Ala Glu Ala
        435                 440                 445

Tyr Tyr Ile Asp Arg Gln Asn His
    450                 455

<210> SEQ ID NO 32
<211> LENGTH: 457
<212> TYPE: PRT
<213> ORGANISM: Artificial Sequence
<220> FEATURE:
<223> OTHER INFORMATION: synthesized

<400> SEQUENCE: 32

Met Asp Ile Lys Glu Ile Val Asn Ser Lys Gly Ala Lys Gly Ala Ala
1               5                   10                  15

Ala Ala Ala Ala Ser Ala Ser Gly Gln Ala Gln Ala Gln Ala Gln
            20                  25                  30

Asp Leu His Leu Leu Gln Thr Ile Ser Gln Ala Asn Gly Met Arg Met
        35                  40                  45

Ser Asp Thr Gly Ser Glu Arg Gly Thr Ser Pro His Gly Ser Glu His
    50                  55                  60

Ser Gln Tyr Ser Thr Pro Arg Met Gly Met Asn Val Met Asn Gly Ala
65                  70                  75                  80

Pro Asn Gly Met Arg Tyr Pro Ser Pro Gly Met Gln Asn Ala Met
                85                  90                  95

Pro Met Met Gln Gln Pro Tyr Arg Pro Asp Ile Pro Phe Asp Asn Ser
            100                 105                 110

Met Met Pro Thr Gln Gln Asp Asn Thr Arg Gln Arg Gln Pro Gly
        115                 120                 125

Asp Val Thr Val Thr Lys Ala Phe Pro Cys Ser Thr Cys Gly Lys Gly
    130                 135                 140
```

```
Phe Ala Arg Arg Ser Asp Leu Ala Arg His Glu Arg Ile His Ser Gly
145                 150                 155                 160

Val Arg Pro His Val Cys Asp Tyr Pro Gly Cys Gly Lys Gln Phe Ile
                165                 170                 175

Gln Arg Ser Ala Leu Thr Val His Leu Arg Val His Thr Gly Glu Lys
            180                 185                 190

Pro His Thr Cys Glu Arg Cys Ala Lys Pro Phe Ser Asp Ser Ser Ser
        195                 200                 205

Leu Ala Arg His Arg Arg Ile His Ser Gly Lys Arg Pro Tyr Lys Cys
210                 215                 220

Pro Tyr Ala Asp Cys Gln Lys Thr Phe Thr Arg Arg Thr Thr Leu Thr
225                 230                 235                 240

Arg His Gln Asn His His Thr Gly Thr Val Glu Glu Ala Ala Ala Ala
                245                 250                 255

Thr Ala Ala Ala Leu Ala Thr Arg Pro Gly Asn Asn Arg Pro Ser Arg
            260                 265                 270

Gln Arg Ser Asp Gly Glu Ser Tyr Ser Asn Asn Gly Ser Pro Met Ser
        275                 280                 285

Thr Pro Ser Pro Gly Arg His Leu Ser Ala Ser Pro Ser Ser Asp Met
290                 295                 300

Ala Pro Met Asn Ser Met Gln Arg His Pro Gly Asp Tyr Gly Tyr Met
305                 310                 315                 320

Asn Asn Ser Ser Leu Pro Gly His Leu Arg Gly Asp Tyr Gly Val Pro
                325                 330                 335

Ser Gln Pro Pro Pro Val Ser Thr Ala Phe Ala Asn Gly Met Gln Gln
            340                 345                 350

Gln Arg Pro Thr Ser His Pro Thr Gly Tyr Gly Pro Pro Asn Ile Leu
        355                 360                 365

Glu Pro Pro Ala Asn Met Glu Gln Arg Gln Pro Gly Ser Ala Asn Gly
370                 375                 380

Ser Pro His Met Thr Asn Met Gly Trp Gln Ser Pro Ser His Met Gly
385                 390                 395                 400

Ser Pro Ser His Asn Asn Asn Tyr Val Tyr Pro Asp Pro Asp Pro Tyr
                405                 410                 415

Gly Ser Gly Ala Ala Ile Gly Gln Met Tyr Tyr Pro Asn Ser Asn Met
            420                 425                 430

Arg Arg Pro Gln Ser Thr Glu Pro Glu Gln Tyr Asp Met Lys Pro Arg
        435                 440                 445

Met Gly Asp Leu Trp Ala Thr Ala Gln
450                 455

<210> SEQ ID NO 33
<211> LENGTH: 472
<212> TYPE: PRT
<213> ORGANISM: Artificial Sequence
<220> FEATURE:
<223> OTHER INFORMATION: synthesized

<400> SEQUENCE: 33

Met Lys Arg Lys Gln Asp Asp Glu Arg Leu Asp Gly His Asp Gly Pro
1               5                   10                  15

Asp His Ala Gln Val Gln Ser Lys Lys Arg Ala Thr Asp Trp Val Gln
            20                  25                  30

Gln Gln Gln Glu Glu Glu Leu Ser Gln Val Glu Gln Leu Glu Ala Pro
        35                  40                  45
```

-continued

```
Ala Leu Pro Ser Gln Ser Arg Ser Pro Pro Ala Gly Ala Glu Ala Ala
 50                  55                  60

Ala Ser Asp Gly Asn Gly Asn Asp Ser Leu Glu Leu Asp Pro Asp Ser
 65                  70                  75                  80

Ala Ser Val Ala Ser Val Ala Asn Thr Ser Leu Thr His Ala Asp Pro
                 85                  90                  95

Thr Thr Thr Val Ala Ala Thr Ser Ile Asn Thr Thr Thr Arg Ala
            100                 105                 110

Ser Arg Arg Phe Pro Ser Asp Leu Lys Thr Ile Arg Cys Thr Phe Ala
            115                 120                 125

Gly Cys Thr Lys Thr Phe Asn Arg Pro Ala Arg Leu Ala Ala His Leu
130                 135                 140

Arg Ser His Thr Asn Asp Arg Pro Phe Lys Cys Pro Tyr Asp Asp Cys
145                 150                 155                 160

Asp Lys Asp Tyr Leu Glu Glu Lys His Leu Ser Gln His Ile Lys Gly
                165                 170                 175

Ser His Thr Asn Asp Arg Lys Tyr Thr Cys Pro Glu Pro Gly Cys Gly
            180                 185                 190

Lys Ser Phe Val Thr Asn Thr Arg Leu Arg Arg His Ala Leu Val His
            195                 200                 205

Glu Gly Ala Asp Arg Tyr Arg Cys Arg Gly Tyr Gly Asp Cys Val Gln
210                 215                 220

Ser Phe Arg Lys His Gln Thr Leu Gln Arg His Ile Arg Thr Val His
225                 230                 235                 240

Leu Gly Lys Ser Ala Tyr Pro Cys Gly Asn Asp Gly Cys Asp Ala Gly
                245                 250                 255

Phe Asp Thr Ala Ser Ala Leu Arg Arg His Val Glu Arg Glu His Gly
            260                 265                 270

Asp Leu Lys Phe Trp Cys Asp Glu Cys Asn Ala Glu Gly Glu Gly Asp
            275                 280                 285

Asp Ser Gly Gly Arg Arg Val Gly Phe Thr Thr Met Leu Leu Leu Gln
290                 295                 300

Ala His Met Lys Lys Glu His Asn Asn Cys Ala Phe Cys Gly Val Arg
305                 310                 315                 320

Cys Gly Thr Gln Ser Asn Met Met Arg His Val Glu Leu Tyr His Ser
                325                 330                 335

Ala Lys Thr Val Glu Asp Arg Lys Thr Ile Ala Cys Thr Trp Glu Gly
            340                 345                 350

Cys Asp Lys Lys Phe Thr Arg Val Ser Asn Leu Asn Thr His Ile Lys
            355                 360                 365

Ser Ala His Glu Gly His Arg Phe Val Cys Gly Gln Thr Asp Thr Tyr
370                 375                 380

Asp Ala Lys Val Ser Glu Ile Ala Asp Trp Asn Phe Ala Glu Glu Gly
385                 390                 395                 400

Cys Gly Gln Gly Phe Thr Thr Arg Val Lys Leu Glu Glu His Val Leu
                405                 410                 415

His Val His Leu Gly Lys Lys Arg Pro Pro Lys Leu Tyr Pro Val Pro
            420                 425                 430

Ser Met Val Ala Gln Ala Gln Gln Ala Gln Ala Leu Leu Asp Thr
            435                 440                 445

Arg Asp Leu Ala Cys Pro Ala Arg Gly Thr Gly Ser Tyr Gly Thr Ile
450                 455                 460
```

Ser Glu Cys Cys Gln Leu Glu Arg
465                 470

<210> SEQ ID NO 34
<211> LENGTH: 441
<212> TYPE: PRT
<213> ORGANISM: Artificial Sequence
<220> FEATURE:
<223> OTHER INFORMATION: synthesized

<400> SEQUENCE: 34

Met Asp Ile Thr Thr Ile Leu Asn Arg Lys Gly Ser Ala Ala Met Val
1               5                   10                  15

Ala Ala Asp Gly Gln Phe Asp His Gln His Leu Val Pro Asn His Ser
            20                  25                  30

Ile Asp His Thr Ser Ser Pro Lys Met Lys Ser Glu Pro Gly Val Ser
        35                  40                  45

Asp Ala Gly Asp Gln Ala Val Leu Ala Tyr Pro Pro His Gly Pro Leu
    50                  55                  60

Gly Gln Val Pro Thr Met Pro His Asp Met Arg Tyr Ala Pro Gln Ala
65                  70                  75                  80

His Pro Ala Pro Gly Leu Pro Leu Leu Gln Asn Pro Phe Val Ser Gly
                85                  90                  95

Gly Tyr Ala Gly Ser Ala Gln Ile Pro Asn Ala Gly Ala Pro Gln Gly
            100                 105                 110

Arg Pro Asp Pro Pro Lys Thr Phe His Cys Gly Thr Cys Gly Lys
        115                 120                 125

Gly Phe Ala Arg Arg Ser Asp Leu Ala Arg His Glu Arg Ile His Ser
130                 135                 140

Gly Val Arg Pro His Ala Cys Asp Trp Pro Gly Cys Gly Lys Gln Phe
145                 150                 155                 160

Ile Gln Arg Ser Ala Leu Thr Val His Ser Arg Val His Thr Gly Glu
                165                 170                 175

Lys Pro His Met Cys Glu Arg Cys Gly Lys Pro Phe Ser Asp Ser Ser
            180                 185                 190

Ser Leu Ala Arg His Arg Arg Ile His Ser Gly Lys Arg Pro Tyr Lys
        195                 200                 205

Cys Pro Tyr Ala Asn Cys Gln Lys Thr Phe Thr Arg Arg Thr Thr Leu
    210                 215                 220

Thr Arg His Gln Asn His His Thr Gly Thr Ile Glu Glu Ala Ala Ala
225                 230                 235                 240

Glu Thr Glu Ala Asn Leu Arg Gln Asn Lys Glu Arg Ala Arg Leu Pro
                245                 250                 255

Gly Asp Met Phe Ser Glu His Gly Ser Val His Ser Thr Pro Ser Pro
            260                 265                 270

Ala His His Pro Ile Ser Pro Val Gly Asp Leu Pro Pro Leu Asn Met
        275                 280                 285

Pro Arg Ser Asp Tyr Tyr Met Pro Asn Gly Ser Ile Pro Ala His Val
    290                 295                 300

Arg Gly Gly Phe Thr Gln Ala Ser Pro Arg Ala Ser Pro Thr Ala Thr
305                 310                 315                 320

Ser Pro Ser Leu Ser Ser Tyr Gly Ser Ala Pro His Pro Arg Pro Ser
                325                 330                 335

Met Thr Ser His Pro Ser Gly Tyr Gly Pro Pro Gln Pro Leu Glu Pro
            340                 345                 350

```
Pro Ala Asn Asn Asp His Arg Pro Asn Ser Val Ser Gly Ser Pro His
            355                 360                 365

Met Thr Ser Leu Gly Trp Ala Ser Pro Ser His Gly Ser Ile Pro Ser
370                 375                 380

Pro Gly Ser Ala Thr Asp Phe Tyr Pro Glu Thr Ser Gly Pro Ala Tyr
385                 390                 395                 400

Pro Thr Ser Met Pro Pro His Met Tyr Phe Pro Asn Ser Thr Ile Arg
                405                 410                 415

Arg Pro Thr Ser Thr Glu Pro Asp Ser Tyr Glu Leu Lys Pro Lys Met
            420                 425                 430

Gly Glu Ser Ala Trp Ser Thr Pro Val
            435                 440

<210> SEQ ID NO 35
<211> LENGTH: 406
<212> TYPE: PRT
<213> ORGANISM: Artificial Sequence
<220> FEATURE:
<223> OTHER INFORMATION: synthesized

<400> SEQUENCE: 35

Met Ala Tyr Leu Ala Asn Gln Leu Asn Gly Gly Val Pro Arg Tyr Pro
1               5                   10                  15

Ser Pro Ser Met Gln Gln Gln Gly Ala Met Pro Leu Ile Gln His Thr
            20                  25                  30

Tyr His Pro Asn Ala Gly Ser Asp Gln Ser Tyr Gln Pro Gln Ala Ser
        35                  40                  45

Met Gly Pro Val Gln Gly Ala Leu Pro Pro Asp Pro Thr Gln Ser Asp
    50                  55                  60

Gly Thr Gly Arg Pro Asn Gly Ser Gly Leu Pro Lys Ala Phe Ala Cys
65                  70                  75                  80

Ser Ser Cys Gly Lys Gly Phe Ala Arg Arg Ser Asp Leu Ala Arg His
                85                  90                  95

Glu Arg Ile His Ser Gly Val Arg Pro His Ala Cys Asp Tyr Pro Gly
            100                 105                 110

Cys Asn Lys Gln Phe Ile Gln Arg Ser Ala Leu Thr Val His Ser Arg
        115                 120                 125

Val His Thr Gly Glu Lys Pro His Met Cys Glu Arg Cys Gly Lys Pro
    130                 135                 140

Phe Ser Asp Ser Ser Ser Leu Ala Arg His Arg Arg Ile His Ser Gly
145                 150                 155                 160

Lys Arg Pro Tyr Lys Cys Pro Tyr Ala Asp Cys Gln Lys Thr Phe Thr
                165                 170                 175

Arg Arg Thr Thr Leu Thr Arg His Gln Asn His His Thr Gly Thr Ile
            180                 185                 190

Glu Glu Ser Glu Ala Ala Thr Ala Ala Leu Ala Ser Arg Val Asn
        195                 200                 205

Met Gln Ser Arg Ser Arg Gly Ser Asp Glu Glu Gly Asp Tyr Ser Asp
    210                 215                 220

Gly Lys Ser Pro Met Pro Gln Gln Pro Asp Arg Val Asn Ser Pro Ala
225                 230                 235                 240

Ile Asn Val Asn Gly Val Pro Gln Met Gln Arg Gln Gly Ser Asp Leu
                245                 250                 255

Tyr Met Gln Val Met Gly Asn Gly Met Ala Ala Ala Ala Phe Pro
            260                 265                 270
```

```
Gln His Leu Arg Ser Glu Met Gln Gly Ser Pro Arg Pro Gln Ser Pro
            275                 280                 285

Ser Gln Tyr Pro Met Pro Pro Thr Thr Gln Pro Gln Arg Pro Gly Leu
        290                 295                 300

Thr Ser Asn Pro Ser Ser Gly Tyr Asn Pro Pro Gln Ile Leu Glu Pro
305                 310                 315                 320

Pro Thr Thr Asn Gly Gln Gln Thr Gly Ser Gly Ser Asn Ser Pro His
                325                 330                 335

Ile Ser Ala Ala Met Gly Trp Gln Ser Pro His Asn Gly Leu Thr Gln
                340                 345                 350

His Gln Gln Ser Asp Tyr Ser Tyr Pro Asp Pro Asn Gly Gln Tyr Ala
            355                 360                 365

Thr Ala Asn Ala Ala Ala Met Tyr Tyr Gln Gln Pro Val Gln Arg Pro
370                 375                 380

His Ser Thr Gly Pro Ile Asp Tyr Gln Gln Leu Arg Gly Ala Glu Met
385                 390                 395                 400

Trp Ala Gln His Gln Gln
                405

<210> SEQ ID NO 36
<211> LENGTH: 406
<212> TYPE: PRT
<213> ORGANISM: Artificial Sequence
<220> FEATURE:
<223> OTHER INFORMATION: synthesized

<400> SEQUENCE: 36

Met Ala Met Gln His Ser His His His Pro Thr Gly Ser Thr Pro Glu
1               5                   10                  15

Arg Gln Met His Gln Leu Pro Gln Leu Thr Ala Arg Asn Leu Pro Glu
            20                  25                  30

Pro Pro Met Asp Arg Ser Gly Ser Pro His Gly Ser Glu His Ser Arg
        35                  40                  45

Tyr Ser Ala Pro Arg Ser His Met Asp Ser Val Pro Arg Ser Tyr Pro
    50                  55                  60

Ser Pro Val Pro Met Asn Gly Pro Pro Met Met Gln Ala His Ala Pro
65                  70                  75                  80

Pro Gln His Gln His Gln His Gln His His Ala Gly Val Pro
            85                  90                  95

Ile Thr Met Ile Leu Pro Gly Gly Pro Pro Asp Met Asn Ala Gly Met
            100                 105                 110

His His Tyr Lys Pro Pro Gly Val Pro Val Glu Pro Gln Pro Ala Gln
        115                 120                 125

Gln Val Lys Ala Tyr Pro Cys Gly Thr Cys Gly Lys Arg Phe Ala Arg
    130                 135                 140

Arg Ser Asp Leu Ala Arg His Glu Arg Ile His Ser Gly Ile Arg Pro
145                 150                 155                 160

His Val Cys Asp Tyr Pro Asn Cys Gly Lys Gln Phe Ile Gln Arg Ser
                165                 170                 175

Ala Leu Thr Val His Gln Arg Val His Thr Gly Glu Lys Pro His Met
            180                 185                 190

Cys Glu Arg Cys Gly Lys Pro Phe Ser Asp Ser Ser Ser Leu Ala Arg
        195                 200                 205

His Arg Arg Ile His Ser Gly Lys Arg Pro Tyr Lys Cys Pro Tyr Ala
    210                 215                 220
```

```
Asp Cys Gln Lys Thr Phe Thr Arg Arg Thr Thr Leu Thr Arg His Gln
225                 230                 235                 240

Asn His His Thr Gly Thr Val Glu Glu Ala Ala Ala Thr Ala Ala
            245                 250                 255

Ala Leu Ala Ala Arg Ala Ser Val Lys Pro Gly Ser Thr Arg Ser Asp
                260                 265                 270

Gly Asp Ser Met Ser Asn Arg Gly Ser Pro Met Thr Thr Pro Ser Pro
                275                 280                 285

Ala Gln Arg Thr Leu Ser Met Ser Pro Ser Ala Asp Gln Met Gln Arg
        290                 295                 300

Ser Asn Ala Glu Phe Gly Tyr Met Gly Asn Thr Ser Leu Pro Val His
305                 310                 315                 320

Leu Gln Arg Asp Met His Val Gly Ser Pro Ala Ser Thr Thr Ser Ala
                325                 330                 335

Gly Tyr Ser Asn Gly Val Arg Pro Thr Ser His Pro Thr Gly Tyr Gly
                340                 345                 350

Met Val Pro Pro Pro Thr Leu Glu Pro Asn Val Glu Gln His Ser Gly
                355                 360                 365

Pro Gly Ser Ala Gly Gly Ser Pro His Met Ser Thr Met Gly Trp Gln
        370                 375                 380

Ser Pro Ser His Val Ala Ser Pro Ser His Ser Asn Asn Gly Ser Ala
385                 390                 395                 400

Tyr Met Tyr Pro Gly Ala
                405

<210> SEQ ID NO 37
<211> LENGTH: 283
<212> TYPE: PRT
<213> ORGANISM: Artificial Sequence
<220> FEATURE:
<223> OTHER INFORMATION: synthesized

<400> SEQUENCE: 37

Met Ala Pro Gly Val Gly Arg Asp Phe Asn Cys Ser Trp Glu His Cys
1               5                   10                  15

Gly Lys Ser Phe Asn Arg Lys Ser Asp Leu Cys Arg His Tyr Arg Ile
                20                  25                  30

His Thr Asn Glu Arg Pro Tyr His Cys Thr Val Lys Asp Cys Asn Lys
            35                  40                  45

Ser Phe Ile Gln Arg Ser Ala Leu Thr Val His Ser Arg Thr His Thr
    50                  55                  60

Gly Glu Lys Pro His Val Cys Asp His Glu Gly Cys His Lys Ala Phe
65                  70                  75                  80

Ser Asp Ser Ser Ser Leu Ala Arg His Arg Arg Ile His Thr Gly Lys
                85                  90                  95

Arg Pro Tyr Ile Cys Gln Glu Pro Thr Cys Glu Arg Ser Phe Cys Arg
                100                 105                 110

Lys Thr Thr Leu Thr Lys His Gln His Arg Ser His Pro Ser Gly Thr
            115                 120                 125

Met Thr Arg Pro Pro Ser Glu Asp Ala Met Ser Glu Gln Ser Tyr Gln
    130                 135                 140

Ala Pro Val Ala Ala Pro Ile Pro Asn Asp Gln Tyr Leu Leu Ala Gln
145                 150                 155                 160

Gln Gln Tyr Tyr His Gln Pro Ser Thr Pro Ser Gln Glu Phe Tyr Pro
                165                 170                 175
```

```
Pro Gln Ser Leu Pro Val Thr His Ile Pro Val His Asp Thr Pro Pro
                180                 185                 190

Ile Met Thr Gln Ser Val Pro Val Thr Ser Pro Leu Asp Val Gln His
                195                 200                 205

Ala Gln Gln Gln Tyr Met Gln Gln Leu Met Gln Gln Arg Tyr Asp Thr
            210                 215                 220

Thr Asn Gln Ser Tyr Ile Pro Pro Gly Phe Gln Gln Gln Gln Gln Thr
225                 230                 235                 240

Phe Val Pro Gln Pro Met Ala Glu Gly His Pro Leu Met Ile Ser Tyr
                245                 250                 255

Asn Gln Asn Phe His Tyr Lys Gln Pro Thr Arg Ile Leu Asn Gln Pro
                260                 265                 270

Glu Gly Thr Asp Trp Gly Phe Leu Gly Val Gly
            275                 280

<210> SEQ ID NO 38
<211> LENGTH: 388
<212> TYPE: PRT
<213> ORGANISM: Artificial Sequence
<220> FEATURE:
<223> OTHER INFORMATION: synthesized

<400> SEQUENCE: 38

Met Ser Gly His Leu Gln Ala Ala Arg Pro Tyr Gly Ser Pro Thr Ser
1               5                   10                  15

Met His Ala Ser Leu His Met Pro Glu Pro Asn Met Gly Pro Ser Gly
                20                  25                  30

Met Ala Phe Pro Ser Met Ala Pro Glu Leu Tyr Ala Pro Pro Gln Pro
            35                  40                  45

Leu Arg Ala Pro Asp Ala Thr Ser Gln Pro Ala Pro Lys Ala Tyr Ala
    50                  55                  60

Cys Ser Thr Cys Gly Lys Gly Phe Ala Arg Arg Ser Asp Leu Ala Arg
65                  70                  75                  80

His Glu Arg Ile His Thr Gly Val Arg Pro His Val Cys Glu Tyr Pro
                85                  90                  95

Asn Cys Gly Lys Gln Phe Ile Gln Arg Ser Ala Leu Thr Val His Gln
                100                 105                 110

Arg Val His Thr Gly Glu Lys Pro His Met Cys Glu Arg Cys Gly Lys
            115                 120                 125

Pro Phe Ser Asp Ser Ser Ser Leu Ala Arg His Arg Arg Ile His Ser
130                 135                 140

Gly Lys Arg Pro Tyr Lys Cys Pro Tyr Ala Asp Cys Gln Lys Thr Phe
145                 150                 155                 160

Thr Arg Arg Thr Thr Leu Thr Arg His Gln Asn His His Thr Gly Thr
                165                 170                 175

Val Glu Asp Ala Ala Arg Ala Thr Ala Glu Val Leu Ala Arg Asn Ser
                180                 185                 190

Val Ala Arg Ser Ala Ser Ala Arg Pro Thr Arg Ser Glu Gly Asp Gln
            195                 200                 205

Ile Ser Asn His Gly Ser Pro Leu Ser Thr Ser Pro Ala Gln Arg
    210                 215                 220

Thr Met Ser Met Ser Pro Ser Ala Glu Leu Ala Ala Asn Gly Met
225                 230                 235                 240

Gln His Gln Tyr Asn Gly Asn Ser Ser Leu Pro Ala His Met Arg Thr
                245                 250                 255
```

```
Asp Leu His Ser Ser Pro Ala Ala Thr Thr Ser Ser Gly Phe Ser
            260             265             270

Ser Asn Val Arg Pro Thr Ser His Pro Asn Ala Tyr Gly Ala Ala Pro
        275                 280             285

Pro Pro Thr Thr Leu Glu Pro Ser Ile Glu Gly Ser Gln Gly Pro Gly
        290                 295             300

Ser Ala Val Gly Ser Pro His Met Ser Ser Val Gly Trp Ala Ser Pro
305             310             315             320

Ser His Val Ala Ser Pro Ala His Ser Asn Ser Gly Gly Asn Ser Ser
                325             330             335

Tyr Val Tyr Pro Asp Pro Asp Ser Ser Tyr Pro Thr Asn Ala Ala Ala
            340             345             350

Gln Gly Gln Met Phe Tyr Ser Ala Ala Met Gly Leu Gln Arg Pro Gly
            355             360             365

Ser Ala Glu Pro Gly Ala Gln Ser Ala Tyr Lys Pro Arg Gln Asn Glu
        370                 375             380

Leu Trp Ala Ala
385

<210> SEQ ID NO 39
<211> LENGTH: 421
<212> TYPE: PRT
<213> ORGANISM: Artificial Sequence
<220> FEATURE:
<223> OTHER INFORMATION: synthesized

<400> SEQUENCE: 39

Met Asp Ile Lys Glu Ile Val Asn Ser Lys Gly Val Lys Gly Ala Ala
1               5                   10                  15

Ala Ala Ala Ala Ser Ala Ser Gly Gln Ala Gln Asp Leu His Leu
            20                  25                  30

Leu Gln Ser Ile Ser Gln Ala Asn Gly Leu Arg Met Ser Asp Ala Gly
            35                  40                  45

Ser Glu Arg Gly Asn Ser Pro His Gly Ser Glu His Ser Gln Tyr Ser
    50                  55                  60

Thr Pro Arg Met Gly Met Asn Gly Met Asn Gly Ala Pro Asn Gly Met
65                  70                  75                  80

Arg Tyr Pro Ser Pro Pro Gly Met Gln Asn Ser Met Pro Met Met Gln
                85                  90                  95

Gln Pro Tyr Arg Pro Asp Val Ala Phe Asp Asn Gly Met Met Ser Thr
            100                 105                 110

Gln Gln Gln Asp Asn Thr Arg Gln Arg Gln Pro Gly Asp Ile Thr Val
            115                 120                 125

Thr Lys Ala Phe Pro Cys Ser Thr Cys Gly Lys Gly Phe Ala Arg Arg
        130                 135                 140

Ser Asp Leu Ala Arg His Glu Arg Ile His Ser Gly Val Arg Pro His
145                 150                 155                 160

Val Cys Asp Tyr Pro Gly Cys Gly Lys Gln Phe Ile Gln Arg Ser Ala
                165                 170                 175

Leu Thr Val His Leu Arg Val His Thr Gly Glu Lys Pro His Thr Cys
            180                 185                 190

Glu Arg Cys Ala Lys Thr Phe Thr Arg Arg Thr Thr Leu Thr Arg His
            195                 200                 205

Gln Asn His His Thr Gly Thr Val Glu Glu Ala Ala Ala Thr Ala
        210                 215                 220
```

```
Ala Ala Leu Ala Gly Arg Pro Gly Asn Asn Arg Pro Ser Arg Gln Arg
225                 230                 235                 240

Ser Asp Gly Glu Ser Tyr Ser Asn Asn Gly Ser Pro Met Ser Thr Pro
            245                 250                 255

Ser Pro Gly Arg His Leu Ser Ala Ser Pro Ser Ser Asp Met Ala Pro
            260                 265                 270

Met Asn Asn Met Gln Arg His Pro Gly Asp Tyr Gly Tyr Met Asn Asn
            275                 280                 285

Ser Ser Leu Pro Gly His Leu Arg Gly Asp Tyr Gly Val Pro Asn Gln
            290                 295                 300

Pro Pro Pro Val Ser Thr Ala Phe Thr Asn Gly Met Gln Arg Pro Thr
305                 310                 315                 320

Ser His Pro Thr Gly Tyr Gly Pro Pro Ser Ile Leu Glu Pro Pro Ala
            325                 330                 335

Asn Met Glu Gln Arg Gln Pro Gly Ser Ala Asn Gly Ser Pro His Met
            340                 345                 350

Thr Asn Met Gly Trp Gln Ser Pro Ser Gln Met Ala Ser Pro Ser His
            355                 360                 365

Asn Asn Asn Tyr Val Tyr Pro Asp Pro Asp Pro Tyr Gly Ser Gly Ala
370                 375                 380

Ala Met Gly Gln Met Tyr Tyr Pro Asn Ser Asn Met Arg Arg Pro Gln
385                 390                 395                 400

Ser Thr Glu Pro Glu Gln Tyr Asp Met Lys Pro Arg Ile Asn Glu Met
            405                 410                 415

Trp Ala Thr Ala Gln
            420

<210> SEQ ID NO 40
<211> LENGTH: 441
<212> TYPE: PRT
<213> ORGANISM: Artificial Sequence
<220> FEATURE:
<223> OTHER INFORMATION: synthesized

<400> SEQUENCE: 40

Met Asp Ile Thr Thr Ile Leu Asn Lys Asn Arg Ser Ala Val Ala Ala
1               5                   10                  15

Ala Ala Glu Ala Gln Leu Gln His Gln Leu Ala Gln Thr Ala Gln Ile
            20                  25                  30

Lys Ser Arg Ser Pro Ser Glu Leu Gly Ser Glu His Asp Ala Gln Gln
            35                  40                  45

Pro Gly Arg His Ser Glu Pro Tyr His Pro Ala His Gln Pro Ile Gln
    50                  55                  60

Leu Pro Thr Ile Ser Gln Tyr His Ser Pro Leu His Thr Asn His His
65                  70                  75                  80

Ala Ser Met Met Arg Gly Asp Tyr Ala Gln Asn Gly His Glu Asn Met
                85                  90                  95

Phe Arg Asn Met Pro Thr Ser Asn Ser Gly Pro Gly Arg Gly Thr Gly
            100                 105                 110

Glu Pro Ala Pro Lys Ser Phe His Cys Gln Thr Cys Ser Lys Gly Phe
            115                 120                 125

Ala Arg Arg Ser Asp Leu Ala Arg His Glu Arg Ile His Ser Gly Ile
    130                 135                 140

Arg Pro His Val Cys Asp Trp Pro Gly Cys Gly Lys Gln Phe Ile Gln
145                 150                 155                 160
```

Arg Ser Ala Leu Thr Val His Thr Arg Val His Thr Gly Glu Lys Pro
            165                 170                 175

His Met Cys Asp Arg Cys Gly Lys Pro Phe Ser Asp Ser Ser Ser Leu
        180                 185                 190

Ala Arg His Arg Arg Ile His Ser Gly Lys Arg Pro Tyr Lys Cys Pro
    195                 200                 205

Tyr Ala Asn Cys Gln Lys Thr Phe Thr Arg Arg Thr Thr Leu Thr Arg
210                 215                 220

His Gln Asn His His Thr Gly Thr Ile Glu Ala Ala Ala Glu Thr
225                 230                 235                 240

Glu Ala Asn Leu Arg Gln Gly Lys Val Val Arg Pro Asp Gly Val Tyr
                245                 250                 255

Ser Glu Thr Ala Ser Pro His Gly Thr Ala Ser Pro Ala Gln Arg Ser
            260                 265                 270

Ser Val Ser Pro Arg His Glu Leu Pro Pro Leu His Ser His Arg Gln
        275                 280                 285

Met Gly Asp Tyr Phe Met Ala Ser Ser Leu Pro Pro His Leu Arg
    290                 295                 300

Asp Phe Gln Gln Ala Ser Pro Arg Ala Ser Pro Ser Thr Pro Ser Pro
305                 310                 315                 320

Thr Leu Ser Thr Phe Ser Ala Ala His His Pro Arg Pro Ser Leu Thr
                325                 330                 335

Ser His Pro Thr Ser Tyr Gly Pro Pro Gln Pro Leu Glu Pro Pro Pro
            340                 345                 350

Asn Ser Gly Ser Arg Pro Gly Ser Val Thr Gly Ser Pro His Met Thr
        355                 360                 365

Thr Val Gly Trp Ala Ser Pro Ser Leu Asn Ser Val Pro Ser Pro Gly
    370                 375                 380

Ser Val Ser Ala Pro Glu Tyr Thr Tyr Pro Glu Pro Ser Gly Pro Pro
385                 390                 395                 400

Phe Ala Gly Gly Met Pro Ala His Met Tyr Tyr Pro Asn Ser Thr Ile
                405                 410                 415

Arg Arg Pro Gln Ser Thr Glu Pro Glu Asn Tyr Glu Leu Lys Pro Lys
            420                 425                 430

Val Glu Glu Pro Trp Ala Thr His Ala
        435                 440

<210> SEQ ID NO 41
<211> LENGTH: 479
<212> TYPE: PRT
<213> ORGANISM: Artificial Sequence
<220> FEATURE:
<223> OTHER INFORMATION: synthesized

<400> SEQUENCE: 41

Met Glu Leu Asp Thr Ile Leu Asn Ala Arg Leu Thr Ala Ser Leu Gly
1               5                   10                  15

Thr Gly Ala Pro Tyr Ala Met Gln His Ala Met Gln Gln His Phe
            20                  25                  30

Gly Ala Pro Pro Ser Tyr Leu Asn Gly Ser His Ile Lys Ser Glu Asn
        35                  40                  45

Gly Ser Glu Arg Gly Val Ser Pro His Pro Ser Asp Ser Ser Arg Tyr
    50                  55                  60

Ser Ser Gln Gln Pro Gln Gln Leu Pro Ser Tyr Pro Ser Ile Pro
65                  70                  75                  80

Gln Gln His Met Asn Gly Leu Arg Tyr Pro Ser Pro Ser Gln Met Gln
            85                  90                  95

Ala Pro Met Pro Met Leu Asn Asn Ser Asn Tyr Ile Pro Thr Pro Pro
            100                 105                 110

Asp His Thr Tyr Ala Gln Gln Gln Leu Pro Asp Ala Gln Val Gly
            115                 120                 125

His Gln His Asn Gly Gly Arg Pro Ala Ser Asp Thr Gly Pro Pro Lys
            130                 135                 140

Ala Phe Ala Cys Ser Thr Cys Gly Lys Gly Phe Ala Arg Arg Ser Asp
145                 150                 155                 160

Leu Ala Arg His Glu Arg Ile His Ser Gly Ile Arg Pro His Val Cys
            165                 170                 175

Asp Tyr Pro Asn Cys Gly Lys Gln Phe Ile Gln Arg Ser Ala Leu Thr
            180                 185                 190

Val His Gln Arg Val His Thr Gly Glu Lys Pro His Met Cys Glu Arg
            195                 200                 205

Cys Gly Lys Pro Phe Ser Asp Ser Ser Leu Ala Arg His Arg Arg
210                 215                 220

Ile His Ser Gly Lys Arg Pro Tyr Lys Cys Pro Tyr Ala Asp Cys Gln
225                 230                 235                 240

Lys Thr Phe Thr Arg Arg Thr Thr Leu Thr Arg His Gln Asn His His
            245                 250                 255

Thr Gly Thr Val Glu Glu Ala Ala Ala Thr Ala Ala Leu Ala
            260                 265                 270

Ser Arg Ala Ser Gln Ser Ser Arg Thr Gly Arg Ser Asp Gly Gly Asp
            275                 280                 285

Tyr Ser Glu Thr Ala Ser Pro Leu Gly Thr Pro Ser Pro Asn Asp Arg
            290                 295                 300

Thr Leu Ser Leu Ser Pro Ala Asn Gly Met Pro Ala Gly Gly Met Pro
305                 310                 315                 320

Gly Leu His Arg Gln Gly Ser Asp Tyr Ala Tyr Met Gly Gly Met Asn
            325                 330                 335

Val Pro Pro His Met Arg His Glu Met Pro Gln Pro Ser Pro Arg Ala
            340                 345                 350

Ser Pro Ala Leu Thr Ala Gln Ser Tyr Ala Ser Asn Val Ser Gly Ser
            355                 360                 365

Arg Pro Ala Ile Thr Ser His Pro Ser Ala Tyr Gly Pro Pro Ile
            370                 375                 380

Leu Glu Pro Pro Ala Ser Ala Asn His Gly Gln Ser Gly Gly Thr Ser
385                 390                 395                 400

Ser Ala Asn Gly Ser Pro His Met Ser Thr Met Gly Trp Gln Ser Pro
            405                 410                 415

Gly Gln Gln Ala Leu Pro Ser Pro Gly Ala Asn Asp Asn Gly Tyr Val
            420                 425                 430

Tyr Pro Glu Pro Gln Tyr Gln Ala Gln Asn Gly Met Tyr Tyr Gln His
            435                 440                 445

Asn Asn Ile Arg Arg Pro Asn Ser Thr Glu Pro Asp His Tyr Asn Pro
450                 455                 460

Asn Gln Gln Arg Met Gly Asn Glu Met Trp Ala Pro Ala Val Gln
465                 470                 475

<210> SEQ ID NO 42
<211> LENGTH: 449
<212> TYPE: PRT

<213> ORGANISM: Artificial Sequence
<220> FEATURE:
<223> OTHER INFORMATION: synthesized

<400> SEQUENCE: 42

```
Met Arg Leu Ser Phe Ser Arg Ile Leu Thr Cys Ala Glu Pro Arg Ala
1               5                   10                  15

Gln Gln Pro Gln Gln Gly Ala Thr Pro Glu Leu Gln Gln Gln Arg Pro
            20                  25                  30

Gln Ala Leu Gln Gln Leu Gln Gln Leu Gln Pro Leu Gln Thr Gln
        35                  40                  45

Ile Asp Arg Gln Pro Ser Pro His Gly Ser Glu Gln Ser Arg Tyr Ser
    50                  55                  60

Gly Pro Met Asn Ala Ser Tyr Pro Ser Pro Thr Ala Met Ala Ala Thr
65                  70                  75                  80

Pro Leu Pro Pro Val Pro Asn Ala Asn Met Ala Pro Ala Pro Met Val
                85                  90                  95

Pro Asn Glu Met Gln Gln Asn Leu Gly Met Pro Pro Ala Gly Tyr Gln
            100                 105                 110

Pro Ala Gln Ala Pro Pro Gln Pro Pro Ala Lys Gln Phe Pro Cys Ser
        115                 120                 125

Thr Cys Gly Lys Pro Phe Ala Arg Arg Ser Asp Leu Ala Arg His Glu
    130                 135                 140

Arg Ile His Ser Gly Ile Arg Pro His Val Cys Asp Tyr Pro Gly Cys
145                 150                 155                 160

Gly Lys Gln Phe Ile Gln Arg Ser Ala Leu Thr Val His Ser Arg Val
                165                 170                 175

His Thr Gly Glu Lys Pro His Arg Cys Glu Arg Cys Gly Lys Pro Phe
            180                 185                 190

Ser Asp Ser Ser Leu Ala Arg His Arg Ile His Ser Gly Lys
        195                 200                 205

Arg Pro Tyr Lys Cys Pro Tyr Ala Asp Cys Gln Lys Thr Phe Thr Arg
    210                 215                 220

Arg Thr Thr Leu Thr Arg His Gln Asn His His Val Gly Thr Val Glu
225                 230                 235                 240

Glu Ser Ala Arg Ala Arg Ala Glu Ala Leu Ala Gln Gly Ala Asn Ala
                245                 250                 255

Ala Ala Ala Ala Val Ala Ala Ala Gln Ser Lys Ser Arg Ser Gly Ser
            260                 265                 270

Glu Gln Ala Ser Asn His Glu Ser Pro Leu Thr Asn Thr Pro Ser Pro
        275                 280                 285

Gly Gln Arg Pro Met Ser Met Ser Pro Gly Ala Glu Leu Ala Gly Ile
    290                 295                 300

Asn Asn Met Gln Tyr Leu Ser Asn Ser Ile Pro Pro His Leu Arg Gly
305                 310                 315                 320

Asp Val His Val Gly Ser Pro Ser Pro Thr Ala Ser Ser Gly Tyr Asn
                325                 330                 335

Asn Gly Met Arg Pro Thr Ser His Pro Thr Gly Tyr Ala Pro Pro Gln
            340                 345                 350

Thr Leu Glu Pro Ser Ile Glu Gln Pro Gln Gln Gly Pro Gly Ser Ala
        355                 360                 365

Val Gly Ser Pro His Ile Gly Ser Val Gly Trp Ala Ser Pro Gly His
    370                 375                 380

Val Gly Ser Pro Thr Gln Ser Pro Ser Gly Asn Gly Tyr Val Tyr Pro
```

```
            385                 390                 395                 400

Asp Pro Glu Ala Tyr Pro Asn Gly Thr Pro Ile Ala Gln Met Phe Phe
                405                 410                 415

Asn Ser Ala Val Ala Ser Arg Arg Pro Asp Ser Ala Glu Pro Gly Asn
                420                 425                 430

Pro Ser Phe Asp Thr Lys Ser Arg Gln Gly Glu Leu Trp Thr Asn Ser
                435                 440                 445

Gln

<210> SEQ ID NO 43
<211> LENGTH: 517
<212> TYPE: PRT
<213> ORGANISM: Artificial Sequence
<220> FEATURE:
<223> OTHER INFORMATION: synthesized

<400> SEQUENCE: 43

Met Asp Leu Arg Gly Leu Leu Gln Ser His Pro His His Thr Ser
1               5                   10                  15

His Gln Gln Pro Tyr Asp His Arg Leu Pro Ala Ala Gln Pro Tyr Thr
                20                  25                  30

Ser Leu Pro Ile Ser Tyr Ala Ser Pro Ser Tyr Ile Ala Ile Gly His
                35                  40                  45

His His Asn His Gln His His Gln Ala Gln Gly Gln Gln Gly Gln
            50                  55                  60

Gly Met Tyr Asp Phe Pro Phe Ser His Pro Gln Gln Gln Gln Gln Gln
65                  70                  75                  80

Gly Glu Gln Ser Thr Tyr Leu Arg Arg His Gln Gly Tyr Gln Asn Gln
                85                  90                  95

Met Pro Thr Ser Ala Gln Gln Gln Gln Ser Ser Tyr Pro Gln Gln
                100                 105                 110

Gln Gln Gln Leu Pro Arg Ser Tyr Gln Ser Gly Asn Ala Gln Ser Met
            115                 120                 125

Tyr Gly Lys Thr Thr Ala Ile Ala Pro Ala Gly Glu Gly Trp Gly Lys
130                 135                 140

His Gln Gln Gln Val Gly Gly Tyr Gln Gln Ser Gln Met Gln Thr Gln
145                 150                 155                 160

Val Val Ala Gln Ser Thr Asp Val Asp Ala Leu Met Arg Ala Ile Gln
                165                 170                 175

Ala Lys Pro Ala Gly Asp Asn Gly Ser Ala Ser Glu Val Ala Ser Ala
            180                 185                 190

Glu Arg Thr Arg Asp Val Ser Ala Glu Arg Glu Lys Asn Ala Ser Arg
        195                 200                 205

Gly Gly Gly Ala Thr Gly Met Lys Asn Gly Asn Gly Arg Glu Glu
210                 215                 220

Pro Lys Lys Arg Tyr Glu Cys His Leu Gly Glu Cys Arg Lys Ala Phe
225                 230                 235                 240

Phe Gln Lys Thr His Leu Glu Ile His Ile Arg Ala His Thr Gly Ala
                245                 250                 255

Lys Pro Tyr Thr Cys Thr His Pro Thr Cys Thr His Ala Phe Ser Gln
            260                 265                 270

Leu Gly Asn Leu Lys Thr His Leu Arg Arg His Thr Gly Glu Arg Pro
        275                 280                 285

Phe Ala Cys Pro Thr Cys Gly Lys Thr Phe Ala Gln Arg Gly Asn Val
    290                 295                 300
```

```
Arg Ala His Ala Ala Val His Asp Ala Gly Gly Ala Ala Lys Lys Phe
305                 310                 315                 320

Val Cys Arg Leu Asp Gly Cys Gly Lys Cys Phe Thr Gln Leu Gly Asn
                325                 330                 335

Leu Lys Ser His Met Asn Lys Phe His Val Glu Thr Leu Arg Gly Leu
                340                 345                 350

Thr Val Arg Phe Gly Glu Ser Glu Lys Arg Gly Arg Asp Gly Gly Glu
                355                 360                 365

Gly Glu Gly Lys Glu Glu Glu Asp Asp Leu Leu Asp Tyr Phe Arg Ser
            370                 375                 380

Leu Tyr Arg Asn Ala Asn Lys Gly Ile Lys Gly Arg Gly Lys Gly Arg
385                 390                 395                 400

Lys Val Ala Ser Thr Thr Ser Thr Ser Ser Thr Pro Pro Ser Leu Ser
                405                 410                 415

Ser Ser Thr Ser Ser Leu Ser Ser Leu Ala Ser Leu Ser Ser Leu Ala
                420                 425                 430

Ser Leu Ala Ser Leu Ala Ser Pro Pro Leu Ser Pro Thr Ser Thr
            435                 440                 445

Ser Ser Tyr Ile Gly Gly Ile Pro Ala His Tyr Arg Met Gly Met Gly
            450                 455                 460

Met Gly Met Ala Pro Gly Met Asp Gly Ile Glu Leu Phe Asp Gly Ser
465                 470                 475                 480

Ser Ser Gly Ile Gly Ser Pro Cys Ala Ser Ser Leu Gly Ser Leu Tyr
                485                 490                 495

Glu Val Gly Gly Thr Tyr Glu Glu Glu Gly Gly Glu Leu Ala Phe
                500                 505                 510

Gly Asp Arg Met Tyr
            515

<210> SEQ ID NO 44
<211> LENGTH: 436
<212> TYPE: PRT
<213> ORGANISM: Artificial Sequence
<220> FEATURE:
<223> OTHER INFORMATION: synthesized

<400> SEQUENCE: 44

Met Ser Gly Met Arg Ser Pro Ala Pro Thr Glu Val Met Asp Ile Thr
1               5                   10                  15

Asn Met Leu Asn Asn Lys Gly Gln Met Gln Gln Leu Thr Ser Gly Leu
                20                  25                  30

Leu Asp His Gln Gln Tyr Gln His Ala Phe Val Lys His Glu Ser Gly
            35                  40                  45

Met Glu Arg Ser Ala Ser Pro His Gly Ser Glu His Ser Gln Tyr Ser
        50                  55                  60

Asn Pro His Ser Ile Ala Arg Ala Tyr Pro Ser Pro Ser Thr Met Gln
65                  70                  75                  80

Ala Pro Met His Met Pro Asn Pro Met Ser Ala Ala Met Thr Met Gln
                85                  90                  95

Gly Tyr Pro Glu Met Pro Asn Met Gly Gly Met Pro His Met His Met
                100                 105                 110

Gln Gln Met Pro Gln Gln Pro Pro Pro Gln Gln Pro Ile Lys
            115                 120                 125

Ala Tyr Pro Cys Ser Thr Cys Gly Lys Gly Phe Ala Arg Arg Ser Asp
    130                 135                 140
```

-continued

```
Leu Ala Arg His Glu Arg Ile His Ser Gly Val Arg Pro His Val Cys
145                 150                 155                 160

Asp Trp Pro Gln Cys Gly Lys Gln Phe Ile Gln Arg Ser Ala Leu Thr
                165                 170                 175

Val His Gln Arg Val His Thr Gly Glu Lys Pro His His Cys Glu Thr
            180                 185                 190

Cys Ala Lys Pro Phe Ser Asp Ser Ser Leu Ala Arg His Arg Arg
        195                 200                 205

Thr His Ser Gly Lys Arg Pro Tyr Lys Cys Pro Tyr Ala Asp Cys Gln
    210                 215                 220

Lys Thr Phe Thr Arg Arg Thr Thr Leu Thr Arg His Gln Asn His His
225                 230                 235                 240

Ser Gly Thr Ile Glu Glu Ala Ala Ala Thr Ala Ala Ala Leu Ala
                245                 250                 255

Ala Ser Lys Ser Lys Gly Leu Ser Gln Thr Arg Ser Glu Ser Asp His
        260                 265                 270

Met Ser Asn His Gly Ser Pro Leu Thr Thr Pro Ser Pro Ser Gln Arg
    275                 280                 285

Thr Met Ser Met Ser Pro Ser Val Asp Leu Ser Gly Asn Asn Ser Ile
    290                 295                 300

Pro Arg His Pro Gly Asp Phe Gln Tyr Leu Ser Gln Asn Gly Ser Leu
305                 310                 315                 320

Pro Met His Met Arg Val Gly Ser Pro Thr Ser Thr Ser Ser Gly Gly
                325                 330                 335

Phe Asn Met Met Arg Pro Thr Ser His Pro Thr Ser Tyr Gly Pro Pro
            340                 345                 350

Pro Thr Leu Glu Pro Asn Leu Asp Asn Ser Gln Gly Thr Pro Ser Ser
        355                 360                 365

Asn Gly Gly Ser Pro His Met Thr Asn Val Gly Trp Gln Ser Pro Ser
370                 375                 380

His Met Ala Ser Pro Ser Gln Asn Asn Ala Ser Tyr Val Tyr Pro Asp
385                 390                 395                 400

Pro Ala Asp Ala Tyr Pro Ala Asn Gln Ala Met Asn Gln Met Tyr Tyr
                405                 410                 415

Ser Ala Ala Ala His Met Arg Arg Pro Gln Ser Thr Glu Pro Gly Leu
            420                 425                 430

Val His Met Ala
        435

<210> SEQ ID NO 45
<211> LENGTH: 507
<212> TYPE: PRT
<213> ORGANISM: Artificial Sequence
<220> FEATURE:
<223> OTHER INFORMATION: synthesized

<400> SEQUENCE: 45

Met Leu Ala Arg Pro Glu Arg Arg Gly Lys Pro Arg Cys Gly Ala Gly
1               5                   10                  15

Ser Ala Leu Lys Pro Glu Gly Val Lys Leu Ser Phe Asp Cys Leu Phe
                20                  25                  30

Phe Gly Ile Glu Thr Ile Ser Glu Pro Glu Val Thr Pro Ala Phe Val
            35                  40                  45

Ala His Ile Leu Gly Cys Glu Ser Leu Glu Thr Ser Pro Ala Val Val
        50                  55                  60
```

```
Asn Phe Ser Ala Asp Pro Thr Arg Lys Gly Ser Ala Ala Met Val Ala
 65                  70                  75                  80

Ala Glu Phe Asp His Gln Gln Phe Ile Gln Asn Pro His Leu Asp Thr
                 85                  90                  95

Ser Ser Pro Lys Met Lys Pro Glu Pro Gly Val Ser Glu Ala Gly Asp
            100                 105                 110

Gln Pro Val Leu Ala Tyr Pro Pro His Ala Pro Leu Gly Gln Val Pro
                115                 120                 125

Asn Met His Pro Asp Met Arg Tyr Gln Pro Gln Thr His Pro Asn Pro
130                 135                 140

Ala Leu Pro Leu Leu Gln Asn Pro Tyr Met Pro Gly Gly Tyr Thr Ser
145                 150                 155                 160

Ala Pro Pro Met Pro Asn Gly Gly Ala Pro Gln Gly Arg Thr Asp Pro
                165                 170                 175

Pro Pro Lys Thr Phe His Cys Gly Thr Cys Ser Lys Gly Phe Ala Arg
            180                 185                 190

Arg Ser Asp Leu Ala Arg His Glu Arg Ile His Ser Gly Ile Arg Pro
        195                 200                 205

His Ala Cys Asp Trp Pro Gly Cys Gly Lys Gln Phe Ile Gln Arg Ser
    210                 215                 220

Ala Leu Thr Val His Ser Arg Val His Thr Gly Glu Lys Pro His Met
225                 230                 235                 240

Cys Glu Arg Cys Gly Lys Pro Phe Ser Asp Ser Ser Leu Ala Arg
                245                 250                 255

His Arg Arg Ile His Ser Gly Lys Arg Pro Tyr Lys Cys Pro Tyr Ala
            260                 265                 270

Asn Cys Gln Lys Thr Phe Thr Arg Arg Thr Thr Leu Thr Arg His Gln
        275                 280                 285

Asn His His Thr Gly Thr Ile Glu Glu Ala Ala Ala Glu Thr Glu Ala
    290                 295                 300

Asn Leu Arg Gln Asn Lys Glu Arg Val Arg Ala Pro Gly Glu Gly Met
305                 310                 315                 320

Tyr Ser Glu His Gly Ser Val His Ser Thr Pro Ser Pro Ala His His
                325                 330                 335

Pro Ala Leu Ser Pro Ala Gly Glu Leu Pro Pro Leu Asn Met Pro Arg
            340                 345                 350

Ser Ser Gly Glu Tyr Tyr Ser Met Gly Asn Gly Ser Ile Pro Pro His
        355                 360                 365

Val Arg Gly Asp Phe Pro Gln Ala Ser Pro Arg Ala Ser Pro Thr Ala
    370                 375                 380

Thr Ser Pro Ser Leu Ser Ser Phe Gly Ser Ala Pro His Thr Arg Pro
385                 390                 395                 400

Ser Met Thr Ser His Pro Ser Gly Tyr Gly Pro Pro Gln Pro Leu Glu
                405                 410                 415

Pro Pro Ala Asn Asn Asp His Arg Pro Asn Ser Val Ser Gly Ser Pro
            420                 425                 430

His Met Thr Ser Leu Gly Trp Ala Ser Pro Ser His Gly Ser Ile Pro
        435                 440                 445

Ser Pro Gly Ser Ala Thr Asp Phe Gly Tyr Ser Asp Pro Asn Gly Pro
    450                 455                 460

Ala Tyr Pro Asn Ser Met Pro Pro His Met Tyr Phe Pro Asn Ser Thr
465                 470                 475                 480
```

Ile Arg Arg Pro Thr Ser Thr Glu Pro Glu Asn Tyr Glu Met Lys Pro
            485                 490                 495

Lys Ile Gly Glu Ser Ala Trp Ser Thr Pro Val
            500                 505

<210> SEQ ID NO 46
<211> LENGTH: 529
<212> TYPE: PRT
<213> ORGANISM: Artificial Sequence
<220> FEATURE:
<223> OTHER INFORMATION: synthesized

<400> SEQUENCE: 46

Met Ser His Thr Ser Gly Asn Ala Trp Arg Trp Ser Glu Asp Ser His
1               5                   10                  15

Ile Pro Phe Cys Tyr Met Asp Thr Ala Gly Met Val Gln Ser Met Asn
            20                  25                  30

Pro Gln Thr Thr Thr Ser Ala Gly Leu Gly Arg Ala Thr Val Ala Ala
        35                  40                  45

Pro Ile Met Pro Ile Ser Ser Tyr Gly Ser Ser Thr Phe Asn Met Thr
    50                  55                  60

Ser Gly His Gln Gln Ile Pro Gln Asn Ser Tyr Gly Phe Thr Ser Tyr
65                  70                  75                  80

Asn Asp Gly Ser Leu Thr Thr Ile Ile Pro Ser Tyr Gly Ala Asn Tyr
                85                  90                  95

Ile Gln Pro Arg Pro Leu Pro Gly Met Met Gln Ser Phe Ala Pro Thr
            100                 105                 110

Pro Lys Gln Ala Pro Phe Asn Gly Ser Ser Arg Gln Glu Phe Val Gly
        115                 120                 125

Ser Ser His Gln Asn Gln Ser Pro Gln Ile Lys Pro Glu Pro Ser Trp
130                 135                 140

Thr Thr Ser Ala Gly His Lys Thr Pro Pro Lys Thr Gln Ser Thr Pro
145                 150                 155                 160

Pro Pro Ser Lys Asp Ile Ser Pro Leu Pro Leu Thr Gly Ser Asp Glu
                165                 170                 175

Ala His Ile Gly Ser Thr Ala Ile Asp Arg Leu Met Lys Val Ile Gln
            180                 185                 190

Thr Lys Ala Gln Thr Leu Gln Thr Gln Leu Pro Pro Ile Pro Gln Ile
        195                 200                 205

Thr Pro Val Val Gly Ala Pro His Thr Leu Ser Arg Gln Asp Ser Met
    210                 215                 220

Tyr Arg Arg Phe Tyr Gly Tyr Glu Lys Glu Lys Gln Met Leu Thr
225                 230                 235                 240

Ser Gly Lys Ala Pro Ser Glu Pro Gly His Ser Lys Arg Lys Glu Lys
                245                 250                 255

Lys Tyr Arg Cys Thr Phe Glu Asn Cys Pro Ser Ser Phe Pro Gln Lys
            260                 265                 270

Thr His Leu Gln Ile His Leu Arg Lys His Thr Gly Ala Lys Pro Tyr
        275                 280                 285

Thr Cys Ser Trp Lys Ser Cys Gly Arg Gln Phe Ser Gln His Gly Asn
    290                 295                 300

Leu Lys Thr His Met Asn Arg His Ser Gly Glu Arg Arg Phe Pro Cys
305                 310                 315                 320

Glu Ile Cys Gly Lys Arg Phe Gly Gln Pro Ser Asn Leu Ser Ala His
                325                 330                 335

```
Arg Ile Val His Thr Gly Glu Lys Pro Phe Thr Cys Lys Leu Asp Gly
            340                 345                 350

Cys Glu Lys Arg Phe Thr Gln Leu Gly Asn Leu Lys Ser His His Asn
        355                 360                 365

Asn Phe His Gln Gln Thr Ile Glu Asn Leu Met Leu Lys Leu Glu Ser
    370                 375                 380

Gly Glu Ile Asp Leu Glu Ala Asn Lys Glu Phe Trp Ser Tyr Phe Phe
385                 390                 395                 400

Thr Leu Tyr Lys Asn Ser Asn Lys Gly Ile Lys Gly Arg Gly Lys Asp
                405                 410                 415

Arg Asn Ile Ser Pro Arg Ser Arg Leu Ser Lys Ser Gly His Ala Ser
            420                 425                 430

Thr Gly Thr Asp Ala Ser Arg Tyr Ile Ser Ser Asn Met Arg Ser Cys
        435                 440                 445

His Gly Leu Met Gly Val Asp Ala Thr Ser Pro Phe Ser Ser Asp Val
    450                 455                 460

Thr Met Tyr Asp Ser Asp Ala Ser Leu Arg Ser His Thr Ser Gly Ser
465                 470                 475                 480

Ile Ser Ala His Ser Ser Phe Gly Ser Val Ser Ser Asp Gly Thr Ser
                485                 490                 495

Ser Ser Cys Ser Ser Phe Ser Asp Glu Ile Thr Gly Asp Tyr Lys Asp
            500                 505                 510

His Arg Gly Gly Asn Ser Arg Gly Gly Leu Ala Phe Gly Glu Arg Leu
        515                 520                 525

Tyr

<210> SEQ ID NO 47
<211> LENGTH: 423
<212> TYPE: PRT
<213> ORGANISM: Artificial Sequence
<220> FEATURE:
<223> OTHER INFORMATION: synthesized

<400> SEQUENCE: 47

Met Asp Ile Pro Thr Ile Leu Asn Glu Lys Gly Thr Ala Ala Ala Ala
1               5                   10                  15

Ala Ala Ala Ala Ala Ala Lys Ala Gln Leu Gln Gln Gln Leu Ala
            20                  25                  30

Gln Gly Thr His Ile Lys Ser Gln Ser Pro Ser Glu Met Gly Ser Glu
        35                  40                  45

Asn Gly Thr Ser Gln Asn Gly Asp Gln Pro Asn Ile Tyr Asn Pro Thr
    50                  55                  60

Ser Gln Pro Gln Pro Leu Ser Thr Ile Pro Gln Tyr His Ser Pro Pro
65                  70                  75                  80

Gln Ser Ser Val Val Asn Ser Ala Ala Arg Ser Asp Tyr Ile Gln Asn
                85                  90                  95

Asp Gln Gly Lys Ile Glu Tyr Leu Gln Asn Asp Ser Ser Gly Arg Thr
            100                 105                 110

Arg Ala Asn Gly Glu Pro Ala Pro Lys Thr Phe His Cys Ser Thr Cys
        115                 120                 125

Gly Lys Gly Phe Ala Arg Arg Ser Asp Leu Ala Arg His Glu Arg Ile
    130                 135                 140

His Ser Gly Ile Arg Pro His Val Cys Asp Trp Pro Gly Cys Gly Lys
145                 150                 155                 160

Gln Phe Ile Gln Arg Ser Ala Leu Thr Val His Thr Arg Val His Thr
```

```
                    165                 170                 175
Gly Glu Lys Pro His Met Cys Asp Arg Cys Gly Lys Pro Phe Ser Asp
            180                 185                 190

Ser Ser Ser Leu Ala Asp Ile Ala Glu Tyr Ile Pro Glu Asn Asp Leu
        195                 200                 205

Thr Asn Ala Gln Ala Ala Ala Gln Thr Glu Ala Asn Leu Arg Gln Asn
    210                 215                 220

Lys Glu Arg Ser Ile Arg Pro Leu Glu Gly Ile Tyr Ser Glu Pro Gly
225                 230                 235                 240

Ser Ala Gln Ser Thr Pro Ser Cys Gln Arg Leu Ser Ala Ser Pro Gly
                245                 250                 255

Asn Glu Leu Pro Pro Met His Leu His Arg Gln Met Gly Glu Tyr Tyr
            260                 265                 270

Met Gly Asn Asn Thr Ser Ile Pro Pro His Leu Arg Ser Asp Phe Gln
        275                 280                 285

Gln Ala Ser Pro Arg Ala Ser Pro Ser Thr Ser Ser Pro Pro Leu Ser
    290                 295                 300

Thr Tyr Asn Ser Val Pro His Ile Arg Pro Ser Leu Thr Ser His Pro
305                 310                 315                 320

Ser Gly Tyr Arg Pro Pro Gln Pro Leu Glu Pro Ala Asn Ser Asp
                325                 330                 335

Pro Arg Pro Asn Ser Val Ala Gly Ser Pro His Ile Ser Ser Met Gly
            340                 345                 350

Trp Ala Ser Pro Thr Leu Asn Ser Ile Ser Ser Pro Gly Ser Ala Ser
        355                 360                 365

Ala Thr Glu Tyr Ser Tyr Pro Glu Pro Ser Leu Pro Pro Tyr Ser Ala
    370                 375                 380

His Ile Pro Pro His Ile Phe Phe Pro Asn Ser Thr Ile Arg Arg Pro
385                 390                 395                 400

Gln Ser Thr Glu Pro Glu Asn Tyr Glu Met Lys Pro Lys Leu Asn Gly
                405                 410                 415

Asp Ser Trp Thr Thr Pro Val
            420

<210> SEQ ID NO 48
<211> LENGTH: 421
<212> TYPE: PRT
<213> ORGANISM: Artificial Sequence
<220> FEATURE:
<223> OTHER INFORMATION: synthesized

<400> SEQUENCE: 48

Met Asn Arg Pro Glu Gln Gln Gln Tyr Asn Gln Tyr Gln Gln Gln Gln
1               5                   10                  15

Gln Gln Gln Phe Arg Gln Pro Gln Leu Pro Tyr Asn Asp Tyr Gln Gln
            20                  25                  30

His Gln Gln His Gln Gln Gln Gln Pro Gln Gln Tyr Gln Gln Tyr
        35                  40                  45

Gln Gln Tyr Gln Gln Thr Pro Gln Gln Phe His Pro Gln Tyr Asn Ile
    50                  55                  60

Ser Pro Ser Thr Gln His Ser His Ile Ser Pro Thr Ser Ser Gln Tyr
65                  70                  75                  80

Ser Asn Thr Ser Glu Gly Gln Arg Leu Lys Ser Ala Gln Asp Thr Val
                85                  90                  95

Thr Thr Asp Asp Gly Arg Pro Leu Leu Gly Ala Thr Lys Val Asp Gln
```

```
                    100                 105                 110
Leu Met Leu Val Ile Gln Ala Arg Lys Lys Gly Val His Asn Pro Ile
        115                 120                 125

Ala Gln Ala Asp Asp Gly Ser Ile Leu Asp Asn Gly Asp Gly Val Leu
130                 135                 140

Pro Gln Glu Thr Glu Leu Val Gly Gly Ile Asp Lys Pro Lys Thr Lys
145                 150                 155                 160

Gly Thr Lys His His Glu Cys Gln Tyr Cys His Lys Thr Phe Thr Gln
                165                 170                 175

Ser Thr His Leu Glu Val His Val Arg Ser His Ile Gly Tyr Lys Pro
            180                 185                 190

Phe Glu Cys Asn Tyr Cys Gly Lys Arg Phe Thr Gln Gly Gly Asn Leu
        195                 200                 205

Arg Thr His Leu Arg Leu His Thr Gly Glu Lys Pro Tyr Ile Cys Glu
210                 215                 220

Thr Cys Gly Arg Ser Phe Ser Arg Lys Gly Asn Leu Ala Ala His Lys
225                 230                 235                 240

Leu Thr His Glu Asn Leu Lys Pro Tyr Glu Cys Lys Leu Asp Gly Cys
                245                 250                 255

Asn Lys Ala Phe Thr Gln Leu Gly Asn Leu Lys Ala His Gln Asn Arg
            260                 265                 270

Phe His Leu Glu Thr Leu Asn Asn Leu Thr Arg Arg Leu Ala Glu Ile
        275                 280                 285

Asp Pro Glu Asp Ala Gln Thr Thr Met Asn Pro Asp Glu Arg Asp Leu
290                 295                 300

Leu Asn Tyr Phe Ala Gly Leu Tyr Lys Asn Ser Asn Arg Gly Ile Lys
305                 310                 315                 320

Gly Arg Gly Lys Arg Thr Ser Pro Val Leu Lys Thr Pro Gln Ile Ala
                325                 330                 335

Asn Gln Ala Ala Pro Val Asn Asn Gln Pro Gln Pro Gln Gln Gln Gln
            340                 345                 350

Gln Gln Gln Gln Arg Pro Gln Gln Gln Ala Lys Gln Glu Gln Gln Gln
        355                 360                 365

Gln Gln Tyr Asn Pro Gln Tyr Gln Gln Tyr Gln Tyr Pro Gln Asp Gln
370                 375                 380

Ser Phe Asn Gln Gln Leu Ala Phe Asn Gln Gln Asn Gly Ala Asn Phe
385                 390                 395                 400

Ala Pro Pro Met Asn Pro Gly Ala Lys Ala Gly Asn Ile Ser Phe Lys
                405                 410                 415

Asn Val Asn Tyr Asn
            420

<210> SEQ ID NO 49
<211> LENGTH: 383
<212> TYPE: PRT
<213> ORGANISM: Artificial Sequence
<220> FEATURE:
<223> OTHER INFORMATION: synthesized

<400> SEQUENCE: 49

Met Asp Arg Ser Ala Ser Pro His Met Ser Glu His Ser Ser Tyr Ser
1               5                   10                  15

Ala His Ser Leu Ser Arg Ala Tyr Pro Ser Pro Thr Ala Met Gln Ala
            20                  25                  30

Pro Met Gln Ile Gln Asn Pro Met His Ser Ala Met Gln Met Gly Gly
```

```
            35                  40                  45
Phe Ala Asp Met Ser Gly Met Gly Ser Val Pro Ser Met Ala Met His
 50                  55                  60
His Ile Pro Gln Gln Pro Gln Gln Gln Thr Pro Thr Ala Pro Val
65                  70                  75                  80
Lys Ala Tyr Pro Cys Ser Thr Cys Gly Lys Gly Phe Ala Arg Arg Ser
                85                  90                  95
Asp Leu Ala Arg His Glu Arg Ile His Thr Gly Val Arg Pro His Val
                100                 105                 110
Cys Asp Tyr Pro Lys Cys Asn Lys Gln Phe Ile Gln Arg Ser Ala Leu
                115                 120                 125
Thr Val His Gln Arg Val His Thr Gly Glu Lys Pro His His Cys Glu
                130                 135                 140
Thr Cys Ala Lys Pro Phe Ser Asp Ser Ser Leu Ala Arg His Arg
145                 150                 155                 160
Arg Thr His Ser Gly Lys Arg Pro Tyr Lys Cys Pro Tyr Ala Asp Cys
                165                 170                 175
Gln Lys Thr Phe Thr Arg Arg Thr Thr Leu Thr Arg His Gln Asn His
                180                 185                 190
His Thr Gly Thr Ile Glu Glu Ala Ala Ala Thr Ala Ala Ala Leu
                195                 200                 205
Ala Ala Ser Arg Ala Lys Asn Gly Ser Gln Ala Arg Ser Glu Gly Asp
                210                 215                 220
His Met Ser Asn His Gly Ser Pro Leu Thr Thr Pro Ser Pro Ser Gln
225                 230                 235                 240
His Thr Met Met Ser Pro Ala Leu Asp Leu Ser Gly Ser Asn Gly Leu
                245                 250                 255
Asn Arg His Pro Ala Asp Phe Gln Tyr Met Thr Gln Gly Gly Thr Leu
                260                 265                 270
Pro Pro His Leu Arg Val Gly Ser Pro Thr Ser Thr Ser Ala Ala
                275                 280                 285
Ser Tyr Asn Asn Gly Ile Arg Pro Thr Ser His Pro Thr Gly Tyr Gly
                290                 295                 300
Pro Pro Pro Thr Leu Glu Pro Asn Leu Glu Gln His Pro Ala Gly Ser
305                 310                 315                 320
Gly Ser Ala Gly Gly Ser Pro His Met Ser Gln Val Gly Trp Gln Ser
                325                 330                 335
Pro Gln Thr His Ser Pro Ala His Asn Ala Gly Ser Tyr Val Tyr Pro
                340                 345                 350
Asp Pro Asp Gly Tyr Pro Pro Asn Pro Ser Met Ser Gln Met Tyr Tyr
                355                 360                 365
Gly Ala Pro Gln Gln Met Arg Arg Pro Gln Ser Thr Glu Pro Gly
                370                 375                 380

<210> SEQ ID NO 50
<211> LENGTH: 507
<212> TYPE: PRT
<213> ORGANISM: Artificial Sequence
<220> FEATURE:
<223> OTHER INFORMATION: synthesized

<400> SEQUENCE: 50

Met Ala Leu Thr Ala Gln Pro Ser Ala Pro Ala Gly Trp Glu Arg Trp
1               5                   10                  15

Pro Gln His His Pro Asn Asn Asp Tyr Val Met Met Asp Ala Asp Val
```

-continued

```
                    20                  25                  30
Met Pro Tyr Asn Ala Arg Pro Met Thr Thr Ala Pro Met Gln Gln Arg
                    35                  40                  45
Pro Ser Leu Val Pro His Tyr Ile Pro Thr Thr Ser Met Ser Thr Ala
                50                  55                  60
Pro Ile Thr Ser Ile Ser Ala Pro Ala His Tyr Gln Pro Ser Val Ser
65                  70                  75                  80
Tyr Gly Gly Tyr Pro Ala Tyr Pro Leu Pro Ser Pro Thr Thr Met
                    85                  90                  95
Ser Ser Gln Tyr Arg His Gln His Tyr Gln Glu Arg Pro Ser Leu His
                100                 105                 110
Met Ile Thr Pro Glu Leu Glu Asp Thr Arg Gly Pro His His Ile Arg
                115                 120                 125
Asp Ala Arg Arg Tyr Ser Glu Glu Ser Arg Ser Pro Ser Glu Arg Ser
            130                 135                 140
Asp Ser Gln Ala Ser Thr Ala Glu Thr Thr Ile Ser Asn His Ser Thr
145                 150                 155                 160
Cys Ser Arg Thr Ile Thr Pro Asn Ala Pro Val Asn Gly Ala Pro Gln
                    165                 170                 175
Val Glu Phe Ser Thr Ala Val Asp Lys Leu Met Lys Val Ile Gln Ser
                180                 185                 190
Lys Met Lys Asp Thr Asp Ala Glu Gln Ser Gly Asp Asp Lys Asp Ile
                195                 200                 205
Lys Val Glu Gln Gln Ser Ser Pro Asp Cys Gln Ala Arg Val Gln Gln
            210                 215                 220
Pro Ala Asp Lys Gln Lys Arg Lys Arg Tyr Glu Cys Gln Ile Glu Gly
225                 230                 235                 240
Cys Asn Lys Lys Phe Ser Gln Lys Thr His Arg Asp Thr His Val Arg
                    245                 250                 255
Ser His Thr Gly Asp Arg Pro Tyr Val Cys Pro Ile Pro Gly Cys Gly
                260                 265                 270
Gly Arg Phe Thr Gln Ala Gly Asn Leu Lys Thr His Lys Arg Arg His
                275                 280                 285
Thr Gly Glu Arg Pro Tyr Arg Cys Glu Val Cys Asp Lys Gly Phe Val
            290                 295                 300
Gln Arg Gly Asp Val Lys Ala His Met Lys Thr His Leu Gly Thr Lys
305                 310                 315                 320
Ala Phe Leu Cys Arg Leu Asp Asn Cys His Lys Gln Phe Thr Gln Arg
                    325                 330                 335
Gly Asn Leu Lys Tyr His Gln Asn Lys Tyr His Asn Glu Thr Ile Lys
                340                 345                 350
Ala Leu Ala Ala Arg Phe Asp Thr Ile Glu Asp Trp Ser Thr Val Ser
                355                 360                 365
Lys Glu Asp Met Glu Ile Phe Lys Asp Phe Ala Val Val His Lys Asn
            370                 375                 380
Ser Asn Lys Gly Ile Lys Gly Arg Gly Lys His Arg Lys Val Lys Ser
385                 390                 395                 400
Val Pro Gln Ser Ser Pro Thr Ser Pro Thr Gly His Ser Pro Leu Pro
                    405                 410                 415
Asn Ile Met Ala Ser Gln Tyr Pro Leu Pro Ser Gly Pro Gly Leu Ser
                420                 425                 430
His Leu Leu His Ser Pro His Pro Leu His Pro Leu His His Gln
                435                 440                 445
```

```
Gly Pro Ser His Ser Ala Met Tyr Gly Met Pro Arg Pro Gly Phe His
            450                 455                 460
Gly His Tyr Glu Thr Tyr Asp His His Glu Val Asp Thr Val Ala Ser
465                 470                 475                 480
Ser Arg Gly Ser Val Ala Glu Pro Ile Tyr His His Glu Glu His
            485                 490                 495
Pro Arg Glu Leu Ala Phe Gly Asp Arg Ile Tyr
            500                 505
```

<210> SEQ ID NO 51
<211> LENGTH: 590
<212> TYPE: PRT
<213> ORGANISM: Artificial Sequence
<220> FEATURE:
<223> OTHER INFORMATION: synthesized

<400> SEQUENCE: 51

```
Met Val Met Val Pro His Thr Leu Gly Thr Thr Trp Arg Trp Ser Glu
1               5                   10                  15
Asp Ser His Ile Pro Phe Cys Tyr Met Asp Ala Ser Gly Met Val Gln
                20                  25                  30
Ser Leu Asp Pro Gln Thr Thr Ser Ala Gly Leu Gly Arg Thr Ile
            35                  40                  45
Ile Ala Pro Pro Ile Met Pro Met Asp Ser Phe Ser Gly Ser Ser Phe
50                  55                  60
Ile Met Asn Gly His Gln Gln Ile Ser Gln Asn Ala Tyr Gly Phe Thr
65                  70                  75                  80
Ser Tyr Thr Asn Gly Ser Ser Thr Asn Leu Ile Thr Thr Tyr Gly Ala
                85                  90                  95
Asn Tyr Ile Gln Pro Arg Ser Leu Pro Pro Met Ile Gln Ser Phe Ser
            100                 105                 110
His Ser Pro Lys Glu Val Ile Phe Asp Glu Ser His Arg Gln Gly Phe
            115                 120                 125
Ile Glu Ser Thr Ser Pro Ser Gln Ser Pro Gln Ile Lys Pro Glu Pro
130                 135                 140
Ser Trp Lys Lys Thr Thr Arg Cys Gln Pro Glu Lys Thr Pro Lys Ala
145                 150                 155                 160
Ser Arg Pro Asn Lys Thr Ile Asn Pro Pro Leu Thr Gly Ser Asn
            165                 170                 175
Glu Ala His Ile Gly Thr Thr Ala Val Asp Arg Leu Met Lys Ile Ile
            180                 185                 190
Gln Asp Lys Ala Arg Thr Ser Lys Ser Pro Ser Pro Ser Val Ser Glu
            195                 200                 205
Ser Thr Ser Val Val Gly Ser Pro His Thr Leu Tyr Asn His Asp Tyr
            210                 215                 220
Ile Ser Ala Tyr Glu Glu Lys Gln Ile Leu Thr Ser Val Lys Val
225                 230                 235                 240
His Asp Glu Ser Gly Arg Ser Lys Val Pro Lys Lys Arg Phe Arg Cys
                245                 250                 255
Thr Phe Glu Gly Cys Met Ser Arg Phe Leu Gln Lys Ala Gln Leu Glu
            260                 265                 270
Ile His Val Arg Lys His Thr Gly Glu Thr Pro Tyr Val Cys Gly Tyr
            275                 280                 285
Val Gln Cys Lys Arg Arg Phe Thr Gln Gln Gly Asn Leu Asn Ile His
            290                 295                 300
```

```
Leu Asp Arg His Arg Gly Ile Arg Arg Tyr Pro Cys Glu Ile Cys Gly
305                 310                 315                 320

Lys Arg Phe Gly Gln Arg Ser Asn Leu Asp Ala His Arg Ile Val His
            325                 330                 335

Thr Gly Ile Lys Pro Phe Ser Cys Lys Leu Asp Gly Cys Gly Lys Arg
        340                 345                 350

Phe Thr Gln Arg Gly Asn Leu Lys Ser His His Asn Lys Phe His Arg
    355                 360                 365

Gln Thr Leu Glu Arg Leu Gln Ser Gln Leu Ile Asn Gly Glu Ile Asp
370                 375                 380

Ile Glu Ala Asn Lys Glu Phe Trp Ser Tyr Phe Asn Leu Tyr Lys
385                 390                 395                 400

Asn Ser Asn Lys Gly Ile Lys Gly Arg Gly Lys Asp Arg Asn Ile Ser
                405                 410                 415

Pro Arg Ser Arg Ser Ser Arg Asn Ser His Ala Ser Thr Gly Ser Asn
            420                 425                 430

Ala Ser Arg Tyr Val Ser Pro Asn Met Arg Ser Cys His Gly Leu Met
        435                 440                 445

Asp Thr Asp Gly Ala Ser Tyr Ser Asp Ala Thr Met Tyr Asp Ser Asp
    450                 455                 460

Gly Ser Met Arg Ser His Thr Ser Gly Ser Met Ser Val Asn Ser Ser
465                 470                 475                 480

Phe Ser Ser Gly Thr Thr Asp Ser Thr Ala Ser Thr Tyr Ser Asn Phe
                485                 490                 495

Ser Asp Asp Ile Ala Thr Asp Tyr Gln Asp Pro His Ala Arg Asn Val
            500                 505                 510

Arg Gly Asp Leu Ala Phe Arg Val Thr Arg Asp Val Glu Met Lys Met
        515                 520                 525

Ser Thr Gln Asp Glu Asn Thr Glu Met Lys Gly Arg Thr Ala Val Leu
    530                 535                 540

His Ser Phe Ile Ile Ile Ile Ile Ile Thr Ile Ile Thr Gln His
545                 550                 555                 560

Ser Thr Thr Pro Asn Thr Asn Ile Pro Pro Lys Lys Ala Arg Cys Ile
                565                 570                 575

Phe Ile Glu Arg Ile Asn Leu Phe Leu Thr His Gln Ser Ser
            580                 585                 590

<210> SEQ ID NO 52
<211> LENGTH: 320
<212> TYPE: PRT
<213> ORGANISM: Artificial Sequence
<220> FEATURE:
<223> OTHER INFORMATION: synthesized

<400> SEQUENCE: 52

Met Ala Pro Gly Gly Ser Arg Gly Phe Asn Cys Ser Trp Glu Arg Cys
1               5                   10                  15

Gly Lys Ser Phe Asn Arg Lys Ser Asp Leu Cys Arg His Tyr Arg Ile
            20                  25                  30

His Thr Asn Glu Arg Pro Tyr His Cys Thr Val Pro Ser Cys Asn Lys
        35                  40                  45

Ser Phe Ile Gln Arg Ser Ala Leu Thr Val His Ser Arg Thr His Thr
    50                  55                  60

Gly Glu Lys Pro His Val Cys Asp His Glu Asp Cys Arg Lys Ala Phe
65                  70                  75                  80
```

```
Ser Asp Ser Ser Ser Leu Ala Arg His Arg Ile His Thr Gly Arg
            85                  90                  95

Arg Pro Tyr Ile Cys Ser Glu Pro Ala Cys Asp Arg Ser Phe Cys Arg
        100                 105                 110

Lys Thr Thr Leu Thr Lys His Gln Ser Arg Thr His Gln Pro Gly Gly
        115                 120                 125

Asn Thr Arg Pro Ser Ser Glu Glu Ala Pro Thr Pro Glu Ser Met Thr
130                 135                 140

Tyr Gln Thr Pro Val Ile Thr Thr Met Ala Pro Asn Thr Thr Gln Tyr
145                 150                 155                 160

Ile Ile Ala Gln Gln Pro Tyr Tyr His Asn Gly Pro Thr Pro Thr Thr
            165                 170                 175

Ala Asp Phe Tyr Gln Thr Pro Gln Pro Ala Ile His Phe Thr Gln Pro
            180                 185                 190

Gln Ala Met Val Pro Gln Gln Ile Pro Thr Ala Gly Leu Pro Thr Pro
            195                 200                 205

Pro Phe Glu Pro Gln His Tyr Ala Gln Ile Met Gln Gln Gln Gln Gln
210                 215                 220

Pro Arg Tyr Asp Pro Thr Pro His Gln Thr Tyr Ile Gln Pro Gln Tyr
225                 230                 235                 240

Gln Ser Pro Thr Pro Pro Phe Val Ala Gln His Gln His His Met Ala
            245                 250                 255

Ala Asp Val Arg Pro Leu Met Ala Thr Tyr His Pro Asp Gln Phe Lys
            260                 265                 270

Pro Pro Ala Arg Ile Leu Ser Ser Gln Glu Gly Thr Asp Trp Ser Phe
            275                 280                 285

Leu Gly Cys Leu Asp Arg Cys Ser Pro Gly Pro Gly Thr Gln Glu Tyr
            290                 295                 300

Ala Ile Pro Phe Ser Val Asp Glu Lys Gln Pro Leu Leu Gly Leu Ser
305                 310                 315                 320

<210> SEQ ID NO 53
<211> LENGTH: 426
<212> TYPE: PRT
<213> ORGANISM: Artificial Sequence
<220> FEATURE:
<223> OTHER INFORMATION: synthesized

<400> SEQUENCE: 53

Met Val Ala Ala Asp Gly His Phe Asp His Gln His Leu Val Pro Asn
1               5                   10                  15

Pro Gly Leu Asp His Thr Ser Ser Pro Lys Met Lys Ser Glu Pro Gly
            20                  25                  30

Val Ser Asp Ala Gly Asp Gln Ala Val Leu Ala Tyr Pro Pro His Gly
        35                  40                  45

Pro Leu Gly Gln Val Pro Asn Met Ala His Asp Met Arg Tyr Ala His
    50                  55                  60

Gln Ala His Pro Gly Pro Gly Leu Pro Leu Leu Gln Asn Pro Phe Val
65                  70                  75                  80

Pro Gly Ala Tyr Ala Gly Asn Ala Gln Ile Pro Asn Ala Gly Ala Pro
            85                  90                  95

Gln Gly Arg Pro Asp Pro Pro Lys Thr Phe His Cys Gly Thr Cys
        100                 105                 110

Gly Lys Gly Phe Ala Arg Arg Ser Asp Leu Ala Arg His Glu Arg Ile
        115                 120                 125
```

```
His Ser Gly Ile Arg Pro His Ala Cys Asp Trp Pro Gly Cys Gly Lys
        130                 135                 140

Gln Phe Ile Gln Arg Ser Ala Leu Thr Val His Ser Arg Val His Thr
145                 150                 155                 160

Gly Glu Lys Pro His Met Cys Glu Arg Cys Gly Lys Pro Phe Ser Asp
                165                 170                 175

Ser Ser Ser Leu Ala Arg His Arg Ile His Ser Gly Lys Arg Pro
            180                 185                 190

Tyr Lys Cys Pro Tyr Ala Asn Cys Gln Lys Thr Phe Thr Arg Arg Thr
        195                 200                 205

Thr Leu Thr Arg His Gln Asn His His Thr Gly Thr Ile Glu Glu Ala
    210                 215                 220

Ala Ala Glu Thr Glu Ala Asn Leu Arg Gln Asn Lys Glu Arg Ala Arg
225                 230                 235                 240

Met Pro Gly Asp Met Phe Ser Glu His Gly Ser Val His Ser Thr Pro
                245                 250                 255

Ser Pro Ala His His Pro Ile Ser Pro Ala Gly Asp Leu Pro Pro Leu
            260                 265                 270

Asn Met Pro Arg Ser Asp Tyr Tyr Met Pro Asn Gly Ser Ile Pro Pro
            275                 280                 285

His Val Arg Gly Gly Phe Thr Gln Ala Ser Pro Arg Ala Ser Pro Thr
    290                 295                 300

Ala Thr Ser Pro Ser Leu Ser Ser Tyr Gly Ser Ala Pro His Pro Arg
305                 310                 315                 320

Pro Ser Met Thr Ser His Pro Ser Gly Tyr Gly Pro Pro Gln Pro Leu
                325                 330                 335

Glu Pro Pro Ala Asn Asn Asp His Arg Pro Asn Ser Val Ser Gly Ser
            340                 345                 350

Pro His Met Thr Ser Leu Gly Trp Pro Ser Pro Ser His Ala Ser Ile
            355                 360                 365

Pro Ser Pro Gly Ser Ala Thr Asp Phe Tyr Pro Glu Thr Ser Gly Pro
370                 375                 380

Ala Tyr Pro Ser Ala Met Pro Pro His Met Tyr Phe Pro Asn Ser Thr
385                 390                 395                 400

Ile Arg Arg Pro Thr Ser Thr Glu Pro Asp Ser Tyr Asp Leu Lys His
                405                 410                 415

Lys Met Glu Ser Ala Trp Ser Thr Pro Val
            420                 425

<210> SEQ ID NO 54
<211> LENGTH: 312
<212> TYPE: PRT
<213> ORGANISM: Artificial Sequence
<220> FEATURE:
<223> OTHER INFORMATION: synthesized

<400> SEQUENCE: 54

Met Val Arg Arg Arg Phe Pro Arg Thr Lys Val Asp Ala Thr Cys Asp
1               5                   10                  15

Gln Cys His Lys Ser Phe Gly Ser Leu Ala Asp Leu Lys Arg His Ser
                20                  25                  30

Met Ile Gln Asp His Leu Asp Leu Arg Pro Tyr Ala Cys Thr Trp Pro
            35                  40                  45

Gly Cys Thr Arg Ala Phe Pro Gln Ser Ala Ala Leu Lys Asn His Phe
    50                  55                  60
```

Asn Thr His Thr Gly Lys Lys Pro Tyr Arg Cys Ala Trp Val His Glu
65                  70                  75                  80

Cys Asp Arg Ala Phe Gly Asp Lys Ser Thr Cys Ser Arg His Glu Ala
                85                  90                  95

Thr Lys His Leu Gly Leu Ile Gly His Lys Cys Pro Val Lys His Cys
            100                 105                 110

Arg Ser Ser Ile Lys Arg Lys Thr Asp Phe Ala Arg His Leu Arg Asp
        115                 120                 125

Lys His Gly Ile Arg Thr Lys Gly Leu Asp Val Ser Gln Tyr Ala Val
    130                 135                 140

Tyr Lys Pro Gly Gly Pro Ile Lys Lys Cys Arg Lys Asn Lys Arg
145                 150                 155                 160

Val Glu Ser Ser Pro Glu Asn Ser Pro Leu Ala Cys Pro Leu Asp Asp
                165                 170                 175

Phe Val Glu Ser Pro Thr Ser Ser Gly Thr Thr Pro Leu Pro Glu
            180                 185                 190

Thr Pro Glu Met Gly Gln Gln Ala Glu Leu Pro Val Thr Asp Phe Ser
        195                 200                 205

His Met Gly Leu Val Val Pro Ala Asp Glu Pro His His Ser Gln Ile
    210                 215                 220

Ser Asn Ala Pro Phe Val Asp Thr Tyr Glu Lys His Asn Tyr Val His
225                 230                 235                 240

Ser Leu Pro Thr Gln Phe Met Ile Pro Pro Ser Ile Ser Pro Ala Val
                245                 250                 255

Gln Pro Gln Tyr Tyr Tyr Val Pro Glu Ala Tyr Gln Gln Thr Phe Ala
            260                 265                 270

Ser Asp Pro Leu Ala Leu Val Ile Asp Pro Val Leu Met Met Glu Ser
        275                 280                 285

Met Leu Tyr Gly Gly His Gly Thr Gln His Tyr Ala Asn Ala Pro Ile
    290                 295                 300

Pro Leu Tyr Tyr Pro Ser Ser Cys
305                 310

<210> SEQ ID NO 55
<211> LENGTH: 454
<212> TYPE: PRT
<213> ORGANISM: Artificial Sequence
<220> FEATURE:
<223> OTHER INFORMATION: synthesized

<400> SEQUENCE: 55

Met Glu Thr Ala Val Pro Val Thr Tyr Asn Val Thr Asn His Asp Met
1               5                   10                  15

Asn Ala Val Ala His Arg Arg Met Met Ala Pro His Gln His His His
            20                  25                  30

His His Asp Gln Asn Ile Ala Tyr Phe Ser Asn Pro Ile Pro Tyr
        35                  40                  45

Ser Thr Pro Leu Gln Pro Pro Ser Phe Ser Gly Phe Gly His Ile Leu
    50                  55                  60

Asn Asn His Pro His His Thr Ser Tyr Gln Gly Tyr Phe Asn Ser Asn
65                  70                  75                  80

Pro Ser His Gln Val Asn Ser His His Pro Arg Leu Pro Thr Glu Thr
                85                  90                  95

Asn Pro Val Gln Gln Leu Ser Asp Val Arg His Val Lys Asn Ala Asn
            100                 105                 110

Pro Arg Leu Ile Arg Pro Ser Pro Lys Glu Asp Thr Leu Pro Pro
        115                 120                 125

Pro Pro Pro Gln Arg Met Cys Val Pro Pro Ala Arg Asn Thr Thr Gln
130                 135                 140

His Glu Asp Ser Lys Pro Met His Lys Pro Glu Val Val Phe Gly Thr
145                 150                 155                 160

Glu Val Asp Thr Leu Met Lys Ala Ile Gln Ala Lys Pro Gln Pro Pro
                165                 170                 175

Ser Pro Gln Ala Glu His Gln Leu Pro Pro Leu Gln Gln Lys Phe Asn
            180                 185                 190

Ser Gly Val Thr Asn Trp Ile His Pro Ala Tyr Ala Asn Gln Met Gly
        195                 200                 205

Gly Asn Gln Ser Ile Phe Pro Asn Pro Gln Asp Arg Ile Pro Pro
    210                 215                 220

Ala Asn Gln Lys Pro Lys Arg Lys Tyr Asp Cys Thr Leu Pro His Cys
225                 230                 235                 240

Arg Lys Ser Phe Phe Gln Lys Thr His Leu Asp Ile His Met Arg Ala
                245                 250                 255

His Thr Gly Asp Lys Pro Phe Thr Cys Lys Glu Pro Ser Cys Gly Gln
            260                 265                 270

Arg Phe Ser Gln Leu Gly Asn Leu Lys Thr His Glu Arg Arg His Thr
        275                 280                 285

Gly Glu Lys Pro Tyr Ser Cys Glu Ile Cys His Lys Lys Phe Ala Gln
    290                 295                 300

Arg Gly Asn Val Arg Ala His Lys Ile Thr His Glu Gln Ala Lys Pro
305                 310                 315                 320

Phe Thr Cys Arg Leu Asp Asp Cys Gly Lys Gln Phe Thr Gln Leu Gly
                325                 330                 335

Asn Leu Lys Ser His Gln Asn Lys Phe His Ala Gln Thr Leu Arg Asn
            340                 345                 350

Leu Thr Leu Arg Phe Ala Ser Ile Ala Asp Ile Glu Arg Met Ser Pro
        355                 360                 365

Gln Asp Lys Glu Leu Trp Ser Tyr Phe Ser Asn Leu Tyr Arg Asn Ser
    370                 375                 380

Asn Lys Gly Ile Lys Gly Arg Gly Lys Asp Arg Arg Val Ser Thr Ala
385                 390                 395                 400

Lys Arg Ser Met Ser Ala Tyr Asp Gly Ser Pro Ser Glu Ser Glu Asp
                405                 410                 415

Asp Gly Lys Asp Arg Asn Arg Thr Tyr Asp Arg Ala Ser Ala Val Met
            420                 425                 430

Thr Ser Asn Asn Asp Glu Pro Asp Tyr Arg Glu Gln Leu Tyr His Asn
        435                 440                 445

Arg Asn Gly Gly His His
    450

<210> SEQ ID NO 56
<211> LENGTH: 398
<212> TYPE: PRT
<213> ORGANISM: Artificial Sequence
<220> FEATURE:
<223> OTHER INFORMATION: synthesized

<400> SEQUENCE: 56

Met Ala Glu Asp Pro Glu Arg Pro Arg Pro Phe Leu Cys Asp Trp Gln
1               5                   10                  15

Gly Cys Gly Lys Arg Phe Asn Arg Lys Ser Asp Leu Gln Arg His His
            20                  25                  30

Arg Ile His Thr Asn Glu Arg Pro Tyr Gly Cys Asn Trp Gln Asp Cys
            35                  40                  45

Gly Lys Arg Phe Ile Gln Arg Ser Ala Leu Thr Val His Leu Arg Thr
 50                  55                  60

His Thr Gly Glu Lys Pro His Gln Cys Glu Val Pro Glu Cys Arg Lys
 65                  70                  75                  80

Pro Phe Ala Asp Ser Ser Leu Ala Arg His Arg Arg Ile His Arg
                85                  90                  95

Gly Glu Lys Pro Tyr Arg Cys Gln Asp Val Gly Cys Asn Lys Ala Phe
            100                 105                 110

Cys Arg Lys Thr Thr Arg Asp Lys His His Thr Asn Ser His Arg Gly
            115                 120                 125

Gly Ile Asn Arg Ser Met Thr Pro Arg Gln Gln Leu His Pro Ser Phe
130                 135                 140

Gly Ser Gly Phe Asp Gln Phe His Met Ser Ala Pro Pro Glu Leu Thr
145                 150                 155                 160

Ala Ser Thr Asp Ser Ser Pro Ala Asp Ser Thr Ala Tyr Ser Pro Ala
            165                 170                 175

Ala Leu Glu Gly Asp Trp Ser Asn Gln Asn Phe Asn Asn Tyr Thr His
            180                 185                 190

Leu Pro Asn Leu Gln Glu Ala Ser Ile Ala Leu Gln Asn Gln Ile Arg
            195                 200                 205

Ser Gln Gln Ile Pro Gln Leu Met Ser Tyr Met Pro Ser Arg Val Leu
210                 215                 220

Pro Ser Tyr Ser Ala Pro Pro Asn Met Ile Thr Pro Gln Met Pro
225                 230                 235                 240

Gln Gln Gly Ser Phe Ser Ser Tyr Ser Pro Ser Pro Val Glu Ser Ala
            245                 250                 255

Gln Gln Gln Pro Trp Ala Thr Gly Phe Gln Asn Asn Gln Arg Gln Tyr
            260                 265                 270

Pro Arg Val Leu Thr Ser Asn Asp Thr Ala Pro Arg Met Phe Ser Pro
            275                 280                 285

Tyr Pro Ala Pro Pro Asn Met Leu Pro Gly Gln Asn Asp Phe Asn Ser
290                 295                 300

Gln Tyr Pro Pro Gln Gln Gln Gln Ser Trp Gly Met Pro Gln Asn
305                 310                 315                 320

Gln Gly Gln Gln Asp Gln Arg Gln Tyr Ser Leu Pro Ser Pro Ser Gln
            325                 330                 335

Pro Leu Thr Pro Val Pro Val Ser Ala Gly Thr Gly Thr Met Gln Pro
            340                 345                 350

Leu Gln Pro Met Pro Gly His Ile Tyr Gly Ala Arg Leu Val Gly Asp
            355                 360                 365

Asp Leu Asn Asp His Phe Phe Lys Val Glu Thr Thr Ala Asp Asp Asn
            370                 375                 380

Asn Pro Gly Met Thr Leu Pro Asp Ala Arg Phe Ala Gly Leu
385                 390                 395

<210> SEQ ID NO 57
<211> LENGTH: 448
<212> TYPE: PRT
<213> ORGANISM: Artificial Sequence
<220> FEATURE:

<223> OTHER INFORMATION: synthesized

<400> SEQUENCE: 57

```
Met Gly Ile Gly Asn Val Leu Asn Ile Lys Ala Glu Ser Gly Gly Gln
1               5                   10                  15

Gln Ala Ser Gln Gln Gly Ala Thr Ser Glu Leu Gln Gln Gln Arg Pro
            20                  25                  30

Pro Gln Gln Leu Gln Gln Leu Gln Val Asp Arg Gln Gly Ser Pro Gln
        35                  40                  45

Gly Ser Glu Gln Pro Arg Tyr Ser Gly Pro Met Ser Ala Ser Tyr Pro
    50                  55                  60

Ser Pro Thr Ala Met Ala Pro Ala Pro Leu Pro Val Pro Asn Ala
65                  70                  75                  80

Asn Met Ala Pro Ala Pro Met Val Pro His Glu Met Gln Gln Asn Ile
                85                  90                  95

Gly Ile Val His Pro Ala Tyr Gln Gln Thr Gln Gln Pro Pro Gln Ala
            100                 105                 110

Pro Ala His Gln Pro Pro Ala Lys Gln Phe Pro Cys Ser Thr Cys Gly
        115                 120                 125

Lys Pro Phe Ala Arg Arg Ser Asp Leu Ala Arg His Glu Arg Ile His
130                 135                 140

Ser Gly Ile Arg Pro His Val Cys Asp Tyr Pro Gly Cys Gly Lys Gln
145                 150                 155                 160

Phe Ile Gln Arg Ser Ala Leu Thr Val His Ser Arg Val His Thr Gly
                165                 170                 175

Glu Lys Pro His Arg Cys Glu Arg Cys Gly Lys Pro Phe Ser Asp Ser
            180                 185                 190

Ser Ser Leu Ala Arg His Arg Ile His Ser Gly Lys Arg Pro Tyr
        195                 200                 205

Lys Cys Pro Tyr Ala Asp Cys Gln Lys Thr Phe Thr Arg Arg Thr Thr
    210                 215                 220

Leu Thr Arg His Gln Asn His His Val Gly Thr Val Glu Asp Ser Ala
225                 230                 235                 240

Arg Ala Arg Ala Glu Ala Leu Ala Gln Gly Ala Asn Ala Ala Ala
                245                 250                 255

Ala Ala Ala Ala Ala Ala Ala Ala Arg Asn Lys Ser Gln Ser Ala Ser
            260                 265                 270

Glu Gln Ala Ser Asn His Glu Ser Pro Ile Thr Thr Pro Ser Pro Gly
        275                 280                 285

Gln Arg Pro Ile Ser Met Ser Pro Gly Ala Glu Leu Ala Gly Met Asn
    290                 295                 300

Asn Met Gln Tyr Leu Ser Asn Ser Ile Pro Ala His Leu Arg Gly Asp
305                 310                 315                 320

Val His Val Gly Ser Pro Ser Pro Thr Ala Ser Thr Gly Tyr Asn Asn
                325                 330                 335

Gly Met Arg Pro Thr Ser His Pro Thr Gly Tyr Ala Pro Pro Gln Thr
            340                 345                 350

Leu Glu Pro Ser Ile Glu Gln Pro Gln Gln Gly Pro Gly Ser Ala Val
        355                 360                 365

Gly Ser Pro His Ile Gly Ser Val Gly Trp Ala Ser Pro Gly Pro Val
    370                 375                 380

Gly Ser Pro Thr Gln Ser Pro Asn Gly Asn Gly Tyr Val Tyr Pro Asp
385                 390                 395                 400
```

```
Pro Glu Ser Tyr Pro Ser Gly Thr Pro Ile Ala Gln Met Phe Tyr Asn
            405                 410                 415

Asn Ala Val Ala Thr Arg Arg Pro Glu Ser Ala Glu Pro Ala Asn Pro
            420                 425                 430

Ser Phe Asp Ala Lys Gly Arg Gln Gly Glu Leu Trp Thr Asn Ala Gln
            435                 440                 445

<210> SEQ ID NO 58
<211> LENGTH: 416
<212> TYPE: PRT
<213> ORGANISM: Artificial Sequence
<220> FEATURE:
<223> OTHER INFORMATION: synthesized

<400> SEQUENCE: 58

Asn Gly Leu Val Ala Ala Pro Thr Ala Pro Ser Thr Thr Thr Thr Ala
1               5                   10                  15

Val Gly Ser Ala Ala Ser Gly Ala Gly Met Gly Ile His Asn Asn Pro
            20                  25                  30

Ala Val Met Pro Pro Arg Thr Val Pro Met Val Asn Ser Phe Gly Glu
            35                  40                  45

Ala Ala Pro Ala Gly Gly Asp His Trp Pro Lys Thr Pro Phe Met Gly
            50                  55                  60

Ser Ser Asp Ala Ser Val Thr Thr Ser Ser Ile Ser Ser Thr Ser Ser
65                  70                  75                  80

Ser Ser His Arg Arg Asp Arg Leu Gly Arg Asp Arg Glu Arg Asp His
                85                  90                  95

His Ser Ser Arg Asp His His His Ala Arg Glu Arg Asp His Ser
            100                 105                 110

Ser Ser Gly Lys Arg His His His His Ser Ser Arg Arg His Ser His
            115                 120                 125

His Arg Ser Ser Arg Arg Gln Ser Asp Asp Ser Asp Ser Ala Gly Ser
130                 135                 140

Asp Glu Asp Gly Ser Tyr Ala Arg Gly Gly Leu Arg Arg Ala Arg Asn
145                 150                 155                 160

His Ser Ser Asp Ser Gly Ser Ser Ala Glu Asp Ser Asp Asp Thr
            165                 170                 175

Asp Ala Glu Asp Asp Ser Arg Arg His Thr Thr Ala Val Thr Arg Ala
            180                 185                 190

Asn Ala Arg His Ala Leu Ala Glu Gly Phe Leu Leu Asp Asp Val Thr
            195                 200                 205

Cys Gly Gln Cys Gly Lys Ile Phe Arg Arg Pro Asp Arg Leu Ser Ala
            210                 215                 220

His Val Arg Thr His Ala Thr Met Arg Pro Phe Val Cys Thr Met Ala
225                 230                 235                 240

Asp Cys Ser Lys Thr Phe Arg Glu Lys Ala Ala Leu Lys Lys His Met
            245                 250                 255

Ile Ser His Gly Asp Ile Arg Pro Tyr Thr Cys Glu Arg Cys Gly Ala
            260                 265                 270

Gly Phe Lys Phe Asn His His Leu Lys Arg His Asp Thr Arg Cys Leu
            275                 280                 285

His Arg Leu Asn Arg Ile Cys Gly Ser Lys Ala Pro Pro Thr Val Gln
            290                 295                 300

Gln Arg Ala Leu Glu Met Leu Ser Gln Ala Gly Phe Arg Ala Val Ala
305                 310                 315                 320
```

```
Gly Thr Asp Ser Val Asn Leu Val Met Phe Asn Pro Glu Ser Met Ala
            325                 330                 335

Thr Thr Lys Pro Glu Glu Ala Met Ser Gly Thr Ala Pro Ser Val Ser
        340                 345                 350

Ser Pro Glu His Glu His Asn Met Ser Ala Ser Asp Asp Ala Ser Glu
        355                 360                 365

Ala Ser Ser Asn Gln His Ser Ala Ser Ser Leu Ser Ala Thr Phe Asp
    370                 375                 380

Leu Pro Thr Ser Trp Lys Pro Glu Asp Ser Gly Ala Ala Asp Ala His
385                 390                 395                 400

Ser Arg Tyr Ser Leu Val Pro Val Ala Pro Ser Ala Thr Pro Val Ala
                405                 410                 415

<210> SEQ ID NO 59
<211> LENGTH: 403
<212> TYPE: PRT
<213> ORGANISM: Artificial Sequence
<220> FEATURE:
<223> OTHER INFORMATION: synthesized

<400> SEQUENCE: 59

Met Glu Arg Ser Val Ser Pro His Met Ser Glu His Ser Ser Tyr Ser
1               5                   10                  15

Thr Pro His Ser Ile Ala Arg Ser Tyr Thr Ser Pro Ser Ala Met Gln
            20                  25                  30

Ala Pro Met His Met Pro Ser Ser Met Thr Gly Gln Met Ala Met Pro
        35                  40                  45

Thr Phe Ser Asp Met Pro Gly Ala Met Gly Thr Val His Asn Met Thr
    50                  55                  60

Met His His Met Pro Gln Gln His Gln Pro Pro Gln Pro Ser Lys
65                  70                  75                  80

Ser Phe Leu Cys Gly Thr Cys Ser Lys Ser Phe Ala Arg Arg Ser Asp
                85                  90                  95

Leu Ala Arg His Gly Leu Arg Pro His Val Cys Asp His Leu Gly Cys
            100                 105                 110

Gly Lys Gln Phe Ile Gln Arg Ser Ala Leu Thr Val His Lys Arg Val
        115                 120                 125

His Thr Gly Glu Lys Pro His His Cys Glu Thr Cys Ala Lys Arg Phe
    130                 135                 140

Ser Asp Ser Ser Ser Leu Ala Arg His Arg Arg Thr His Thr Gly Asn
145                 150                 155                 160

Arg Pro Tyr Lys Cys Pro Tyr Ala Asp Cys Gln Lys Thr Phe Thr Arg
                165                 170                 175

Arg Thr Thr Leu Thr Arg His Gln Asn His His Ser Gly Thr Ile Glu
            180                 185                 190

Glu Ala Ala Ala Thr Ala Ala Ala Leu Ala Ser Lys Ala Gln
        195                 200                 205

Lys Gly Gly Thr Arg Thr Arg Ala Asp Gly Asp His Leu Ser Ser His
    210                 215                 220

Gly Ser Pro Met Thr Thr Pro Ser Pro Ser His Arg Thr Met Ser Met
225                 230                 235                 240

Ser Pro Ser Leu Asp Met Gly Ala Ala Asn Asn Met Asn Arg His Pro
                245                 250                 255

Gly Asp Phe Gln Tyr Leu Gln Gln Thr Gly Ser Leu Pro Pro His Leu
            260                 265                 270
```

```
Arg Gly Val Gly Ser Pro Asn Ser Thr Ser Ser Asn Gly Tyr Asn Asn
            275                 280                 285

Asn Asn Asn Asn Asn Asn Asn Asn Asn Asn Asn Asn Ser Asn Ser
            290                 295                 300

Asn Asn Gly Met Arg Pro Thr Ser His Pro Asn Thr Tyr Gly Pro Pro
305                 310                 315                 320

Pro Ile Leu Glu Pro Asn Leu Glu Gln His Gln Ser Gly Pro Gly Ser
                325                 330                 335

Met Gly Gly Ser Pro His Met Thr Ser Leu Gly Trp Gln Ser Pro Ser
            340                 345                 350

His Val Pro Ser Pro Ser Gln Asn Gly Ala Ser Tyr Val Tyr Pro Glu
            355                 360                 365

Pro Asp Thr Tyr Ser Gln Asn Ala Ala Met Asn Gln Met Tyr Tyr Gly
            370                 375                 380

Ala Pro Pro Gln Met Arg Arg Gln Gln Ser Thr Glu Pro Gly Leu Val
385                 390                 395                 400

His Met Ala

<210> SEQ ID NO 60
<211> LENGTH: 453
<212> TYPE: PRT
<213> ORGANISM: Artificial Sequence
<220> FEATURE:
<223> OTHER INFORMATION: synthesized

<400> SEQUENCE: 60

Met Gln Gln Gln His Phe Gly Ala Pro Pro Ser Tyr Leu Asn Gly Gly
1               5                   10                  15

His Ile Lys Ser Glu Asn Gly Ser Glu Arg Gly Val Ser Pro His Pro
            20                  25                  30

Ser Asp Ser Ser Arg Tyr Ser Ser Gln Gln Pro Gln Gln Gln Leu Pro
            35                  40                  45

Ser Tyr Pro Ser Ile Pro Gln Gln His Met Asn Gly Leu Arg Tyr Pro
        50                  55                  60

Ser Pro Ser Gln Met Gln Ala Pro Met Pro Met Leu Asn Asn Ser Asn
65                  70                  75                  80

Tyr Ile Pro Thr Pro Pro Glu His Thr Tyr Ala Gln Gln Gln Gln Leu
                85                  90                  95

Pro Asp Ala Gln Val Gly His Gln His Asn Gly Gly Arg Pro Ala Ser
            100                 105                 110

Asp Thr Gly Pro Pro Lys Ala Phe Ala Cys Ser Thr Cys Gly Lys Gly
            115                 120                 125

Phe Ala Arg Arg Ser Asp Leu Ala Arg His Glu Arg Ile His Ser Gly
        130                 135                 140

Ile Arg Pro His Val Cys Asp Tyr Pro Asn Cys Gly Lys Gln Phe Ile
145                 150                 155                 160

Gln Arg Ser Ala Leu Thr Val His Gln Arg Val His Thr Gly Glu Lys
                165                 170                 175

Pro His Met Cys Glu Arg Cys Gly Lys Pro Phe Ser Asp Ser Ser Ser
            180                 185                 190

Leu Ala Arg His Arg Arg Ile His Ser Gly Lys Arg Pro Tyr Lys Cys
            195                 200                 205

Pro Tyr Ala Asp Cys Gln Lys Thr Phe Thr Arg Arg Thr Thr Leu Thr
        210                 215                 220

Arg His Gln Asn His His Thr Gly Thr Val Glu Glu Ala Ala Ala Ala
```

-continued

```
                225                 230                 235                 240
        Thr Ala Ala Ala Leu Ala Ser Arg Ala Ser Gln Ser Ser Arg Thr Gly
                        245                 250                 255

Arg Ser Asp Gly Gly Asp Tyr Ser Glu Thr Ala Ser Pro Leu Gly Thr
                        260                 265                 270

Pro Ser Pro Asn Asp Arg Thr Leu Ser Leu Ser Pro Ala Asn Gly Met
                        275                 280                 285

Pro Ala Gly Gly Met Pro Gly Leu His Arg Gln Gly Ser Asp Tyr Ala
                        290                 295                 300

Tyr Met Gly Gly Met Asn Val Pro Pro His Met Arg His Glu Met Pro
        305                 310                 315                 320

Gln Pro Ser Pro Arg Ala Ser Pro Ala Leu Thr Ala Gln Ser Tyr Ala
                        325                 330                 335

Ser Asn Val Ser Gly Ser Arg Pro Ala Ile Thr Ser His Pro Ser Ala
                        340                 345                 350

Tyr Gly Pro Pro Pro Ile Leu Glu Pro Pro Ala Ser Ala Asn His Gly
                        355                 360                 365

Gln Ser Gly Gly Thr Ser Ser Ala Asn Gly Ser Pro His Met Ser Thr
                        370                 375                 380

Met Gly Trp Gln Ser Pro Gly Gln Gln Ala Leu Pro Ser Pro Gly Ala
        385                 390                 395                 400

Asn Asp Asn Gly Tyr Val Tyr Pro Glu Pro Gln Tyr Gln Ala Gln Asn
                        405                 410                 415

Gly Met Tyr Tyr Gln His Asn Asn Ile Arg Arg Pro Asn Ser Thr Glu
                        420                 425                 430

Pro Asp His Tyr Asn Pro Asn Gln Gln Arg Met Gly Asn Glu Met Trp
                        435                 440                 445

Ala Pro Ala Val Gln
                        450

<210> SEQ ID NO 61
<211> LENGTH: 381
<212> TYPE: PRT
<213> ORGANISM: Artificial Sequence
<220> FEATURE:
<223> OTHER INFORMATION: synthesized

<400> SEQUENCE: 61

Met Glu Leu Phe Gln Ile Met Ala Glu Asp Pro Glu Arg Pro Arg Pro
1               5                   10                  15

Phe Leu Cys Asp Trp Gln Gly Cys Gly Lys Arg Phe Asn Arg Lys Ser
                20                  25                  30

Asp Leu Gln Arg His His Arg Ile His Thr Asn Glu Arg Pro Tyr Gly
            35                  40                  45

Cys Asn Trp Gln Asp Cys Gly Lys Arg Phe Ile Gln Arg Ser Ala Leu
        50                  55                  60

Thr Val His Leu Arg Thr His Thr Gly Glu Lys Pro His Gln Cys Glu
65                  70                  75                  80

Val Pro Glu Cys Arg Lys Pro Phe Ala Asp Ser Ser Leu Ala Arg
                85                  90                  95

His Arg Arg Ile His Arg Gly Glu Lys Pro Tyr Arg Cys Gln Asp Val
                100                 105                 110

Gly Cys Asn Lys Ala Lys Thr Thr Arg Asp Lys His His Ser Asn Ser
                115                 120                 125

His Arg Gly Gly Ile Asn Arg Ser Met Thr Pro Arg Gln Gln Leu His
```

```
            130                 135                 140
Pro Thr Phe Ser Ser Glu Phe Asp Gln Phe His Met Ser Ala Pro Pro
145                 150                 155                 160

Asp Leu Thr Ala Ser Thr Glu Ser Ser Pro Ala Asp Ser Thr Ala Tyr
                165                 170                 175

Ser Pro Ala Ala Leu Glu Gly Asp Trp Ser Asn Gln Ser Phe Asn Asn
            180                 185                 190

Tyr Thr His Leu Pro Asn Leu Gln Glu Ala Ser Leu Ala Leu Gln Asn
        195                 200                 205

Gln Ile Arg Ser Gln Gln Ile Pro Gln Leu Met Pro Tyr Met Pro Ser
    210                 215                 220

Arg Val Met Pro Ser Tyr Ser Ala Pro Ser Asn Met Met Thr Gln Gln
225                 230                 235                 240

Gln Met Pro Gln Gln Gly Asn Phe Ser Ser Tyr Ser Pro Ser Pro Val
                245                 250                 255

Glu Ser Thr Gln Gln Gln Pro Trp Gly Thr Gly Cys Ser Arg Pro Ile
            260                 265                 270

Arg Leu Pro Pro Asn Met Met Pro Gly Gln Asn Asp Phe Asn Ser Gln
        275                 280                 285

Tyr Pro Pro Gln Gln Gln Ser Trp Gly Met Pro Gln Asn Gln
    290                 295                 300

Gly Gln Gln Glu Gln Arg Gln Tyr Ser Leu Pro Ala Pro Ser Gln Pro
305                 310                 315                 320

Met Thr Pro Val Pro Val Ser Ala Gly Thr Gly Asn Ile Gln Pro Met
                325                 330                 335

Gln Pro Met Pro Gly His Ile Tyr Gly Ala Arg Leu Val Gly Asp Asp
            340                 345                 350

Leu Ser Asp His Phe Phe Lys Val Glu Thr Ser Ala Asp Asn Asn
        355                 360                 365

Pro Gly Met Thr Leu Pro Asp Ala Arg Phe Ala Gly Leu
    370                 375                 380

<210> SEQ ID NO 62
<211> LENGTH: 411
<212> TYPE: PRT
<213> ORGANISM: Artificial Sequence
<220> FEATURE:
<223> OTHER INFORMATION: synthesized

<400> SEQUENCE: 62

Met Asp Val Met Glu Leu Val Glu Asn Glu Gln Asn Ala Arg Pro Phe
1               5                   10                  15

Gln Cys Asp Trp Lys Thr Cys Thr Lys Ser Phe Asn Arg Lys Ser Asp
                20                  25                  30

Leu Gln Arg His Tyr Arg Ile His Thr Asn Glu Arg Pro Tyr Ser Cys
            35                  40                  45

Val Thr Pro Gly Cys Gly Lys Ser Phe Ile Gln Arg Ser Ala Leu Thr
        50                  55                  60

Val His Ile Arg Thr His Thr Gly Glu Lys Pro His Gln Cys Gln His
65                  70                  75                  80

Ile Gly Cys Gly Lys Arg Phe Ser Asp Ser Ser Leu Ala Arg His
                85                  90                  95

Arg Arg Ile His Thr Gly Lys Arg Pro Tyr Lys Cys Ala His Asp Gly
            100                 105                 110

Cys Leu Lys Ser Phe Cys Arg Lys Thr Thr Met Val Lys His Gln Arg
```

```
                115                 120                 125
Arg Ser His Gln Arg Gly Ile His Ser Glu Leu Asp Asp Gly Glu
    130                 135                 140

Thr Ser Asp Ser Asp Ser Gly Glu Ser Pro Thr Thr Pro Gln His His
145                 150                 155                 160

Ser Ser Gln Ile Gln Trp Pro Gln His Leu Thr Val Pro Gly Val Pro
                165                 170                 175

His Gly His Gln Met His Arg Ala His Ser Phe Ala Asp Phe Gly Gln
            180                 185                 190

His Gln His Ile Asp Gly Tyr Pro Met Pro Gln Ala Tyr Ala His Arg
        195                 200                 205

His Ser Leu Ser Gly Gly Pro Gln Ala Tyr Gly Pro Ile Pro Asp Gln
    210                 215                 220

His His His Val Met Gln Arg Gln Pro Ser Leu Gln His Ala Ser Tyr
225                 230                 235                 240

Tyr Val Pro Glu Gln Asn Asn Pro Gly Val Ala Thr Leu Asn Thr Asn
                245                 250                 255

Pro Ala Pro Ile Gln Thr Tyr His Ile Pro Arg His Ser Met Glu Arg
            260                 265                 270

His Pro Gln Glu Ile Leu Gln Ser Ser Pro Gly Ser Tyr Ser Ser His
        275                 280                 285

Ser Arg Ala Ser Pro Val Ser Gln Glu Pro Tyr Tyr Thr His Ala Gln
    290                 295                 300

His Ser Val His Val Pro Thr Tyr Ala Ile His Gly Gln Ser Pro Thr
305                 310                 315                 320

Glu Ser Gln Pro Met Ile His Tyr Gln Gln His Val Pro Thr Pro Gln
                325                 330                 335

Ser Ile Pro Ser Pro Val Ala Gln Val Gln His Gln Leu Gln His Gln
            340                 345                 350

Tyr Pro Gln Pro Pro Glu His Gly Gln Trp Tyr Glu Ser Thr Pro Tyr
        355                 360                 365

Gln Gln Pro Glu Val Ile Ser Asn Val Pro Met Tyr Pro Gln Val Thr
    370                 375                 380

Val Phe Ser Asp Pro Trp His Lys Leu Glu Thr Phe Asp Asp Pro Ser
385                 390                 395                 400

Leu Gln Met Pro Ser Ala Arg Ile Glu Asn Leu
                405                 410

<210> SEQ ID NO 63
<211> LENGTH: 367
<212> TYPE: PRT
<213> ORGANISM: Artificial Sequence
<220> FEATURE:
<223> OTHER INFORMATION: synthesized

<400> SEQUENCE: 63

Met Asp Ile Val Asn Leu Val Asn Asn Ala Asp Thr Arg Lys Ser Ser
1               5                   10                  15

Lys Asn Ala Ser Thr Gln Pro Arg Pro Phe Ala Cys Thr Tyr Gly Asn
            20                  25                  30

Cys Thr Lys Ala Phe Ala Arg Arg Ser Asp Leu Gln His Leu Arg
        35                  40                  45

Ile His Leu Asn Glu Arg Pro Phe Ala Cys Pro Ile Asp Gly Cys Ser
    50                  55                  60

Lys Thr Phe Ile Gln Arg Ser Ala Leu Thr Val His Ile Arg Val His
```

```
                65                  70                  75                  80
Thr Gly Glu Arg Pro His Thr Cys Glu Gln Cys Gly Lys Ala Phe Ser
                    85                  90                  95

Asp Ser Ser Ser Leu Ala Arg His Arg Ile His Thr Gly Lys Arg
                    100                 105                 110

Pro Tyr Lys Cys Pro Val Glu Gly Cys Asn Lys Thr Phe Cys Arg Lys
                    115                 120                 125

Thr Thr Leu Thr Lys His Thr Lys Arg Asn His Gln Ser Gln Ser Ser
130                 135                 140

Leu Ser Asn Ser Pro Ser Pro Ser Pro Glu Ala Gln Ser
145                 150                 155                 160

Asn Val Pro Ala Leu Thr Ile Pro Gln Pro Leu Thr Gln Gln Leu Ser
                    165                 170                 175

Gln Ser Pro Leu Gln Cys Leu Pro Ile Thr Gln Pro Ser Leu Tyr Ala
                    180                 185                 190

Leu Ser Gln Glu Glu Lys Pro Gln Phe Met Asp Asn Ser Gln Phe Arg
                    195                 200                 205

Leu Gln Ser Pro Ile Cys Met Ser Ser Tyr Gln Ser Gln Glu Ser Pro
210                 215                 220

Ser Asn Ser Thr Val Phe Ser Ser Pro Thr Thr Pro Thr Tyr Ala Thr
225                 230                 235                 240

Glu Ala Gln Phe Leu Tyr Gln His Pro Pro Pro Gln Gly Ala Phe
                    245                 250                 255

Ser Tyr Tyr Glu Ser Thr Ser Pro Phe Leu Tyr Val Asp Thr Ser Asn
                    260                 265                 270

Gln Lys Ser Gln Met Gly Leu Asn Asn Gln Ser Gln Leu Leu Thr Pro
                    275                 280                 285

Pro Gln Ser Ala Asp Pro Asn Asn Phe Gly Pro Phe Ala Tyr Val Pro
                    290                 295                 300

Pro Pro Leu Ala Val Thr Asp Asp Tyr Asn Thr Tyr Pro Phe Val Pro
305                 310                 315                 320

Pro Ser Pro Pro Leu Thr Gly Asn Cys Glu Thr Ser Tyr Ser Asn Gln
                    325                 330                 335

Ser Leu Ile Asp Glu Ser His Tyr His His Glu Thr Tyr Pro His Pro
                    340                 345                 350

Asn Val Leu Thr Gly Leu Gly Leu Asp Leu Val Gln Asp Gly Glu
                    355                 360                 365

<210> SEQ ID NO 64
<211> LENGTH: 320
<212> TYPE: PRT
<213> ORGANISM: Artificial Sequence
<220> FEATURE:
<223> OTHER INFORMATION: synthesized

<400> SEQUENCE: 64

Met Ala Pro Gly Gly Ser Arg Gly Phe Asn Cys Ser Trp Glu Asn Cys
1               5                   10                  15

Gly Lys Ser Phe Asn Arg Lys Ser Asp Leu Cys Arg His Tyr Arg Ile
                20                  25                  30

His Thr Asn Glu Arg Pro Tyr His Cys Thr Val Pro Ser Cys Asn Lys
                35                  40                  45

Ser Phe Ile Gln Arg Ser Ala Leu Thr Val His Ser Arg Thr His Thr
                50                  55                  60

Gly Glu Lys Pro His Val Cys Asp His Glu Asp Cys Arg Lys Ala Phe
```

```
                65                  70                  75                  80
Ser Asp Ser Ser Ser Leu Ala Arg His Arg Arg Ile His Thr Gly Arg
                    85                  90                  95

Arg Pro Tyr Ile Cys Ser Glu Pro Ala Cys Asp Arg Ser Phe Cys Arg
                100                 105                 110

Lys Thr Thr Leu Thr Lys His Gln Ser Arg Thr His Gln Pro Gly Val
                115                 120                 125

Asn Thr Arg Pro Ser Ser Glu Glu Ala Pro Thr Pro Glu Ser Met Thr
130                 135                 140

Tyr Gln Thr Pro Val Met Thr Thr Met Pro Pro Asn Ser Asn Gln Tyr
145                 150                 155                 160

Ile Leu Ala Gln Gln Pro Tyr Tyr His Asn Gly Pro Thr Pro Thr Thr
                165                 170                 175

Ala Asp Phe Tyr Gln Thr Pro Gln Pro Ala Ile His Phe Pro Gln Pro
                180                 185                 190

Gln Ala Met Val Pro Gln Pro Ile Pro Thr Ala Gly Leu Pro Thr Pro
                195                 200                 205

Pro Phe Glu Pro Gln His Tyr Ala Gln Ile Met Gln Gln Gln Gln Pro
                210                 215                 220

Arg Tyr Asp Pro Thr Tyr Ile Gln Pro Gln Tyr Gln Ser Pro Thr Pro
225                 230                 235                 240

Pro Phe Val Ala Gln Pro Gln His His Met Thr Ala Asp Gly Arg Pro
                245                 250                 255

Ile Val Ala Thr Tyr His Pro Asp Gln Phe Lys Pro Pro Ala Arg Ile
                260                 265                 270

Leu Ser Ser Gln Glu Ala Met Leu Ile Arg Phe Ser Pro Ala Leu Ser
                275                 280                 285

Thr Leu Ala Gly Gly Ala Thr Pro Asp Pro Glu His Arg Thr Pro Asn
                290                 295                 300

Phe Gly Ser Gly Val Met Arg Thr Ser His Ser Trp Pro Phe Pro Pro
305                 310                 315                 320

<210> SEQ ID NO 65
<211> LENGTH: 295
<212> TYPE: PRT
<213> ORGANISM: Artificial Sequence
<220> FEATURE:
<223> OTHER INFORMATION: synthesized

<400> SEQUENCE: 65

Gln Gln Gln Gln Gln Gln Arg Gln Gln His Arg Gln Gln Thr Pro
1               5                   10                  15

Gln Gln His Glu Arg Tyr Glu Lys Gln Gln His Pro Gln Asp Tyr Asn
                20                  25                  30

Ser Asn Ser Asn Asn Ser Asn Asn His Asn Asn Asn Ile Ser Ser
            35                  40                  45

Ser Asn Thr Asn Asn Thr Lys Glu Lys Lys Leu Ile Asn Ser Asn Ser
50                  55                  60

Ser Leu Lys Arg Asp Asp Gly Arg Pro Leu Val Gly Ala Thr Lys Val
65                  70                  75                  80

Asp Gln Leu Met Leu Ile Ile Gln Ala Arg Gln Lys Gly Val Cys Gly
                85                  90                  95

Asn Ile Glu Gln Ser Glu Asp Gly Asn Ile Asp Glu Glu Asn Ile Leu
                100                 105                 110

Pro Asn Pro Ile Glu Leu Val Gly Gly Val Glu Lys Thr Ser Leu Lys
```

-continued

```
            115                 120                 125
Gly Asp Lys Ser His Gln Cys Lys Tyr Cys Gln Lys Lys Phe Thr Gln
        130                 135                 140

Ser Thr His Leu Asp Val His Leu Arg Ser His Met Gly Val Lys Pro
145                 150                 155                 160

Tyr Lys Cys Glu Phe Cys Asp Lys Arg Phe Thr Gln Gly Gly Asn Leu
                165                 170                 175

Arg Thr His Met Arg Leu His Thr Gly Glu Lys Pro Phe Lys Cys Asn
            180                 185                 190

Ile Cys Asp Lys Gln Phe Ser Arg Lys Gly Asn Leu Gln Ala His His
        195                 200                 205

Leu Thr His Asp Asn Ser Lys Pro Phe Ile Cys Lys Phe Asp Gly Cys
    210                 215                 220

Asn Lys Gly Phe Thr Gln Leu Gly Asn Leu Lys Ala His Gln Asn Arg
225                 230                 235                 240

Phe His Leu Asp Thr Ile Asn Glu Leu Phe Asn Lys Leu Ala Gln Leu
                245                 250                 255

Gly Glu Gly Ile Gly Ser Tyr Asp Ser Leu Pro Lys Ser Glu Lys Asp
            260                 265                 270

Leu Leu Asp Tyr Phe Ser Ser Leu Tyr Lys Asn Leu Asn Lys Gly Ile
        275                 280                 285

Lys Gly Arg Gly Lys Ala Arg
    290                 295

<210> SEQ ID NO 66
<211> LENGTH: 494
<212> TYPE: PRT
<213> ORGANISM: Artificial Sequence
<220> FEATURE:
<223> OTHER INFORMATION: synthesized

<400> SEQUENCE: 66

Met Ser Gln Ser Pro Ser Ala Ser Gly Ala Met Gly Ile Gly Ser Val
1               5                   10                  15

Leu Asn Asn Lys Gly Ala Ala Ala Gln Ala Leu Gln Gln Ala Gly
            20                  25                  30

Ala Met Pro Val Asp Gln Gln Val Gln Gln Leu Gln Gln Val
        35                  40                  45

Gln Gln Val Gln Gln Val Gln Gln Val Gln Gln Ala Gln Gln
    50                  55                  60

Val Gln Gln Ala Gln Gln Leu Gln Gln Ala Gln Gln Pro Leu Gln Gln
65                  70                  75                  80

Val Gln Gln Gln Gln Gln His Gln Gln Gly Gln Thr Ile Pro Gln Gln
                85                  90                  95

Val Pro Met Asn Arg Pro Asn Ser Pro His Gly Ser Glu Asn Ser Gly
            100                 105                 110

Tyr Thr Tyr Pro Ser Pro Thr Ala Ile Gly Gly Ala Pro Leu Pro Pro
        115                 120                 125

Ala Asn Met Ala Pro Ala Pro Met Gly Ile Pro Met Gln Gln Thr Met
    130                 135                 140

Gln Gln Pro Met Pro Gln Ser Met Ile Pro Val Met His Pro Gly Phe
145                 150                 155                 160

Lys Thr Glu Pro Thr Pro Ala Pro Gln Gln Pro Pro Lys Ala Tyr
                165                 170                 175

Pro Cys Gln Thr Cys Gly Lys Gly Phe Ala Arg Arg Ser Asp Leu Ala
```

```
                180             185             190
Arg His Glu Arg Ile His Ser Gly Ile Arg Pro His Val Cys Asp Tyr
                195             200             205
Pro Gly Cys Gly Lys Gln Phe Ile Gln Arg Ser Ala Leu Thr Val His
                210             215             220
Gln Arg Val His Thr Gly Glu Lys Pro His Gln Cys Glu Arg Cys Gly
225             230             235             240
Lys Pro Phe Ser Asp Ser Ser Leu Ala Arg His Arg Arg Ile His
                245             250             255
Ser Gly Lys Arg Pro Tyr Lys Cys Pro Tyr Val Asp Cys Gln Lys Thr
                260             265             270
Phe Thr Arg Arg Thr Thr Leu Thr Arg His Gln Asn His His Thr Gly
                275             280             285
Thr Val Glu Asp Ser Gln Arg Ala Arg Asn Glu Ala Leu Ala Gln Gly
                290             295             300
Ser Asn Thr Ala Leu Ala Ala Ala Ile Arg Asn Lys Arg Gly Asp
305             310             315             320
Ser Glu Gln Ala Ser Asn Gln Glu Ser Pro Ile Thr Thr Pro Ser Pro
                325             330             335
Ala Gln Arg Pro Met Ser Met Ser Pro Asn Glu Asp Leu Ala Asn Ile
                340             345             350
Asn Asn Met Gln Gln Tyr Leu Thr Asn Thr Ser Leu Pro Pro His Ile
                355             360             365
Arg Gly Asp Val His Gly Gly Ser Pro Val Ser Thr Ala Ser Ser Gly
                370             375             380
Tyr Asn Asn Gly Met Arg Pro Thr Ser His Pro Ser Gly Gly Tyr Ala
385             390             395             400
Pro Pro Pro Pro Leu Glu Pro Ser Leu Asp Gln Phe Gln Gln Gly Pro
                405             410             415
Gly Ser Ala Ser Gly Ser Pro His Ile Gly Ser Val Gly Trp Ala Ser
                420             425             430
Pro Gly Pro Val Gly Ser Pro Thr Glu Ser His Gly Gln Gly Ala Ser
                435             440             445
Val Tyr Pro Asp Pro Glu Pro Ser Tyr Gln Asn Thr Ala Gln Met Gly
                450             455             460
Gln Ile Tyr Tyr Ala Ser Ala Ala Thr Gln Gly Arg Arg Pro Gly Ser
465             470             475             480
Thr Glu Pro Gly Gln Arg Pro Ser Glu Met Trp Thr Gly Gln
                485             490

<210> SEQ ID NO 67
<211> LENGTH: 498
<212> TYPE: PRT
<213> ORGANISM: Artificial Sequence
<220> FEATURE:
<223> OTHER INFORMATION: synthesized

<400> SEQUENCE: 67

Met Pro Arg Ala Leu Ile Pro Lys Pro Asp Gln Pro Arg Gly Ala His
1               5               10              15
Glu Cys Ala Val Cys Glu Lys Ala Phe Lys Asn Arg Ser Glu Leu Ala
                20              25              30
Arg His Gln Asn Ile His Arg Glu Asp Lys Pro Phe Val Cys Thr Glu
                35              40              45
Cys Gly Lys Lys Phe Ala Gln Asn Gly Gln Leu Thr Asn His Arg Asn
```

```
                50                  55                  60
Thr His Phe Gly Phe Arg Pro Ser Lys Cys Ala Phe Cys Pro Arg Asp
 65                  70                  75                  80

Phe Ala Glu Gly Gly Ser Thr Gly Arg His Glu Arg Glu Gln His Ser
                 85                  90                  95

Asn Phe Ala Gly Phe Gln Cys Pro Val Ser Gly Cys Glu Phe Met His
                100                 105                 110

Lys Arg Lys Gly Asp Tyr Asn Val His Leu Ala Gly His Gly Val Ser
                115                 120                 125

Pro Ser Ser Val Asn Pro Trp His His Ala Tyr Thr Thr Asp Gly Ser
            130                 135                 140

Lys Ile Asp Pro Thr Arg Gly Leu Arg Glu Gln Leu Glu Trp Glu Pro
145                 150                 155                 160

Phe Leu Lys Asp Gly Arg Asp Gly Ala Gly His Pro Asn Arg Ala Arg
                165                 170                 175

Ala Lys Arg Thr Ala Thr Ser Leu Gly Lys Glu Arg Gln Thr Ala Pro
                180                 185                 190

Ala Gln Ala Pro Arg Thr Arg Ser Ser Arg Lys Arg Arg Ala Asp Glu
                195                 200                 205

Thr Asp Glu Asp Asp Asp Glu Asp Glu Tyr Lys Pro Asn Thr Arg
210                 215                 220

Ala Arg Ala Ala Lys Arg Val Arg Gln Ser Pro Pro Glu Pro Glu Pro
225                 230                 235                 240

Glu Val Lys Pro Ala His Ala Val Ser Glu Asp Ala Phe Asp His Leu
                245                 250                 255

Phe Thr Ile Ser Pro Thr Ser Asp His Gly Ser Asn Val Gly Leu Pro
                260                 265                 270

Ser Gly Ser Ser Ser Leu Thr Ser Leu Ala Ala Thr Pro Asp Pro
            275                 280                 285

Gln Gln Gly Glu Leu Gln Tyr Ala Leu Asp Ala Tyr Gly Cys Ala Ser
            290                 295                 300

Pro Val Ala Gly Pro Ser Ala Ser Tyr Asn Pro His Asn Val Leu Gly
305                 310                 315                 320

Leu Ala Leu Pro Asp Gln Ser Ser Ala Tyr Leu Gly Tyr Gln Ser Pro
                325                 330                 335

Leu Ser Gly His Gln Ala Leu Asp Gln Cys Gly Ala Thr Ser Asp Leu
                340                 345                 350

Gly Leu Leu Met Ala Gln Gln Ala Pro His Gly His Tyr Glu Phe Asp
                355                 360                 365

Met Ala Ala Phe Glu Ala Ser Leu Cys Asp Gly Thr Phe Phe Asp
370                 375                 380

Asn Asn Asp Leu Val His Ala Gln Pro Met Gln Phe Gln Ala Ser Tyr
385                 390                 395                 400

Asp Ser Tyr Asn Ile Pro Pro Asn Val Ser Ser Tyr Leu His Gly
                405                 410                 415

Gly Leu Tyr Gln Tyr Asp Asn Leu Ala Pro Ala Met Ser Ala Asp Leu
                420                 425                 430

Leu Ser Ala Ser Ser Pro Leu Thr Ser Ser Gln Gly Thr Ser Arg
            435                 440                 445

Ser Pro Ser Pro Leu Gly Leu Gly Leu Gly Ser Asn Gly Phe Ser Val
            450                 455                 460

Pro Ser Ile Ser Ser Leu Gly Arg Ala Arg Ala Asn Ala Gln Leu Ile
465                 470                 475                 480
```

```
Met Pro Gln Val Tyr Gln Asp Ile Ala Leu Leu His Gly Tyr Pro Thr
                485                 490                 495
Ser Met

<210> SEQ ID NO 68
<211> LENGTH: 501
<212> TYPE: PRT
<213> ORGANISM: Artificial Sequence
<220> FEATURE:
<223> OTHER INFORMATION: synthesized

<400> SEQUENCE: 68

Met Glu Leu Asp Thr Ile Leu Asn Ala Arg Leu Thr Gln Tyr Ala Gly
1               5                   10                  15
His Gly His Pro His Pro Phe Gly Met Gln His Ala Met Gln His Glu
                20                  25                  30
Met Gln Gln Gln His Phe Gly Ala Pro Pro Tyr Met Ala Asn Gly Arg
            35                  40                  45
Ile Lys Ser Glu Asn Gly Ser Glu Arg Gly Val Ser Pro His Pro Ser
    50                  55                  60
Asp Ser Ser Arg Tyr Ser Ser Gln Gln Pro Gln Gln Pro Leu Pro Ser
65                  70                  75                  80
Tyr Pro Ala Met Pro Pro Gln His Met Asn Gly Met Arg Tyr Pro Ser
                85                  90                  95
Pro Ser Gln Met Gln Ala Pro Met Pro Met Leu Asn Asn Asn Asn Tyr
                100                 105                 110
Ile Pro Gln Pro Pro Asp His Ala Tyr Gly Gln Gln Gln Gln Gln Gln
            115                 120                 125
Val Pro Asp Gln Gln Gln His Gln Gly Gly Arg Pro Ala Ser Asp Thr
    130                 135                 140
Gly Pro Pro Lys Ala Phe Ala Cys Ser Thr Cys Gly Lys Gly Phe Ala
145                 150                 155                 160
Arg Arg Ser Asp Leu Ala Arg His Glu Arg Ile His Ser Gly Ile Arg
                165                 170                 175
Pro His Val Cys Asp Tyr Pro Asn Cys Gly Lys Gln Phe Ile Gln Arg
                180                 185                 190
Ser Ala Leu Thr Val His Gln Arg Val His Thr Gly Glu Lys Pro His
            195                 200                 205
Met Cys Glu Arg Ser Trp Lys Gly Thr Phe Ala His Ser Thr Ala Lys
    210                 215                 220
Gly Leu Ala Asn Ile Thr Gln Pro Phe Ser Asp Ser Ser Ser Leu Ala
225                 230                 235                 240
Arg His Arg Arg Ile His Ser Gly Lys Arg Pro Tyr Lys Cys Pro Tyr
                245                 250                 255
Ala Asp Cys Gln Lys Thr Phe Thr Arg Arg Thr Thr Leu Thr Arg His
                260                 265                 270
Gln Asn His His Thr Gly Thr Val Glu Glu Ala Ala Ala Thr Ala
            275                 280                 285
Ala Ala Leu Ala Ser Arg Ala Ala Pro Ser Arg Thr Gly Arg Ser
        290                 295                 300
Asp Gly Gly Asp Tyr Ser Glu Asn Ala Ser Pro Leu Asn Thr Pro Ser
305                 310                 315                 320
Pro Gly Asp Arg Thr Leu Ser Met Ser Pro Ala Asn Gly Met Pro Ala
                325                 330                 335
```

```
Gly Val Val Pro Gly Met His Arg Gln Ala Thr Asp Tyr Ala Tyr Met
                340                 345                 350

Gly Gly Met Asn Val Pro Pro His Met Arg Ser Glu Met Pro Gln Pro
            355                 360                 365

Ser Pro Arg Ala Ser Pro Ala Leu Thr Thr Gln Ser Tyr Ser Ser Val
        370                 375                 380

Gly Ser Ser Arg Pro Pro His His Leu Pro Pro His Arg Ile Trp Thr
385                 390                 395                 400

Ser Pro His Pro Gly Ser Leu Pro Arg Leu Pro Asn His Asn Gln Phe
                405                 410                 415

Arg His His Ser Ala Pro Thr Ala Ala Pro His Met Phe Cys His Gly
            420                 425                 430

Ala Gly Gln Ser Pro Gly Gln Gln Ala Leu Pro Ser Pro Gly Gln Ala
        435                 440                 445

Asp Asn Gly Tyr Val Tyr Pro Glu Pro Gln Tyr Gly Asn Thr Gln Asn
    450                 455                 460

Ser Met Tyr Tyr Gln Asn His Asn Ile Arg Arg Pro Asn Ser Thr Glu
465                 470                 475                 480

Pro Asp His Tyr Asn Ala Asn Pro Gln Arg Met Gly Asn Asp Leu Trp
                485                 490                 495

Ala Pro Ala Val Gln
                500

<210> SEQ ID NO 69
<211> LENGTH: 428
<212> TYPE: PRT
<213> ORGANISM: Artificial Sequence
<220> FEATURE:
<223> OTHER INFORMATION: synthesized

<400> SEQUENCE: 69

Met Ala Asp Val Leu Pro Ala Lys Ala Pro Ser Gln Leu Leu Gln Arg
1               5                   10                  15

Arg Leu Ser Gln Ala His Phe Asn Ala Met Gln Val Gln Gly Met Met
            20                  25                  30

Ala Gln Phe Asn Met Ala Phe Arg Pro Asp Ser Ala Ala Thr Ile Pro
        35                  40                  45

Leu Gln Met Leu Gln Ala Gln Glu Gln Gln Thr Leu Ala Met His Ala
    50                  55                  60

Ala Ser Val Ala Pro Ser Glu Leu Leu Asn Thr His Pro Ala Gln Thr
65                  70                  75                  80

Met Asn Asn Ser Met Tyr Met Asp His Ser Ala Phe Gln Asn Ser Tyr
                85                  90                  95

Ser Ile Pro Val Gly Met Asn Asn Ala Thr Phe Gly Ser Leu Ala Trp
            100                 105                 110

Pro Ala Ser Ile Val Thr Asn Pro Asn Thr Met Ala Val Leu Pro Leu
        115                 120                 125

Val Arg Asn Glu Ser Tyr Ser Ser Val Glu Gly Ser Glu Pro Ser Ile
    130                 135                 140

Lys Thr Glu Asp Arg Ser Pro Ile His Pro Ser Gln Val Tyr Phe Asp
145                 150                 155                 160

Ala Thr Ala Tyr Ala Ser Ser Pro Glu Ser Gln Thr Ala Thr Asp Ser
                165                 170                 175

Ser Glu Glu Thr Lys Pro Val Val Phe Ser Thr Glu Ile Asp Thr Leu
            180                 185                 190
```

```
Met Lys Ala Ile Gln Met Lys Thr Gln Pro Ala Glu Gln Arg Glu Ala
            195                 200                 205

Pro Lys Pro Lys Pro Ala Ala Ser Asn Asn Arg Ala Lys Lys Arg Tyr
        210                 215                 220

Thr Cys Asp Val Pro Asp Cys Gly Lys Ala Phe Tyr Gln Lys Thr His
225                 230                 235                 240

Leu Glu Ile His Thr Arg Ala His Thr Gly Ile Lys Pro Phe Leu Cys
                245                 250                 255

Lys Glu Pro Ser Cys Gly Gln Arg Phe Ser Gln Leu Gly Asn Leu Lys
            260                 265                 270

Thr His Glu Arg Arg His Thr Gly Glu Arg Pro Tyr His Cys Asp Ile
        275                 280                 285

Cys Gly Lys Thr Phe Ala Gln His Gly Asn Val Arg Ala His Lys Ile
        290                 295                 300

Val His Thr Ala Ala Lys Pro Phe Thr Cys Lys Leu Asp Asn Cys Asn
305                 310                 315                 320

Lys Gln Phe Thr Gln Leu Gly Asn Leu Lys Ser His Gln Asn Lys Phe
                325                 330                 335

His Val Glu Thr Ile Arg Arg Leu Lys Ser Arg Phe Glu Asp Ile Lys
            340                 345                 350

Ala Gly Asp Val Val Glu Lys Trp Glu Lys Asp Met Trp Glu Tyr Phe
        355                 360                 365

Ala Gly Leu Tyr Lys Asn Cys Asn Lys Gly Ile Lys Gly Arg Gly Lys
        370                 375                 380

Asp Arg Arg Ile Ser Thr Thr Leu Leu Gly Ala Ala Gln Arg Arg Asp
385                 390                 395                 400

Ser Met Val Ser Ala Glu Cys Ser Gly Gly Glu Gly Leu Ala Met Gln
                405                 410                 415

Ala Arg Arg Asp Ser Leu Thr Gly Thr Met His Gln
            420                 425

<210> SEQ ID NO 70
<211> LENGTH: 292
<212> TYPE: PRT
<213> ORGANISM: Artificial Sequence
<220> FEATURE:
<223> OTHER INFORMATION: synthesized

<400> SEQUENCE: 70

Met Ala Pro Gly Gly Ser Arg Gly Phe Asn Cys Ser Trp Glu Arg Cys
1               5                   10                  15

Gly Lys Ser Phe Asn Arg Lys Ser Asp Leu Cys Arg His Tyr Arg Ile
            20                  25                  30

His Thr Asn Glu Arg Pro Tyr His Cys Thr Val Pro Ser Cys Asn Lys
        35                  40                  45

Ser Phe Ile Gln Arg Ser Ala Leu Thr Val His Ser Arg Thr His Thr
    50                  55                  60

Gly Glu Lys Pro His Val Cys Asp His Glu Cys Arg Lys Ala Phe
65                  70                  75                  80

Ser Asp Ser Ser Ser Leu Ala Arg His Arg Arg Ile His Thr Gly Arg
                85                  90                  95

Arg Pro Tyr Ile Cys Ser Glu Pro Ala Cys Asp Arg Ser Phe Cys Arg
            100                 105                 110

Lys Thr Thr Leu Thr Lys His Gln Ser Arg Thr His Gln Pro Gly Gly
        115                 120                 125
```

```
Asn Thr Arg Pro Ser Ser Glu Glu Ala Pro Thr Pro Glu Ser Met Thr
    130                 135                 140

Tyr Gln Thr Pro Val Ile Thr Thr Met Ala Pro Asn Thr Thr Gln Tyr
145                 150                 155                 160

Ile Ile Ala Gln Gln Pro Tyr Tyr His Asn Gly Pro Thr Pro Thr Thr
                165                 170                 175

Ala Asp Phe Tyr Gln Thr Pro Gln Pro Ala Ile His Phe Thr Gln Pro
            180                 185                 190

Gln Ala Met Val Pro Gln Ile Pro Thr Ala Gly Leu Pro Thr Pro
        195                 200                 205

Pro Phe Glu Pro Gln His Tyr Ala Gln Ile Met Gln Gln Gln Gln
210                 215                 220

Pro Arg Tyr Asp Pro Thr Pro His Gln Thr Tyr Ile Gln Pro Gln Tyr
225                 230                 235                 240

Gln Ser Pro Thr Pro Pro Phe Val Ala Gln His Gln His His Met Ala
                245                 250                 255

Ala Asp Val Arg Pro Leu Met Ala Thr Tyr His Pro Asp Gln Phe Lys
                260                 265                 270

Pro Pro Ala Arg Ile Leu Ser Ser Gln Glu Gly Thr Asp Trp Ser Phe
                275                 280                 285

Leu Gly Val Ser
    290

<210> SEQ ID NO 71
<211> LENGTH: 416
<212> TYPE: PRT
<213> ORGANISM: Artificial Sequence
<220> FEATURE:
<223> OTHER INFORMATION: synthesized

<400> SEQUENCE: 71

Met Leu Asn Lys Lys Gly Gln Leu Gln Gln Leu Asn Pro Gly Leu Leu
1               5                   10                  15

Asp His Gln His Gln Ala Phe Val Lys His Glu Pro Gly Met Glu Arg
                20                  25                  30

Ser Ala Ser Pro His Gly Ser Glu His Ser Gln Tyr Ser Asn Pro His
            35                  40                  45

Ile Ala Arg Ala Tyr Pro Ser Pro Ala Ala Met Gln Ala Pro Met His
50                  55                  60

Ile Pro Asn Pro Met Pro Ala Ala Met Gln Leu Pro Gly Phe Pro Glu
65                  70                  75                  80

Met Pro Asn Met Gly Gly Met Pro Asn Met His Met Gln Gln Met Gln
                85                  90                  95

Gln Gln Pro Pro Pro Pro Gln Gln Pro Ile Lys Ala Tyr Pro Cys
            100                 105                 110

Ser Thr Cys Gly Lys Gly Phe Ala Arg Arg Ser Asp Leu Ala Arg His
        115                 120                 125

Glu Arg Ile His Ser Gly Val Arg Pro His Val Cys Asp Trp Pro Asn
    130                 135                 140

Cys Gly Lys Gln Phe Ile Gln Arg Ser Ala Leu Thr Val His Gln Arg
145                 150                 155                 160

Val His Thr Gly Glu Lys Pro His His Cys Glu Thr Cys Ala Lys Pro
                165                 170                 175

Phe Ser Asp Ser Ser Ser Leu Ala Arg His Arg Arg Thr His Ser Gly
            180                 185                 190
```

Lys Arg Pro Tyr Lys Cys Pro Tyr Ala Asp Cys Gln Lys Thr Phe Thr
            195                 200                 205

Arg Arg Thr Thr Leu Thr Arg His Gln Asn His His Ser Gly Thr Ile
    210                 215                 220

Glu Glu Ala Ala Ala Ala Thr Ala Ala Ala Leu Ala Ala Ser Lys Ser
225                 230                 235                 240

Lys Gly Met Ser Gln Pro Arg Ser Glu Ser Asp Leu Met Ser Asn Asn
            245                 250                 255

Gly Ser Pro His Thr Thr Pro Ser Pro Gly Gln Arg Thr Met Ser Met
            260                 265                 270

Ser Pro Ser Val Asp Leu Ser Gly Thr Asn Ser Ile Pro Arg His Pro
            275                 280                 285

Gly Asp Phe Gln Tyr Leu Gln Gln Ser Gly Ser Leu Pro Met His Met
    290                 295                 300

Arg Val Gly Ser Pro Thr Ser Thr Ser Ser Gly Gly Tyr Asn Met Met
305                 310                 315                 320

Arg Pro Thr Ser His Pro Thr Ser Tyr Gly Pro Pro Thr Leu Glu
            325                 330                 335

Pro Asn Leu Glu His Ser Gln Gly Ala Pro Ser Ser Asn Gly Gly Ser
            340                 345                 350

Pro His Met Ala Asn Val Gly Trp Gln Ser Pro Ser His Val Pro Ser
    355                 360                 365

Pro Ser Gln Asn Asn Ala Ser Tyr Val Tyr Pro Asp Pro Ser Glu Ala
    370                 375                 380

Tyr Pro Thr Asn Pro Ala Met Asn Gln Met Tyr Tyr Gly Ala Ala Ala
385                 390                 395                 400

His Met Arg Arg Pro Gln Ser Ala Glu Pro Gly Leu Val His Met Ala
            405                 410                 415

<210> SEQ ID NO 72
<211> LENGTH: 446
<212> TYPE: PRT
<213> ORGANISM: Artificial Sequence
<220> FEATURE:
<223> OTHER INFORMATION: synthesized

<400> SEQUENCE: 72

Met Asp Ile Thr Thr Ile Leu Asn Lys Lys Gly Thr Ala Ala Val Ala
1               5                   10                  15

Ala Ala Glu Ala His Leu Gln Gln His Leu Val His Ala Thr His Met
            20                  25                  30

Lys Ser Lys Thr Pro Ser Glu Ile Ser Ser Glu His Gly Thr Pro Gln
        35                  40                  45

Asn Gly Asp Gln Ser Asn Ile Tyr His Pro Thr Ser Gln Pro Asn Pro
    50                  55                  60

Gln Leu Val Gly Ser Ser Lys Tyr His Ser Gln Ser Gln Gly His Thr
65                  70                  75                  80

Gly Ile Ala Pro Val Arg Ser Asp Tyr Val Gln Asp Gly Gln Gly Ile
            85                  90                  95

Val Lys Tyr Leu Gln Asn Gly Ser Gly Gly Asn Gly Arg Ser Ser Gly
            100                 105                 110

Glu Pro Val Pro Lys Thr Phe His Cys Ser Thr Cys Ser Lys Gly Phe
        115                 120                 125

Ala Arg Arg Ser Asp Leu Ala Arg His Glu Arg Ile His Ser Gly Ile
    130                 135                 140

Arg Pro His Val Cys Asp Trp Pro Gly Cys Gly Lys Gln Phe Ile Gln
145                 150                 155                 160

Arg Ser Ala Leu Thr Val His Thr Arg Val His Thr Gly Glu Lys Pro
            165                 170                 175

His Met Cys Asp Arg Cys Gly Lys Pro Phe Ser Asp Ser Ser Ser Leu
            180                 185                 190

Ala Arg His Arg Arg Ile His Ser Gly Lys Arg Pro Tyr Lys Cys Pro
            195                 200                 205

Tyr Ala Asn Cys Gln Lys Thr Phe Thr Arg Arg Thr Thr Leu Thr Arg
            210                 215                 220

His Gln Asn His His Thr Gly Thr Ile Glu Glu Ala Ala Ala Glu Thr
225                 230                 235                 240

Glu Ala Asn Leu Arg Gln Asn Lys Glu Arg Ala Val Arg Pro Pro Asp
            245                 250                 255

Gly Met Tyr Ser Glu Ala Gly Ser Thr Gln Ser Thr Pro Ser Pro Gly
            260                 265                 270

Gln Arg His Ser Leu Ser Pro Gly Asn Glu Leu Pro Pro Met Tyr Leu
            275                 280                 285

Pro Arg Gln Met Ser Asp Tyr Tyr Met Gly Asn Thr Pro Ile Pro Ala
            290                 295                 300

His Leu Arg Gly Asp Phe Gln Gln Ala Ser Pro Arg Ala Ser Pro Ser
305                 310                 315                 320

Thr Ser Ser Pro Pro Leu Ser Thr Tyr Ser Ser Val Pro His Ala Arg
            325                 330                 335

Pro Ser Met Thr Ser His Pro Ser Gly Tyr Gly Pro Pro Gln Pro Val
            340                 345                 350

Glu Pro Pro Ala Asn Ser Asp Pro Arg Pro Asn Ser Val Ala Gly Ser
            355                 360                 365

Pro His Ile Thr Ser Met Gly Trp Ala Ser Pro Thr Leu His Ser Ile
370                 375                 380

Gly Ser Pro Asp Ser Ala Ser Ala Thr Glu Tyr Ser Tyr Pro Glu Pro
385                 390                 395                 400

Ser Ala Pro Ser Tyr Ser Ser Gln Ile Pro Pro His Met Tyr Phe Pro
            405                 410                 415

Asn Ser Thr Ile Arg Arg Pro Gln Ser Thr Glu Pro Glu Asn Tyr Glu
            420                 425                 430

Leu Lys Pro Lys Leu Asn Gly Asp Ser Trp Thr Thr Pro Val
            435                 440                 445

<210> SEQ ID NO 73
<211> LENGTH: 467
<212> TYPE: PRT
<213> ORGANISM: Artificial Sequence
<220> FEATURE:
<223> OTHER INFORMATION: synthesized

<400> SEQUENCE: 73

Met Asp Ile Thr Thr Ile Leu Asn Lys Lys Ala Ser Val Ser Ile Val
1               5                   10                  15

Ala Ala Asp Val His Gln Leu Gln Gln His Leu Ala Gln Ala Gln Ser
            20                  25                  30

Gln Ser Gln Thr Asp Asp Ala Val Lys Ser Arg Ser Pro Ser Glu Leu
            35                  40                  45

Gly Ala Ser Glu His His Arg Ser Ala Ser Ala Pro Pro Ser Glu His
        50                  55                  60

-continued

```
His His His His His His His Gln Pro Thr Ser Ser Phe Pro Ser
 65                  70                  75                  80

Ser Thr Gln Ser Leu Pro Gln Met Ala His Leu Ala Gln Tyr His Val
                 85                  90                  95

Gln Ala Gln Ala Asn His Ala Gly Thr Ser Pro Gly Tyr Ala His Ser
            100                 105                 110

Ala His Gly Ser Asp Tyr Gly Arg Ser Ser Thr Ser Met Arg Pro Thr
        115                 120                 125

Gly Leu Pro Ala Leu Lys Thr Phe His Cys Gln Thr Cys Ser Lys Gly
    130                 135                 140

Phe Ala Arg Arg Ser Asp Leu Ala Arg His Glu Arg Ile His Ser Gly
145                 150                 155                 160

Ile Arg Pro His Ala Cys Asp Trp Pro Gly Cys Gly Lys Gln Phe Ile
                165                 170                 175

Gln Arg Ser Ala Leu Thr Val His Thr Arg Val His Thr Gly Glu Lys
            180                 185                 190

Pro His Met Cys Asp Arg Cys Gly Lys Pro Phe Ser Asp Ser Ser Ser
        195                 200                 205

Leu Ala Arg His Arg Arg Ile His Ser Gly Lys Arg Pro Tyr Lys Cys
    210                 215                 220

Pro Tyr Ala Asn Cys Gln Lys Thr Phe Thr Arg Arg Thr Thr Leu Thr
225                 230                 235                 240

Arg His Gln Asn His His Thr Gly Thr Ile Glu Glu Ala Ala Ala Glu
                245                 250                 255

Thr Glu Ala Asn Leu Arg His Ser Lys Asp Arg Ser Thr Ala Ser Arg
            260                 265                 270

Pro Ser Glu Tyr Ser Glu Pro Gly Ser Ala His Ser Thr Pro Ser Pro
        275                 280                 285

Ala Gln Arg Pro Ser Leu Ser Pro Gly Asn Glu Leu Pro Pro Leu Asn
    290                 295                 300

Leu Ser Ser Arg Pro Ser Ala Ala Gly Gly Pro Thr Ser Ala Gly Gly
305                 310                 315                 320

Ser Ala Asp Tyr Tyr Thr Ser Leu Pro Pro His Leu Arg Thr Asp Phe
                325                 330                 335

Ala Asn Ser Ser Pro Arg Ala Ser Pro Thr Ser Pro Ser Pro Thr Leu
            340                 345                 350

Thr Ser Leu Ser Gly Pro Ala Ser Phe His His His Asn His Asn Arg
        355                 360                 365

Pro Ser Leu Thr Ser His Pro Ser Gly Tyr Ala Pro Gln Pro Leu
    370                 375                 380

Glu Pro Pro Ala Asn Ser Asp Pro Arg Pro Asn Ser Val Ala Gly Ser
385                 390                 395                 400

Pro His Leu Ser Ser Val Gly Trp Ala Ser Pro Thr Leu Ser Ser Met
                405                 410                 415

Pro Ser Pro Ser Ser Ala Ser Ala Pro Glu Tyr Pro Tyr Pro Glu Pro
            420                 425                 430

Ser Ser His Gln Tyr Pro Gly Ser Ile Thr Pro His Met Phe Phe Pro
        435                 440                 445

Arg Arg Pro Gln Ser Ser Glu Pro Glu Asn Tyr Glu Leu Lys Pro Lys
    450                 455                 460

Leu Glu Leu
465
```

-continued

<210> SEQ ID NO 74
<211> LENGTH: 490
<212> TYPE: PRT
<213> ORGANISM: Artificial Sequence
<220> FEATURE:
<223> OTHER INFORMATION: synthesized

<400> SEQUENCE: 74

Met Gln Tyr Glu Val Pro Leu Pro Ile Ala Met Asn His Asp Val Ser
1               5                   10                  15

Thr Ser Asn Gly His Tyr Ala Gln Thr Leu Tyr Val Pro Asn Gly Asn
            20                  25                  30

Asn Arg Ile Lys Ser Glu Asn Gly Ser Glu Arg Gly Val Ser Pro His
        35                  40                  45

Thr Ser Asp His Ser Ser Arg Tyr Ser Gln Thr Pro Gln Asn Ser
    50                  55                  60

Val Ala Tyr Gln Gln Ile Ala Ala Gln Leu Thr Asn Gly Met Arg Tyr
65                  70                  75                  80

Pro Ser Pro Asn Gln Met Gln Gln Asn Asn Met Pro Met Leu Gln
            85                  90                  95

His Ser Tyr His Pro Asn Thr Thr Gln Asp Gln Gly Tyr Gln Thr Gln
            100                 105                 110

Ala Gly Ala Thr Met Gly Ala Val Gln Gln Ala Val Pro Gln Ser Thr
        115                 120                 125

Asp Gln Thr Ala Met Asp Gly Gly Arg Ala Ser Thr Gly Ser Ser Gly
    130                 135                 140

Leu Pro Lys Ala Phe Ala Cys Ser Thr Cys Gln Lys Gly Phe Ala Arg
145                 150                 155                 160

Arg Ser Asp Leu Ala Arg His Glu Arg Ile His Ser Gly Val Arg Pro
                165                 170                 175

His Val Cys Asp His Pro Gly Cys Gly Lys Gln Phe Ile Gln Arg Ser
            180                 185                 190

Ala Leu Thr Val His Ser Arg Val His Thr Gly Glu Lys Pro His Met
        195                 200                 205

Cys Glu Arg Cys Gly Lys Pro Phe Ser Asp Ser Ser Leu Ala Arg
    210                 215                 220

His Arg Arg Ile His Ser Gly Lys Arg Pro Tyr Lys Cys Pro Tyr Ala
225                 230                 235                 240

Asp Cys Gln Lys Thr Phe Thr Arg Arg Thr Thr Leu Thr Arg His Gln
                245                 250                 255

Asn His His Thr Gly Thr Ile Glu Glu Ser Glu Ala Ala Thr Ala Ala
            260                 265                 270

Ala Leu Ala Ser Arg Val Gln Met Ser Thr Asn Arg Ser Arg Gly Ser
        275                 280                 285

Asp Glu Glu Asp Gly Tyr Ser Gly Asp Gly Lys Ser Pro Leu Pro Gln
    290                 295                 300

Gln Gln Asp Arg Ala Ala Thr Gly Ser Pro Ala Ala Val Leu Asn Gly
305                 310                 315                 320

Met Pro Gln Leu Gln Arg Gln Ala Ser Asp Tyr Tyr Met Asn Ala Met
                325                 330                 335

Asn Gly Gly Met Ala Ala Val Pro Pro His Leu Arg Asn Ala Met Gln
            340                 345                 350

Pro Ser Pro Arg Ala Gln Ser Pro Gln Gln Tyr Pro Met Pro Val Asn
        355                 360                 365

Gly Asn Thr Pro Gln Ser Arg Pro Ser Leu Thr Ser Asn Pro Ser Ser

```
                        370                 375                 380
Ser Ala His Leu Pro Gln Ile Leu Glu Pro Pro Thr Thr Asn Gly Gln
385                 390                 395                 400

Gln Gln Thr Gly Ser Gly Asn Asn Ser Pro His Leu Asn Asn Asn Asn
                405                 410                 415

Asn Asn Pro Met Asn Gly Trp Gln Ser Pro His Pro Gly Met Pro Ala
            420                 425                 430

Asn Ala Ser Gln Thr Thr Asp Tyr Thr Tyr Pro Asp Pro Asn Asn His
            435                 440                 445

Tyr Gly Val Ser Asn Val Asn Thr Ala Gln Met Tyr Tyr Gln Gln Gln
            450                 455                 460

Gly Val Pro Arg Pro His Ser Thr Gln Pro Leu Asp Tyr Gln His Gln
465                 470                 475                 480

Gly Gln Pro Met Trp Ala Gln His Gln Gln
                485                 490

<210> SEQ ID NO 75
<211> LENGTH: 535
<212> TYPE: PRT
<213> ORGANISM: Artificial Sequence
<220> FEATURE:
<223> OTHER INFORMATION: synthesized

<400> SEQUENCE: 75

Met Gln Leu Pro Thr Pro Ser Gly Trp Gly Trp Gln Gln Asn Glu
1               5                   10                  15

Val Glu Ser Gly Tyr Val His Met Gly Ser Pro Met Met Gly Thr Gln
                20                  25                  30

Ala Pro Leu Pro Gln Pro Thr Leu Ser Pro Gln Tyr Pro Val Thr Leu
            35                  40                  45

Ala Pro Ser Pro Ser Leu Gln Gln Pro Met Ser Tyr Gly Pro Tyr Ala
        50                  55                  60

His Gly Leu Pro Ser Val Ala Pro Leu Gln Ile Pro Thr Ile Gly Ser
65                  70                  75                  80

Gln His Ser His His Tyr Gln His Gln His Gln Gln His Gln
                85                  90                  95

Ile Gln Leu Ser Asp Ser Ile Asp Arg Thr Arg Lys Arg Leu Val Asn
                100                 105                 110

Arg Arg Ser Leu Arg Asp Thr Thr Met Glu Ile Met Glu Ala Arg His
            115                 120                 125

Arg Gly His Thr Thr Pro Glu Arg Ala Thr His Arg Ile Pro Gln Thr
        130                 135                 140

Val Val Ala Asn Ala Ser Thr Val Gly Ala Ser His Ala Gly Asn His
145                 150                 155                 160

Val Glu Phe Asn Thr Ser Val Asp Lys Leu Met Lys Val Ile Gln Ala
                165                 170                 175

Met Pro Asp Thr Gly Pro Leu Val Glu Ser Leu Glu Ala Ala Val Lys
            180                 185                 190

Gln Glu Leu Pro Gln Val Glu Glu Ser Glu Gln Ala Ala Ser Pro Pro
        195                 200                 205

His Glu Ser Lys Pro Ala Lys Gln Lys Ala Ala Met Arg Lys Phe Ala
        210                 215                 220

Cys His Phe Arg Gly Cys Gln Lys Lys Phe Ala Gln Lys Ala Gln Leu
225                 230                 235                 240

Asp Thr His Val Arg Ser His Thr Gly Glu Arg Pro Tyr Val Cys Glu
```

```
                    245                 250                 255
Phe Pro Asn Cys Gly Lys Arg Phe Thr Gln Ser Gly Asn Leu His Thr
            260                 265                 270

His Glu Arg Lys His Thr Gly Glu Arg Pro Tyr Val Cys Asp Val Cys
        275                 280                 285

Gly Arg Arg Phe Ala Gln Gly Asn Arg Gln Ala His Lys Lys Val
    290                 295                 300

His Gln Lys Thr Lys Asp Phe Ile Cys Arg Leu Glu Asn Cys Gly Lys
305                 310                 315                 320

Glu Phe Thr Gln Arg Gly Asn Leu Lys Asn His Gln Asn Asn Thr His
                325                 330                 335

Lys Gln Phe Met Asp Gln Thr Met Ala Arg Leu Glu Arg Ile Ser Pro
            340                 345                 350

Glu Asn Met Ser Pro Glu Asp Arg Asp Leu Val Val Tyr Leu Ala Pro
        355                 360                 365

Leu Tyr Lys Asn Ser Asn Lys Gly Ile Lys Gly Arg Gly Ala Arg Pro
    370                 375                 380

Ala Gly Tyr Arg Leu Ser Arg Ser Arg Arg Ala Pro Ser Val Ser Ser
385                 390                 395                 400

Ser Thr Gln Ser Tyr Ser Pro Thr Lys Ser Glu Ala Ser Leu Thr Ser
                405                 410                 415

Ser Pro Cys Thr Ala Gly Pro Pro Ser Gln His His Tyr Gly Gly His
            420                 425                 430

Ala Gln His Gln Tyr His His Gln His His His Gln Gln Gln
        435                 440                 445

Gln Gln Arg Pro Gln Gln Gly Leu Ala Tyr Pro Pro Val Ser Phe Gly
    450                 455                 460

Ser Ala Pro Ser Asp Ser Phe Arg Tyr Pro Tyr Asn Gly Ile Val His
465                 470                 475                 480

Arg Tyr Glu Met Pro Glu His Ser His Thr Tyr Ser Gly Ile Pro Val
                485                 490                 495

Thr Thr Ser Ser Ser Thr Pro Ser Pro Val Ala Thr Val Tyr Ser Asp
            500                 505                 510

Asp Ser Gly Ala Val Tyr His Ser Asp Asp Asn Gly Ala Arg Glu Leu
        515                 520                 525

Ala Phe Gly Glu Arg Ile Cys
    530                 535

<210> SEQ ID NO 76
<211> LENGTH: 341
<212> TYPE: PRT
<213> ORGANISM: Artificial Sequence
<220> FEATURE:
<223> OTHER INFORMATION: synthesized

<400> SEQUENCE: 76

Met Val Arg Thr Arg Ser Phe Pro Cys Ser Trp Val Ser Cys Lys Lys
1               5                   10                  15

Val Phe Asn Arg Lys Ser Asp Leu Cys Arg His Tyr Arg Ile His Thr
            20                  25                  30

Asn Glu Arg Pro Tyr Arg Cys Asn Phe Pro Asn Cys Thr Lys Ser Phe
        35                  40                  45

Ile Gln Arg Ser Ala Leu Thr Val His Ser Arg Thr His Thr Gly Glu
    50                  55                  60

Lys Pro His Val Cys Asn Phe Ala Asn Cys Ser Lys Ala Phe Ser Asp
```

```
                65                  70                  75                  80
        Ser Ser Ser Leu Ala Arg His Arg Ile His Thr Gly Arg Arg Pro
                        85                  90                  95

Tyr Lys Cys Leu Glu Pro Thr Cys Asp Arg Ser Phe Cys Arg Lys Thr
                        100                 105                 110

Thr Leu Thr Lys His Gln Ser Arg Ser His Gln Pro Glu Ala Val Ser
                        115                 120                 125

Pro Ser Ala Gln Ser Cys Glu Ser Glu Leu Tyr Ser Gln Pro Thr Gln
                    130                 135                 140

His Ser Met Ser Met Met Pro Gln Ser Ser Pro Val Ser Gln His Gln
        145                 150                 155                 160

Leu Gln Ser Gln Gln Gln Glu Gln Gln Gln His Gln Gln Gln His Leu
                        165                 170                 175

Gln Pro Gln Pro Arg Pro Gln Gln His Ser Pro Tyr Gln Gln His
                        180                 185                 190

Ser Pro Ile Ile Ala Val Pro Val Ser Asp Tyr Phe His His Ala Gln
                        195                 200                 205

Ser Gln Pro Thr Thr Val His Ser Ile Pro Ile Ser Ala Glu Gln Pro
                    210                 215                 220

Ile Leu Pro Pro Gln Val His Tyr Val Ser Thr Gly Ile Leu Pro Pro
        225                 230                 235                 240

Gln Ile Pro Arg Tyr Asp Ile Pro Ile Thr Thr Ser Ala Ala Val Ser
                        245                 250                 255

Ile Pro Thr Thr Ile Asp Gln Leu Thr Tyr Ala His Pro Val Ser Val
                        260                 265                 270

Ser Met Pro Gln Gln Arg Ile Gln Ala Pro Gln Pro Ile Gln Val
                    275                 280                 285

Ser His Gln Thr Asp Gly Gly Phe Gln Val Leu Pro Val Val Ala Gly
                    290                 295                 300

Gly Ala Gly Gly Gln Tyr Met Lys Glu Phe Asp His Met Lys His Gly
        305                 310                 315                 320

Gln Gln Arg Phe Phe Gly Ser Thr Tyr Pro Glu His Met Asn Trp Asp
                        325                 330                 335

Phe Leu Gly Leu Ser
                    340

<210> SEQ ID NO 77
<211> LENGTH: 441
<212> TYPE: PRT
<213> ORGANISM: Artificial Sequence
<220> FEATURE:
<223> OTHER INFORMATION: synthesized

<400> SEQUENCE: 77

Met Glu Ile Pro Thr Ile Leu Asn Arg Lys Ala Ser Ala Ala Val Val
1               5                   10                  15

Ala Asp Pro Arg Phe Gln Ala Gln Leu Ala Gln Ala Val His Leu His
                20                  25                  30

Gln Gln Glu Met Ser Glu Gln Ala Asn Ser Gln Pro Gly Thr His Ala
            35                  40                  45

Val Met Gly Tyr Pro Pro Asn Ala Gln Pro Leu His Gln Gly Pro Met
        50                  55                  60

Pro Gly Gln His Trp Pro Ile His Pro Asn Gly Ala Pro Met Met Pro
65                  70                  75                  80

Asn Asn Trp Asp Pro Asn Pro Phe Ala Gly Ala Pro Pro Gln Pro Pro
```

85                  90                  95

Gln Pro Ser His Thr Pro Pro Val Pro Gln Gln Gln Pro Arg Ala Glu
                100                 105                 110

Pro Ala Pro Arg Val Phe His Cys Ser Thr Cys Gln Lys Gly Phe Ala
            115                 120                 125

Arg Arg Ser Asp Leu Ala Arg His Glu Arg Ile His Ser Gly Ile Arg
        130                 135                 140

Pro His Ala Cys Asp Trp Pro Gly Cys Gly Lys Gln Phe Ile Gln Arg
145                 150                 155                 160

Ser Ala Leu Thr Val His Ala Arg Val His Thr Gly Glu Lys Pro His
                165                 170                 175

Met Cys Glu Arg Cys Gly Lys Pro Phe Ser Asp Ser Ser Leu Ala
                180                 185                 190

Arg His Arg Arg Ile His Ser Gly Lys Arg Pro Tyr Lys Cys Pro Tyr
            195                 200                 205

Ala Asn Cys Gln Lys Thr Phe Thr Arg Arg Thr Thr Leu Thr Arg His
        210                 215                 220

Gln Asn His His Thr Gly Thr Ile Glu Glu Ala Ala Ala Gln Thr Glu
225                 230                 235                 240

Ala Ser Leu Arg Gln Asn Arg Glu Lys Ser Ala Arg Ala Ser Glu Gly
                245                 250                 255

Ile Tyr Ser Glu Thr Gly Ser Gly His Ser Thr Pro Ser Pro Gly Gln
                260                 265                 270

Gln Ala Ala Met Gly Leu Gly Ser Glu Leu Pro Pro Leu Asn Ile Ile
            275                 280                 285

Arg Ser Thr Gly Glu Tyr Tyr Ile Pro Asn Gly Gly Ile Pro Pro His
        290                 295                 300

Val Arg Gly Asp Phe Gln Gln Ala Ser Pro Arg Ala Ser Pro Ala Ala
305                 310                 315                 320

Thr Ser Pro Ala Leu Ser Ser Tyr Ser Ser His Pro Arg Pro Ser Met
                325                 330                 335

Thr Ser His Pro Ser Ser Tyr Gly Pro Pro Gln Pro Leu Glu Pro Pro
            340                 345                 350

Ala Asn Thr Asp His Arg Pro Gly Ser Val Thr Gly Ser Pro His Met
        355                 360                 365

Thr Ser Met Gly Trp Ala Ser Pro Ser His Ala Ser Met Pro Ser Pro
    370                 375                 380

Gly Ser Pro His Glu Phe Gly Tyr Pro Glu Pro Ser Val Ala Ala Tyr
385                 390                 395                 400

Ala Ser Ala Met Pro Pro His Met Tyr Phe Pro Asn Ser Thr Ile Arg
                405                 410                 415

Arg Pro Gly Ser Thr Glu Pro Glu Asn Tyr Glu Met Lys Pro Lys Ile
            420                 425                 430

Gly Pro Asp Gly Trp Ser Thr Pro Ile
            435                 440

<210> SEQ ID NO 78
<211> LENGTH: 444
<212> TYPE: PRT
<213> ORGANISM: Artificial Sequence
<220> FEATURE:
<223> OTHER INFORMATION: synthesized

<400> SEQUENCE: 78

Met Asp Ile Thr Thr Ile Leu Asn Arg Lys Gly Ser Thr Ala Ala Ile

-continued

```
1               5                   10                  15
Ala Ala Glu Ala Gln Phe Gln Gln Phe Val His His Asn Leu Asp
                20                  25                  30
Pro Ser Ser Ser Pro Lys Met Lys Pro Glu Pro Gly Val Ser Glu Ala
                35                  40                  45
Ser Asp Gln Gln Val Leu Ser Tyr Pro Ser His Ala Pro Leu Asn Pro
    50                  55                  60
Met Pro Asn Met Ala Gln Asp Met Arg Tyr Pro Pro His Gly Gln Pro
65                  70                  75                  80
Asn Ser Gly Met Pro Val Leu Gln Asn Pro Tyr Val Pro Gly Ala Tyr
                85                  90                  95
Thr Gly Ser Ala Gln Ile Pro Ser Ser Ala Thr Pro Gln Arg Ala Asp
                100                 105                 110
Pro Pro Pro Lys Thr Phe His Cys Ser Thr Cys Gly Lys Gly Phe Ala
                115                 120                 125
Arg Arg Ser Asp Leu Ala Arg His Glu Arg Ile His Thr Gly Ile Arg
                130                 135                 140
Pro His Ala Cys Asp Trp Pro Gly Cys Gly Lys Gln Phe Ile Gln Arg
145                 150                 155                 160
Ser Ala Leu Thr Val His Ser Arg Val His Thr Gly Glu Lys Pro His
                165                 170                 175
Met Cys Glu Arg Cys Gly Lys Pro Phe Ser Asp Ser Ser Ser Leu Ala
                180                 185                 190
Arg His Arg Arg Ile His Ser Gly Lys Arg Pro Tyr Lys Cys Pro Tyr
                195                 200                 205
Ala Asn Cys Gln Lys Thr Phe Thr Arg Arg Thr Thr Leu Thr Arg His
                210                 215                 220
Gln Asn His His Thr Gly Thr Ile Glu Glu Ala Ala Glu Thr Glu
225                 230                 235                 240
Ala Asn Leu Arg Gln Asn Lys Glu Arg Ala Arg Ala Pro Gly Asp Gly
                245                 250                 255
Val Phe Ser Glu His Ala Ser Val His Ser Thr Pro Ser Pro Ala His
                260                 265                 270
His Pro Val Ser Ile Pro Pro Gly Asp Leu Pro Pro Leu Asn Met
                275                 280                 285
Pro Arg Ser Ala Gly Asp Tyr Tyr Met Gly Asn Gly Ser Ile Pro Pro
                290                 295                 300
His Val Arg Gly Asp Phe Ser Gln Ala Ser Pro Arg Ser Ser Pro Thr
305                 310                 315                 320
Ala Thr Ser Pro Ser Leu Ser Ser Phe Ser Ser Ala Pro His Gln Arg
                325                 330                 335
Pro Ser Met Thr Ser His Pro Ser Gly Tyr Ala Pro Pro Gln Pro Leu
                340                 345                 350
Glu Pro Pro Ala Asn Ser Asp His Arg Pro Asn Ser Val Ser Gly Ser
                355                 360                 365
Pro His Met Thr Ser Leu Gly Trp Ala Ser Pro Ser His Gly Ser Ile
                370                 375                 380
Pro Ser Pro Gly Ser Val Asn Asp Phe Asn Tyr Pro Glu Pro Ser Gly
385                 390                 395                 400
Pro Ala Tyr Pro Ser Ser Met Pro Pro His Met Tyr Phe Pro Asn Ser
                405                 410                 415
Thr Ile Arg Arg Pro Thr Ser Thr Glu Pro Glu Asn Tyr Glu Leu Lys
                420                 425                 430
```

```
Pro Arg Leu Gly Asp Asn Gly Trp Ser Thr Pro Val
        435                 440

<210> SEQ ID NO 79
<211> LENGTH: 456
<212> TYPE: PRT
<213> ORGANISM: Artificial Sequence
<220> FEATURE:
<223> OTHER INFORMATION: synthesized

<400> SEQUENCE: 79

Met Glu Thr Ala Glu Pro Val Ser Tyr Glu Phe Pro Gly His Thr Ile
1               5                   10                  15

Gly Ala Val Ala Pro Arg Arg Met Met Thr Ser Asn Leu Gly His Asn
            20                  25                  30

Phe Pro Phe Tyr Ala Thr Pro Ala Ala Ser Phe Pro Leu Pro Phe His
        35                  40                  45

Gln Ser Ser Ser Thr Ala Tyr Gly Phe Gly His Ala Leu Asn His His
    50                  55                  60

His His Asn His His Gln Pro Ser Tyr Pro Gln Phe Phe Val Ala Ser
65                  70                  75                  80

His Glu Ser Ile Asn Ser Gln Pro Met Arg Leu Ser Ser Glu Pro Pro
                85                  90                  95

Pro Val Gln Ser Ile Pro Asp Ile Arg Pro Ala Lys Asn Ala Val Asn
            100                 105                 110

Arg Val Ser Arg Asp Pro Leu Val Lys Asn Asp Pro Ser Ser Asn Thr
        115                 120                 125

Gln Gln Thr Pro Met Ala Arg Ser Ser Thr His Gly Ala Ala Ala Gln
    130                 135                 140

Ser Lys Ser Pro Ser Val Ser Glu Ile Glu Phe Thr Thr Glu Val Asp
145                 150                 155                 160

Ile Leu Met Lys Ala Ile Gln Ser Arg Asn Ser Val Gln Pro Pro Asn
                165                 170                 175

Thr Gln Ser Leu Pro Pro Leu Gln Gln Leu Thr His Arg Gly Cys His
            180                 185                 190

Gly Tyr Pro Gln Thr Phe Ser Leu His Pro Ser Gly Asn Thr Arg Cys
        195                 200                 205

Asn Met Met Ala Glu Val Gln Ser Arg Ser Gly Lys Lys Arg Lys
    210                 215                 220

Tyr Val Cys Thr Leu Pro His Cys Gly Lys Ser Phe Ala Gln Lys Thr
225                 230                 235                 240

His Leu Asp Ile His Thr Arg Ala His Thr Gly Asp Lys Pro Phe Ile
                245                 250                 255

Cys Lys Glu Pro Ser Cys Gly Gln Arg Phe Ser Gln Leu Gly Asn Leu
            260                 265                 270

Lys Arg Glu Lys Thr Asp Ser Asn Pro Gly Ala His Lys Gln Thr His
        275                 280                 285

Gln Arg Arg His Thr Gly Glu Lys Pro Phe Ser Cys Asp Ile Cys Gln
    290                 295                 300

Lys Arg Phe Ala Gln Arg Gly Asn Val Arg Ala His Lys Ile Thr His
305                 310                 315                 320

Gln His Ala Lys Pro Phe Thr Cys Leu Leu Asp Asp Cys Gly Lys Gln
                325                 330                 335

Phe Thr Gln Leu Gly Asn Leu Lys Ser His Gln Asn Lys Phe His Ala
            340                 345                 350
```

```
Thr Thr Leu Arg Asp Leu Thr Leu Lys Phe Ser Gln Val Thr Ile Gly
            355                 360                 365

Asp Pro Met Ser Pro Gln Asp Arg Lys Leu Trp Glu Tyr Phe Ala Thr
    370                 375                 380

Leu Tyr Lys Asn Ser Asn Lys Gly Ile Lys Gly Arg Gly Lys Asp Arg
385                 390                 395                 400

Arg Ile Ser Pro Thr Ser Arg Ser Gly Pro Gly Lys Arg His Gln Thr
                405                 410                 415

Leu Gly Asn Asn Asp Asp Lys Leu Gln Arg Pro Ile Tyr Glu Glu Ser
                420                 425                 430

Ser Val Tyr Thr Gly Gly Ser Ser Ser Asp Glu Glu Asp Ala Glu Ala
            435                 440                 445

Tyr Tyr Ile Asp Arg Gln Asn His
    450                 455

<210> SEQ ID NO 80
<211> LENGTH: 423
<212> TYPE: PRT
<213> ORGANISM: Artificial Sequence
<220> FEATURE:
<223> OTHER INFORMATION: synthesized

<400> SEQUENCE: 80

Ser Glu Thr Gly Ser Glu Arg Gly Ala Ser Pro His Thr Ser Asp Gln
1               5                   10                  15

Ser Ser Arg Tyr Ser Ser Gln Thr Pro Gln Asn Ser Ala Val Tyr Gln
            20                  25                  30

Gln Met Ala Ala Gln Leu Thr Asn Gly Leu Gln Tyr Thr Ala Pro Pro
        35                  40                  45

Gln Met Gln Gln Gln Asn Gly Met Ser Leu Leu Gln His Ser Tyr His
    50                  55                  60

Pro Ala Thr Gly Gln Glu Pro Ser Tyr Gln Thr Gln Pro Gln Gln
65                  70                  75                  80

Gln Gln Ser Gln Gln Ser Thr Gln Leu Gly Leu Pro Lys Ala Phe
            85                  90                  95

Ser Cys Asn Thr Cys Gln Lys Gly Phe Ala Arg Arg Ser Asp Leu Ala
            100                 105                 110

Arg His Glu Arg Ile His Ser Gly Val Arg Pro His Val Cys Glu His
        115                 120                 125

Pro Asn Cys Gly Lys Gln Phe Ile Gln Arg Ser Ala Leu Thr Val His
    130                 135                 140

Ser Arg Val His Thr Gly Glu Lys Pro His Met Cys Glu Arg Cys Gly
145                 150                 155                 160

Lys Pro Phe Ser Asp Ser Ser Leu Ala Arg His Arg Arg Ile His
                165                 170                 175

Ser Gly Lys Arg Pro Tyr Lys Cys Pro Tyr Ala Asp Cys Gln Lys Thr
            180                 185                 190

Phe Thr Arg Arg Thr Thr Leu Thr Arg His Gln Asn His His Thr Gly
        195                 200                 205

Thr Ile Glu Glu Ser Glu Ala Ala Thr Ala Ala Leu Ala Ser Arg
    210                 215                 220

Ala Ser Leu Pro Gln Gln Arg Ser Arg Gly Ser Asp Glu Glu Asn Asp
225                 230                 235                 240

Phe Ser Ala Asp Gly Lys Ser Pro Met Pro Pro Gln His Asp Arg Pro
                245                 250                 255
```

```
Ser Ala Ser Pro Ala Asn Gly Met Asn Gly Ala Pro Gln Leu Gln Arg
            260                 265                 270

Gln Ala Ser Asp Tyr Tyr Leu Asn Ala Met Asn Gly Gly Met Ala Ser
            275                 280                 285

Val Pro Ala His Leu Arg Asn Asp Met Gln Pro Thr Pro Arg Ser Gln
            290                 295                 300

Ser Pro Ala Gln Tyr Thr Met Pro Val Asn Pro Gln Ser Arg Pro
305                 310                 315                 320

Thr Leu Ala Ser Asn Pro Ser Ala Ser Tyr Ala Ser Arg Gln Ile Leu
                325                 330                 335

Glu Pro Asn Gly Ala Ser Val Gln Gln Gln Gly Thr Ser Gly Thr Asn
            340                 345                 350

Ser Pro His Met Asn Gly Asn Ile Ala Trp Gln Pro Ser His His Gly
            355                 360                 365

Leu Pro Thr Thr Gln Thr Thr Asp Tyr Thr Tyr Pro Asp His Thr Gly
            370                 375                 380

Tyr Ser Val Ala Asn Pro Met Tyr Tyr Gln Gln Gly Ser Val Gln Arg
385                 390                 395                 400

Pro His Ser Thr Gly Pro Ile Asp His Tyr Gly Pro Met Arg Gly Gln
                405                 410                 415

Glu Met Trp Ala Gln His Gln
            420

<210> SEQ ID NO 81
<211> LENGTH: 503
<212> TYPE: PRT
<213> ORGANISM: Artificial Sequence
<220> FEATURE:
<223> OTHER INFORMATION: synthesized

<400> SEQUENCE: 81

Lys Leu Ala Leu Ala Ala Gln Pro Thr Ala Asn Pro Asn Trp Gly Arg
1               5                   10                  15

Trp Pro Gln Gln Leu Ser Gly Glu Tyr Thr Met Met Glu Ser Pro Ser
            20                  25                  30

Met Leu Pro Phe Asp Ser Arg Thr Ala Thr Ala Pro Leu Gln Arg
            35                  40                  45

Pro Ile Met Ala Pro Tyr Met Val Pro Asn Ser Tyr Ser Ser Ala Gln
    50                  55                  60

Met Asn Ser Leu Thr Ala Thr His Tyr Gln Ala Pro Asn Pro Tyr Gln
65                  70                  75                  80

Phe Ser Gly Tyr Gln Gly Pro Pro Thr Pro Pro His Asn Ser Ser Pro
                85                  90                  95

Phe Lys Val Glu Tyr His Asp Arg Pro Met Gly Pro Asp Ser Asp
            100                 105                 110

Asn Gly Arg Val Pro Ser Tyr His Arg Gly Ala Lys Tyr Ser Tyr Ala
            115                 120                 125

Glu Gln Ala Pro Ser Pro Ala Arg Ser Asp Ser Gln Ala Ser Thr Ala
    130                 135                 140

Arg Ser Ser Val Asn Asn Pro Thr Leu Cys Ser Lys Thr Ile Thr Ser
145                 150                 155                 160

Asn Glu Thr Ile Asn Pro Asp Asp Gln Val Asn Phe Glu Thr Glu Val
                165                 170                 175

Asp Glu Leu Met Lys Ala Ile Gln Arg Lys Gly Glu Lys Glu Leu Asp
            180                 185                 190
```

```
Val Ala Gln Gln Pro Leu Thr Pro Gly Met Ser Pro Val Ser Glu Ala
        195                 200                 205

Ser Leu Glu Asn Asn Gly Thr Pro Ala Pro Ala Asp Ser Lys Thr Ser
    210                 215                 220

Lys Lys Arg Tyr Val Cys Asn Gly Pro Asn Cys Arg Lys Ser Phe Thr
225                 230                 235                 240

Gln Lys Thr His Leu Asp Ile His Arg Thr His Thr Gly Asp Lys
                245                 250                 255

Pro Tyr Thr Cys Glu Phe Pro Gly Cys Lys Leu Thr Phe Ser Gln Leu
                260                 265                 270

Gly Asn Leu Lys Thr His Met Arg Arg His Thr Gly Glu Arg Pro Tyr
                275                 280                 285

Ser Cys Gly Lys Cys Gly Arg Lys Phe Ala Gln Arg Gly Asn Val Arg
                290                 295                 300

Ala His Glu Gln Thr His Gln Gly Leu Lys Pro Phe Ile Cys Arg Leu
305                 310                 315                 320

Asp Asp Cys Asn Lys Thr Phe Ser Gln Leu Gly Asn Met Lys Thr His
                325                 330                 335

Gln Asn Asn Phe His Lys Lys Thr Leu Lys Asn Leu Thr Met Arg Phe
                340                 345                 350

Ala Gln Ile Leu Asn Ser Gly Glu Glu Val Pro Glu Ala Glu Arg Glu
                355                 360                 365

Leu Phe Glu Tyr Phe Ala Thr His Tyr Lys Asn Ser Asn Lys Gly Ile
                370                 375                 380

Lys Gly Arg Gly Lys Ala Arg Thr Val Ala Arg Lys Thr Lys Pro
385                 390                 395                 400

Ser Gln Ser Pro Pro Thr Asn Pro Asn Thr Val Thr Pro Gln Tyr Pro
                405                 410                 415

Leu Pro Gln Ile Pro Pro Thr Gln Gln Ile Pro Ser Pro His Gln Pro
                420                 425                 430

His Gly Leu Ser His Pro Gly Ser Leu Ala Ala Tyr Ser Met Ser Arg
                435                 440                 445

Gly His Pro Asn Val Ile Asn Asn Met Pro Arg Glu Ser His Ala Gly
                450                 455                 460

Gly Tyr Glu Met Tyr Asp Met Gln Gly Gly His His Val Gln Pro
465                 470                 475                 480

Ser Asn Asn Asn Gly Met Met Tyr Glu Glu His Ala Arg Glu Met
                485                 490                 495

Gly Phe Asn Glu Arg Met Tyr
                500

<210> SEQ ID NO 82
<211> LENGTH: 446
<212> TYPE: PRT
<213> ORGANISM: Artificial Sequence
<220> FEATURE:
<223> OTHER INFORMATION: synthesized

<400> SEQUENCE: 82

Met Gln His Glu Gln Leu Gln Gln His Phe Gly Pro Thr Ser Phe Leu
1               5                   10                  15

Asn Gly Arg Ile Lys Ser Glu Asn Gly Ser Asp Arg Gly Val Ser Pro
                20                  25                  30

His Pro Ser Asp Ser Ser Arg Tyr Ser Ser Gln Ala Pro Gln Pro Leu
                35                  40                  45
```

Gln Ser Tyr Pro Pro Met Thr Asn Asn Met Asn Gly Met Arg Tyr
            50                  55                  60

Pro Ser Pro Ser Gln Met Asn Thr Pro Met Pro Met Leu Asn Asn Asn
65                  70                  75                  80

Asn Tyr Ile Pro Asn Pro Pro Glu His Ala Tyr Pro Gln Gln Ala Thr
                85                  90                  95

Pro Asp Pro Gln Gln Gln His Leu Gly Gly Arg Pro Ala Ser Asp Thr
            100                 105                 110

Gly Pro Pro Lys Ala Phe Ala Cys Ser Thr Cys Ala Lys Gly Phe Ala
            115                 120                 125

Arg Arg Ser Asp Leu Ala Arg His Glu Arg Ile His Ser Gly Ile Arg
            130                 135                 140

Pro His Val Cys Asp His Pro Gly Cys Gly Lys Gln Phe Ile Gln Arg
145                 150                 155                 160

Ser Ala Leu Thr Val His Gln Arg Val His Thr Gly Glu Lys Pro His
                165                 170                 175

Met Cys Glu Arg Cys Gly Lys Pro Phe Ser Asp Ser Ser Leu Ala
            180                 185                 190

Arg His Arg Arg Ile His Ser Gly Lys Arg Pro Tyr Lys Cys Pro Tyr
            195                 200                 205

Ala Asp Cys Gln Lys Thr Phe Thr Arg Arg Thr Thr Leu Thr Arg His
            210                 215                 220

Gln Asn His His Thr Gly Thr Val Glu Glu Ala Ala Ala Thr Ala
225                 230                 235                 240

Ala Ala Leu Ala Ser Arg Ala Ser Ala Pro Ser Arg Ser Ala Arg Ser
                245                 250                 255

Asp Ala Asp Glu Tyr Ser Glu Thr Ala Ser Pro Leu Gly Thr Pro Ser
            260                 265                 270

Pro His Glu Arg Pro Leu Ser Leu Ser Pro Ala Asn Gly Met Pro Val
            275                 280                 285

Val Pro Ala Met His Arg Gln Ala Ser Asp Tyr Ala Tyr Met Gly Ser
            290                 295                 300

Met Asn Val Pro Pro His Leu Arg Asn Glu Met Pro Gln Pro Ser Pro
305                 310                 315                 320

Arg Ser Ser Pro Ala Leu Thr Ser Gln Ser Tyr Asn Ser Ala Val Ser
                325                 330                 335

Asn Thr Arg Pro Thr Ile Thr Ser His Pro Ser Gly Tyr Gly Pro Pro
            340                 345                 350

Pro Ile Leu Glu Pro Pro Ala Ser Ala Asn His Asn Gln Pro Gly Ser
            355                 360                 365

Val Asn Gly Ser Pro His Met Gly Ala Met Gly Trp Gln Ser Pro Ser
            370                 375                 380

Gln Gln Ala Met Pro Ser Pro Gly Pro Gly Asp Asn Tyr Val Tyr Pro
385                 390                 395                 400

Glu Pro His Tyr Ala Asn Asn Gly Ser Asn Met Tyr Tyr Ala Asn Ser
                405                 410                 415

Asn Ile Arg Arg Pro Asn Ser Thr Glu Pro Asp Gln Tyr Asn Pro Gln
            420                 425                 430

Gln Gln Arg Met Ala Gly Asp Met Trp Ala Pro Pro Val Gln
            435                 440                 445

<210> SEQ ID NO 83
<211> LENGTH: 442

<212> TYPE: PRT
<213> ORGANISM: Artificial Sequence
<220> FEATURE:
<223> OTHER INFORMATION: synthesized

<400> SEQUENCE: 83

| | | | | | | | | | | | | | | |
|---|---|---|---|---|---|---|---|---|---|---|---|---|---|---|
| Met | Asp | Ile | Thr | Thr | Ile | Leu | Asn | Arg | Lys | Ala | Ser | Val | Ala | Met | Val |
| 1 | | | | 5 | | | | | 10 | | | | | 15 | |
| Ala | Pro | Asp | Ala | Gln | Phe | Asp | Gln | Gln | Gln | Phe | Met | Gln | Ala | Ser | Asn |
| | | | 20 | | | | | 25 | | | | | 30 | | |
| Leu | Asn | Thr | Ser | Pro | Ser | Pro | Gly | Met | Lys | Ser | Glu | Pro | Asn | Val | Ser |
| | | | 35 | | | | | 40 | | | | | 45 | | |
| Glu | Ala | Ala | Asn | Gln | Ser | Val | Leu | Ser | Tyr | Pro | Pro | His | Ala | Pro | Met |
| | 50 | | | | | 55 | | | | | 60 | | | | |
| Asn | Gln | Pro | Pro | Asn | Met | Asn | Gln | Asp | Ile | Arg | Tyr | Ala | Val | Gln | Gln |
| 65 | | | | | 70 | | | | | 75 | | | | | 80 |
| Pro | Asn | Pro | Gln | Leu | Pro | Met | Leu | Gln | Ser | Pro | Tyr | Ala | Pro | Ser | Gly |
| | | | | 85 | | | | | 90 | | | | | 95 | |
| Tyr | Ser | Ala | Ala | Ser | Val | Pro | Ile | Ser | Ala | Pro | Gln | Gly | Arg | Pro | Glu |
| | | | | 100 | | | | | 105 | | | | | 110 | |
| Pro | Pro | Pro | Lys | Thr | Phe | His | Cys | Gly | Thr | Cys | Gly | Lys | Gly | Phe | Ala |
| | | | | 115 | | | | | 120 | | | | | 125 | |
| Arg | Arg | Ser | Asp | Leu | Ala | Arg | His | Glu | Arg | Ile | His | Ser | Gly | Ile | Arg |
| | | 130 | | | | | 135 | | | | | 140 | | | |
| Pro | His | Ala | Cys | Asp | Trp | Pro | Gly | Cys | Gly | Lys | Gln | Phe | Ile | Gln | Arg |
| 145 | | | | | 150 | | | | | 155 | | | | | 160 |
| Ser | Ala | Leu | Thr | Val | His | Ser | Arg | Val | His | Thr | Gly | Glu | Lys | Pro | His |
| | | | | 165 | | | | | 170 | | | | | 175 | |
| Met | Cys | Glu | Arg | Cys | Gly | Lys | Pro | Phe | Ser | Asp | Ser | Ser | Ser | Leu | Ala |
| | | | 180 | | | | | 185 | | | | | 190 | | |
| Arg | His | Arg | Arg | Ile | His | Ser | Gly | Lys | Arg | Pro | Tyr | Lys | Cys | Pro | Tyr |
| | | | | 195 | | | | | 200 | | | | | 205 | |
| Ala | Asn | Cys | Gln | Lys | Thr | Phe | Thr | Arg | Arg | Thr | Thr | Leu | Thr | Arg | His |
| | | 210 | | | | | 215 | | | | | 220 | | | |
| Gln | Asn | His | His | Thr | Gly | Thr | Ile | Glu | Glu | Ala | Ala | Ala | Glu | Thr | Glu |
| 225 | | | | | 230 | | | | | 235 | | | | | 240 |
| Ala | Asn | Leu | Arg | Gln | Asn | Lys | Glu | Arg | Ala | Lys | Val | Pro | Gly | Asp | Gly |
| | | | | 245 | | | | | 250 | | | | | 255 | |
| Met | Phe | Ser | Asp | His | Gly | Ser | Val | His | Gly | Ser | Val | His | Ser | Thr | Pro |
| | | | 260 | | | | | 265 | | | | | 270 | | |
| Ser | Pro | Ala | His | His | Pro | Ile | Ser | Pro | Gly | Gly | Glu | Leu | Pro | Pro | Leu |
| | | | | 275 | | | | | 280 | | | | | 285 | |
| Thr | Ile | Pro | Arg | Ser | Thr | Gly | Glu | Tyr | Tyr | Leu | Gly | Asn | Gly | Ser | Ile |
| | | | | 290 | | | | | 295 | | | | | 300 | |
| Pro | Ala | His | Val | Arg | Gly | Asp | Phe | Gln | Gln | Ala | Ser | Pro | Arg | Ala | Ser |
| 305 | | | | | 310 | | | | | 315 | | | | | 320 |
| Pro | Thr | Ala | Thr | Ser | Pro | Ser | Leu | Ser | Ser | Tyr | Ser | Ser | Ala | Pro | Leu |
| | | | | 325 | | | | | 330 | | | | | 335 | |
| Pro | Arg | Pro | Ser | Met | Thr | Ser | His | Pro | Ser | Thr | Tyr | Ala | Pro | Pro | Gln |
| | | | | 340 | | | | | 345 | | | | | 350 | |
| Pro | Leu | Glu | Pro | Pro | Ala | Thr | Lys | Asp | His | Arg | Pro | Asn | Ser | Val | Gly |
| | | | | 355 | | | | | 360 | | | | | 365 | |
| Gly | Ser | Pro | His | Met | Ser | Ser | Leu | Gly | Trp | Pro | Ser | Pro | Ser | His | Ser |
| | | | 370 | | | | | 375 | | | | | 380 | | |

```
Pro Val Ser Ala Pro Asp Phe Gly Tyr Pro Glu Ser Gly Pro Pro
385                 390                 395                 400

Tyr Pro Gly Ser Val Pro Pro His Met Tyr Phe Pro Asn Ser Thr Ile
            405                 410                 415

Arg Arg Pro Ala Ser Thr Glu Pro Glu Asn Tyr Glu Leu Arg Pro Arg
            420                 425                 430

Leu Gly Asp Asn Ser Trp Ser Thr Pro Ala
        435                 440
```

<210> SEQ ID NO 84
<211> LENGTH: 460
<212> TYPE: PRT
<213> ORGANISM: Artificial Sequence
<220> FEATURE:
<223> OTHER INFORMATION: synthesized

<400> SEQUENCE: 84

```
Met Asp Ile Thr Thr Ile Leu Asn Arg Lys Ala Ser Val Ser Val Val
1               5                   10                  15

Ala Ala Asp Val His Arg Leu Gln Gln His Ile Val His Ala Gln Ala
            20                  25                  30

Gln Thr Asp Asp Val Leu Lys Ser Arg Pro Ser Glu Met Gly Ser
        35                  40                  45

Glu His His Arg Ser Ala Ser Ala Pro Pro Ser Glu His His His His
    50                  55                  60

His His His His Gln Pro Thr Ser Ser Phe Pro Ser Ser Thr Gln Ser
65                  70                  75                  80

Leu Pro Gln Met Ala His Leu Ala Gln Tyr His Val Gln Ala Gln Ala
                85                  90                  95

Asn His Ser Ser Pro Asn Pro Gly Tyr Ala His Ser Ala His Gly Ser
            100                 105                 110

Asp Tyr Gly Arg Ser Ser Gly Gly Asn Met Arg Pro Thr Gly Leu Pro
            115                 120                 125

Ala Leu Lys Thr Phe His Cys Gln Thr Cys Ser Lys Gly Phe Ala Arg
130                 135                 140

Arg Ser Asp Leu Ala Arg His Glu Arg Ile His Ser Gly Ile Arg Pro
145                 150                 155                 160

His Ala Cys Asp Trp Pro Gly Cys Gly Lys Gln Phe Ile Gln Arg Ser
            165                 170                 175

Ala Leu Thr Val His Thr Arg Val His Thr Gly Glu Lys Pro His Met
            180                 185                 190

Cys Asp Arg Cys Gly Lys Pro Phe Ser Asp Ser Ser Leu Ala Arg
            195                 200                 205

His Arg Arg Ile His Ser Gly Lys Arg Pro Tyr Lys Cys Pro Tyr Ala
210                 215                 220

Asn Cys Gln Lys Thr Phe Thr Arg Arg Thr Thr Leu Thr Arg His Gln
225                 230                 235                 240

Asn His His Thr Gly Thr Ile Glu Glu Ala Ala Glu Thr Glu Ala
            245                 250                 255

Asn Leu Arg His Ser Lys Asp Arg Thr Thr Thr Arg Pro Ser Asp
            260                 265                 270

Tyr Ser Glu Pro Gly Ser Ala His Ser Thr Pro Ser Pro Ala Gln Arg
            275                 280                 285

Pro Ser Leu Ser Pro Gly Asn Glu Leu Pro Pro Leu Asn Leu Ser Arg
            290                 295                 300
```

Pro Ser Ala Gly Pro Thr Ser Ser Gly Gly Ala Asp Tyr Tyr Thr Ser
305                 310                 315                 320

Leu Pro Pro His Leu Arg Thr Asp Phe Ala Asn Ser Ser Pro Arg Ala
            325                 330                 335

Ser Pro Thr Ser Pro Ser Pro Thr Leu Thr Ser Leu Ser Gly Pro Ala
            340                 345                 350

Ser Phe His His His Asn His Asn Arg Pro Ser Leu Thr Ser His Pro
            355                 360                 365

Ser Gly Tyr Ala Pro Pro Gln Pro Leu Glu Pro Ala Asn Ser Asp
            370                 375                 380

Pro Arg Pro Asn Ser Val Ala Gly Ser Pro His Leu Ser Ser Val Gly
385                 390                 395                 400

Trp Ala Ser Pro Thr Leu Ser Ser Met Pro Ser Pro Ser Ser Ala Ser
                405                 410                 415

Ala Pro Glu Tyr Ser Tyr Pro Glu Pro Ala Ser His Gln Tyr Pro Gly
            420                 425                 430

Gly Ile Thr Pro His Met Phe Phe Pro Arg Arg Pro Gln Ser Ser Glu
            435                 440                 445

Pro Glu Asn Tyr Glu Met Lys Pro Lys Leu Glu Leu
450                 455                 460

<210> SEQ ID NO 85
<211> LENGTH: 439
<212> TYPE: PRT
<213> ORGANISM: Artificial Sequence
<220> FEATURE:
<223> OTHER INFORMATION: synthesized

<400> SEQUENCE: 85

Met Ser Pro Ser Pro Thr Pro Gln Pro Trp Asp Gln Trp Ser Gln Gln
1               5                   10                  15

Gln Gln Gln Gln Gln Gln Pro Gln His His Ser Gly Tyr Pro Leu Met
                20                  25                  30

Asp Gln Ser Val Phe Pro Gln Tyr Ala Pro Pro Thr Gln Tyr Asp
            35                  40                  45

Pro Arg Thr Ser Gln Tyr Asp Pro Arg Thr Val Val Thr Ser Gly Pro
50                  55                  60

Leu Ile Ala Pro His Met Ala Pro His Tyr Val Thr Ala Pro Ala Tyr
65                  70                  75                  80

Gly Val Ser Pro Ile Ser Asn Met Lys Pro His Phe Ser Thr Gln Thr
                85                  90                  95

His Tyr Ser Tyr Gly Gln Tyr Asp Gln Pro Thr Gly His Leu Ala Met
                100                 105                 110

Pro Tyr Ser Arg Met Ser Pro Gln Gln Glu Arg Leu Gly Leu Pro Met
            115                 120                 125

Val Ser Gln Met Pro Gln Gln Gln His Leu His Ser Gln Gln Arg Gln
130                 135                 140

Gln Arg Ser Pro Ser Ala Ala Arg Ser Glu Thr Leu Ser Ala Pro Lys
145                 150                 155                 160

Thr Pro Asp Pro Met Asn Thr Lys Glu Ile Thr Tyr Asn Lys Pro Val
                165                 170                 175

Met Thr Asp Asp Val Val Phe Thr Thr Pro Val Asp Val Met Met Lys
            180                 185                 190

Ala Leu Gln Lys Arg Lys Asp Lys Glu Asp Leu Ala Ser Ser Asn Ser
            195                 200                 205

```
Ser Glu Val Gly Ala Gly Ser Val Lys Ser Glu Pro Ser Pro His
    210                 215                 220
Pro Ser Ser Thr Asp Gly Ser Gln Glu Thr Thr Asp Lys Val Lys
225                 230                 235                 240
Tyr Arg Cys Pro Tyr Asp Gly Cys Pro Lys Ser Phe Gln Gln Ser Thr
                245                 250                 255
His Leu Glu Thr His Lys Arg Ala His Thr Gly Asp Lys Pro Tyr Lys
                260                 265                 270
Cys Glu Trp His Gly Cys Gly Arg Arg Phe Ser Gln Pro Gly Asn Leu
            275                 280                 285
Lys Thr His Thr Arg Leu His Thr Gly Glu Arg Pro Phe Glu Cys Glu
    290                 295                 300
Met Cys Gly Ala Cys Phe Ala Gln Arg Gly Asn Leu Thr Ala His Lys
305                 310                 315                 320
Ala Thr His Ser Lys Thr Lys Pro Phe Val Cys Lys Leu Asp Thr Cys
                325                 330                 335
Asn Lys Cys Phe Thr Thr Arg Gly Asn Leu Lys Asn His Gln Asn Lys
                340                 345                 350
Tyr His Lys Glu Thr Ile Ala Gln Leu Val Asp Trp Ile Ile Ser Leu
            355                 360                 365
Thr Asp Val Asp Ala Leu Ser Ala Lys Asp Arg Asp Leu Leu Trp Tyr
    370                 375                 380
Phe Ser Asn Ile Tyr Lys Asn Ser Asn Lys Gly Ile Lys Gly Arg Gly
385                 390                 395                 400
Arg Asp Arg Arg Val Ser Glu Val Arg Met Gly Lys Thr Lys Leu Ser
                405                 410                 415
Ser Pro Gly Met Gly Leu Pro Arg Ser Lys Met Leu Asp Ser Ser Phe
            420                 425                 430
Ser Arg Leu Gly Leu Gly Phe
            435

<210> SEQ ID NO 86
<211> LENGTH: 405
<212> TYPE: PRT
<213> ORGANISM: Artificial Sequence
<220> FEATURE:
<223> OTHER INFORMATION: synthesized

<400> SEQUENCE: 86

Met Lys Pro Glu Pro Gly Val Pro Glu Ala Pro Asp Gln Gln Val Leu
1               5                   10                  15
Ser Tyr Pro Pro His Ala Pro Leu Asn Ser Met Pro Ser Met Val Pro
                20                  25                  30
Asp Met Arg Tyr Ser Gln Gly Gln Pro Asn Ser Gly Met Pro Leu Leu
            35                  40                  45
Gln Asn Ala Tyr Val Pro Gly Val Tyr Thr Thr Asn Ala Gln Ile Pro
    50                  55                  60
Asn Gly Ala Thr Pro Gln Arg Ala Asp Pro Pro Lys Thr Phe His
65                  70                  75                  80
Cys Ser Thr Cys Gly Lys Gly Phe Ala Arg Arg Ser Asp Leu Ala Arg
                85                  90                  95
His Glu Arg Ile His Thr Gly Ile Arg Pro His Ala Cys Asp Trp Pro
            100                 105                 110
Gly Cys Gly Lys Gln Phe Ile Gln Arg Ser Ala Leu Thr Val His Ser
    115                 120                 125
```

```
Arg Val His Thr Gly Glu Lys Pro His Met Cys Glu Arg Cys Gly Lys
130                 135                 140

Pro Phe Ser Asp Ser Ser Leu Ala Arg His Arg Ile His Ser
145                 150                 155                 160

Gly Lys Arg Pro Tyr Lys Cys Pro Tyr Ala Asn Cys Gln Lys Thr Phe
                165                 170                 175

Thr Arg Arg Thr Thr Leu Thr Arg His Gln Asn His His Thr Gly Thr
                180                 185                 190

Ile Glu Glu Ala Ala Ala Glu Thr Glu Ala Asn Leu Arg Gln Asn Lys
                195                 200                 205

Glu Arg Ala Arg Val Pro Gly Asp Gly Ala Phe Ser Glu His Ala Ser
210                 215                 220

Val His Ser Thr Pro Ser Pro Ala His His Pro Ala Ala Asn Pro Pro
225                 230                 235                 240

Pro Gly Asp Leu Pro Pro Leu Asn Met Pro Arg Ser Thr Gly Asp Tyr
                245                 250                 255

Tyr Met Gly Asn Gly Ser Ile Pro Pro His Val Arg Gly Asp Phe Ser
                260                 265                 270

Gln Ala Ser Pro Arg Ala Ser Pro Thr Ala Thr Ser Pro Ser Leu Ser
                275                 280                 285

Ser Phe Ser Asn Ala Pro His Pro Arg Pro Ser Met Thr Ser His Pro
290                 295                 300

Ser Gly Tyr Ala Pro Pro Gln Pro Leu Glu Pro Ala Asn Ser Asp
305                 310                 315                 320

His Arg Pro Asn Ser Val Ser Gly Ser Pro His Met Thr Ser Leu Gly
                325                 330                 335

Trp Ala Ser Pro Ser His Gly Ser Ile Pro Ser Pro Gly Ser Val Asn
                340                 345                 350

Asp Phe Asn Tyr Pro Glu Pro Ser Gly Pro Ala Tyr Pro Asn Ser Met
                355                 360                 365

Pro Pro His Met Tyr Phe Pro Asn Ser Thr Ile Arg Arg Pro Gly Ser
                370                 375                 380

Thr Glu Pro Glu Asn Tyr Glu Met Lys Pro Arg Leu Gly Asp Asn Gly
385                 390                 395                 400

Trp Ser Thr Pro Val
                405

<210> SEQ ID NO 87
<211> LENGTH: 463
<212> TYPE: PRT
<213> ORGANISM: Artificial Sequence
<220> FEATURE:
<223> OTHER INFORMATION: synthesized

<400> SEQUENCE: 87

Met Ser Asp Pro Arg Pro Ala Val Ser Pro Thr Val Ser Val Ser Gly
1               5                   10                  15

Ala Gly Ala Ala Ala Leu Gln Ser His Met Ser Leu Glu Ala Val Lys
                20                  25                  30

Gln Glu Thr His Gly Leu Gln Pro Leu Gln Gln His Tyr His His Gln
                35                  40                  45

Leu Ala Pro Gly Pro Met Asp Arg Ala Asp Ser Pro His Gly Ser Glu
            50                  55                  60

His Ser Arg Tyr Ser Val Pro Pro Leu Asn Gly Met Asp Gln Pro Arg
65                  70                  75                  80
```

Pro Tyr Gly Ser Pro Thr Ala Met His Ala Pro Leu His Leu Ser Asp
            85                  90                  95

Met Asn Arg Pro Pro Thr Ser Leu Pro Met Asn Ser Leu Pro Leu Pro
        100                 105                 110

Ala Ile Gln Pro Thr Leu Ala Pro Ala Pro Gln Ala Ala Gly Ala Val
            115                 120                 125

Tyr Gly Ser Gln Glu Thr Pro Gln Pro Pro Lys Ala Tyr Pro Cys
        130                 135                 140

Ser Thr Cys Gly Lys Gly Phe Ala Arg Arg Ser Asp Leu Ala Arg His
145                 150                 155                 160

Glu Arg Ile His Ser Gly Val Arg Pro His Ile Cys Glu Phe Pro Gly
                165                 170                 175

Cys Asn Lys Lys Phe Ile Gln Arg Ser Ala Leu Thr Val His Gln Arg
            180                 185                 190

Val His Thr Gly Glu Lys Pro His Gln Cys Glu Arg Cys Gly Lys Pro
        195                 200                 205

Phe Ser Asp Ser Ser Ser Leu Ala Arg His Arg Arg Ile His Ser Gly
    210                 215                 220

Lys Arg Pro Tyr Lys Cys Pro Tyr Ala Asp Cys Gln Lys Thr Phe Thr
225                 230                 235                 240

Arg Arg Thr Thr Leu Thr Arg His Gln Asn His His Thr Gly Thr Ile
                245                 250                 255

Glu Glu Ala Ala Ala Ala Thr Arg Glu Ala Leu Ala Arg Gly Pro Thr
            260                 265                 270

Gly Thr Ala Arg Met Thr Pro Thr His Val Thr Arg Ser Glu Gly Asp
        275                 280                 285

Ala Gly Ser Gly Ser Asn His Ala Ser Pro Met Ser Thr Pro Ser Pro
    290                 295                 300

Ala His Arg Thr Asn Ser Met Ser Pro Ser Asn Glu Leu Ala Gly Ile
305                 310                 315                 320

Gly Ser Ile Gln Ser Gln Tyr Val Asn Asn Ser Leu Pro Ser His Leu
                325                 330                 335

Arg Gly Asp Val His Ala Ala Ser Pro Thr Ser Thr Thr Ser Ser Gly
            340                 345                 350

Tyr Thr Asn Asn Arg Pro Thr Ser His Pro Thr Gly Tyr Gly Pro Pro
        355                 360                 365

Gln Val Leu Glu Pro Asn Val Glu Thr Arg Pro Gly Pro Gly Ser Ala
    370                 375                 380

Ser Gly Ser Pro His Leu Gly Ser Val Gly Trp Gln Ser Pro Ser His
385                 390                 395                 400

Val Gly Ser Pro Ser His Ser Thr Ser Gly Phe Val Tyr Pro Asp Pro
                405                 410                 415

Glu Ala Tyr Pro Ser Ser Ala Gly Met Gly Pro Leu Phe Tyr Ser Asn
            420                 425                 430

Ala Ile Ala Gly Val Arg Ser Gly Ser Ala Pro Gly Gln Asn Asn
        435                 440                 445

Asp Tyr Pro Lys Ser Arg Ser Ser Glu Leu Trp Ala Ser Ala Gln
450                 455                 460

<210> SEQ ID NO 88
<211> LENGTH: 462
<212> TYPE: PRT
<213> ORGANISM: Artificial Sequence
<220> FEATURE:
<223> OTHER INFORMATION: synthesized

<400> SEQUENCE: 88

```
Met Leu Pro Leu Asp Ser Arg Thr Thr Thr Gly Pro Pro Gln Arg
1               5                   10                  15

Pro Ala Met Ala Pro Tyr Met Met Tyr Gln Ser His Gly Pro Gly Pro
                20                  25                  30

Val Asn Ser Phe Ala Ala Ser Tyr Tyr Gln Thr Pro Asn Pro Tyr Gln
            35                  40                  45

Phe Gly Glu Tyr Gln Gly Pro Pro Thr Pro Pro His Leu Val Ala Pro
    50                  55                  60

Pro Lys Ile Gln Tyr Tyr Asp His Asn Ala Val Gly His Asp Lys Asp
65                  70                  75                  80

Asp Gly Arg Thr Pro Ser Tyr Pro Arg Glu Met Glu Tyr Thr Tyr Ala
                85                  90                  95

Glu Gln Ala Pro Ser Pro Ala Arg Ser Asp Leu Gln Ala Ser Thr Val
                100                 105                 110

Arg Tyr Ser Gly Thr Lys Pro Ser Met Thr Ser Lys Thr Ile Ile Ser
            115                 120                 125

Asn Glu Thr Leu Asn Pro Gly Asp Gln Thr Asn Phe Val Thr Glu Val
130                 135                 140

Asp Glu Leu Met Lys Val Ile Gln Arg Lys Ala Asp Leu Gln Val Gly
145                 150                 155                 160

Ala Gly Gln Gln Pro Leu Ala Pro Val Met Ser Ser Val Ser Val Ile
                165                 170                 175

Ser Gln Gly Thr Pro Gly Ser Ile Asp Asn Lys Thr Ala Arg Lys Arg
            180                 185                 190

Tyr Arg Cys Asp Gly Pro Ser Cys Gln Lys Ser Phe Thr Gly Lys Thr
            195                 200                 205

His Leu Asp Ile His Arg Arg Thr His Thr Gly Ile Lys Pro Tyr Ile
        210                 215                 220

Cys Asp Phe Pro Gly Cys Asp Leu Thr Phe Ser Gln Leu Gly Asn Leu
225                 230                 235                 240

Lys Thr His Lys Arg Arg His Thr Gly Glu Arg Pro Phe Ala Cys Glu
                245                 250                 255

Gln Cys Asp Arg His Phe Ser Gln Arg Gly Asn Leu Gln Ala His Leu
            260                 265                 270

Glu Ser His Lys Gly Leu Lys Pro Phe Ile Cys Ile Leu Asp Asp Cys
        275                 280                 285

Asn Lys Thr Phe Thr Leu Leu Gly Asn Met Lys Thr His Gln Asn Ser
    290                 295                 300

Leu His Lys Glu Thr Leu Glu Glu Leu Thr Met Lys Phe Thr Lys Ile
305                 310                 315                 320

Ile Ala Ser Gly Glu Lys Val Cys Glu Ala Asp Arg Glu Leu Phe Glu
                325                 330                 335

Tyr Phe Ala Thr His Tyr Lys Asn Ser Asn Lys Gly Ile Arg Gly Arg
            340                 345                 350

Gly Asp Ala Arg Thr Val Ala Asp His Lys Thr Arg Met Glu Met Asn
        355                 360                 365

His Pro Val Asn Thr Met Thr Ala Val Pro Gln His Pro Leu Pro Gln
    370                 375                 380

Ile Val Ser Thr Pro Ile Pro Leu His Gly Leu Pro Val Ser Val Ser
385                 390                 395                 400

Leu Ala Ser Tyr Ser Val Ser Arg Val Gln Pro Gly Pro Ile Asn Pro
```

```
                    405                 410                 415
Met Ser Thr Gln Thr His Ala Gly Gly Tyr Glu Met Tyr Asp Met Asn
            420                 425                 430

Gly His His Arg Ile Gln Pro Leu Asn Ser His Gly Leu Ser Tyr Asp
        435                 440                 445

Thr Asn Ser Ala Arg Glu Met Gly Tyr His Glu Arg Met Tyr
    450                 455                 460

<210> SEQ ID NO 89
<211> LENGTH: 440
<212> TYPE: PRT
<213> ORGANISM: Artificial Sequence
<220> FEATURE:
<223> OTHER INFORMATION: synthesized

<400> SEQUENCE: 89

Met Asp Phe Thr Thr Ile Leu Asn Arg Lys Asn Ser Ala Ala Ala Ala
1               5                   10                  15

Ala Ala Ala Glu Ala Gln Leu Gln Gln Gln Tyr Phe Gln Gln Ser Ala
            20                  25                  30

Gln Leu His Thr Gly Ala Ser Pro Thr Met Lys Ser Glu Ser Gly Gly
        35                  40                  45

Ser Asp Asn Pro Val Asn Ala Tyr Pro Pro His Gly Pro Pro Pro Met
    50                  55                  60

Gln Met Asp Ala Gly Leu Ala Asp Ser Phe Tyr Tyr Ala Gln Pro Thr
65                  70                  75                  80

Gly Ser Thr Pro Arg Asn Met Ala Tyr Ala Pro Ala Gly Tyr Ala Gly
                85                  90                  95

Asp Pro Gln Met Gln Gln Glu Pro Val Pro Gln Gly Arg Ala Gly Val
            100                 105                 110

Glu Pro Pro Pro Lys Thr Phe His Cys Ser Thr Cys Asn Lys Gly Phe
        115                 120                 125

Ala Arg Arg Ser Asp Leu Ala Arg His Glu Arg Ile His Thr Gly Val
    130                 135                 140

Arg Pro His Ala Cys Glu Trp Pro Gly Cys Gly Lys Gln Phe Ile Gln
145                 150                 155                 160

Arg Ser Ala Leu Thr Val His Ser Arg Val His Thr Gly Glu Lys Pro
                165                 170                 175

His Met Cys Glu Arg Cys Gly Lys Pro Phe Ser Asp Ser Ser Ser Leu
            180                 185                 190

Ala Arg His Arg Arg Ile His Ser Gly Lys Arg Pro Tyr Lys Cys Pro
        195                 200                 205

Tyr Ala Asn Cys Gln Lys Thr Phe Thr Arg Arg Thr Thr Leu Thr Arg
    210                 215                 220

His Gln Asn His His Thr Gly Thr Ile Glu Glu Ala Ala Ala Glu Thr
225                 230                 235                 240

Glu Ala Gln Leu Arg Gln Asn Lys Asp Arg Gly Arg Pro Gly Glu Gly
                245                 250                 255

Met Phe Ser Glu His Ala Ser Ile His Ser Thr Pro Ser Pro Ala Gln
            260                 265                 270

His Pro Ser Met Ser Pro Gly Gly Glu Leu Pro Leu Asn Met His
        275                 280                 285

Arg Ser Ala Gly Asp Tyr Tyr Met Gly Thr Gly Pro Ile Pro Pro His
    290                 295                 300

Val Arg Gly Asp Phe Pro Gln Gly Ser Pro Arg Ala Ser Pro Thr Ala
```

```
                305                 310                 315                 320
        Thr Ser Pro Ser Leu Ser Ser Tyr Gly Ser Ala Pro His Thr Arg Pro
                        325                 330                 335

Ser Met Thr Ser His Pro Tyr Ala Pro Pro Gln Pro Leu Glu Pro Pro
                        340                 345                 350

Ala Asn Ser Asp His Arg Pro Asn Ser Val Asn Gly Ser Pro His Met
                        355                 360                 365

Thr Ser Leu Gly Trp Ala Ser Pro Ser His Gly Ser Met Pro Ser Pro
                        370                 375                 380

Gly Ser Ala Asn Asp Phe Thr Tyr Pro Glu Pro Thr Gly Pro Ala Tyr
        385                 390                 395                 400

Pro Thr Ser Met Pro Pro His Met Tyr Phe Pro Asn Ser Thr Ile Arg
                        405                 410                 415

Arg Pro Thr Ser Thr Glu Pro Glu Asn Tyr Glu Met Lys Pro Arg Gly
                        420                 425                 430

Asp His Ser Trp Ser Thr Ala Val
                        435                 440

<210> SEQ ID NO 90
<211> LENGTH: 395
<212> TYPE: PRT
<213> ORGANISM: Artificial Sequence
<220> FEATURE:
<223> OTHER INFORMATION: synthesized

<400> SEQUENCE: 90

Met Ala Glu Asp Pro Glu Arg Pro Arg Pro Phe Leu Cys Asp Trp Gln
        1               5                   10                  15

Gly Cys Gly Lys Arg Phe Asn Arg Lys Ser Asp Leu Gln Arg His His
                        20                  25                  30

Arg Ile His Thr Asn Glu Arg Pro Tyr Gly Cys Asn Trp Gln Asp Cys
                        35                  40                  45

Gly Lys Arg Phe Ile Gln Arg Ser Ala Leu Thr Val His Leu Arg Thr
                        50                  55                  60

His Thr Gly Glu Lys Pro His Gln Cys Glu Val Pro Glu Cys Arg Lys
        65                  70                  75                  80

Pro Phe Ala Asp Ser Ser Ser Leu Ala Arg His Arg Ile His Arg
                        85                  90                  95

Gly Glu Lys Pro Tyr Arg Cys Gln Asp Val Gly Cys Asn Lys Ala Lys
                        100                 105                 110

Thr Thr Arg Asp Lys His His Thr Asn Ser His Arg Gly Gly Ile Asn
                        115                 120                 125

Arg Ser Met Thr Pro Arg Gln Gln Leu His Pro Ser Phe Gly Ser Gly
                        130                 135                 140

Phe Asp Gln Phe His Met Ser Ala Pro Pro Glu Leu Thr Ala Ser Thr
        145                 150                 155                 160

Asp Ser Ser Pro Ala Asp Ser Thr Ala Tyr Ser Pro Ala Ala Leu Glu
                        165                 170                 175

Gly Asp Trp Ser Ser Gln Asn Phe Asn Asn Tyr Thr His Met Pro Asn
                        180                 185                 190

Leu Gln Glu Ala Ser Ile Ala Leu Gln Asn Gln Ile Arg Ser Gln Gln
                        195                 200                 205

Ile Pro Gln Leu Met Pro Tyr Met Ser Ser Arg Val Val Pro Ser Tyr
                        210                 215                 220

Ser Ala Pro Pro Pro Asn Met Met Gly Gln Gln Met Pro Gln Gln Gly
```

-continued

```
            225                 230                 235                 240
        Ser Phe Ser Ser Tyr Ser Pro Ser Pro Val Asp Ser Thr Gln Gln Gln
                        245                 250                 255

Pro Trp Ala Thr Gly Leu Gln Asn Asn Gln Arg His Tyr Gln Arg Val
                        260                 265                 270

Leu Thr Ser Asn Asp Thr Ala Pro Arg Met Phe Ser Pro Tyr Pro Ala
                        275                 280                 285

Pro Pro Asn Met Met Thr Ser Gln Asn Asp Phe Asn Asn Gln Tyr Pro
                        290                 295                 300

Pro Pro Gln Gln Gln Gln Ser Trp Gly Met Pro Gln Asn Gln Gly Gln
        305                 310                 315                 320

Gln Asp Gln Arg His Tyr Ser Leu Ser Ser Pro Ser Gln Pro Leu Thr
                        325                 330                 335

Pro Val Pro Val Ser Ala Gly Pro Gly Thr Met Gln Pro Leu Gln Ser
                        340                 345                 350

Met Pro Gly His Ile Tyr Gly Ala Arg Leu Val Gly Asp Asp Leu Ser
                        355                 360                 365

Asp His Phe Phe Lys Val Glu Thr Thr Ala Asp Glu Asn Asn Pro Gly
                        370                 375                 380

Met Thr Leu Pro Asp Ala Arg Phe Ala Gly Leu
        385                 390                 395

<210> SEQ ID NO 91
<211> LENGTH: 471
<212> TYPE: PRT
<213> ORGANISM: Artificial Sequence
<220> FEATURE:
<223> OTHER INFORMATION: synthesized

<400> SEQUENCE: 91

Met Ser Asn Ile Asn Gln Asn Gln Asn Pro Gly Ala Asn Gly Gly Ala
1               5                   10                  15

Ser Met Asp Ile Thr Asn Ile Leu Asn Thr Lys Gly Gly Ala Ala Ala
                20                  25                  30

Ala Ala Ala Ala Gly Ala Ser Pro Ser Asp His Thr Phe His Gln
            35                  40                  45

Gln Leu Met His Ala Ser Gly Gly Gln Ala Asn Ser Glu Thr Ala Ser
    50                  55                  60

Glu Arg Gly Gly Ser Pro His Gly Ser Glu His Ser Ser Arg Tyr Ser
65                  70                  75                  80

Gly Pro Pro Ser Met Gly His Met Asn Gly Met Gly Asn Gly Met Arg
                85                  90                  95

Tyr Pro Ser Pro Thr Ala Met Gln Ser Pro Leu Pro Met Gln Ala Gly
                100                 105                 110

Phe Arg Asn Asp Gly Phe Asp Gly Ser Ala Pro Gln His Gln Glu Ile
            115                 120                 125

Pro Arg Ser Thr Gly Arg Leu Pro Pro Gly His Gly Val Thr Gln Gln
        130                 135                 140

Lys Ala Phe Pro Cys Thr Val Cys Gln Lys Gly Phe Ala Arg Arg Ser
145                 150                 155                 160

Asp Leu Ala Arg His Glu Arg Ile His Ser Gly Ile Arg Pro His Val
                165                 170                 175

Cys Asp Tyr Pro Asn Cys Gly Lys Gln Phe Ile Gln Arg Ser Ala Leu
                180                 185                 190

Thr Val His Ala Arg Val His Thr Gly Glu Lys Pro His Met Cys Glu
```

```
                195                 200                 205
Arg Cys Gly Lys Arg Phe Ser Asp Ser Ser Leu Ala Arg His Arg
    210                 215                 220
Arg Ile His Ser Gly Lys Arg Pro Tyr Lys Cys Pro Tyr Ala Asp Cys
225                 230                 235                 240
Gln Lys Thr Phe Thr Arg Arg Thr Thr Leu Thr Arg His Gln Asn His
                245                 250                 255
His Thr Gly Thr Val Glu Glu Ala Ala Ala Thr Ala Ala Leu
            260                 265                 270
Ala Ser Arg Ala Gly Ser Asn Arg Ser Gly Arg Gly Pro Arg Ser Asp
            275                 280                 285
Gly Glu Gln Tyr Ser Ala Thr Gly Ser Pro Met Ser Thr Pro Ser Pro
        290                 295                 300
Gly Gln Arg Thr His Ser Met Ser Pro Asn Ala Glu Leu Ala Pro Met
305                 310                 315                 320
Asn Gly Met Gln Arg His Met Gly Asp Tyr Pro Tyr Met Asn Asn Ser
                325                 330                 335
Ser Leu Pro Val His Leu Arg Asn Asp Tyr Ala Gln His Val Pro Met
            340                 345                 350
Gln Asn Ala Pro Leu Pro Gln Lys Gln Ser Gln Tyr Pro Asn Asn Gln
        355                 360                 365
Arg Pro Thr Ser His Pro Thr Gly Tyr Gly Pro Pro Gln Ile Leu Glu
    370                 375                 380
Pro Pro Ala Asn Pro Gln Ser Ala Gly Ser Ala Ser Gly Gly Ser Pro
385                 390                 395                 400
His Met Ser Asn Ala Gly Trp His Ser Pro Ser Asn Met Pro Ser Pro
                405                 410                 415
Thr Ser Gln Ser Asn Gly Tyr Val Tyr Pro Asp Pro Asp Pro Tyr Gly
            420                 425                 430
Ser Gly Gly Met Gly His Met Tyr Tyr Pro Asn Ser Asn Ile Arg Arg
            435                 440                 445
Pro Gln Ser Thr Glu Pro Asp Ser Tyr Glu Thr Lys Pro Arg Leu Asn
    450                 455                 460
Glu Leu Trp Thr Ala Ala Gln
465                 470

<210> SEQ ID NO 92
<211> LENGTH: 424
<212> TYPE: PRT
<213> ORGANISM: Artificial Sequence
<220> FEATURE:
<223> OTHER INFORMATION: synthesized

<400> SEQUENCE: 92

Met Val Ala Ala Asp Thr Pro Phe Asp Pro Ala His Leu Val Pro Asn
1               5                   10                  15
Pro Gly Met Asp His Ser Pro Lys Met Lys Ala Glu Pro Gly Ala Glu
            20                  25                  30
Ser Thr Asp Gln Gln Val Leu Ser Tyr Pro His His Ala Gln Leu Ser
        35                  40                  45
Gln Met Pro Ser Met Gln Gln Asp Leu Arg Tyr Ala Pro Gln Ala His
    50                  55                  60
Pro Asn Gln Gly Leu Pro Leu Leu Gln Asn Thr Phe Ile Pro Gly Ala
65                  70                  75                  80
Tyr Ala Gly Ala Gly Gln Leu Pro Ala Asn Val Pro Gln Gly Arg Pro
```

```
                    85                  90                  95
Asp Pro Pro Lys Thr Phe His Cys Gly Thr Cys Ser Lys Gly Phe
                100                 105                 110

Ala Arg Arg Ser Asp Leu Ala Arg His Glu Arg Ile His Ser Gly Ile
                115                 120                 125

Arg Pro His Ala Cys Asp Trp Pro Gly Cys Gly Lys Gln Phe Ile Gln
            130                 135                 140

Arg Ser Ala Leu Thr Val His Ala Arg Val His Thr Gly Glu Lys Pro
145                 150                 155                 160

His Met Cys Glu Arg Cys Gly Lys Pro Phe Ser Asp Ser Ser Ser Leu
                165                 170                 175

Ala Arg His Arg Arg Ile His Ser Gly Lys Arg Pro Tyr Lys Cys Pro
                180                 185                 190

Tyr Ala Asn Cys Gln Lys Thr Phe Thr Arg Arg Thr Thr Leu Thr Arg
            195                 200                 205

His Gln Asn His His Thr Gly Thr Ile Glu Glu Ala Ala Ala Glu Thr
        210                 215                 220

Glu Ala Asn Leu Arg Gln Asn Lys Glu Arg Ala Arg Val Ser Gly Asp
225                 230                 235                 240

Met Phe Ser Asp His Gly Ser Val His Ser Thr Pro Ser Pro Ala His
                245                 250                 255

His Pro Val Ser Pro Val Gly Asp Leu Pro Pro Leu Asn Met Pro Arg
                260                 265                 270

Ser Asp Tyr Tyr Met Thr Asn Gly Ser Ile Pro Pro His Val Arg Gly
            275                 280                 285

Gly Phe Pro Gln Val Ser Pro Arg Ala Ser Pro Thr Ala Thr Ser Pro
        290                 295                 300

Ser Leu Ser Ser Tyr Gly Ser Ala Pro His Val Arg Pro Ser Met Thr
305                 310                 315                 320

Ser His Pro Ser Gly Tyr Gly Pro Pro Gln Pro Leu Glu Pro Pro Ala
                325                 330                 335

Asn Asn Asp His Arg Pro Asn Ser Val Ser Gly Ser Pro His Met Thr
            340                 345                 350

Ser Leu Gly Trp Ala Ser Pro Ser His Ser Ser Ile Pro Ser Pro Gly
        355                 360                 365

Ser Ala Thr Asp Phe Gly Tyr Pro Glu Pro Ser Gly Ala Ala Tyr Ala
            370                 375                 380

Ser Ser Met Pro Pro His Met Tyr Phe Pro Ser Ser Thr Ile Arg Arg
385                 390                 395                 400

Pro Ala Ser Thr Glu Pro Asp Asn Tyr Glu Met Lys Pro Arg Leu Gly
                405                 410                 415

Asp Ser Ala Trp Ser Thr Pro Val
            420

<210> SEQ ID NO 93
<211> LENGTH: 555
<212> TYPE: PRT
<213> ORGANISM: Artificial Sequence
<220> FEATURE:
<223> OTHER INFORMATION: synthesized

<400> SEQUENCE: 93

Met His Thr Tyr Thr Asp Met Tyr Thr Phe Ala His Arg Leu His Thr
1               5                  10                  15

Pro Arg Ser Val Gln Ser Glu Cys Ala Ser Thr Cys Arg Ala Arg Leu
```

```
                20                  25                  30
Leu Ser Arg Val Pro Pro Ile Trp Arg Gly Thr Tyr Pro Thr Asn Arg
            35                  40                  45
Met Ala Leu Thr Ala Gln Pro Ser Ala Pro Ala Gly Trp Glu Arg Trp
        50                  55                  60
Pro Gln His His Pro Ser Asn Asp Tyr Val Met Asp Ala Asp Val
 65                 70                  75                  80
Met Pro Tyr Asn Ala Arg Pro Met Thr Thr Ala Pro Met Gln Gln Arg
                85                  90                  95
Pro Ser Leu Val Pro His Tyr Met Pro Thr Thr Ser Met Ser Thr Ala
            100                 105                 110
Ser Ile Asn Ser Ile Ser Ala Pro Ala His Tyr Gln Ser Pro Val Ser
            115                 120                 125
Tyr Gly Gly Gly Tyr Pro Ala Tyr Pro Leu Pro Thr Pro Thr Thr Met
            130                 135                 140
Asn Ser Ser Tyr Asn Lys His Gln Gln Tyr Gln Glu Arg Pro Ser Leu
145                 150                 155                 160
His Met Ile Thr Pro Glu Phe Glu Glu Thr Arg Gly Pro His His Ile
                165                 170                 175
Arg Asn Ala Arg Arg Tyr Ser Glu Glu Ser Arg Ser Pro Ser Glu Arg
                180                 185                 190
Ser Asp Ser Gln Gly Ser Thr Thr Glu Thr Thr Ile Ser Asn His Ser
            195                 200                 205
Ser Cys Ser Arg Thr Ile Thr Pro Asn Thr Pro Val Asn Gly Ala Pro
        210                 215                 220
Gln Val Glu Phe Ser Thr Ala Val Asp Lys Leu Met Lys Val Ile Gln
225                 230                 235                 240
Ser Lys Met Lys Asp Ala Asp Pro Glu Gln Ser Gly Asp Asp Lys Asp
                245                 250                 255
Ile Lys Ala Glu Gln Gln Ser Ser Pro Val Cys Gln Ala Arg Val Gln
                260                 265                 270
Gln Pro Ala Asp Lys His Lys Arg Lys Arg Tyr Glu Cys Gln Ile Glu
            275                 280                 285
Gly Cys Asn Lys Lys Phe Ser Gln Lys Thr His Arg Asp Thr His Val
        290                 295                 300
Arg Ser His Thr Gly Asp Arg Pro Tyr Val Cys Pro Ile Pro Gly Cys
305                 310                 315                 320
Gly Gly Arg Phe Thr Gln Ala Gly Asn Leu Lys Thr His Lys Arg Arg
                325                 330                 335
His Thr Gly Glu Arg Pro Tyr Arg Cys Glu Val Cys Asp Lys Gly Phe
            340                 345                 350
Val Gln Arg Gly Asp Val Lys Ala His Met Lys Thr His Leu Gly Thr
            355                 360                 365
Lys Ala Phe Leu Cys Arg Leu Asp Asn Cys His Lys Gln Phe Thr Gln
        370                 375                 380
Arg Gly Asn Leu Lys Tyr His Gln Asn Lys Tyr His Asn Glu Thr Ile
385                 390                 395                 400
Lys Ala Leu Ala Ala Arg Phe Asp Ala Ile Glu Asp Trp Ser Thr Val
                405                 410                 415
Leu Lys Glu Asp Met Glu Ile Phe Lys Asp Phe Ala Glu Val His Lys
                420                 425                 430
Asn Ser Asn Lys Gly Ile Lys Gly Arg Gly Lys His Arg Lys Val Lys
            435                 440                 445
```

Ser Val Pro Leu Ser Ser Pro Thr Ser Pro Thr Gly His Ser Pro Leu
    450                 455                 460

Pro Asn Ile Met Ala Ser Gln Tyr Pro Leu Pro Ser Ala Pro Gly Val
465                 470                 475                 480

Ser Gln Leu Leu His Thr Pro His Pro Leu His Pro Pro Leu His His
                485                 490                 495

Gln Gly Pro Ser His Ser Ala Met Tyr Gly Met Pro Arg Ser Ser Leu
            500                 505                 510

His Ser His Tyr Glu Thr Tyr Asp His His Glu Val Asp Thr Val Ala
        515                 520                 525

Ser Ser Arg Ala Ser Val Ala Glu Pro Ile Tyr His His Glu Glu His
    530                 535                 540

Pro Arg Glu Leu Ala Phe Gly Asp Arg Met Tyr
545                 550                 555

<210> SEQ ID NO 94
<211> LENGTH: 421
<212> TYPE: PRT
<213> ORGANISM: Artificial Sequence
<220> FEATURE:
<223> OTHER INFORMATION: synthesized

<400> SEQUENCE: 94

Met Arg Asn Gln Leu Pro Ala Gln Gln Gln Ser Asn Tyr Tyr Thr Asn
1               5                   10                  15

Ser Gln Pro Ala Gln Leu Pro Tyr Gln Gln Gln Gln Gln Gln Gln Gln
                20                  25                  30

Gln Gln Gln Gln Gln Gln Gln Gln Gln Gln Gln Gln Gln Gln Gln Gln
            35                  40                  45

Arg Gln Gln Thr Ser Lys Pro Arg Arg Asn Ser Asn Asn Arg Asp Ala
    50                  55                  60

Ile Ser Asp Gln Ser Leu Lys Ser Pro Ile Glu Ser Ser Ser Asn Glu
65                  70                  75                  80

Gly Asn Leu Val Pro Ala Gln Gln Tyr Val Lys Ser Glu Asp Gly Arg
                85                  90                  95

Pro Leu Leu Gly Ala Thr Lys Ile Asp Gln Leu Met Leu Val Ile Gln
            100                 105                 110

Ala Arg Asp Lys Gly Ile Thr Ser Pro Ile Gln Gln Ala Pro Asp Gly
        115                 120                 125

Ser Ile Leu Ala Ala Pro Asp Tyr Ser Leu Ser Arg Asp Lys Ser Glu
    130                 135                 140

Leu Asp Asn Gly Val Leu Pro Arg Pro Ile Ser Leu Val Gly Gly Val
145                 150                 155                 160

Asp Lys Pro Ser Lys Ala Lys Ile Lys Glu Asp Glu Gly Ser Asp Asp
                165                 170                 175

Glu Glu Ser Lys Gly Lys Arg Arg Lys His Lys Asn Gln Gln Cys Pro
            180                 185                 190

Tyr Cys Phe Lys Tyr Phe Thr Gln Ser Thr His Leu Glu Val His Ile
        195                 200                 205

Arg Ser His Ile Gly Tyr Lys Pro Phe Glu Cys Asn Tyr Cys His Lys
    210                 215                 220

Lys Phe Thr Gln Gly Gly Asn Leu Arg Thr His Leu Arg Leu His Thr
225                 230                 235                 240

Gly Glu Lys Pro Phe Thr Cys Asp Ile Cys Asn Arg Gln Phe Asn Arg
                245                 250                 255

```
Lys Gly Asn Leu Gly Ala His Lys Leu Thr His Glu Asn Leu Lys Pro
                260                 265                 270

Tyr Glu Cys Lys Leu Asp Gly Cys Asp Lys Ser Phe Thr Gln Leu Gly
            275                 280                 285

Asn Leu Lys Ser His Gln Asn Arg Phe His Leu Ser Thr Leu Asn His
        290                 295                 300

Leu Thr Gln Lys Leu Ala Glu Leu Ser Gly Leu Ser Ile Glu Asn Leu
305                 310                 315                 320

Pro Pro Asp Glu Lys Asp Leu Leu Met Tyr Phe Lys Asp Leu Tyr Lys
                325                 330                 335

Asn Ser Asn Lys Gly Ile Arg Gly Arg Gly Lys Ala Lys Leu Ser Lys
            340                 345                 350

Asp Asp Thr Gly Gly Ala Thr Ser Ser Ser Pro Asp Asn Ser Gln Phe
        355                 360                 365

Asn Leu Gln Ser Gln Ser Pro Gln Leu Gln Leu Gln Asn Leu Gln Ala
    370                 375                 380

Leu Pro Arg Gln Gln Asp Gln Gln Gln Gly Ser Pro Glu Tyr Ser Gln
385                 390                 395                 400

Ser Gln His Ser Leu Asp Phe Met Asn Pro His Leu Ala Gly Ser Ile
                405                 410                 415

Asn Gly Tyr Gln Gly
            420

<210> SEQ ID NO 95
<211> LENGTH: 444
<212> TYPE: PRT
<213> ORGANISM: Artificial Sequence
<220> FEATURE:
<223> OTHER INFORMATION: synthesized

<400> SEQUENCE: 95

Met Glu Ile Pro Thr Ile Leu Asn Arg Lys Ala Ser Ala Ala Val Ala
1               5                   10                  15

Ala Asp Pro Arg Phe Gln Ala Gln Leu Ala Gln Ala Val His Met His
            20                  25                  30

Thr Gln Glu Met Ser Glu Gln Ala Thr Ser Gln Pro Gly Asp His Thr
        35                  40                  45

Val Met Gly Tyr Pro Pro Asn Ala Gln Pro Leu His Gln Thr Gln Gln
    50                  55                  60

Met Ala Pro Gln Leu Trp Pro Thr His Pro Asn Gly Ala Pro Val Met
65                  70                  75                  80

Pro Pro Asn Gly Tyr Val His Thr Gly Phe Pro Ala Val Pro Pro Gln
                85                  90                  95

Gln Ser His Thr Pro Pro Val Gln Gln Gln Gln Gln Gln Gln Gln Ser
            100                 105                 110

Arg Pro Glu Pro Ala Pro Arg Val Phe His Cys Ser Thr Cys Gln Lys
        115                 120                 125

Gly Phe Ala Arg Arg Ser Asp Leu Ala Arg His Glu Arg Ile His Ser
    130                 135                 140

Gly Ile Arg Pro His Ala Cys Asp Trp Pro Gly Cys Gly Lys Gln Phe
145                 150                 155                 160

Ile Gln Arg Ser Ala Leu Thr Val His Ala Arg Val His Thr Gly Glu
                165                 170                 175

Lys Pro His Met Cys Glu Arg Cys Gly Lys Pro Phe Ser Asp Ser Ser
            180                 185                 190
```

```
Ser Leu Ala Arg His Arg Ile His Ser Gly Lys Arg Pro Tyr Lys
        195                 200                 205

Cys Pro Tyr Ala Asn Cys Gln Lys Thr Phe Thr Arg Arg Thr Thr Leu
210                 215                 220

Thr Arg His Gln Asn His His Thr Gly Thr Ile Glu Glu Ala Ala Ala
225                 230                 235                 240

Gln Thr Glu Ala Ser Leu Arg Gln Asn Arg Glu Arg Ser Ala Arg Ala
                245                 250                 255

Ser Glu Gly Ile Tyr Ser Glu Thr Gly Ser Gly His Ser Thr Pro Ser
                260                 265                 270

Pro Gly Gln Gln Ala Ser Met Gly Met Gly Ser Glu Leu Pro Pro Leu
                275                 280                 285

Asn Ile Ile Arg Ser Thr Gly Glu Tyr Tyr Ile Pro Asn Gly Gly Ile
            290                 295                 300

Pro Ala His Val Arg Gly Asp Phe Gln Gln Gly Ser Pro Arg Ala Ser
305                 310                 315                 320

Pro Ala Ala Thr Ser Pro Ser Leu Ser Ser Tyr Ser His Pro Arg
                    325                 330                 335

Pro Ser Met Thr Ser His Pro Ser Gly Tyr Gly Pro Gln Pro Leu
                340                 345                 350

Glu Pro Pro Ala Asn Asn Asp His Arg Pro Gly Ser Val Thr Gly Ser
                355                 360                 365

Pro His Met Thr Ser Met Gly Trp Ala Ser Pro Ser His Gly Ser Met
        370                 375                 380

Pro Ser Pro Gly Ser Pro His Asp Phe Gly Tyr Pro Glu Ser Asn Val
385                 390                 395                 400

Ala Ala Tyr Ala Ser Ala Met Pro Pro His Met Tyr Phe Pro Asn Ser
                405                 410                 415

Thr Ile Arg Arg Pro Gly Ser Thr Glu Pro Glu Asn Tyr Glu Met Lys
                420                 425                 430

Pro Arg Ile Gly Pro Asp Gly Trp Ser Thr Pro Met
            435                 440

<210> SEQ ID NO 96
<211> LENGTH: 344
<212> TYPE: PRT
<213> ORGANISM: Artificial Sequence
<220> FEATURE:
<223> OTHER INFORMATION: synthesized

<400> SEQUENCE: 96

Met Pro Arg Thr Arg Ser Phe Pro Cys Ser Trp Val Ser Cys Lys Lys
1                   5                   10                  15

Val Phe Asn Arg Lys Ser Asp Leu Cys Arg His Tyr Arg Ile His Thr
                20                  25                  30

Asn Glu Arg Pro Tyr Arg Cys Asn Phe Pro Asn Cys Thr Lys Ser Phe
            35                  40                  45

Ile Gln Arg Ser Ala Leu Thr Val His Ser Arg Thr His Thr Gly Glu
    50                  55                  60

Lys Pro His Val Cys Asn Phe Ala Asn Cys Ser Lys Ala Phe Ser Asp
65                  70                  75                  80

Ser Ser Ser Leu Ala Arg His Arg Arg Ile His Thr Gly Arg Arg Pro
                85                  90                  95

Tyr Lys Cys Leu Glu Pro Thr Cys Asp Arg Ser Phe Cys Arg Lys Thr
                100                 105                 110
```

Thr Leu Thr Lys His Gln Ser Arg Ser His Gln Pro Glu Ala Val Ser
        115                 120                 125

Pro Ser Ala Gln Ser Cys Glu Ser Glu Leu Tyr Ser Gln Gln Ala Gln
130                 135                 140

His Ser Ile Ser Met Met Ser Gln Ser Pro Gln Val Pro Gln His Gln
145                 150                 155                 160

Leu Gln Ser Gln Gln Pro Gln Pro Gln Asp Gln Gln Leu Gln Ser Gln
                165                 170                 175

Pro Gln His Leu Gln Ser Gln Pro Arg Pro Gln Gln His Ser Pro Tyr
            180                 185                 190

Gln Gln Gln His Ser Pro Ile Ile Ala Val Pro Val Ala Asp Tyr Phe
        195                 200                 205

His Ala Gln Ala Gln Pro Thr Thr Val His Ser Ile Pro Ile Ser Ala
210                 215                 220

Glu Gln Pro Ile Leu Pro Pro Gln Val His Tyr Val Thr Thr Gly Met
225                 230                 235                 240

Ile Ser Ser Gln Ile Pro Arg Tyr Asp Ile Pro Ile Thr Thr Ser Ala
                245                 250                 255

Pro Val Ser Thr Pro Thr Ser Met Asp His Leu Ala Tyr Asn His Pro
            260                 265                 270

Ile Ser Val Ser Met Pro Gln Gln Gln Arg Ile Gln Ala Pro Gln Pro
        275                 280                 285

Val Pro Ile Pro His Gln Ala Asp Gly Gly Phe Gln Val Leu Pro Val
290                 295                 300

Val Ala Gly Gly Ala Gly Gly Tyr Met Lys Glu Phe Asp Gln Met
305                 310                 315                 320

Lys His Gly Gln Gln Arg Phe Phe Gly Ser Ala Tyr Pro Asp Gln Met
                325                 330                 335

Asn Trp Glu Phe Leu Gly Leu Ser
            340

<210> SEQ ID NO 97
<211> LENGTH: 507
<212> TYPE: PRT
<213> ORGANISM: Artificial Sequence
<220> FEATURE:
<223> OTHER INFORMATION: synthesized

<400> SEQUENCE: 97

Met Ala Leu Thr Ala Gln Pro Ser Ala Pro Ala Gly Trp Glu Arg Trp
1               5                   10                  15

Pro Gln His His Pro Ser Asn Asp Tyr Val Met Met Asp Ala Asp Val
            20                  25                  30

Met Pro Tyr Asn Ala Arg Pro Met Thr Thr Ala Pro Met Gln Gln Arg
        35                  40                  45

Pro Ser Leu Val Pro His Tyr Met Pro Thr Thr Ser Met Ser Thr Ala
    50                  55                  60

Ser Ile Asn Ser Ile Ser Ala Pro Ala His Tyr Gln Ser Pro Val Pro
65                  70                  75                  80

Tyr Gly Gly Gly Tyr Pro Ala Tyr Pro Leu Pro Thr Pro Thr Thr Met
                85                  90                  95

Asn Ser Ser Tyr His Lys His Gln Gln Tyr Gln Glu Arg Pro Ser Leu
            100                 105                 110

His Met Ile Thr Pro Glu Phe Glu Asp Thr Arg Gly Pro His His Ile
        115                 120                 125

```
Arg Asn Ala Arg Arg Tyr Ser Glu Glu Ser Arg Ser Pro Ser Glu Arg
        130                 135                 140

Ser Asp Ser Gln Gly Ser Thr Thr Glu Thr Thr Ile Ser Asn His Ser
145                 150                 155                 160

Ser Cys Ser Arg Thr Ile Thr Pro Asn Thr Pro Val Asn Gly Ala Pro
                165                 170                 175

Gln Val Glu Phe Ser Thr Ala Val Asp Lys Leu Met Lys Val Ile Gln
            180                 185                 190

Ser Lys Met Lys Asp Ala Asp Pro Glu Gln Ser Gly Asp Asp Lys Asp
        195                 200                 205

Ile Lys Ala Glu Gln Gln Ser Ser Pro Val Cys Gln Ala Arg Val Gln
210                 215                 220

Gln Pro Ala Asp Lys His Lys Arg Lys Arg Tyr Glu Cys Gln Ile Glu
225                 230                 235                 240

Gly Cys Asn Lys Lys Phe Ser Gln Lys Thr His Arg Asp Thr His Val
                245                 250                 255

Arg Ser His Thr Gly Asp Arg Pro Tyr Val Cys Pro Ile Pro Gly Cys
            260                 265                 270

Gly Gly Arg Phe Thr Gln Ala Gly Asn Leu Lys Thr His Lys Arg Arg
        275                 280                 285

His Thr Gly Glu Arg Pro Tyr Arg Cys Glu Val Cys Asp Lys Gly Phe
290                 295                 300

Val Gln Arg Gly Asp Val Lys Ala His Met Lys Thr His Leu Gly Thr
305                 310                 315                 320

Lys Ala Phe Leu Cys Arg Leu Asp Asn Cys His Lys Gln Phe Thr Gln
                325                 330                 335

Arg Gly Asn Leu Lys Tyr His Gln Asn Lys Tyr His Asn Glu Thr Ile
            340                 345                 350

Lys Ala Leu Ala Ala Arg Phe Asp Ala Ile Glu Asp Trp Ser Thr Val
        355                 360                 365

Leu Lys Glu Asp Met Glu Ile Phe Lys Asp Phe Ala Glu Val His Lys
370                 375                 380

Asn Ser Asn Lys Gly Ile Lys Gly Arg Gly Lys His Arg Lys Val Lys
385                 390                 395                 400

Ser Val Pro Leu Ser Pro Thr Ser Pro Thr Gly His Ser Pro Leu
                405                 410                 415

Pro Asn Ile Met Ala Ser Gln Tyr Pro Leu Pro Ser Ala Pro Gly Val
            420                 425                 430

Ser Gln Leu Leu His Thr Pro His Pro Leu His Pro Pro Leu His His
        435                 440                 445

Gln Gly Pro Ser His Ser Ala Met Tyr Gly Met Pro Arg Ser Ser Leu
450                 455                 460

His Ser His Tyr Glu Thr Tyr Asp His His Glu Val Asp Thr Val Ala
465                 470                 475                 480

Ser Ser Arg Gly Ser Val Ala Glu Pro Ile Tyr His His Glu Glu His
                485                 490                 495

Pro Arg Glu Leu Ala Phe Gly Asp Arg Met Tyr
            500                 505

<210> SEQ ID NO 98
<211> LENGTH: 308
<212> TYPE: PRT
<213> ORGANISM: Artificial Sequence
<220> FEATURE:
```

<223> OTHER INFORMATION: synthesized

<400> SEQUENCE: 98

Met Asp Ile Thr Thr Ile Leu Asn Lys Lys Ala Ser Val Ser Ile Val
1               5                   10                  15

Ala Ala Asp Val His Gln Leu Gln Gln His Leu Ala Gln Ala Thr Ala
            20                  25                  30

Gln Ser Gln Thr Asp Asp Ala Val Lys Ser Arg Ser Pro Ser Glu Leu
        35                  40                  45

Gly Ala Ser Glu His His Arg Ser Ala Ser Ala Pro Pro Ser Glu His
    50                  55                  60

His His His His His His His Gln Pro Thr Ser Ser Phe Pro Ser Ser
65                  70                  75                  80

Thr Gln Ser Leu Pro Gln Met Ala His Leu Ala Gln Tyr His Val Gln
                85                  90                  95

Ala Gln Ala Asn His Ala Ser Thr Ser Pro Gly Tyr Ala His Ser Ala
            100                 105                 110

His Gly Ser Asp Tyr Gly Arg Ser Thr Thr Ser Met Arg Pro Thr Gly
        115                 120                 125

Leu Pro Ala Leu Lys Thr Phe His Cys Gln Thr Cys Ser Lys Gly Phe
    130                 135                 140

Ala Arg Arg Ser Asp Leu Ala Arg His Glu Arg Ile His Ser Gly Ile
145                 150                 155                 160

Arg Pro His Ala Cys Asp Trp Pro Gly Cys Gly Lys Gln Phe Ile Gln
                165                 170                 175

Arg Ser Ala Leu Thr Val His Thr Arg Val His Thr Gly Glu Lys Pro
            180                 185                 190

His Met Cys Asp Arg Cys Gly Lys Pro Phe Ser Asp Ser Ser Ser Leu
        195                 200                 205

Ala Arg His Arg Arg Ile His Ser Gly Lys Arg Pro Tyr Lys Cys Pro
    210                 215                 220

Tyr Ala Asn Cys Gln Lys Thr Phe Thr Arg Arg Thr Thr Leu Thr Arg
225                 230                 235                 240

His Gln Asn His His Thr Gly Thr Ile Glu Glu Ala Ala Ala Glu Thr
                245                 250                 255

Glu Ala Asn Leu Arg His Ser Lys Asp Arg Ser Thr Thr Ser Arg Pro
            260                 265                 270

Ser Glu Tyr Ser Glu Pro Gly Ser Ala His Ser Thr Pro Ser Pro Ala
        275                 280                 285

Gln Arg Pro Ser Leu Ser Pro Gly Asn Glu Leu Pro Leu Asn Leu
    290                 295                 300

Ser Ser Arg Pro
305

<210> SEQ ID NO 99
<211> LENGTH: 430
<212> TYPE: PRT
<213> ORGANISM: Artificial Sequence
<220> FEATURE:
<223> OTHER INFORMATION: synthesized

<400> SEQUENCE: 99

Met Val Ala Ala Glu Phe Asp His Gln Gln Phe Ile Gln Asn Pro His
1               5                   10                  15

Leu Asp Thr Ser Ser Pro Lys Met Lys Pro Glu Pro Gly Val Ser Glu
            20                  25                  30

Ala Gly Asp Gln Pro Val Leu Ala Tyr Pro His Ala Pro Leu Gly
            35                  40                  45

Gln Val Pro Asn Met His Pro Asp Met Arg Tyr Gln Pro Gln Thr His
 50                  55                  60

Pro Asn Pro Ala Leu Pro Leu Leu Gln Asn Pro Tyr Met Pro Gly Gly
 65                  70                  75                  80

Tyr Thr Ser Ala Pro Pro Met Pro Asn Gly Gly Ala Pro Gln Gly Arg
                85                  90                  95

Thr Asp Pro Pro Pro Lys Thr Phe His Cys Gly Thr Cys Ser Lys Gly
            100                 105                 110

Phe Ala Arg Arg Ser Asp Leu Ala Arg His Glu Arg Ile His Ser Gly
            115                 120                 125

Ile Arg Pro His Ala Cys Asp Trp Pro Gly Cys Gly Lys Gln Phe Ile
130                 135                 140

Gln Arg Ser Ala Leu Thr Val His Ser Arg Val His Thr Gly Glu Lys
145                 150                 155                 160

Pro His Met Cys Glu Arg Cys Gly Lys Pro Phe Ser Asp Ser Ser Ser
                165                 170                 175

Leu Ala Arg His Arg Arg Ile His Ser Gly Lys Arg Pro Tyr Lys Cys
            180                 185                 190

Pro Tyr Ala Asn Cys Gln Lys Thr Phe Thr Arg Arg Thr Thr Leu Thr
            195                 200                 205

Arg His Gln Asn His His Thr Gly Thr Ile Glu Glu Ala Ala Ala Glu
210                 215                 220

Thr Glu Ala Asn Leu Arg Gln Asn Lys Glu Arg Val Arg Ala Pro Gly
225                 230                 235                 240

Glu Gly Met Tyr Ser Glu His Gly Ser Val His Ser Thr Pro Ser Pro
                245                 250                 255

Ala His His Pro Ala Leu Ser Pro Ala Gly Glu Leu Pro Pro Leu Asn
            260                 265                 270

Met Pro Arg Ser Ser Gly Glu Tyr Tyr Ser Met Gly Asn Gly Ser Ile
            275                 280                 285

Pro Pro His Val Arg Gly Asp Phe Pro Gln Ala Ser Pro Arg Ala Ser
            290                 295                 300

Pro Thr Ala Thr Ser Pro Ser Leu Ser Ser Phe Gly Ser Ala Pro His
305                 310                 315                 320

Thr Arg Pro Ser Met Thr Ser His Pro Ser Gly Tyr Gly Pro Pro Gln
                325                 330                 335

Pro Leu Glu Pro Pro Ala Asn Asn Asp His Arg Pro Asn Ser Val Ser
            340                 345                 350

Gly Ser Pro His Met Thr Ser Leu Gly Trp Ala Ser Pro Ser His Gly
            355                 360                 365

Ser Ile Pro Ser Pro Gly Ser Ala Thr Asp Phe Gly Tyr Ser Asp Pro
370                 375                 380

Asn Gly Pro Ala Tyr Pro Asn Ser Met Pro Pro His Met Tyr Phe Pro
385                 390                 395                 400

Asn Ser Thr Ile Arg Arg Pro Thr Ser Thr Glu Pro Glu Asn Tyr Glu
                405                 410                 415

Met Lys Pro Lys Ile Gly Glu Ser Ala Trp Ser Thr Pro Val
            420                 425                 430

<210> SEQ ID NO 100
<211> LENGTH: 540

```
<212> TYPE: PRT
<213> ORGANISM: Artificial Sequence
<220> FEATURE:
<223> OTHER INFORMATION: synthesized

<400> SEQUENCE: 100

Met Cys Arg Ala Arg Leu Leu Ser Arg Val Pro Pro Gly Trp Arg Glu
1               5                   10                  15

Val Pro Ser Pro Phe Pro Ile Leu Pro Pro Ile Asp Arg Tyr Ser Thr
            20                  25                  30

Asp Arg Met Ala Leu Thr Ala Gln Pro Ser Ala Pro Ala Gly Trp Glu
        35                  40                  45

Arg Trp Pro Gln His His Pro Asn Asn Asp Tyr Val Met Met Asp Ala
    50                  55                  60

Asp Val Met Pro Tyr Asn Ala Arg Pro Met Thr Thr Ala Pro Met Gln
65                  70                  75                  80

Gln Arg Pro Ser Leu Val Pro His Tyr Met Pro Thr Thr Ser Met Ser
                85                  90                  95

Thr Ala Ser Ile Asn Ser Ile Ser Ala Pro Ala His Tyr Gln Ser Pro
            100                 105                 110

Met Ser Tyr Gly Gly Gly Tyr Pro Ala Tyr Pro Leu Pro Thr Pro Thr
        115                 120                 125

Thr Met Asn Ser Pro Tyr Lys His Gln Gln Tyr Gln Glu Arg Pro Thr
    130                 135                 140

Leu His Met Ile Thr Pro Glu Ile Glu Asp Thr Arg Gly Pro His His
145                 150                 155                 160

Ile Arg Asn Ala Arg Arg Tyr Ser Ala Glu Ser Arg Ser Pro Ser Glu
                165                 170                 175

Arg Ser Asp Ser Gln Val Ser Thr Thr Glu Ile Thr Ile Ser Asn His
            180                 185                 190

Ser Ser Cys Ser Arg Thr Ile Thr Pro Asn Thr Pro Val Asn Gly Ala
        195                 200                 205

Pro Gln Val Glu Phe Ser Thr Ala Val Asp Lys Leu Met Lys Val Ile
    210                 215                 220

Gln Ser Lys Met Lys Asp Ala Asp Pro Glu Gln Ser Gly Asp Asp Arg
225                 230                 235                 240

Asp Ile Lys Ala Glu Gln Gln Ser Ser Pro Val Cys Gln Ala Arg Val
                245                 250                 255

Gln Gln Pro Ala Asp Lys Leu Lys Arg Lys Tyr Glu Cys Gln Ile
            260                 265                 270

Glu Gly Cys Asn Lys Lys Phe Ser Gln Lys Thr His Arg Asp Thr His
        275                 280                 285

Val Arg Ser His Thr Gly Asp Arg Pro Tyr Val Cys Pro Ile Pro Gly
    290                 295                 300

Cys Gly Arg Phe Thr Gln Ala Gly Asn Leu Lys Thr His Lys Arg
305                 310                 315                 320

Arg His Thr Gly Glu Arg Pro Tyr Arg Cys Glu Val Cys Asp Lys Gly
                325                 330                 335

Phe Val Gln Arg Gly Asp Val Lys Ala His Met Lys Thr His Leu Gly
            340                 345                 350

Thr Lys Ala Phe Leu Cys Lys Leu Asp Asn Cys His Lys Gln Phe Thr
        355                 360                 365

Gln Arg Gly Asn Leu Lys Tyr His Gln Asn Lys Tyr His Asn Glu Thr
    370                 375                 380
```

```
Ile Lys Ala Leu Ala Ala Arg Phe Asp Ala Ile Glu Asp Trp Ser Thr
385                 390                 395                 400

Val Leu Lys Glu Asp Met Glu Ile Phe Lys Asp Phe Ala Glu Val His
                405                 410                 415

Lys Asn Ser Asn Lys Gly Ile Lys Gly Arg Gly Lys His Arg Lys Val
            420                 425                 430

Lys Ser Val Pro Leu Ser Ser Pro Thr Ser Pro Thr Gly His Ser Pro
        435                 440                 445

Leu Pro Asn Ile Met Ala Ser Gln Tyr Pro Leu Pro Ser Ala Pro Gly
    450                 455                 460

Val Ser Gln Leu Leu His Thr Pro His Pro Leu His Pro Leu His
465                 470                 475                 480

His Gln Gly Pro Ser His Ser Ala Met Tyr Gly Met Pro Arg Gln Ser
                485                 490                 495

Leu His Ser His Tyr Glu Thr Tyr Asp His His Glu Val Asp Thr Val
            500                 505                 510

Pro Ser Ser Arg Gly Pro Val Ala Glu Pro Ile Tyr His His Glu Glu
        515                 520                 525

His Pro Arg Glu Leu Ala Ser Gly Asp Arg Met Tyr
530                 535                 540

<210> SEQ ID NO 101
<211> LENGTH: 432
<212> TYPE: PRT
<213> ORGANISM: Artificial Sequence
<220> FEATURE:
<223> OTHER INFORMATION: synthesized

<400> SEQUENCE: 101

Met Glu Ile His Glu Leu Ile Ile Asp Glu Arg His Ala Pro Lys Gln
1               5                   10                  15

Phe Pro Cys Asp Trp Pro Asp Cys Asn Lys Lys Phe Asn Arg Lys Ser
                20                  25                  30

Asp Leu Gln Arg His His Arg Ile His Thr Asn Thr Arg Pro Tyr Ala
            35                  40                  45

Cys Thr Phe Ala Gly Cys Lys Lys Ser Phe Ile Gln Arg Ser Ala Leu
    50                  55                  60

Thr Val His Ile Arg Thr His Thr Gly Glu Lys Pro His Gln Cys Glu
65                  70                  75                  80

Phe Ile Gly Cys Gly Lys Cys Phe Ser Asp Ser Ser Leu Ala Arg
                85                  90                  95

His Arg Arg Ile His Thr Gly Arg Arg Pro Tyr Leu Cys Gly Val Asn
                100                 105                 110

Arg Cys Gly Lys Ser Phe Cys Arg Lys Thr Thr Leu Ile Lys His Ala
            115                 120                 125

Arg Arg Ala His Gly Ile Gly Gln Asn Leu Asp Val Ser Asp Asp
130                 135                 140

Ser Glu Asn Asp Asp Ser Thr Thr Thr Glu Arg Ser His Pro Lys Pro
145                 150                 155                 160

Val Ser Gln Ala Arg Ala Glu Val Ile Arg Asn His Gly Pro Glu Ser
                165                 170                 175

Val Leu Gln Asn Gln Gly Arg His Leu Ser Leu Phe Arg Pro Glu Leu
            180                 185                 190

Ser Leu Pro Ser Ser Pro Arg Ser Asn Ser Asn Thr Ile Gly Phe Gly
    195                 200                 205
```

```
Asp Thr Tyr Gly Ser Ala Ser Ala Val Tyr His Pro Gln Asn Leu Val
    210                 215                 220

Ser Asp His Pro Met Thr Pro Thr Ser Pro Tyr Cys Phe Gln Glu Thr
225                 230                 235                 240

Pro Pro His Ala His Val Pro Pro Phe Pro Asn Leu Pro Arg Thr Cys
                245                 250                 255

Ala Glu Asp Phe Ile Pro Thr Gly Thr Gly Leu Pro Gln His Pro Gln
            260                 265                 270

Asn Pro Gln Tyr Asn Pro Asn Leu Arg Ile Ile Cys Ser Ser Ser Pro
        275                 280                 285

Thr Gln Gln Ala Leu Ala Ala Gly His Cys Val Gly Ser Pro Gly Glu
290                 295                 300

Leu Ser Asn Cys Ser Thr Ala Thr Ser Gly Ala Ser Val Asp Tyr Phe
305                 310                 315                 320

Tyr Arg Asn Pro Ser Thr Val Asp Gly Val Gly Asn Val Thr Leu Phe
                325                 330                 335

Met Gln Gln Ser Ala Ala Ser Asp His Ile Ser His Val Gln Asp
            340                 345                 350

Gln Gly Ile Ala Glu Met Pro Ile Ala Val Met Ser Gln Gln His
        355                 360                 365

Gln His His Pro Gln Gln Pro Gly Ala Ala Ile Trp Tyr Gly Tyr Ser
370                 375                 380

Gln Phe Asp Gln Pro Gln Phe His Ser Gly Ser Glu Gln Arg Leu Phe
385                 390                 395                 400

Tyr Glu Asn Gly Asn Met Glu Asn Ile Thr Pro Val Lys Ala Thr Thr
                405                 410                 415

Ser Glu Val Val Leu His Pro Leu Leu Thr Pro Arg Ala Ser Leu Cys
            420                 425                 430

<210> SEQ ID NO 102
<211> LENGTH: 457
<212> TYPE: PRT
<213> ORGANISM: Artificial Sequence
<220> FEATURE:
<223> OTHER INFORMATION: synthesized

<400> SEQUENCE: 102

Met Glu Thr Ala Glu Pro Val Ser Tyr Glu Phe Pro Gly His Ala Val
1               5                   10                  15

Gly Ala Val Ala Ser Arg Arg Met Leu Gly Ser Asn Ile Asn His Asn
            20                  25                  30

Phe Ser Phe Tyr Thr Asn Pro Thr Ala Ser Phe Pro Leu Pro Tyr His
        35                  40                  45

Gln Pro Pro Ser Ala Thr Tyr Ser Phe Ser His Pro Leu Asn Thr His
    50                  55                  60

His His Gln His His Gln Pro Gln Pro Gln His Pro Gln His His
65                  70                  75                  80

Asn His His His Gln His Pro Gly Tyr Gln His Phe Phe Val Pro Asn
                85                  90                  95

His Ser Leu Asn Ala Gln Ser Ala Arg Leu Ala Ser Glu Pro Pro Leu
            100                 105                 110

Ala Gln Pro Ile Pro Asp Ile Arg Pro Ala Arg Asn Ala Val Asn Arg
        115                 120                 125

Val Ser Gly Asp Ser Val Ala Lys Val Glu Gln Arg Ala Ala Pro Gln
    130                 135                 140
```

```
Ser Ser Ser Val Ala Ala Ala Pro Gly Asn Gly Val Ser Ala His Glu
145                 150                 155                 160

Lys Asn Pro Asn Ala Ser Glu Val Glu Phe Ser Thr Glu Val Asp Val
            165                 170                 175

Leu Met Lys Ala Ile Gln Ala Lys Glu Ala Ser Gln Pro Ala Ala Leu
        180                 185                 190

Gln Ser Leu Pro Pro Leu Gln Gln Leu Thr His Gly Gly Asn Gly
    195                 200                 205

Phe Ala Gln Gly Tyr Met Ser Ala Val Val Asn His Arg Gly Ala Val
210                 215                 220

Ile Ala Asp Glu Ser Gln Ser Arg Ser Ala Lys Lys Arg Lys Tyr Thr
225                 230                 235                 240

Cys Thr Leu Pro His Cys Gly Lys Ser Phe Ala Gln Lys Thr His Leu
                245                 250                 255

Asp Ile His Met Arg Ala His Thr Gly Asp Lys Pro Phe Val Cys Lys
            260                 265                 270

Glu Pro Thr Cys Gly Gln Arg Phe Ser Gln Leu Gly Asn Leu Lys Thr
        275                 280                 285

His Gln Arg Arg His Thr Gly Glu Lys Pro Phe Thr Cys Asp Val Cys
    290                 295                 300

Gln Lys Arg Phe Ala Gln Arg Gly Asn Val Arg Ala His Lys Ile Thr
305                 310                 315                 320

His Leu Lys Thr Lys Pro Phe Thr Cys Leu Leu Glu Gly Cys Gly Lys
                325                 330                 335

Gln Phe Thr Gln Leu Gly Asn Leu Lys Ser His Gln Asn Lys Phe His
            340                 345                 350

Thr Gln Thr Leu Gln Ala Leu Thr Lys Lys Phe Ser Ala Met Ile Asp
        355                 360                 365

Gly Glu His Met Ser Pro Gln Asp Arg Lys Leu Trp Glu Tyr Phe Ala
    370                 375                 380

Gly Leu Tyr Lys Asn Ser Asn Lys Gly Ile Lys Gly Arg Gly Lys Asp
385                 390                 395                 400

Arg Arg Ile Ser Pro Ser Ser Lys Thr Asn Val Ser Ala Asp Gly Ser
                405                 410                 415

Arg Arg Pro Gly Ala Asp Asp Gln Ala Arg Arg Gly Ser Tyr Glu Asp
            420                 425                 430

Ser Val Tyr Thr Gly Ala Ser Ser Asp Glu Asp Asn Glu Asp Pro
        435                 440                 445

Tyr Phe Ile Glu Lys Arg Gly Asp Glu
    450                 455

<210> SEQ ID NO 103
<211> LENGTH: 478
<212> TYPE: PRT
<213> ORGANISM: Artificial Sequence
<220> FEATURE:
<223> OTHER INFORMATION: synthesized

<400> SEQUENCE: 103

Met Glu Leu Asp Thr Ile Leu Asn Ala Arg Leu Thr Ala Ser Leu Gly
1               5                   10                  15

Thr Gly Ala Leu Phe Thr Met Gln His Ala Met Gln Gln His Phe
            20                  25                  30

Gly Ala Pro Pro Ser Tyr Leu Asn Gly Gly His Ile Lys Ser Glu Asn
        35                  40                  45
```

```
Gly Ser Glu Arg Gly Val Ser Pro His Pro Ser Asp Ser Ser Arg Tyr
    50                  55                  60
Ser Ser Gln Gln Pro Gln Gln Ser Leu Pro Ser Tyr Pro Ser Ile Pro
65                  70                  75                  80
Gln Gln His Met Asn Gly Leu Arg Tyr Pro Ser Pro Ser Gln Met Gln
                85                  90                  95
Ala Pro Met Pro Met Leu Asn Asn Ser Asn Tyr Ile Pro Asn Pro Pro
            100                 105                 110
Asp His Ala Tyr Ala Gln Gln Gln Met Pro Asp Thr Gln Val Gln
            115                 120                 125
His Gln His Asn Gly Gly Arg Pro Ala Ser Asp Thr Gly Pro Pro Lys
    130                 135                 140
Ala Phe Ala Cys Ser Thr Cys Gly Lys Gly Phe Ala Arg Arg Ser Asp
145                 150                 155                 160
Leu Ala Arg His Glu Arg Ile His Ser Gly Ile Arg Pro His Val Cys
                165                 170                 175
Asp Tyr Pro Asn Cys Gly Lys Gln Phe Ile Gln Arg Ser Ala Leu Thr
            180                 185                 190
Val His Gln Arg Val His Thr Gly Glu Lys Pro His Met Cys Glu Arg
    195                 200                 205
Cys Gly Lys Pro Phe Ser Asp Ser Ser Ser Leu Ala Arg His Arg Arg
    210                 215                 220
Ile His Ser Gly Lys Arg Pro Tyr Lys Cys Pro Tyr Ala Asp Cys Gln
225                 230                 235                 240
Lys Thr Phe Thr Arg Arg Thr Thr Leu Thr Arg His Gln Asn His His
                245                 250                 255
Thr Gly Thr Val Glu Glu Ala Ala Ala Ala Thr Ala Ala Ala Leu Ala
            260                 265                 270
Ser Arg Ala Ser Ala Ser Ser Arg Thr Gly Arg Ser Asp Gly Gly Asp
    275                 280                 285
Tyr Ser Glu Thr Ala Ser Pro Leu Gly Thr Pro Ser Pro Asn Asp Arg
    290                 295                 300
Thr Leu Ser Leu Ser Pro Ala Asn Gly Met Pro Ala Gly Gly Met Pro
305                 310                 315                 320
Gly Leu His Arg Gln Gly Ser Asp Tyr Ala Tyr Met Gly Gly Met Asn
                325                 330                 335
Val Pro Pro His Met Arg His Glu Met Pro Gln Pro Ser Pro Arg Ala
            340                 345                 350
Ser Pro Ala Leu Thr Ala Gln Ser Tyr Ala Ser Asn Val Ser Gly Thr
    355                 360                 365
Arg Pro Ala Ile Thr Ser His Pro Ser Ala Tyr Gly Pro Pro Ile
    370                 375                 380
Leu Glu Pro Pro Ala Ser Ala Asn His Asn Gln Ser Gly Thr Asn Ser
385                 390                 395                 400
Ala Asn Ala Ser Pro His Met Ser Ala Met Gly Trp Gln Ser Pro Gly
                405                 410                 415
Gln Gln Ala Leu Pro Ser Pro Gly Ala Ala Asp Asn Gly Tyr Val Tyr
            420                 425                 430
Pro Glu Pro Gln Tyr Gln Ala Gln Asn Gly Met Tyr Tyr Gln His Asn
            435                 440                 445
Asn Ile Arg Arg Pro Asn Ser Thr Glu Pro Asp His Tyr Asn Pro Asn
    450                 455                 460
Gln Gln Arg Met Gly Asn Glu Met Trp Ala Pro Ala Val Gln
```

-continued

```
465                 470                 475
```

<210> SEQ ID NO 104
<211> LENGTH: 369
<212> TYPE: PRT
<213> ORGANISM: Artificial Sequence
<220> FEATURE:
<223> OTHER INFORMATION: synthesized

<400> SEQUENCE: 104

```
Met Asn Arg Ala Asp Ile Ala Met His Thr Tyr Ala His His Ser His
1               5                   10                  15

Val Ala His Gly Ala Ile Pro Ala Ser Asn Phe Glu Leu Thr Ser Ser
            20                  25                  30

Phe Phe Ala Asn Pro Ala Phe Thr Tyr Pro Ala Gln Tyr Asn Ser Ile
        35                  40                  45

Asp Leu Gly Tyr Asp Leu Gly Leu Gly Tyr Gly Cys Asn Leu Gly
    50                  55                  60

His Gly Ala Asn Ala Ser Pro Gln Gln Ile Phe Gly Gln His Ser Ala
65                  70                  75                  80

Ser Tyr Ser Glu Gln Gly Leu His Val Pro Ala Ser Gln Gln Pro Ala
                85                  90                  95

Pro Gly Glu Pro Ala Gln Arg Ser Pro Ala Ile Lys Val Glu Ala Ala
            100                 105                 110

Ser Gln Asp Ala Asp Asn Val Glu Phe Gln Pro Tyr Ser Val Pro Thr
        115                 120                 125

Ser Thr Leu Pro Thr Ser Ala Thr Asp Ala Asp Val Gly Thr Asp Val
    130                 135                 140

Asp Thr Leu Met Arg Ala Ile Gln Thr Lys Ala Lys Thr Ser Ser Thr
145                 150                 155                 160

Gln Ala Pro Ser Ser Ala Ala Leu Ile Asp Gln Arg Arg Ser Lys Ala
                165                 170                 175

Arg Arg Lys Tyr Pro Cys Lys Val Gln Ser Cys Ala Lys Val Phe Thr
            180                 185                 190

Gln Lys Thr His Leu Glu Ile His Met Arg Ala His Thr Gly Tyr Lys
        195                 200                 205

Pro Tyr Leu Cys Arg Glu Thr Ser Cys Gly Gln Arg Phe Ser Gln Leu
    210                 215                 220

Gly Asn Leu Lys Thr His Glu Arg Arg His Thr Gly Glu Arg Pro Tyr
225                 230                 235                 240

Ser Cys Asp Arg Cys Gly Arg Ser Phe Ala Gln Arg Gly Asn Val Gln
                245                 250                 255

Ala His Arg Ile Val His Glu Arg Ile Lys Pro Tyr Cys Cys Gln Leu
            260                 265                 270

Glu Gly Cys Ser Lys Arg Phe Thr Gln Leu Gly Asn Leu Lys Ser His
        275                 280                 285

Gln Asn Lys Phe His Thr Glu Thr Leu Arg Val Leu Ala Val Lys Phe
    290                 295                 300

Ala Ser Leu Arg Glu Glu Asp Ala Met Ser Glu Ala Asp Arg Glu Leu
305                 310                 315                 320

Trp Glu Tyr Phe Ser Thr Leu Tyr Lys Asn Ser Asn Lys Gly Ile Lys
                325                 330                 335

Gly Arg Gly Lys Asp Arg Arg Ile Ala Ala Val Asp Arg Asn Gly Asp
            340                 345                 350

Gly Leu Lys Gln Glu Thr Gln Asp Cys Glu Ser Ser Ser Ser Val Ser
```

355                 360                 365

Pro

<210> SEQ ID NO 105
<211> LENGTH: 437
<212> TYPE: PRT
<213> ORGANISM: Artificial Sequence
<220> FEATURE:
<223> OTHER INFORMATION: synthesized

<400> SEQUENCE: 105

Met Ser Ser Ala Ser Pro Glu Val Met Asp Ile Thr Asn Met Leu Asn
1               5                   10                  15

Asn Lys Gly Gly Ala Met Ala His Gly Leu Gly Gly Ser Met Pro Asp
            20                  25                  30

His His Gln Gln His His Leu Gly Leu Val Lys His Glu Ser Ala
        35                  40                  45

Leu Asp Arg Ser Gly Ser Pro His Met Ser Glu His Ser Ser Tyr Ser
50                  55                  60

Ala His Ser Met Pro Arg Ala Tyr Pro Ser Pro Thr Ala Met Gln Thr
65                  70                  75                  80

Pro Met Gln Met Gln Asn His Met His Asn Ala Met Gln Met Gly Gly
                85                  90                  95

Phe Thr Asp Met Ser Gly Met Gly Ser Val Pro Ser Met Ala Met His
            100                 105                 110

His Met Pro Gln Gln Pro Gln Gln Gln Ala Pro Thr Ala Pro Val
        115                 120                 125

Lys Ala Tyr Pro Cys Ser Thr Cys Gly Lys Gly Phe Ala Arg Arg Ser
130                 135                 140

Asp Leu Ala Arg His Glu Arg Ile His Thr Gly Val Arg Pro His Val
145                 150                 155                 160

Cys Asp Tyr Pro Lys Cys His Lys Gly Phe Ile Gln Arg Ser Ala Leu
                165                 170                 175

Thr Val His Gln Arg Val His Thr Gly Glu Lys Pro His Arg Cys Glu
            180                 185                 190

Thr Cys Ala Lys Leu Phe Ser Asp Ser Ser Leu Ala Arg His Arg
        195                 200                 205

Arg Thr His Ser Gly Thr Arg Pro Tyr Lys Cys Pro Tyr Ala Asp Cys
210                 215                 220

Gln Lys Thr Phe Thr Arg Arg Thr Thr Leu Thr Arg His Gln Asn Gln
225                 230                 235                 240

His Thr Gly Thr Ile Glu Glu Ala Ala Ala Thr Ala Ala Ala Leu
                245                 250                 255

Ala Ala Ser Arg Val Lys Asn Gly Ser Gln Ala Arg Ser Asp Gly Asp
            260                 265                 270

His Met Ser Asn Gln Gly Ser Pro Leu Thr Thr Pro Ser Pro Asn His
        275                 280                 285

His Ala Met Met Ser Pro Ala Met Asp Leu Ser Gly Ala Asn Gly Leu
290                 295                 300

Gly Arg His Gln Ala Asp Phe Thr Gln Tyr Met Thr Gln Gly Gly Thr
305                 310                 315                 320

Leu Pro Pro His Leu Arg Val Gly Ser Pro Thr Ser Thr Asn Ser Ala
                325                 330                 335

Ala Ser Tyr Asn Ser Gly Ile Arg Pro Thr Ser His Pro Thr Gly Tyr
            340                 345                 350

```
Gly Pro Pro Pro Thr Leu Glu Pro Ser Leu Glu Gln His Thr Gly Ala
            355                 360                 365

Thr Gly Ser Ala Val Gly Ser Pro His Met Ala Ser Gln Leu Gly Trp
    370                 375                 380

Gln Ser Pro His Ser Ser Pro Ser Gln His Gly Gly Ser Tyr Val
385                 390                 395                 400

Tyr Pro Asp Pro Asp Gly Tyr Pro Pro Asn Pro Ser Met Ser Gln Met
                405                 410                 415

Tyr Tyr Gly Ala Pro Gln Gln Met Arg Arg Pro Gln Ser Ala Glu Pro
            420                 425                 430

Gly Met Val His Met
            435

<210> SEQ ID NO 106
<211> LENGTH: 453
<212> TYPE: PRT
<213> ORGANISM: Artificial Sequence
<220> FEATURE:
<223> OTHER INFORMATION: synthesized

<400> SEQUENCE: 106

Met Gln Gln Gln His Phe Gly Ala Pro Pro Ser Tyr Leu Asn Gly Gly
1               5                   10                  15

His Ile Lys Ser Glu Asn Gly Ser Glu Arg Gly Val Ser Pro His Pro
            20                  25                  30

Ser Asp Ser Ser Arg Tyr Ser Ser Gln Gln Pro Gln Gln Gln Leu Pro
        35                  40                  45

Ser Tyr Pro Ser Ile Pro Gln Gln His Met Asn Gly Leu Arg Tyr Pro
    50                  55                  60

Ser Pro Ser Gln Met Gln Ala Pro Met Pro Met Leu Asn Asn Ser Asn
65                  70                  75                  80

Tyr Ile Pro Asn Pro Asp His Ala Tyr Ala Gln Gln Gln Gln Gln Met
                85                  90                  95

Pro Asp Asn Gln Val Gln His Gln His Asn Gly Gly Arg Pro Ala Ser
            100                 105                 110

Asp Thr Gly Pro Pro Lys Ala Phe Ala Cys Ser Thr Cys Gly Lys Gly
        115                 120                 125

Phe Ala Arg Arg Ser Asp Leu Ala Arg His Glu Arg Ile His Ser Gly
    130                 135                 140

Ile Arg Pro His Val Cys Asp Tyr Pro Asn Cys Gly Lys Gln Phe Ile
145                 150                 155                 160

Gln Arg Ser Ala Leu Thr Val His Gln Arg Val His Thr Gly Glu Lys
                165                 170                 175

Pro His Met Cys Glu Arg Cys Gly Lys Pro Phe Ser Asp Ser Ser Ser
            180                 185                 190

Leu Ala Arg His Arg Arg Ile His Ser Gly Lys Arg Pro Tyr Lys Cys
        195                 200                 205

Pro Tyr Ala Asp Cys Gln Lys Thr Phe Thr Arg Arg Thr Thr Leu Thr
    210                 215                 220

Arg His Gln Asn His His Thr Gly Thr Val Glu Glu Ala Ala Ala Ala
225                 230                 235                 240

Thr Ala Ala Ala Leu Ala Ser Arg Ala Ser Ala Ser Ser Arg Thr Gly
                245                 250                 255

Arg Ser Asp Gly Gly Asp Tyr Ser Glu Thr Ala Ser Pro Leu Gly Thr
            260                 265                 270
```

```
Pro Ser Pro Asn Asp Arg Thr Leu Ser Leu Ser Pro Ala Asn Gly Met
            275                 280                 285

Pro Ala Gly Gly Met Pro Gly Leu His Arg Gln Gly Ser Asp Tyr Ala
        290                 295                 300

Tyr Met Gly Gly Ile Asn Val Pro Pro His Met Arg His Glu Met Pro
305                 310                 315                 320

Gln Pro Ser Pro Arg Ala Ser Pro Ala Leu Thr Ala Gln Ser Tyr Ala
                325                 330                 335

Ser Asn Val Ser Gly Ser Arg Pro Ala Ile Thr Ser His Pro Ser Ala
            340                 345                 350

Tyr Gly Pro Pro Pro Ile Leu Glu Pro Ala Ser Ala Asn His Asn
            355                 360                 365

Gln Ser Gly Gly Thr Asn Ser Ala Asn Gly Ser Pro His Met Ser Ala
        370                 375                 380

Met Gly Trp Gln Ser Pro Gly Gln Gln Ala Leu Pro Ser Pro Gly Ala
385                 390                 395                 400

Gly Asp Asn Gly Tyr Val Tyr Pro Glu Pro Gln Tyr Gln Ala Gln Asn
                405                 410                 415

Gly Met Tyr Tyr Gln His Asn Asn Ile Arg Arg Pro Asn Ser Thr Glu
            420                 425                 430

Pro Asp His Tyr Asn Pro Asn Gln Gln Arg Met Gly Asn Glu Met Trp
            435                 440                 445

Ala Pro Ala Val Gln
            450

<210> SEQ ID NO 107
<211> LENGTH: 518
<212> TYPE: PRT
<213> ORGANISM: Artificial Sequence
<220> FEATURE:
<223> OTHER INFORMATION: synthesized

<400> SEQUENCE: 107

Met Ala Leu Gly Phe Leu Pro Pro Asn Pro Glu Thr Trp Gly Arg Trp
1               5                   10                  15

Pro Gln His Gln His Thr Gly Ala Asp Cys Gly Met Met Asp Ala Gly
            20                  25                  30

Met Val Pro Tyr Asp Cys Arg Pro Gly Ala Thr Ala Ser Ile Pro Arg
        35                  40                  45

Pro Glu Leu Ala Gln His Phe Leu Pro Gly Pro Phe Asn Pro Ala Ser
    50                  55                  60

Val Pro Ser Pro Ala Ser Pro Gln Tyr His Ala Pro Val Ser Tyr Gly
65                  70                  75                  80

Gly Tyr Ser Pro Tyr Asn Pro Ser Ser Met Leu Glu Ala Pro Phe Lys
                85                  90                  95

Pro His Gly Leu Gln Gly Arg Met Asp Gly Leu Pro Leu Val Gly Arg
            100                 105                 110

Ser Ser Ser Pro Ser Val Lys Ser Glu Ala Lys Ser Thr Lys Ser Glu
        115                 120                 125

Ser Pro Ser Pro Ser Thr Lys Val Val Ile Pro Asn Val Arg Val Gln
    130                 135                 140

Gly Ala Pro Val His Glu Phe Asn Thr Ala Ile Asp Arg Leu Ala Lys
145                 150                 155                 160

Val Ile Glu Thr Lys Arg Glu Ile Leu Ser Ser Pro Asn Pro Ala Lys
                165                 170                 175
```

Glu Glu Pro Gly Gln Pro Asn Glu Gly Val Glu Gly Gly Glu Met Gln
            180                 185                 190

Gln Ala Arg Gly Lys Ala Lys Arg Lys Arg Phe Cys Cys Asp Ile Pro
        195                 200                 205

Gly Cys Ser Lys Met Phe Ala Gln Lys Asn Asn Leu Asp Thr His Arg
    210                 215                 220

Arg Ala His Thr Gly Glu Ser Pro Tyr Val Cys Pro Ile Cys Leu His
225                 230                 235                 240

Arg Phe Thr Gln Ser Val Asn Leu Lys Ser His Ile Arg Arg His Leu
                245                 250                 255

Gly Glu Arg Pro Tyr Lys Cys Pro Gln Cys Pro Lys Ala Phe Ser Gln
            260                 265                 270

Pro Ser Asn Val Lys Ala His Met Lys Thr His Glu Arg Arg Glu Leu
        275                 280                 285

Arg Ala Arg Trp Val Cys Arg Phe Gly Ser Cys Arg Lys Ser Phe Thr
    290                 295                 300

Ala Lys Gly Asn Leu Lys Ser His Gln Asn Thr Tyr His Val Glu Ala
305                 310                 315                 320

Ile Glu Ala Phe His Ala Lys Leu Ala Ser Ile Glu Asp Lys Ser Met
                325                 330                 335

Ile Thr Glu Glu Asp Lys Glu Met Ala Arg Tyr Ile Thr Glu Val His
            340                 345                 350

Asn Leu Ala Asn Lys Gly Ile Lys Gly Arg Gly Lys Gly Arg Lys Val
        355                 360                 365

Lys Arg Leu Leu Pro Leu Pro Met Gln Pro Ser Ala Ala Ala Ala
    370                 375                 380

Ala Thr Thr Thr Thr Thr Thr Thr Ser Leu Ser Ala Ala Thr Ala Ile
385                 390                 395                 400

Val His Gly Asn Pro Tyr Ser Met Pro Pro Leu Leu Pro His Ala Pro
                405                 410                 415

Pro His His Leu Gln Ala Ala Pro Gln Pro Ser Ala Ala His His Gly
            420                 425                 430

His Gln His His His Phe Tyr Gly Leu Ser Asn Pro Ala Ala Tyr Ser
        435                 440                 445

Met Ser Arg Pro Ser Val Ser Ser Ala Met Leu Phe Gly Val Gly Leu
    450                 455                 460

Gly Ile Asn Thr Arg Asp Val Val His Gly His Gly Ala Tyr Gly Met
465                 470                 475                 480

Leu Asp Ser Asp Gln Ile Ser Glu Ala Ser Val His Ser Pro Pro
                485                 490                 495

Pro Val Met His His Val Tyr Asp Asp Glu His Ala Arg Glu Leu Ala
            500                 505                 510

Phe Gly Glu Arg Leu Tyr
        515

<210> SEQ ID NO 108
<211> LENGTH: 414
<212> TYPE: PRT
<213> ORGANISM: Artificial Sequence
<220> FEATURE:
<223> OTHER INFORMATION: synthesized

<400> SEQUENCE: 108

Met Asp Ile Thr Thr Ile Leu Asn Lys Asn Arg Ser Ala Val Ala Ala
1               5                   10                  15

Ala Ala Glu Ala Gln Leu Gln His Gln Leu Ser Gln Thr Ser His Met
                20                  25                  30

Lys Ser Arg Ser Pro Ser Glu Met Gly Ser Glu His Asp Pro Gln His
                35                  40                  45

Pro Gly Arg His Thr Glu Ser Tyr Gln Gln Val Pro Gln Pro Ile Gln
 50                  55                  60

Leu Pro Asn Ile Ser Gln Tyr His Ser Pro Ile His Ala Asn His His
 65                  70                  75                  80

Pro Ser Ile Leu Arg Gly Asp Tyr Ser Gln Asn Gly His Glu Thr Met
                85                  90                  95

Phe Arg Asn Val Pro Gly Thr Ser Ser Pro Thr Ser Arg Thr Asn Gly
                100                 105                 110

Glu Pro Ala Pro Lys Ser Phe His Cys Gln Thr Cys Gly Lys Gly Phe
                115                 120                 125

Ala Arg Arg Ser Asp Leu Ala Arg His Glu Arg Ile His Ser Gly Ile
130                 135                 140

Arg Pro His Val Cys Asp Trp Pro Gly Cys Gly Lys Gln Phe Ile Gln
145                 150                 155                 160

Arg Ser Ala Leu Thr Val His Thr Arg Val His Thr Gly Glu Lys Pro
                165                 170                 175

His Met Cys Asp Arg Cys Gly Lys Lys Thr Phe Thr Arg Arg Thr Thr
                180                 185                 190

Leu Thr Arg His Gln Asn His His Thr Gly Thr Ile Glu Glu Ala Ala
                195                 200                 205

Ala Glu Thr Glu Ala Asn Leu Arg Gln Gly Lys Val Val Arg Pro Gly
                210                 215                 220

Asp Gly Val Tyr Ser Glu Thr Ala Ser Thr His Gly Thr Ala Ser Pro
225                 230                 235                 240

Ala Gln Arg Ser Ser Pro Ser Pro Arg His Glu Leu Pro Pro Leu His
                245                 250                 255

Ala His Arg Gln Met Gly Asp Tyr Phe Met Gly Asn Ser Ser Leu Pro
                260                 265                 270

Pro His Leu Arg Gly Asp Phe Gln Gln Ala Ser Pro Arg Ala Ser Pro
                275                 280                 285

Ser Ala Pro Ser Pro Thr Leu Ser Thr Phe Ser Thr Ser His Pro Ala
290                 295                 300

Arg Pro Ser Leu Thr Ser His Pro Thr Gly Tyr Gly Pro Pro Gln Pro
305                 310                 315                 320

Leu Glu Pro Pro Pro Asn Gly Gly Ser Arg Pro Gly Ser Val Thr Gly
                325                 330                 335

Ser Pro His Met Thr Thr Val Gly Trp Ala Ser Pro Ser Leu Asn Ser
                340                 345                 350

Ile Pro Ser Pro Gly Ser Ile Ser Ala Pro Glu Tyr Thr Tyr Pro Glu
                355                 360                 365

Pro Ser Gly Pro Pro Phe Ala Gly Gly Val Pro Ala His Met Tyr Tyr
                370                 375                 380

Pro Asn Ser Thr Ile Arg Arg Pro Gln Ser Thr Glu Pro Glu Asn Tyr
385                 390                 395                 400

Glu Leu Lys Pro Lys Met Glu Glu Asn Trp Thr Ala His Ser
                405                 410

<210> SEQ ID NO 109
<211> LENGTH: 553

<212> TYPE: PRT
<213> ORGANISM: Artificial Sequence
<220> FEATURE:
<223> OTHER INFORMATION: synthesized

<400> SEQUENCE: 109

Met Gln Leu Pro Thr Pro Pro Gly Trp Gly Gln Trp Gln Gln Asn Glu
1               5                   10                  15

Val Glu Ser Gly Tyr Val His Ile Gly Ser Pro Met Met Gly Thr Gln
            20                  25                  30

Thr Pro Leu Gln Gln Pro Thr Leu Ser Ser Gln Tyr Pro Val Thr Leu
        35                  40                  45

Ala Pro Ser Pro Ser Leu Gln Gln Pro Ile Ser Tyr Ala Pro Tyr Thr
    50                  55                  60

His Gly Leu Pro Ser Val Ala Pro Leu Gln Met Pro Thr Val Gly Ser
65                  70                  75                  80

Gln His Asn His Gln His Gln His His His Ser Gln His His
                85                  90                  95

His Gln Gln His Gln Ile Gln Phe Pro Asp His Ser Ile Gln Arg Pro
            100                 105                 110

Arg Arg Lys Leu Val Asn Thr Arg Ser Leu Arg Asp Thr Thr Ala Glu
            115                 120                 125

Ala Met Glu Ala Gly His Arg Gly Arg Thr Thr Pro Glu Arg Ala Thr
        130                 135                 140

Arg Arg Val Pro Lys Thr Ile Val Ala Asn Ala Pro Val Val Gly Ala
145                 150                 155                 160

Ser His Val Gly Asn His Val Glu Phe Asn Thr Ser Val Asp Lys Leu
                165                 170                 175

Met Lys Ile Ile Gln Ser Met Pro Glu Thr Gly Thr Leu Val Glu Ser
            180                 185                 190

Ile Glu Ser Val Val Lys Pro Glu Pro Ala Val Ser Pro Ile Asp Glu
        195                 200                 205

Gln Lys Pro Ala Ser Glu Lys Leu Thr Val Arg Arg Phe Val Cys His
    210                 215                 220

Phe Arg Gly Cys Leu Lys Lys Phe Ala Gln Lys Ala Gln Leu Asp Thr
225                 230                 235                 240

His Val Arg Ser His Thr Gly Glu Arg Pro Tyr Val Cys Glu Phe Pro
                245                 250                 255

Asn Cys Gly Lys Arg Phe Ser Gln Ser Gly Asn Leu His Thr His Glu
            260                 265                 270

Arg Lys His Thr Gly Glu Arg Pro Tyr Val Cys Asp Ile Cys Gly Arg
        275                 280                 285

Arg Phe Ala Gln Gly Gly Asn Arg Gln Ala His Lys Lys Val His Gln
    290                 295                 300

Lys Thr Lys Asp Phe Ile Cys Arg Leu Glu Gly Cys Gly Lys Glu Phe
305                 310                 315                 320

Thr Gln Arg Gly Asn Leu Lys Ser His Gln Asn Lys Ser His Gln Gln
                325                 330                 335

Phe Met Asp Gln Thr Met Ala Arg Leu Glu Lys Ile Ser Leu Glu Asn
            340                 345                 350

Met Ser Pro Glu Asp Arg Glu Leu Val Ile Tyr Leu Ala Pro Leu Tyr
        355                 360                 365

Lys Asn Ser Asn Lys Gly Ile Lys Gly Arg Gly Val Arg Pro Pro Gly
    370                 375                 380

Tyr Arg Leu Ser Arg Ser Asp Arg Ser Ser Ser Met Ser Ser Ser Ala
385                 390                 395                 400

His Ser Tyr Ser Pro Thr Lys Ser Glu Ala Ser Leu Thr Ser Ser Pro
            405                 410                 415

Cys Thr Ala Gly Pro Pro Pro Gln His His Tyr Gly Gly His Ala Gln
            420                 425                 430

Gln His His His Gln Gln Gln Gln Gln His Gln Gln Arg His Pro
            435                 440                 445

Asp His Gln Asp Met Ser Ser Tyr His Pro Ser Asn Pro Val Pro Thr
            450                 455                 460

His His His Gln Arg Pro Gln Gln Gly Leu Ala Tyr Pro Pro Val Ser
465                 470                 475                 480

Phe Gly Ser Ala Pro Ser Gly Asn Ile Arg Tyr Pro Tyr Asn Gly Ile
            485                 490                 495

Val His Arg Tyr Glu Met Pro Glu His Ser His Pro Tyr Ser Gly Ile
            500                 505                 510

Pro Val Thr Thr Ser Ser Ser Ser Ser Pro Val Ala Thr Val Tyr
            515                 520                 525

Ser Asp Asp Ser Gly Ala Val Tyr Gln Ser Asp Asp Asn Gly Ala Arg
530                 535                 540

Glu Leu Ala Phe Gly Glu Arg Met Cys
545                 550

<210> SEQ ID NO 110
<211> LENGTH: 463
<212> TYPE: PRT
<213> ORGANISM: Artificial Sequence
<220> FEATURE:
<223> OTHER INFORMATION: synthesized

<400> SEQUENCE: 110

Met Ala Ala Val Val Ala Ser His His Val Gly Phe Trp His Glu Arg
1               5                   10                  15

Arg Asp Pro Thr Ile His Val Thr Asn Leu His Leu Ala Asn Met Met
            20                  25                  30

Ser Pro Tyr Asp Ile Pro Arg Thr Val Ala Asn Thr Ser Ala Ser Arg
            35                  40                  45

Ser Tyr Gln Pro Thr Thr Thr Gln Met Asp Met Gly Met Pro Ile Phe
50                  55                  60

Ser Ala Thr Gly Leu Ser Ser Val Pro Tyr Gln Ser Gly Ala Phe
65                  70                  75                  80

Ala Phe Asp Pro Ile Ser Thr Asn Pro Tyr Asn Met Gln Gln Ser Ser
            85                  90                  95

Tyr Tyr Ser Ser Asn Ile Ala Gln Ala Val Thr Tyr Gly Thr Ala Pro
            100                 105                 110

Asp Val Gln Ser His Pro Thr Val Arg Asp Ala His Ser Ser Phe Leu
            115                 120                 125

Met Asn Arg Asn Thr Met Val Lys Ser Glu Ser Ala Ser Pro Ile Ser
130                 135                 140

Ser Ala Pro Met Tyr Asn Asp His Ser Tyr Val Ala Glu Cys Arg Arg
145                 150                 155                 160

Ala Ala Ser Glu Gln Thr Asp Arg Thr Gly Val Asn Phe Ala Thr Asp
            165                 170                 175

Val Asp Thr Leu Met Arg Ala Ile Gln Ala Lys Glu Pro Thr Thr Pro
            180                 185                 190

Gln Ala Lys Glu Ala Lys Gln Glu Thr Glu Val Lys Ile Ser Gln Lys
            195                 200                 205

Thr Arg Lys Arg Tyr Gln Cys Asn Ile Pro Asp Cys Ser Lys Ser Phe
210                 215                 220

Phe Gln Lys Thr His Leu Asp Ile His Ile Arg Ala His Thr Gly Ala
225                 230                 235                 240

Lys Pro Phe Asn Cys Lys Ala Pro Gly Cys Gly Gln Ser Phe Ser Gln
            245                 250                 255

Leu Gly Asn Leu Lys Thr His Glu Arg Arg His Thr Gly Glu Arg Pro
            260                 265                 270

Tyr Ser Cys Asp Ile Cys Gly Lys Thr Phe Ala Gln Arg Gly Asn Val
            275                 280                 285

Arg Ala His Lys Ile Val His Gln Gln Ile Lys Pro Phe Thr Cys Arg
            290                 295                 300

Leu Asp Asp Cys Gly Lys Gln Phe Thr Gln Leu Gly Asn Leu Lys Ser
305                 310                 315                 320

His Gln Asn Lys Phe His Ala Ala Thr Leu Arg Tyr Leu Thr Gln Lys
                325                 330                 335

Phe Ala Thr Ile Thr Pro Ser Asp Tyr Val Ser Gln Glu Asp Lys Glu
            340                 345                 350

Leu Trp Glu Tyr Phe Ala Ser Leu Tyr Lys Asn Ser Asn Lys Gly Ile
            355                 360                 365

Lys Gly Arg Gly Lys Asp Arg Arg Ile Ser Ala Ile Ser Ser Met Ala
            370                 375                 380

Asn Ser Asn Pro Ser Ser Tyr Ala Pro Met Pro Met Thr Ser Met Ser
385                 390                 395                 400

Gln Ser Tyr Ser Gly Tyr Leu His His Ser Gly Ser Asp Arg Ser Ser
                405                 410                 415

Arg Ser Ser Ser Met Ser Thr Asp Ala Ile Arg Arg Ile Asp Asn Ser
                420                 425                 430

Tyr Asp Phe Asn Ala Pro Met Pro Thr Gly Tyr His His Gln Thr Gln
            435                 440                 445

Gly Thr Gly Tyr Asp Asp Met Val Phe Pro Glu Arg Lys Leu Tyr
            450                 455                 460

<210> SEQ ID NO 111
<211> LENGTH: 449
<212> TYPE: PRT
<213> ORGANISM: Artificial Sequence
<220> FEATURE:
<223> OTHER INFORMATION: synthesized

<400> SEQUENCE: 111

Met Asp Ile Gly Asn Leu Met Asn Gln Arg Gly Ala Ala Met Gln Gln
1               5                   10                  15

His Ala Ser Ile His Thr Gly Ser Thr Pro Glu Arg Gln Met His Gln
                20                  25                  30

Leu Pro Gln Leu Thr Ala Arg Asn Met Pro Glu Pro Pro Met Asp Arg
            35                  40                  45

Ala Gly Ser Pro His Gly Ser Glu His Ser Gln Phe Ser Arg His Thr
        50                  55                  60

Met Asp Gly Val Pro Arg Ser Tyr Pro Ser Pro Ser Ala Met Val Gly
65                  70                  75                  80

Ala Pro Met Gln Met Gln Val Pro Val Ser His Met Gly Pro Gly Pro
                85                  90                  95

Val Ile Leu Pro Gly Ile Pro Gln His Asp Met Ser Gln Gly Met Pro
              100                 105                 110

Gln Tyr Lys Ala Pro Glu Gln Val Ser Gln Pro Thr Lys Ala
        115                 120                 125

Tyr Pro Cys Ser Thr Cys Gly Lys Gly Phe Ala Arg Arg Ser Asp Leu
    130                 135                 140

Ala Arg His Glu Arg Ile His Ser Gly Ile Arg Pro His Val Cys Asp
145                 150                 155                 160

Phe Pro Asn Cys Gly Lys Gln Phe Ile Gln Arg Ser Ala Leu Thr Val
                165                 170                 175

His Gln Arg Val His Thr Gly Glu Lys Pro His Met Cys Glu Arg Cys
            180                 185                 190

Gly Lys Pro Phe Ser Asp Ser Ser Leu Ala Arg His Arg Arg Ile
        195                 200                 205

His Ser Gly Lys Arg Pro Tyr Lys Cys Pro Tyr Ala Asp Cys Gln Lys
    210                 215                 220

Thr Phe Thr Arg Arg Thr Thr Leu Thr Arg His Gln Asn His His Thr
225                 230                 235                 240

Gly Thr Val Glu Glu Ala Ala Ala Ala Thr Ala Ala Ala Leu Ala Ala
                245                 250                 255

Arg Gly Ala Thr Met Lys Pro Asn Ala Thr Arg Ser Asp Gly Asp Ala
            260                 265                 270

Met Ser Asn Arg Gly Ser Pro Leu Thr Thr Pro Ser Pro Gly Gln Arg
        275                 280                 285

Thr Leu Ser Met Ser Pro Ser Ala Asp Ser Met His Arg Ala Asn Ser
    290                 295                 300

Glu Phe Gln Tyr Met Gly Asn Ser Ser Leu Pro Val His Leu Gln Arg
305                 310                 315                 320

Asp Met His Val Gly Ser Pro Ala Ser Thr Ser Ser Gly Gly Tyr Asn
                325                 330                 335

Thr Gly Met Arg Pro Thr Ser His Pro Thr Ser Tyr Gly Pro Pro
            340                 345                 350

Thr Leu Glu Pro Ser Val Glu Gln His Ser Gly Pro Gly Ser Ala Gly
        355                 360                 365

Gly Ser Pro His Met Ser Asn Val Gly Trp Gln Ser Pro Ser His Val
    370                 375                 380

Ala Ser Pro Ser His Ser Ser Asn Gly Gly Gly Tyr Thr Tyr Pro Asp
385                 390                 395                 400

Pro Asp Gly Tyr Pro Ala Ala Pro Ser Leu Gly Gly Gln Met Phe Tyr
                405                 410                 415

Gly Asn Pro Gly Gln Val Arg Arg Pro Gln Ser Thr Glu Pro Pro Ala
            420                 425                 430

Gly Ala Tyr Asp Ile Lys Gly Arg Gln Ser Glu Leu Trp Ala Gly Ala
        435                 440                 445

His

<210> SEQ ID NO 112
<211> LENGTH: 396
<212> TYPE: PRT
<213> ORGANISM: Artificial Sequence
<220> FEATURE:
<223> OTHER INFORMATION: synthesized

<400> SEQUENCE: 112

Met Asn Gly Leu Arg Tyr Pro Ser Pro Ser Gln Met Gln Ala Pro Met

-continued

```
1               5                   10                  15
Pro Met Leu Asn Asn Ser Asn Tyr Ile Pro Asn Pro Pro Asp His Ala
                20                  25                  30
Tyr Ala Gln Gln Gln Met Pro Asp Asn Gln Val Gln His Gln His
                35                  40                  45
Asn Gly Gly Arg Pro Ala Ser Asp Thr Gly Pro Pro Lys Ala Phe Ala
 50                  55                  60
Cys Ser Thr Cys Gly Lys Gly Phe Ala Arg Arg Ser Asp Leu Ala Arg
 65                  70                  75                  80
His Glu Arg Ile His Ser Gly Ile Arg Pro His Val Cys Asp Tyr Pro
                85                  90                  95
Asn Cys Gly Lys Gln Phe Ile Gln Arg Ser Ala Leu Thr Val His Gln
                100                 105                 110
Arg Val His Thr Gly Glu Lys Pro His Met Cys Glu Arg Cys Gly Lys
                115                 120                 125
Pro Phe Ser Asp Ser Ser Ser Leu Ala Arg His Arg Arg Ile His Ser
                130                 135                 140
Gly Lys Arg Pro Tyr Lys Cys Pro Tyr Ala Asp Cys Gln Lys Thr Phe
145                 150                 155                 160
Thr Arg Arg Thr Thr Leu Thr Arg His Gln Asn His His Thr Gly Thr
                165                 170                 175
Val Glu Glu Ala Ala Ala Ala Thr Ala Ala Leu Ala Ser Arg Ala
                180                 185                 190
Ser Ala Ser Ser Arg Thr Gly Arg Ser Asp Gly Gly Asp Tyr Ser Glu
                195                 200                 205
Thr Ala Ser Pro Leu Gly Thr Pro Ser Pro Asn Asp Arg Thr Leu Ser
                210                 215                 220
Leu Ser Pro Ala Asn Gly Met Pro Ala Gly Met Pro Gly Leu His
225                 230                 235                 240
Arg Gln Gly Ser Asp Tyr Ala Tyr Met Gly Gly Ile Asn Val Pro Pro
                245                 250                 255
His Met Arg His Glu Met Pro Gln Pro Ser Pro Arg Ala Ser Pro Ala
                260                 265                 270
Leu Thr Ala Gln Ser Tyr Thr Ser Asn Val Ser Gly Ser Arg Pro Ala
                275                 280                 285
Ile Thr Ser His Pro Ser Ala Tyr Gly Pro Pro Ile Leu Glu Pro
                290                 295                 300
Pro Ala Ser Ala Asn His Asn Gln Ser Gly Gly Thr Asn Ser Ala Asn
305                 310                 315                 320
Gly Ser Pro His Met Ser Ala Met Gly Trp Gln Ser Pro Gly Gln Gln
                325                 330                 335
Ala Leu Pro Ser Pro Gly Ala Gly Asp Asn Gly Tyr Val Tyr Pro Glu
                340                 345                 350
Pro Gln Tyr Gln Ala Gln Asn Gly Met Tyr Tyr Gln His Asn Asn Ile
                355                 360                 365
Arg Arg Pro Asn Ser Thr Glu Pro Asp His Tyr Asn Pro Asn Gln Gln
                370                 375                 380
Arg Met Gly Asn Glu Met Trp Ala Pro Ala Val Gln
385                 390                 395

<210> SEQ ID NO 113
<211> LENGTH: 330
<212> TYPE: PRT
<213> ORGANISM: Artificial Sequence
```

<220> FEATURE:
<223> OTHER INFORMATION: synthesized

<400> SEQUENCE: 113

Met Asn Ala Gly Ile His His Tyr Lys Pro Pro Gly Val Pro Val Glu
1               5                   10                  15

Pro Gln Pro Ala Gln Gln Val Lys Ala Tyr Pro Cys Gly Thr Cys Gly
            20                  25                  30

Lys Arg Phe Ala Arg Arg Ser Asp Leu Ala Arg His Glu Arg Ile His
        35                  40                  45

Ser Gly Ile Arg Pro His Val Cys Asp Tyr Pro Asn Cys Gly Lys Gln
    50                  55                  60

Phe Ile Gln Arg Ser Ala Leu Thr Val His Gln Arg Val His Thr Gly
65                  70                  75                  80

Glu Lys Pro His Met Cys Glu Arg Cys Gly Lys Pro Phe Ser Asp Ser
                85                  90                  95

Ser Ser Leu Ala Arg His Arg Arg Ile His Ser Gly Lys Arg Pro Tyr
            100                 105                 110

Lys Cys Pro Tyr Ala Asp Cys Gln Lys Thr Phe Thr Arg Arg Thr Thr
        115                 120                 125

Leu Thr Arg His Gln Asn His His Thr Gly Thr Val Glu Glu Ala Ala
    130                 135                 140

Ala Ala Thr Ala Ala Leu Ala Arg Ala Ser Val Lys Pro Gly
145                 150                 155                 160

Ser Thr Arg Ser Asp Gly Asp Ser Met Ser Asn Arg Gly Ser Pro Met
                165                 170                 175

Thr Thr Pro Ser Pro Ala Gln Arg Thr Leu Ser Met Ser Pro Ser Ala
            180                 185                 190

Asp Gln Met Gln Arg Ser Asn Ala Glu Phe Gly Tyr Met Gly Asn Thr
        195                 200                 205

Ser Leu Pro Val His Leu Gln Arg Asp Met His Val Gly Ser Pro Ala
    210                 215                 220

Ser Thr Thr Ser Ala Gly Tyr Ser Asn Gly Val Arg Pro Thr Ser His
225                 230                 235                 240

Pro Thr Gly Tyr Gly Met Val Pro Pro Thr Leu Glu Pro Asn Val
                245                 250                 255

Glu Gln His Ser Gly Pro Gly Ala Gly Gly Ser Pro His Met Ser
            260                 265                 270

Thr Met Gly Trp Gln Ser Pro Ser His Val Ala Ser Pro Ser His Ser
            275                 280                 285

Asn Asn Gly Ser Ala Tyr Met Tyr Pro Glu Pro Glu His Tyr Pro Ala
    290                 295                 300

Gly Pro Thr Leu Gly Asn Gln Met Phe Phe Gly Gln Val Arg Arg Pro
305                 310                 315                 320

Gln Ser Thr Glu Pro Pro Ala Ala Ala Tyr
                325                 330

<210> SEQ ID NO 114
<211> LENGTH: 447
<212> TYPE: PRT
<213> ORGANISM: Artificial Sequence
<220> FEATURE:
<223> OTHER INFORMATION: synthesized

<400> SEQUENCE: 114

Met Asp Ile Thr Asn Ile Leu Asn Glu Lys Gly Thr Ala Ala Ala Ala

-continued

```
1               5                   10                  15
Val Ala Lys Ala Gln Leu His Gln His Leu Thr Gln Gly Thr His Ile
                20                  25                  30
Lys Ser Gln Thr Pro Ser Glu Met Gly Ser Glu Asn Gly Thr Ser Gln
                35                  40                  45
Asn Gly Asp Gln Ser Asn Ile Tyr Pro Pro Thr Ser Gln Pro His Ser
            50                  55                  60
His Leu Ala Gly Ile Pro Gln Tyr His Pro Ser Gln Gly Ala Gly
65                  70                  75                  80
Gly Val Pro Ala Ala Arg Ser Asp Phe Val Gln Ala Asp Gln Gly Asp
                85                  90                  95
Val Lys Tyr Leu Pro Asn Ala Asn Thr Gly Arg Gly Arg Ala Ser Gly
                100                 105                 110
Glu Pro Ala Pro Lys Thr Phe His Cys Ser Thr Cys Gly Lys Gly Phe
                115                 120                 125
Ala Arg Arg Ser Asp Leu Ala Arg His Glu Arg Ile His Ser Gly Ile
            130                 135                 140
Arg Pro His Val Cys Asp Trp Pro Gly Cys Gly Lys Gln Phe Ile Gln
145                 150                 155                 160
Arg Ser Ala Leu Thr Val His Thr Arg Val His Thr Gly Glu Lys Pro
                165                 170                 175
His Met Cys Asp Arg Cys Gly Lys Pro Phe Ser Asp Ser Ser Ser Leu
                180                 185                 190
Ala Arg His Arg Arg Ile His Ser Gly Lys Arg Pro Tyr Lys Cys Pro
                195                 200                 205
Tyr Ala Asn Cys Gln Lys Thr Phe Thr Arg Arg Thr Thr Leu Thr Arg
            210                 215                 220
His Gln Asn His His Thr Gly Thr Ile Glu Glu Ala Ala Ala Glu Thr
225                 230                 235                 240
Glu Ala Asn Leu Arg Gln Asn Lys Glu Arg Val Ile Arg Pro Pro Asp
                245                 250                 255
Gly Ile Tyr Ser Glu Thr Gly Ser Thr His Ser Thr Pro Ser Pro Gly
                260                 265                 270
Gln Arg His Ser Leu Ser Pro Gly Asn Glu Leu Pro Pro Met Asn Leu
                275                 280                 285
His Arg Gln Met Gly Asp Tyr Tyr Met Gly Asn Asn Thr Ser Ile Pro
                290                 295                 300
Pro His Leu Arg Gly Asp Phe Gln Gln Pro Ser Pro Arg Ala Ser Pro
305                 310                 315                 320
Ser Thr Ser Ser Pro Pro Val Ser Thr Tyr Asn Asn Val Pro His Ala
                325                 330                 335
Arg Pro Ser Leu Thr Ser His Pro Ser Gly Tyr Gly Pro Pro Gln Pro
                340                 345                 350
Leu Glu Pro Pro Ala Asn Ser Asp Pro Arg Pro Asn Ser Gly Ser Gly
                355                 360                 365
Ser Pro His Ile Ser Ser Met Gly Trp Ala Ser Pro Thr Leu Asn Ser
                370                 375                 380
Val Gly Ser Pro Ala Ser Ala Ser Ala Thr Glu Tyr Ser Tyr Pro Glu
385                 390                 395                 400
Pro Ser Gly Pro Pro Tyr Ser Ala His Met Pro Pro His Met Tyr Phe
                405                 410                 415
Pro Asn Ser Thr Ile Arg Arg Pro Gln Ser Thr Glu Pro Glu Asn Tyr
                420                 425                 430
```

Glu Met Lys Pro Lys Leu Asn Gly Asp Ser Trp Thr Thr Pro Val
         435                 440                 445

<210> SEQ ID NO 115
<211> LENGTH: 423
<212> TYPE: PRT
<213> ORGANISM: Artificial Sequence
<220> FEATURE:
<223> OTHER INFORMATION: synthesized

<400> SEQUENCE: 115

Met Ala His Thr Glu Leu Leu Pro Arg Pro Thr Phe Gln Pro Ala Pro
1               5                   10                  15

Tyr Gly Ser Ala Gly Gly Val Val Ala Leu Gln Gln Leu Gln Leu Asp
            20                  25                  30

His Arg Pro Leu Gln Gln His Gln His His Pro Gln Pro Pro Gln Gln
        35                  40                  45

Gln Gln Gln Gln Gln Gln Gln Gln Gln Gln Gln Gln Gln Gln Arg Leu
    50                  55                  60

Gln Gly Phe Val Pro Tyr Gln Gln Thr Ala Leu Ala Gln Ser Ala Pro
65                  70                  75                  80

Ser Pro Val Tyr Tyr Ala Ser Ser Gln Met Ala Pro Ile Gly Gln His
                85                  90                  95

Val Pro Phe Ala Ser Asp Ala Gln Arg Gln Ser Val Met His Tyr Gln
            100                 105                 110

Met Gly Ser Ser Thr His Pro Leu Pro Gln Ser Phe Met Pro His Pro
        115                 120                 125

Val Pro Val Thr Leu His Asp Leu Gln Ala Gln Leu Val Gln Asn Pro
    130                 135                 140

Ile Ser Gly Leu Ser Gln Pro Gln His Leu His Leu Val Gln Pro Ala
145                 150                 155                 160

Thr Thr Gln Gln Gly Gly Met Pro Gln Pro Gln Met Ser Ser Arg Gln
                165                 170                 175

Arg Val Arg Arg Lys Ser Ser Thr Glu Gly Ser Thr Thr Ser Ser Asp
            180                 185                 190

Asp Lys Thr Ala Gly Leu Ala Gln Ala Ala Ser Ala Gln Val Thr Ala
        195                 200                 205

Thr Pro Val Ser Ser Val Gln Ala Ala Thr Ala Pro Ala Val Ala Pro
    210                 215                 220

Ala Val Pro Arg Thr Val Phe Val Asp Asn Ser Val Ala Gly Ala Ser
225                 230                 235                 240

Ser Thr Phe Gln Cys Glu Trp Gln Gly Cys Ser Asp Ser Phe Leu Ser
                245                 250                 255

Phe Ser Asp Phe Val Ser His Val Thr Asp Glu His Ile Gly Ser Gly
            260                 265                 270

Leu Arg Phe Tyr Phe Cys Asp Trp Lys Asn Cys Met Gln Ala Gly Asn
        275                 280                 285

Pro Phe Arg Lys Arg His Lys Ile Met Thr His Val Arg Ile His Thr
    290                 295                 300

Gly Glu Lys Pro His Ser Cys Ser Val Pro Gly Cys Gly Lys Arg Phe
305                 310                 315                 320

Pro Arg Ile Asp Ser Leu Arg Ala His Met Gln Val His Ser Gly Thr
                325                 330                 335

Arg Lys Phe Thr Cys Pro Leu Ala Thr Cys Met Arg Ser Tyr Tyr His
            340                 345                 350

```
Pro Arg Ser Leu Arg Lys His Val Arg Thr Lys Gln His Gly Asp Ala
        355                 360                 365

Asp Ala Ile Ile Arg Glu Ile Leu Glu Ser Arg Arg Ala Thr Gly Asp
    370                 375                 380

Ala Gln Asp Asp Ser Asp Asn Leu Glu Glu Glu Glu Glu Glu Glu Glu
385                 390                 395                 400

Glu Asp Thr Asp Gly Asp Asp Ser Ala Asp Gly Ser Gly Asp Gly Gly
                405                 410                 415

Ser Gln Ser His Ser Pro Arg
                420

<210> SEQ ID NO 116
<211> LENGTH: 356
<212> TYPE: PRT
<213> ORGANISM: Artificial Sequence
<220> FEATURE:
<223> OTHER INFORMATION: synthesized

<400> SEQUENCE: 116

Met His Ser Ser Ser Met Ile Pro Gln Tyr Asp Thr Ser Arg Ala Ala
1               5                   10                  15

Thr Ser Ala Pro Val Ser Arg Ser Phe Gln Pro Thr Ser Thr Gln Met
            20                  25                  30

Asp Met Ser Met Pro Leu Tyr Ser Ser Asn Gly Leu Pro Thr Thr Val
        35                  40                  45

Pro Tyr Gln Pro Gly Gln Phe Ala Tyr Asp Thr Ala Pro Val Asn Pro
    50                  55                  60

Tyr Thr Met Gln Gln Pro Ser Tyr Tyr Gln Ser Gly Ile Pro His Pro
65                  70                  75                  80

Val Ser Tyr Pro Pro Ser Thr Asp Val Gln Gln Leu Pro Thr Glu Asp
                85                  90                  95

Ala Thr Lys Pro Ser Gln Lys Pro Arg Lys Arg Tyr Gln Cys Thr Val
            100                 105                 110

Pro Asn Cys Asn Lys Ser Phe Tyr Gln Lys Thr His Leu Glu Ile His
        115                 120                 125

Ile Arg Ala His Thr Gly Ala Lys Pro Phe Asn Cys Lys Ala Pro Gly
    130                 135                 140

Cys Gly Gln Ser Phe Ser Gln Leu Gly Asn Leu Lys Thr His Glu Arg
145                 150                 155                 160

Arg His Thr Gly Glu Arg Pro Tyr Ser Cys Asp Ile Cys Gly Lys Thr
                165                 170                 175

Phe Ala Gln Arg Gly Asn Val Arg Ala His Lys Ile Val His Gln Gln
            180                 185                 190

Ile Lys Pro Phe Thr Cys Lys Leu Asp Asp Cys Gly Lys Gln Phe Thr
        195                 200                 205

Gln Leu Gly Asn Leu Lys Ser His Gln Asn Lys Phe His Ala Thr Thr
    210                 215                 220

Leu Arg Tyr Leu Thr Thr Lys Phe Ala Thr Ile Ser Met Gly Asp Trp
225                 230                 235                 240

Val Ser Lys Glu Asp Lys Glu Leu Trp Glu Tyr Phe Ala Ser Leu Tyr
                245                 250                 255

Lys Asn Ser Asn Lys Gly Ile Lys Gly Arg Gly Lys Asp Arg Arg Ile
            260                 265                 270

Ser Ala Met Ser Ser Ser Ala Ser Ser Tyr Pro Ser Ser Tyr Pro Ala
        275                 280                 285
```

```
Met Pro Met Ala Ser Met Ser Arg Ser Tyr Gly Gly Ser Phe His His
        290                 295                 300
Ser Ser Glu Arg Ser Ser Arg Ser Ser Met Ser Ser Asp Thr Ile
305                 310                 315                 320
Gln Arg Val Asp Ser Gly Tyr Asp Phe Asn Val Pro Met Pro Thr Ser
                    325                 330                 335
Tyr His Gln Pro Pro Ala Ser Gly Tyr Asp Asp Met Val Phe Pro Glu
                340                 345                 350
Arg Lys Leu Tyr
            355

<210> SEQ ID NO 117
<211> LENGTH: 475
<212> TYPE: PRT
<213> ORGANISM: Artificial Sequence
<220> FEATURE:
<223> OTHER INFORMATION: synthesized

<400> SEQUENCE: 117

Met Glu Leu Met Glu Leu Val Asp Asn Glu Pro Thr Ala Arg Pro Phe
1               5                   10                  15
Gln Cys Asp Trp Asp Gly Cys Glu Thr Lys Lys Gln Ser Phe Asn Arg
                20                  25                  30
Lys Ser Asp Leu Gln Arg His Tyr Arg Ile His Thr Asn Glu Arg Pro
            35                  40                  45
Tyr Gln Cys Asn Gln Pro Gly Cys Gly Lys Ser Phe Ile Gln Arg Ser
        50                  55                  60
Ala Leu Thr Val His Ile Arg Thr His Thr Gly Glu Lys Pro His Gln
65                  70                  75                  80
Cys Gln His His Gly Cys Gly Lys Arg Phe Ser Asp Ser Ser Ser Leu
                85                  90                  95
Ala Arg His Arg Arg Ile His Thr Gly Lys Arg Pro Tyr Lys Cys Ala
                100                 105                 110
His Asp Gly Cys Leu Lys Ser Ser Phe Cys Arg Lys Thr Thr Met Val
            115                 120                 125
Lys His Gln Arg Arg Ser His Gln Arg Gly Ile His Ser Ser Glu Leu
        130                 135                 140
Asp Asp Ser Met Ser Asp Thr Gly Ser Glu Asp Ser Pro Ser Thr Pro
145                 150                 155                 160
Lys Ser His Ser Ala Met Pro Trp Ala Thr Ala Gln Gln His His His
                165                 170                 175
His Ile Pro Met Met Gly Pro His Gly His His Leu Gln Arg Ala Ala
                180                 185                 190
Ser Phe Ala Asp Phe Gly Gln His Met Asn Gly Tyr Ser Leu Gln Gln
            195                 200                 205
Gln Tyr Asn Asn Gln His Arg His Ser Leu Ser Ser Gly Gly Ala Ala
        210                 215                 220
Glu Tyr His Gly Leu His Gln Asp Pro His Pro Gln Ala Val His His
225                 230                 235                 240
His His Gln Gln Gln Pro Gln Pro Gln His His His His Gln Asn
                245                 250                 255
Val Pro Val Val Leu Gln Arg Thr Ser Ser Leu Pro His His Ser Tyr
                260                 265                 270
Phe Val Ala Asp Ser Asn Asn Pro Gly Val Ala Thr Met Asn Thr Asn
            275                 280                 285
```

```
His Pro Gly Ala Pro Gln Val His His Gln His Ala Pro Gln Tyr
    290                 295                 300

Gln Thr Ile Pro Arg Gln Ala Pro Val Glu Met Thr Tyr Pro Ser Ala
305                 310                 315                 320

Pro Gly Leu Ala Ala Ser Ile Gln Ser Ser Pro Ser Ser Phe Ser Ala
                325                 330                 335

Gly Ser Gly Arg Ser Pro Ser Thr Gln Glu Gly Phe Tyr Thr His Ala
                340                 345                 350

Pro Pro Ala Gln Ala Ala Thr Tyr Ala Leu His Ala Thr Ser Pro Val
                355                 360                 365

Val Glu Thr Gln Gln Gln Gln Gln Gln Gln Gln Gln Gln Gln Gln Gln
                370                 375                 380

Gln Gln Gln Asn Met Tyr Pro Pro Gln Gln Ala Gln Ala Gln Pro
385                 390                 395                 400

Thr Ser Gln Pro Gln Glu Gln Lys Tyr Tyr Glu Pro Gln Pro Val Arg
                405                 410                 415

Glu Glu Glu Pro Gln Gln Asn Trp Tyr Ser Gly Ala His Ala Val Tyr
                420                 425                 430

Gln Pro Pro Val Glu Val Ala Thr Ile Gly Gly Tyr Ala Ala Gly Gly
                435                 440                 445

Val Tyr Asp Pro Trp Gly Thr Gly Pro Lys Leu Glu Phe Asp Asp Gly
                450                 455                 460

Met Gln Leu Pro Ser Ala Arg Ile Glu Ser Met
465                 470                 475

<210> SEQ ID NO 118
<211> LENGTH: 464
<212> TYPE: PRT
<213> ORGANISM: Artificial Sequence
<220> FEATURE:
<223> OTHER INFORMATION: synthesized

<400> SEQUENCE: 118

Met Ala Ala Val Val Ala Pro His Gln Thr Pro Gly Leu Trp Gln Glu
1               5                   10                  15

Arg Arg Glu Pro Ser Phe Gln Met Pro Ser Ser Met His Gln Ser Ser
                20                  25                  30

Met Met Pro Gln Tyr Asp Ala Thr Arg Ser Val Thr Ser Ala Pro Val
                35                  40                  45

Ser Arg Ser Phe Gln Pro Thr Ser Thr Gln Met Asp Met Ser Met Pro
                50                  55                  60

Leu Tyr Thr Ser Asn Gly Leu Pro Thr Ser Ala Pro Tyr Gln Ser Gly
65                  70                  75                  80

Gly Ala Phe Ala Tyr Asp Pro Ala Ser Val Asn Pro Tyr Thr Met Pro
                85                  90                  95

Gln Ser Ser Tyr Tyr Ser Ser Ser Ile Pro Asn Pro Val Ser Tyr Pro
                100                 105                 110

Pro Ser Ser Asp Val Gln Ser Leu Pro Thr Val Arg Asp Gly Arg Asn
                115                 120                 125

Leu Phe Asn Pro Met Val Lys Ala Glu Ser Thr Ser Pro Leu Gln Ser
            130                 135                 140

Asn Pro Ile Tyr Asn Asn Ser Asn Ser Asp Thr Asn Tyr Ser Ala Asp
145                 150                 155                 160

Cys Lys Arg Ser Asn Ser Glu Pro Thr Glu Ser Asn Thr Val Asn Phe
                165                 170                 175
```

```
Ser Thr Asp Val Asp Thr Leu Met Arg Ala Ile Gln Ala Lys Gln Thr
            180                 185                 190

Asn Ala Pro Glu Pro Thr Glu Pro Lys Asp Glu Thr Thr Lys Pro Ser
        195                 200                 205

Gln Lys Pro Arg Lys Arg Tyr Gln Cys Thr Val Pro Asn Cys Asn Lys
    210                 215                 220

Ser Phe Tyr Gln Lys Thr His Leu Glu Ile His Ile Arg Ala His Thr
225                 230                 235                 240

Gly Ala Lys Pro Phe Asn Cys Lys Ala Pro Gly Cys Gly Gln Ser Phe
                245                 250                 255

Ser Gln Leu Gly Asn Leu Lys Thr His Glu Arg Arg His Thr Gly Glu
            260                 265                 270

Arg Pro Tyr Ser Cys Asp Ile Cys Gly Lys Thr Phe Ala Gln Arg Gly
        275                 280                 285

Asn Val Arg Ala His Lys Ile Val His Gln Gln Ile Lys Pro Phe Thr
    290                 295                 300

Cys Lys Leu Asp Asp Cys Gly Lys Gln Phe Thr Gln Leu Gly Asn Leu
305                 310                 315                 320

Lys Ser His Gln Asn Lys Phe His Ala Ala Thr Leu Arg Tyr Leu Thr
                325                 330                 335

Thr Lys Phe Ala Thr Ile Ser Met Gly Asp Trp Val Ser Lys Glu Asp
            340                 345                 350

Lys Glu Leu Trp Glu Tyr Phe Ala Ser Leu Tyr Lys Asn Ser Asn Lys
        355                 360                 365

Gly Ile Lys Gly Arg Gly Lys Asp Arg Arg Ile Ser Ala Met Ser Ser
    370                 375                 380

Ser Ala Ser Ser Tyr Pro Ser Ser Tyr Ala Ala Leu Pro Met Ser Ser
385                 390                 395                 400

Leu Ser Arg Ser Phe Gly Gly Pro Phe His Gln His Ser Ser Glu Arg
                405                 410                 415

Ser Ser Arg Ser Ser Ser Met Ser Ser Asp Ser Ile Gln Arg Val Asp
            420                 425                 430

Ser Gly Tyr Asp Phe Asn Val Pro Met Pro Thr Gly Tyr His Gln Pro
        435                 440                 445

Pro Ala Ser Gly Tyr Asp Asp Met Val Phe Pro Glu Arg Lys Leu Tyr
    450                 455                 460

<210> SEQ ID NO 119
<211> LENGTH: 312
<212> TYPE: PRT
<213> ORGANISM: Artificial Sequence
<220> FEATURE:
<223> OTHER INFORMATION: synthesized

<400> SEQUENCE: 119

Met Ala Thr Leu Tyr Leu Gly Leu Glu Glu Asn Leu Leu Ser Ser Ser
1               5                   10                  15

Pro Asn Leu Arg Ser Tyr Ser Ile Ser Ser Thr Ser Ser Gly Ala Ser
            20                  25                  30

Cys Ser Thr Thr Gln Ser His Pro Ser Cys Tyr Arg Thr Leu Ala Pro
        35                  40                  45

Lys Ala Asp Asn Thr Ser Pro Met Ser Phe Ser Arg Pro Phe Glu
    50                  55                  60

Asp Gly Phe Leu Gly Leu Arg Glu Arg Lys Thr His Asn Gly Gln Ser
65                  70                  75                  80
```

```
Ile Ala Pro Asn Leu Leu Ser Ile Lys Val Glu Gly Ala His Gln Thr
                85                  90                  95

Ser Asn Pro Pro Leu Asp Pro Ala Phe His Pro Ser Gln Gln Met Glu
               100                 105                 110

Asp Met Leu Gln Gln Gln Gln Gln Asn Phe Ser Thr Pro Asn Tyr Asp
           115                 120                 125

Gln Ser Tyr Pro Arg Ile Thr Asn Tyr Pro Glu Tyr Gly Pro Gln Arg
       130                 135                 140

Tyr Ser Ser Asn Ser Leu Ser Pro Ser Ser Asn Gly Asp Cys Leu
145                 150                 155                 160

Tyr Thr Thr His Asn Arg Met Phe Asp Cys Ser Gln Ser Phe Ala Pro
               165                 170                 175

Trp Gly His Glu Ser Asn Ser Arg Glu Ala Cys Ala Ala Met Thr Ala
           180                 185                 190

Leu Glu Leu Leu Met Pro Lys Val Gly Ile Gly Ser Glu Gly Glu Glu
       195                 200                 205

Asp Val Asp Met Ser Asp Arg Asp Ser Ala Gly Ser Ser Pro Gly Pro
   210                 215                 220

Thr Val Ala Arg Arg Lys Arg Arg Ala Pro His Pro Leu Val Ile Ser
225                 230                 235                 240

Ser Arg Asp Lys Pro His Val Cys Ser Val Gly Asp Cys Glu Ser Arg
               245                 250                 255

Phe Lys Arg Pro Glu His Leu Arg Arg His Glu Lys Thr His Thr Gly
           260                 265                 270

Glu Arg Pro Phe Ser Cys Thr Ile Cys Gly Arg Arg Phe Gly Arg Asn
       275                 280                 285

Asp Asn Leu Gln Thr His Lys Lys Thr His Met Lys Met Thr Gly Arg
   290                 295                 300

Asn Glu Tyr Ile Pro Gly Leu Ala
305                 310

<210> SEQ ID NO 120
<211> LENGTH: 467
<212> TYPE: PRT
<213> ORGANISM: Artificial Sequence
<220> FEATURE:
<223> OTHER INFORMATION: synthesized

<400> SEQUENCE: 120

Met Asp Ile Thr Thr Ile Leu Asn Lys Lys Ala Ser Val Ser Ile Val
1               5                   10                  15

Ala Ala Asp Val His Gln Leu Gln Gln His Leu Ala Gln Ala Thr Ala
                20                  25                  30

Gln Ser Gln Thr Asp Asp Ala Val Lys Ser Arg Ser Pro Ser Glu Leu
            35                  40                  45

Gly Ala Ser Glu His His Arg Ser Ala Ser Ala Pro Pro Ser Glu His
        50                  55                  60

His His His His His His Gln Pro Thr Ser Ser Phe Pro Ser Ser
65                  70                  75                  80

Thr Gln Ser Leu Pro Gln Met Ala His Leu Ala Gln Tyr His Val Gln
                85                  90                  95

Ala Gln Ala Asn His Ala Ser Thr Ser Pro Gly Tyr Ala His Ser Ala
            100                 105                 110

His Gly Ser Asp Tyr Gly Arg Ser Thr Thr Ser Met Arg Pro Thr Gly
        115                 120                 125
```

Leu Pro Ala Leu Lys Thr Phe His Cys Gln Thr Cys Ser Lys Gly Phe
            130                 135                 140

Ala Arg Arg Ser Asp Leu Ala Arg His Glu Arg Ile His Ser Gly Ile
145                 150                 155                 160

Arg Pro His Ala Cys Asp Trp Pro Gly Cys Gly Lys Gln Phe Ile Gln
                165                 170                 175

Arg Ser Ala Leu Thr Val His Thr Arg Val His Thr Gly Glu Lys Pro
            180                 185                 190

His Met Cys Asp Arg Cys Gly Lys Pro Phe Ser Asp Ser Ser Ser Leu
        195                 200                 205

Ala Arg His Arg Arg Ile His Ser Gly Lys Arg Pro Tyr Lys Cys Pro
210                 215                 220

Tyr Ala Asn Cys Gln Lys Thr Phe Thr Arg Arg Thr Thr Leu Thr Arg
225                 230                 235                 240

His Gln Asn His His Thr Gly Thr Ile Glu Glu Ala Ala Glu Thr
                245                 250                 255

Glu Ala Asn Leu Arg His Ser Lys Asp Arg Ser Thr Thr Ser Arg Pro
                260                 265                 270

Ser Glu Tyr Ser Glu Pro Gly Ser Ala His Ser Thr Pro Ser Pro Ala
        275                 280                 285

Gln Arg Pro Ser Leu Ser Pro Gly Asn Glu Leu Pro Pro Leu Asn Leu
    290                 295                 300

Ser Ser Arg Pro Pro Ala Ala Gly Gly Pro Thr Ser Ala Gly Gly Ala
305                 310                 315                 320

Ala Asp Tyr Tyr Thr Ser Leu Pro Pro His Leu Arg Thr Asp Phe Ala
                325                 330                 335

Asn Ser Ser Pro Arg Ala Ser Pro Thr Ser Pro Ser Pro Thr Leu Thr
            340                 345                 350

Ser Leu Ser Gly Pro Ala Ser Phe His His His Asn His Asn Arg
        355                 360                 365

Pro Ser Leu Thr Ser His Pro Ser Gly Tyr Ala Pro Pro Gln Pro Leu
    370                 375                 380

Glu Pro Pro Ala Asn Ser Asp Pro Arg Pro Asn Ser Val Ala Gly Ser
385                 390                 395                 400

Pro His Leu Ser Ser Val Gly Trp Ala Ser Pro Thr Leu Ser Ser Met
                405                 410                 415

Pro Ser Pro Ser Ser Ala Ser Ala Pro Glu Tyr Pro Tyr Pro Glu Pro
                420                 425                 430

Ser Asn His Gln Tyr Pro Gly Ser Ile Thr Pro His Met Phe Phe Pro
            435                 440                 445

Arg Arg Pro Gln Ser Ser Glu Pro Glu Asn Tyr Glu Leu Lys Pro Lys
450                 455                 460

Leu Glu Leu
465

<210> SEQ ID NO 121
<211> LENGTH: 402
<212> TYPE: PRT
<213> ORGANISM: Artificial Sequence
<220> FEATURE:
<223> OTHER INFORMATION: synthesized

<400> SEQUENCE: 121

Met Lys Ser Glu Pro Gly Val Thr Glu Ser Ala Asp Gln Pro Val Leu
1               5                   10                  15

Ser Tyr Pro Pro His Ala Pro Leu Pro Ser Met Pro Gln Asp Val Arg
         20                  25                  30

Tyr Ala Pro Gln Ser His Pro Ala Pro Gly Met Pro Leu Met Gln Thr
     35                  40                  45

Pro Tyr Val Pro Gly Gly Tyr Ala Ser Gly Ala Pro Met His Asn Gly
 50                  55                  60

Ala Ala Pro Pro Arg Thr Glu Pro Pro Lys Thr Phe His Cys
65                   70                  75                  80

Gly Thr Cys Gly Lys Gly Phe Ala Arg Arg Ser Asp Leu Ala Arg His
             85                  90                  95

Glu Arg Ile His Ser Gly Ile Arg Pro His Ala Cys Asp Trp Pro Gly
             100                 105                 110

Cys Gly Lys Gln Phe Ile Gln Arg Ser Ala Leu Thr Val His Ser Arg
             115                 120                 125

Val His Thr Gly Glu Lys Pro His Met Cys Glu Arg Cys Gly Lys Pro
 130                 135                 140

Phe Ser Asp Ser Ser Ser Leu Ala Arg His Arg Ile His Ser Gly
145                 150                 155                 160

Lys Arg Pro Tyr Lys Cys Pro Tyr Ala Asn Cys Gln Lys Thr Phe Thr
                 165                 170                 175

Arg Arg Thr Thr Leu Thr Arg His Gln Asn His His Thr Gly Thr Ile
             180                 185                 190

Glu Glu Ala Ala Ala Glu Thr Glu Ala Asn Leu Arg Gln Asn Lys Glu
             195                 200                 205

Arg Ser Arg Gly Pro Gly Glu Pro Met Phe Ser Asp His Ala Ser Val
210                 215                 220

His Ser Thr Pro Ser Pro Ala His Ser Gly Ile Ser Ala Gly Gly Glu
225                 230                 235                 240

Leu Pro Pro Leu Asn Met Pro Arg Ser Thr Gly Asp Tyr Tyr Met Gly
                 245                 250                 255

Ser Gly Ser Ile Pro Pro His Val Arg Gly Asp Phe Ser Gln Ala Ser
                 260                 265                 270

Pro Arg Ala Ser Pro Thr Ala Thr Ser Pro Ser Leu Ser Ser Phe Gly
     275                 280                 285

Ser Ala Pro His Ser Arg Pro Ser Met Thr Ser His Pro Thr Gly Tyr
 290                 295                 300

Gly Pro Pro Gln Pro Leu Glu Pro Ala Asn Asn Asp His Arg Pro
305                 310                 315                 320

Asn Ser Val Ser Gly Ser Pro His Met Pro Thr Leu Gly Trp Ala Ser
                 325                 330                 335

Pro Ser His Gly Ser Ile Pro Ser Pro Gly Ser Ala Asn Asp Phe Pro
             340                 345                 350

Tyr Pro Glu Pro Gly Ala Pro Ala Tyr Pro Ser Ser Val Pro Pro His
         355                 360                 365

Met Tyr Phe Ser His Ser Ala Gly Arg Arg Pro Thr Ser Thr Glu Pro
         370                 375                 380

Glu Asn Tyr Glu Met Lys Pro Lys Met Gly Asp Asn Ser Trp Ser Thr
385                 390                 395                 400

Pro Val

<210> SEQ ID NO 122
<211> LENGTH: 404
<212> TYPE: PRT

<213> ORGANISM: Artificial Sequence
<220> FEATURE:
<223> OTHER INFORMATION: synthesized

<400> SEQUENCE: 122

```
Met Leu Asn Asn Lys Val Thr Ser Ala Gln Tyr Gln Gln His Met Ala
1               5                   10                  15

Gln Ala Ser Tyr Pro Ser Pro Ser Gln Leu Gln Asp Pro Leu Ser Met
            20                  25                  30

Leu Gly Thr Asn Tyr Ser Glu Arg Pro Phe Glu Asn Met Tyr Leu Pro
        35                  40                  45

Gln His Gln Asn Glu His His Met Ser Ser His Asp Ala Ser Asp Ser
50                  55                  60

Gln Arg Gln Ser Ser Asn Gly Ala Ile Lys Ala Phe Ala Cys Thr Asn
65                  70                  75                  80

Cys Gly Lys Gly Phe Ala Arg Arg Ser Asp Leu Ala Arg His Glu Arg
                85                  90                  95

Ile His Thr Gly Asp Arg Pro His Val Cys Pro Glu Lys Gly Cys Gly
            100                 105                 110

Lys Gln Phe Ile Gln Arg Ser Ala Leu Thr Val His Met Arg Val His
        115                 120                 125

Ser Gly Glu Lys Pro His Met Cys Glu Arg Leu Ile Arg Val Leu Trp
130                 135                 140

Leu Gly Ile Val Ala Tyr Ile Leu Gly Lys Arg Pro Tyr Lys Cys Pro
145                 150                 155                 160

Phe Ala Asp Cys Gln Lys Thr Phe Thr Arg Arg Thr Thr Leu Thr Arg
                165                 170                 175

His Gln Asn His His Thr Gly Thr Val Glu Glu Ala Ala Val Ala Thr
            180                 185                 190

Ala Ala Ala Leu Ala Ser Arg Thr Pro Gly Ile His Pro Arg Asn Gly
        195                 200                 205

Ser Asp Gly Gly Asn Phe Ser Asp Thr Ala Ser Met Ser Ser Ala Met
210                 215                 220

Thr Arg Thr Pro Ser Pro Pro Glu Arg Gln Leu Ser Met Ser Pro Asn
225                 230                 235                 240

Asp Asp Val Pro His Met Pro His Leu Asn Arg Arg Thr Ser Gly Val
                245                 250                 255

Ser Tyr Ser Ser Ser Asp Ser Cys Pro Leu Pro Ala His Phe Arg Pro
            260                 265                 270

Gly Leu Gln Gln Pro Ser Pro Arg Ser Ser Pro Ser Val Ser Ser Pro
        275                 280                 285

Thr Leu Ser Ala Phe Gly Gly Asn Asn Ser Tyr His Arg Pro Ser Leu
290                 295                 300

Thr Ser His Pro Thr Leu Pro Val Leu Glu Pro Pro Thr Tyr His Asp
305                 310                 315                 320

Leu Arg Gln Pro Ala Ser Gly Ser Gly Ser Pro His Phe Gly Ser Thr
                325                 330                 335

Gly Trp Gln Ser Pro Val Ala Ala Gly Leu Pro Ser Pro Gly His Asn
            340                 345                 350

Asp Gly Gly Phe Trp Asn Pro Asp Pro Gln Tyr Gly Pro Asn Gln His
        355                 360                 365

Leu Tyr Tyr Pro Ser Ser Asn Met Arg Arg Pro Gln Ser Thr Glu Pro
370                 375                 380

Asp His Tyr Glu Leu Lys Pro Arg Leu Pro Ser Thr Gly Val Trp Ala
```

-continued

```
              385                 390                 395                 400
Gly Thr Met Gly

<210> SEQ ID NO 123
<211> LENGTH: 457
<212> TYPE: PRT
<213> ORGANISM: Artificial Sequence
<220> FEATURE:
<223> OTHER INFORMATION: synthesized

<400> SEQUENCE: 123

Met Ala Ala Val Val Ala Ser His His Met Gly Leu Trp Gln Asp Arg
1               5                   10                  15

Arg Glu Thr Pro Ala His Leu Ser Asn Met His Leu Ser Asn Met Met
                20                  25                  30

Pro Ser Tyr Asp Ala Ser Arg Thr Val Ser Asn Ala Pro Val Ser Arg
            35                  40                  45

Ser Tyr Gln Pro Thr Ser Ser His Met Asp Ile Asn Met Pro Leu Tyr
        50                  55                  60

Ser Ala Asn Gly Leu Pro Thr Ser Val Pro Tyr Gln Ser Gly Ala Phe
65                  70                  75                  80

Ala Tyr Asp Pro Thr Pro Val Asn Ala Tyr Asn Met Gln Gln Pro Ser
                85                  90                  95

Tyr Tyr Gln Ser Asn Ile Gln His Pro Val Ser Tyr Ala Pro Thr Ser
            100                 105                 110

Asp Val Gln Gln Leu Pro Thr Val Arg Asp Ala Arg Asn Val Phe Asn
        115                 120                 125

Asn Met Val Lys Ser Glu Ser Thr Ser Pro Val Gln Ser Asn Pro Met
130                 135                 140

Tyr Asn Asn Thr Ala Tyr Ser Ala Asp Ile Lys Arg Ser Thr Ser Glu
145                 150                 155                 160

Pro Thr Glu Gly Ser Ser Ala Ser Phe Ala Thr Asp Val Asp Thr Leu
                165                 170                 175

Met Arg Ala Ile Gln Ala Lys Gln Thr Thr Ser Pro Gln Ala Ser Glu
            180                 185                 190

Pro Lys Glu Glu Ala Val Lys Val Ser Gln Lys Pro Arg Lys Arg Tyr
        195                 200                 205

Gln Cys Thr Ile Pro Asn Cys Asn Lys Ser Phe Tyr Gln Lys Thr His
    210                 215                 220

Leu Glu Ile His Ile Arg Ala His Thr Gly Ala Lys Pro Phe Asn Cys
225                 230                 235                 240

Lys Ala Pro Gly Cys Gly Gln Ser Phe Ser Gln Leu Gly Asn Leu Lys
                245                 250                 255

Thr His Glu Arg Arg His Thr Gly Glu Arg Pro Tyr Ser Cys Asp Ile
            260                 265                 270

Cys Gly Lys Thr Phe Ala Gln Arg Gly Asn Val Arg Ala His Lys Ile
        275                 280                 285

Val His Gln Gln Ile Lys Pro Phe Thr Cys Lys Leu Asp Asp Cys Gly
    290                 295                 300

Lys Gln Phe Thr Gln Leu Gly Asn Leu Lys Ser His Gln Asn Lys Phe
305                 310                 315                 320

His Ala Ala Thr Leu Arg Tyr Leu Thr Gln Lys Phe Ala Thr Ile Thr
                325                 330                 335

Ser Gly Asp Trp Val Ser Gln Glu Asp Lys Glu Leu Trp Glu Tyr Phe
            340                 345                 350
```

```
Ala Ser Leu Tyr Lys Asn Ser Asn Lys Gly Ile Lys Gly Arg Gly Lys
            355                 360                 365

Asp Arg Arg Ile Ser Ala Met Ser Ser Ser Ala Ser Ser Tyr Pro Ser
370                 375                 380

Ser Tyr Ala Gly Met Pro Met Val Pro Met Ser Arg Ser Tyr Ala Gly
385                 390                 395                 400

Ser Phe His Gln Gln Ser Ser Asp Arg Ser Arg Ser Ser Ser Met
                405                 410                 415

Ser Ser Asp Ser Leu His Arg Val Asp Ser Ala Tyr Asp Phe Gly Ala
            420                 425                 430

Pro Ile Pro Asn Pro Tyr His Gln Gln Pro Gly Thr Gly Tyr Asp Asp
            435                 440                 445

Met Val Phe Pro Glu Arg Lys Leu Tyr
450                 455

<210> SEQ ID NO 124
<211> LENGTH: 437
<212> TYPE: PRT
<213> ORGANISM: Artificial Sequence
<220> FEATURE:
<223> OTHER INFORMATION: synthesized

<400> SEQUENCE: 124

Met Gln Gln Pro His His Gly Ser Gly Ala Thr Pro Asp Arg Gln Ile
1               5                   10                  15

Pro Gln Leu Ser Gln Leu Thr Ala Arg Asn Leu Pro Glu Pro Pro Met
            20                  25                  30

Asp Arg Ala Ala Ser Pro His Gly Ser Glu His Ser Arg Tyr Ser Ala
        35                  40                  45

Pro Arg Ser Thr Leu Asp Thr Met Pro Arg Ser Tyr Pro Ser Pro Asn
    50                  55                  60

Pro Met His Gly Pro Pro Met Thr Met Pro Leu Pro Gly His Gly Gln
65                  70                  75                  80

Gln Gln His Ile Ala Ala Pro Ala Ile Thr Met Ile Leu Pro Gly Ala
                85                  90                  95

Pro Pro Asp Met Gly Met Pro Lys Pro Ala Pro Ala Pro Gln Ala Pro
            100                 105                 110

Val Lys Ala Phe Pro Cys Ser Thr Cys Gly Lys Arg Phe Ala Arg Arg
        115                 120                 125

Ser Asp Leu Ala Arg His Glu Arg Ile His Ser Gly Ile Arg Pro His
    130                 135                 140

Val Cys Asp Phe Pro Gln Cys Gly Lys Gln Phe Ile Gln Arg Ser Ala
145                 150                 155                 160

Leu Thr Val His Gln Arg Val His Thr Gly Glu Lys Pro His Met Cys
                165                 170                 175

Glu Arg Cys Gly Lys Pro Phe Ser Asp Ser Ser Ser Leu Ala Arg His
            180                 185                 190

Arg Arg Ile His Ser Gly Lys Arg Pro Tyr Lys Cys Pro Tyr Ala Asp
        195                 200                 205

Cys Gln Lys Thr Phe Thr Arg Arg Thr Thr Leu Thr Arg His Gln Asn
    210                 215                 220

His His Thr Gly Thr Val Glu Glu Ala Ala Ala Thr Ala Ala Val
225                 230                 235                 240

Leu Ala Ala Arg Thr Asn Ala Lys Pro Gly Ser Val Arg Ser Glu Gly
                245                 250                 255
```

```
Glu Gly Ile Ser Asn His Ala Ser Pro Leu Thr Thr Pro Ser Pro Gly
            260                 265                 270

Gln Arg Thr Leu Ser Met Ser Pro Ser Ala Asp Gln Met Gln Arg Ser
        275                 280                 285

Ala Thr Glu Phe Gln Tyr Met Gly Asn Ala Ser Leu Pro Val His Met
    290                 295                 300

Gln Arg Asp Met His Val Gly Ser Pro Val Pro Thr Thr Ser Ala Thr
305                 310                 315                 320

Tyr Ser Asn Gly Met Arg Pro Thr Ser His Pro Thr Gly Tyr Gly Met
                325                 330                 335

Ile Pro Pro Pro Thr Leu Glu Pro Asn Val Glu Gln His Ser Gly Thr
            340                 345                 350

Gly Ser Ala Gly Gly Ser Pro Ala Met Ala Asn Met Gly Trp Gln Ser
        355                 360                 365

Pro Ser His Val Ala Ser Pro Ser His Asn Thr Asn Gly Asn Gly Tyr
    370                 375                 380

Met Tyr Pro Glu Pro Glu Asn Tyr Pro Ser Gly Pro Thr Leu Gly Gly
385                 390                 395                 400

Gln Met Phe Tyr Ser Asn Pro Ala Pro Val Arg Arg Pro Gln Ser Thr
                405                 410                 415

Glu Pro Pro Ala Ala Ala Tyr Asp Val Lys Pro Arg Gln Asn Glu Leu
            420                 425                 430

Trp Thr Ser Ala His
        435

<210> SEQ ID NO 125
<211> LENGTH: 463
<212> TYPE: PRT
<213> ORGANISM: Artificial Sequence
<220> FEATURE:
<223> OTHER INFORMATION: synthesized

<400> SEQUENCE: 125

Met Ser Asp Pro Arg Pro Ala Val Ser Pro Ala Val Ser Val Ser Gly
1               5                   10                  15

Val Gly Ser Ala Pro Leu Gln Ser His Met Ser Leu Glu Ala Val Lys
            20                  25                  30

Gln Glu Thr His Gly Leu Gln Pro Leu Gln Gln His Tyr His His Gln
        35                  40                  45

Leu Ala Pro Leu Pro Met Asp Arg Ala Asp Ser Pro His Gly Ser Glu
    50                  55                  60

His Ser Arg Tyr Ser Val Pro Pro Leu Asn Gly Met Asp Gln Pro Arg
65                  70                  75                  80

Pro Tyr Gly Ser Pro Ala Ala Met His Ala Pro Leu His Met Ser Asp
                85                  90                  95

Met Asn Arg Pro Pro Thr Ser Leu Pro Met Ser Ser Leu Pro Leu Pro
            100                 105                 110

Ser Ile Gln Pro Val Leu Ala Pro Ala Pro Ala Ala Gly Ala Met
        115                 120                 125

Tyr Gly Thr Gln Glu Ala Pro Gln Pro Pro Lys Ala Tyr Pro Cys
    130                 135                 140

Ser Thr Cys Gly Lys Gly Phe Ala Arg Ser Asp Leu Ala Arg His
145                 150                 155                 160

Glu Arg Ile His Ser Gly Val Arg Pro His Ile Cys Asp Phe Pro Gly
                165                 170                 175
```

Cys Asn Lys Lys Phe Ile Gln Arg Ser Ala Leu Thr Val His Gln Arg
            180                 185                 190

Val His Thr Gly Glu Lys Pro His Gln Cys Glu Arg Cys Gly Lys Pro
        195                 200                 205

Phe Ser Asp Ser Ser Ser Leu Ala Arg His Arg Ile His Ser Gly
    210                 215                 220

Lys Arg Pro Tyr Lys Cys Pro Tyr Ala Asp Cys Gln Lys Thr Phe Thr
225                 230                 235                 240

Arg Arg Thr Thr Leu Thr Arg His Gln Asn His His Thr Gly Thr Ile
                245                 250                 255

Glu Glu Ala Ala Ala Thr Arg Glu Ala Leu Ala Arg Gly Pro Thr
            260                 265                 270

Gly Thr Ala Arg Met Thr Pro Thr His Val Thr Arg Ser Glu Gly Asp
        275                 280                 285

Ala Gly Ser Gly Ser Asn His Ala Ser Pro Met Ser Thr Pro Ser Pro
    290                 295                 300

Ala His Arg Thr Asn Ser Met Ser Pro Ser Asn Glu Leu Ala Gly Ile
305                 310                 315                 320

Gly Ser Ile Gln Ser Gln Tyr Val Asn Asn Ser Leu Pro Ser His Leu
                325                 330                 335

Arg Gly Asp Val His Ala Gly Ser Pro Thr Ser Thr Thr Ser Ser Gly
            340                 345                 350

Tyr Thr Asn Asn Arg Pro Thr Ser His Pro Thr Gly Tyr Gly Pro Pro
        355                 360                 365

Gln Val Leu Glu Pro Asn Ile Glu Thr Arg Pro Gly Pro Gly Ser Ala
    370                 375                 380

Ser Gly Ser Pro His Leu Gly Ser Val Gly Trp Gln Ser Pro Ser His
385                 390                 395                 400

Ala Pro Ser Pro Ser His Ser Thr Ser Gly Phe Val Tyr Pro Asp Pro
                405                 410                 415

Glu Ala Tyr Pro Ser Ser Ala Gly Met Gly Pro Leu Phe Tyr Ser Ser
            420                 425                 430

Ala Ile Ala Gly Val Arg Ser Gly Ser Ala Glu Pro Gly Gln Asn Asn
        435                 440                 445

Asp Tyr Pro Lys Ser Arg Ser Ala Glu Leu Trp Ala Ser Ala Gln
    450                 455                 460

<210> SEQ ID NO 126
<211> LENGTH: 440
<212> TYPE: PRT
<213> ORGANISM: Artificial Sequence
<220> FEATURE:
<223> OTHER INFORMATION: synthesized

<400> SEQUENCE: 126

Met Glu Thr Ala Val Pro Val Thr Tyr Asn Val Pro Asn His Asp Met
1               5                   10                  15

Asn Ala Val Pro Pro Arg Arg Met Met Thr Pro Ser His His Asp Gln
            20                  25                  30

Asn Ile Ala Tyr Phe Ser Asn Pro Ser Ile Pro Tyr Ser Thr Ala Leu
        35                  40                  45

Gln Pro Pro Pro Phe Ser Gly Phe Gly His Ile Leu Asn Asn His His
    50                  55                  60

His Pro Ser Tyr His Ser Tyr Phe Ser Ser Asn Pro Asn His His Val
65                  70                  75                  80

```
Asn Ser His His Pro Arg Leu Pro Ile Glu Ala Leu Pro Val Gln Pro
                 85                  90                  95

Gln Leu Ser Asp Val Arg His Val Lys Asn Phe Ile Pro Arg Ser Ile
            100                 105                 110

Arg Pro Ser Pro Pro Lys Glu Asp His Ile Pro His Pro Pro Pro Gln
        115                 120                 125

Arg Val Asn Val Ala Pro Ala Arg Ala Arg Asn Val Thr Thr Gln His
    130                 135                 140

Asp Asp Pro Lys Gly Pro Thr Lys Pro Glu Val Asp Phe Gly Thr Glu
145                 150                 155                 160

Val Asp Thr Leu Met Lys Thr Ile Gln Ala Lys Pro Gln Ser Ser Ser
                165                 170                 175

Pro Gln Val Glu His Gln Leu Pro Pro Leu Gln Gln Lys Phe Asn Asn
            180                 185                 190

Gly Val Pro Ser Trp Ile Gln Pro Ala Tyr Ala Asn Gln Met Pro Gly
        195                 200                 205

Asn Gln Gly Ile Phe Pro Thr Pro Pro Gln Asp Arg Ile Met Ser Thr
    210                 215                 220

Asn Gln Lys Pro Arg Arg Lys Tyr Glu Cys Thr Leu Pro Gln Cys Arg
225                 230                 235                 240

Lys Ser Phe Phe Gln Lys Thr His Leu Asp Ile His Met Arg Ala His
                245                 250                 255

Thr Gly Asp Lys Pro Phe Thr Cys Lys Glu Pro Ser Cys Gly Gln Arg
            260                 265                 270

Phe Ser Gln Leu Gly Asn Leu Lys Thr His Glu Arg Arg His Thr Gly
        275                 280                 285

Glu Lys Pro Tyr Ser Cys Glu Ile Cys His Lys Lys Phe Ala Gln Arg
    290                 295                 300

Gly Asn Val Arg Ala His Lys Ile Thr His Glu Gln Ala Lys Pro Phe
305                 310                 315                 320

Thr Cys Arg Leu Asp Asp Cys Gly Lys Gln Phe Thr Gln Leu Gly Asn
                325                 330                 335

Leu Lys Ser His Gln Asn Lys Phe His Thr Gln Thr Leu Arg Asn Leu
            340                 345                 350

Thr Leu Arg Phe Glu Ser Ile Gly Asn Ser Asp Arg Met Ser Pro Gln
        355                 360                 365

Asp Lys Glu Leu Trp Asp Tyr Phe Ser Thr Leu Tyr Arg Asn Ser Asn
    370                 375                 380

Lys Gly Ile Lys Gly Arg Gly Lys Asp Arg Arg Val Ser Thr Ala Lys
385                 390                 395                 400

Arg Ser Thr Ser Thr Tyr Glu Gly Ser Val Ser Asp Ser Asp Glu Asp
                405                 410                 415

Leu Lys Ile Arg Ser Arg Ser Tyr Asp Arg Val Ser Ala Val Met Thr
            420                 425                 430

Leu Gly Gly Glu Asp Leu Gly Arg
        435                 440

<210> SEQ ID NO 127
<211> LENGTH: 415
<212> TYPE: PRT
<213> ORGANISM: Artificial Sequence
<220> FEATURE:
<223> OTHER INFORMATION: synthesized

<400> SEQUENCE: 127
```

-continued

```
Met Ala Phe Tyr Ala Val Ala Ala Phe Lys Gly Ile Lys Asp Ser Lys
1               5                   10                  15

Pro Lys Phe Gly Gly Ile Gln Cys Val Asp Val Asn Met Leu Ser Pro
            20                  25                  30

Gly Thr Leu Asn Pro Gln Ser Gln Leu Ala Lys Leu Ile Gly Leu Met
        35                  40                  45

Lys Val Ile Pro Glu Asp Asp Leu His Thr Lys Arg Thr Phe Ile Ile
50                  55                  60

Ile Thr Lys Phe Gln Val Val Leu Phe Ile Met Tyr Ile Tyr Gln Pro
65                  70                  75                  80

Asp Ser Pro Glu Leu Phe Ser Asn Gly Tyr Met Leu Phe Val Glu Arg
            85                  90                  95

Trp Thr Gly Lys Ala Val Thr Thr Leu Asn Glu Ala Val Ser Arg Leu
            100                 105                 110

Gly Gly Met Phe Asp Gly Cys Trp Gln Asp Lys Ser Val Tyr Asn Val
            115                 120                 125

Asp Asn His Ser Thr Ala Arg Ile Leu Asn His Gln Val Pro Pro Ala
130                 135                 140

Cys Ser Thr Arg Phe Thr Glu Ser Met Gln Ala Leu Ala Gly Met Pro
145                 150                 155                 160

Met Glu Tyr Gly Gly Phe Pro Ile Thr Thr Thr Ser Thr Glu Cys
            165                 170                 175

Thr Thr Lys Asp His Ser Gln Tyr Gln Gln Ser Asp Phe Asn Thr Ile
            180                 185                 190

Lys Asn Val Ala Leu Pro Gln Gln Tyr Gln Gln Ser Asp Phe Asn Thr
            195                 200                 205

Ile Lys Asn Val Ala Leu Pro Gln Gln Tyr Gln Gln Ser Asp Phe Asn
            210                 215                 220

Thr Thr Lys Asn Val Ala Leu Pro Gln Gln Tyr Gln Gln Ser Asp Phe
225                 230                 235                 240

Asn Thr Thr Lys Asn Val Ala Leu Pro Gln Gln Tyr Gln Thr Ile Thr
                245                 250                 255

Asn Ser Asn Glu Arg Pro His Lys Cys Lys Glu Pro Gly Cys Gly Lys
            260                 265                 270

Ala Phe Thr Leu Ser Ser Gly Leu Lys Glu His Lys Asn Phe Thr His
            275                 280                 285

Ser Glu Lys Arg Pro His Lys Cys Lys Val Pro Asn Cys Gly Lys Ala
            290                 295                 300

Leu Lys Arg Arg Ser Ala Leu Val Ala His Lys Asn Gly Val His Ser
305                 310                 315                 320

Asn Val Arg Pro His Lys Cys Glu Val Gln Asn Cys Gly Lys Ala Phe
                325                 330                 335

Lys Arg Pro Ser Glu Leu Lys Asn His Gln Asn Phe Thr His Ser Lys
            340                 345                 350

Glu Arg Pro Tyr Lys Cys Arg Val Pro Asn Cys Val Lys Ala Phe Arg
            355                 360                 365

Arg Pro Ser Asp Leu Tyr Gln His Glu His Gln Val His Ser Asn Glu
370                 375                 380

Lys Pro Tyr Lys Cys Glu Val Pro Asn Cys Gly Lys Ala Tyr Lys Arg
385                 390                 395                 400

Phe Thr Ser Leu Gly Lys His Tyr Ile Thr His Thr Asn Asn Ala
                405                 410                 415
```

```
<210> SEQ ID NO 128
<211> LENGTH: 475
<212> TYPE: PRT
<213> ORGANISM: Artificial Sequence
<220> FEATURE:
<223> OTHER INFORMATION: synthesized

<400> SEQUENCE: 128

Met Asp Ala Pro Val Thr Ser Ser Asp Ile Pro Gly Leu Ser Leu
1               5                   10                  15

Val Asp Gln Arg Val Thr Pro Ser Pro Val Pro Ser Met His Leu Pro
                20                  25                  30

Ala Pro Val Pro Thr Pro Pro His Gly His Gln Glu Pro Leu Gln Leu
            35                  40                  45

Gln Pro Leu Gln Gln Tyr His Gln Leu Ser Gln Met Pro Val Asp Arg
50                  55                  60

Ala Asp Ser Pro His Gly Ser Glu His Ser Arg Tyr Ser Ala Pro Pro
65                  70                  75                  80

Met Asn Gly Ser Gly Met Asp Asn Ser Arg Pro Tyr Gly Ser Pro Ser
                85                  90                  95

Ala Met His Ala Pro Leu His Ile Ser Pro Pro Thr Ser Leu Pro Leu
            100                 105                 110

Gly Ser Asn Ile Ser Leu Pro Ala Ile Gln Gln Pro Ile Leu Ala Pro
        115                 120                 125

Ala Pro Pro Ala Met Met Ser Val Tyr Pro Pro Val Asn Gln Pro Pro
130                 135                 140

Pro Pro Val Lys Ala Tyr Pro Cys Ser Thr Cys Gly Lys Gly Phe Ala
145                 150                 155                 160

Arg Arg Ser Asp Leu Ala Arg His Glu Arg Ile His Ser Gly Ile Arg
                165                 170                 175

Pro His Val Cys Asp His Pro Gly Cys Gly Lys Gln Phe Ile Gln Arg
            180                 185                 190

Ser Ala Leu Thr Val His Met Arg Val His Thr Gly Glu Lys Pro His
        195                 200                 205

Met Cys Glu Arg Cys Gly Lys Pro Phe Ser Asp Ser Ser Ser Leu Ala
210                 215                 220

Arg His Arg Arg Ile His Ser Gly Lys Arg Pro Tyr Lys Cys Pro Tyr
225                 230                 235                 240

Ala Asn Cys Gln Lys Thr Phe Thr Arg Arg Thr Thr Leu Thr Arg His
                245                 250                 255

Gln Asn His His Thr Gly Thr Ile Glu Ala Ala Leu Ala Thr Arg
            260                 265                 270

Glu Ala Leu Ser Arg Asp Pro Asn Thr Thr Ala Arg Leu Thr Pro Gly
        275                 280                 285

Ala His His Arg Ser Asp Gly Glu Ala Val Val Thr Ser Asn His Ala
290                 295                 300

Ser Pro Leu Thr Thr Pro Ser Pro Ala His Arg Thr His Ser Met Ser
305                 310                 315                 320

Pro Ser Asn Glu Leu Ala Gly Ile His Thr Leu Gln Thr Gln Tyr Pro
                325                 330                 335

Asn Ser Ser Leu Pro Ser His Leu Arg Ser Asp Val His Ile Ala Ser
            340                 345                 350

Pro Thr Ser Thr Thr Ser Ser Gly Tyr Asn Gly Asn Arg Pro Thr Ser
        355                 360                 365
```

-continued

```
His Pro Ser Gly Tyr Gly Pro Pro Ser Val Leu Glu Pro Ser Ile Glu
        370                 375                 380

Thr Arg Pro Gly Pro Gly Ser Ala Ser Gly Ser Pro His Met Gly Ser
385                 390                 395                 400

Val Gly Trp Gln Ser Pro Ser His Ala Gly Ser Pro Ser His Ser Ala
                405                 410                 415

Ser Gly Phe Val Tyr Pro Asp Pro Glu Ala Tyr Pro Gly His Ala Gly
                420                 425                 430

Leu Ser Gly Asn Leu Gly Ser Leu Phe Tyr Gly Ser Ala Val Asn Ser
                435                 440                 445

Thr Arg Ala Gly Ser Ser Glu Pro Gly Gln Gly Asp Tyr Pro Lys
450                 455                 460

Pro Arg Thr Ser Glu Leu Trp Ala Ser Ala Gln
465                 470                 475

<210> SEQ ID NO 129
<211> LENGTH: 447
<212> TYPE: PRT
<213> ORGANISM: Artificial Sequence
<220> FEATURE:
<223> OTHER INFORMATION: synthesized

<400> SEQUENCE: 129

Met Glu Thr Ala Glu Pro Val Ser Tyr Glu Phe Pro Gly His Ala Val
1               5                   10                  15

Gly Ala Val Ala Pro Arg Arg Met Met Gly Ser Asn Val Gly His Asn
                20                  25                  30

Phe Pro Phe Tyr Thr Asn Pro Thr Gly Gly Tyr Thr Leu Pro Phe His
            35                  40                  45

Gln Ser Ser Ser Pro Ala Tyr Ser Phe Gly His Thr Leu Asn His His
50                  55                  60

His His His His His His Pro Gly Tyr Gln His Tyr Phe Val Ala
65                  70                  75                  80

Gly Gln Gln Pro Ile Asn Pro Gln Pro Val Arg Leu Ser Ser Glu Pro
                85                  90                  95

Pro Ser Ile Gln Gln Ile Pro Asp Ile Arg Pro Ala Lys Asn Ala Val
            100                 105                 110

Asn Arg Val Ala Arg Asp Pro Leu Met Lys Ile Glu His Asn Gly Ala
            115                 120                 125

Ser Gln Gln Pro Pro Gly Ala Gln Ser Ser Asn Glu Glu Gly Ala
130                 135                 140

Gln Gly Lys Ser Ser Ser Ser Asn Glu Val Glu Phe Ser Thr Glu Val
145                 150                 155                 160

Asp Ile Leu Met Lys Ala Ile Gln Ala Lys Ala Ser Ala Gln Ser Pro
                165                 170                 175

Gly Val Gln Ser Leu Pro Pro Leu Gln Gln Leu Thr His Gly Gly Ser
                180                 185                 190

Asn Gly Tyr Pro Gln Ser Tyr Ser Met Pro Val Thr Thr Pro Arg Cys
            195                 200                 205

Thr Val Met Val Glu Glu Ala Pro Ser Arg Ser Gly Lys Lys Arg Lys
210                 215                 220

Tyr Ala Cys Thr Leu Pro Gln Cys Gly Lys Ser Phe Ala Gln Lys Thr
225                 230                 235                 240

His Leu Asp Ile His Met Arg Ala His Thr Gly Asp Lys Pro Phe Val
                245                 250                 255
```

-continued

```
Cys Lys Glu Pro Ser Cys Gly Gln Arg Phe Ser Gln Leu Gly Asn Leu
            260                 265                 270

Lys Thr His Gln Arg Arg His Thr Gly Glu Lys Pro Phe Ser Cys Asp
        275                 280                 285

Ile Cys Gln Lys Arg Phe Ala Gln Arg Gly Asn Val Arg Ala His Lys
    290                 295                 300

Ile Thr His Gln His Ala Lys Pro Phe Thr Cys Leu Leu Asp Asp Cys
305                 310                 315                 320

Gly Lys Gln Phe Thr Gln Leu Gly Asn Leu Lys Ser His Gln Asn Lys
                325                 330                 335

Phe His Ala Thr Thr Leu Arg Asn Leu Thr Met Lys Phe Ser Gln Val
            340                 345                 350

Thr Glu Gly Asp His Met Ser Pro Gln Asp Arg Lys Leu Trp Glu Tyr
        355                 360                 365

Phe Ala Thr Leu Tyr Lys Asn Ser Asn Lys Gly Ile Lys Gly Arg Gly
    370                 375                 380

Lys Asp Arg Arg Ile Ser Pro Thr Ser Arg Ser Asp Pro Gly Ser Glu
385                 390                 395                 400

Ser Arg Arg Arg Ile Glu Pro Leu Ser Ser Thr Asp Asp Lys Met Arg
                405                 410                 415

Arg Ala Ser Tyr Gly Asp Thr Ser Met Tyr Asn Gly Gly Ser Ser Ser
            420                 425                 430

Asp Asp Asp Asp Ala Glu Pro Tyr Phe Ile Glu Arg Gln Ala His
                435                 440                 445

<210> SEQ ID NO 130
<211> LENGTH: 439
<212> TYPE: PRT
<213> ORGANISM: Artificial Sequence
<220> FEATURE:
<223> OTHER INFORMATION: synthesized

<400> SEQUENCE: 130

Met Ser Gly Met Arg Ser Pro Ala Pro Thr Glu Val Met Asp Ile Thr
1               5                   10                  15

Asn Met Leu Asn Lys Lys Gly Gln Met Gln Gln Leu Thr Ser Gly Leu
            20                  25                  30

Leu Asp His His Gln Tyr Gln His Ser Phe Val Lys His Glu Pro Gly
        35                  40                  45

Met Glu Arg Ser Ala Ser Pro His Gly Ser Glu His Ser Gln Tyr Ser
    50                  55                  60

Asn Pro His Asn Ile Ala Arg Ala Tyr Pro Ser Pro Ser Thr Met Gln
65                  70                  75                  80

Ala Pro Met His Ile Pro Asn Pro Met Pro Ser Ala Met Gly Leu Ser
                85                  90                  95

Gly Tyr Pro Glu Met Pro Asn Met Gly Gly Met Pro His Met His Met
            100                 105                 110

Gln His Met Pro Gln Gln Gln His His Gln Pro Pro Gln Gln
        115                 120                 125

Pro Ile Lys Ala Tyr Pro Cys Ser Thr Cys Gly Lys Gly Phe Ala Arg
    130                 135                 140

Arg Ser Asp Leu Ala Arg His Glu Arg Ile His Ser Gly Val Arg Pro
145                 150                 155                 160

His Val Cys Asp Trp Pro Gly Cys Gly Lys Gln Phe Ile Gln Arg Ser
                165                 170                 175
```

Ala Leu Thr Val His Gln Arg Val His Thr Gly Glu Lys Pro His His
            180                 185                 190

Cys Glu Thr Cys Ala Lys Pro Phe Ser Asp Ser Ser Leu Ala Arg
        195                 200                 205

His Arg Arg Thr His Ser Gly Lys Arg Pro Tyr Lys Cys Pro Tyr Ala
    210                 215                 220

Asp Cys Gln Lys Thr Phe Thr Arg Arg Thr Thr Leu Thr Arg His Gln
225                 230                 235                 240

Asn His His Ser Gly Thr Ile Glu Glu Ala Ala Ala Thr Ala Ala
            245                 250                 255

Ala Leu Ala Ala Ser Lys Thr Lys Gly Met Ser Gln Ala Arg Ser Glu
        260                 265                 270

Ser Asp His Met Ser Asn His Gly Ser Pro Met Thr Thr Pro Ser Pro
            275                 280                 285

Ser Gln Arg Thr Met Ser Met Ser Pro Ser Val Asp Leu Ser Gly Thr
        290                 295                 300

Asn Ser Ile Pro Arg His Pro Gly Asp Phe Gln Tyr Leu Gln Gln Thr
305                 310                 315                 320

Gly Ser Leu Pro Met His Met Arg Val Gly Ser Pro Thr Ser Thr Ser
            325                 330                 335

Ser Gly Gly Tyr Asn Met Met Arg Pro Thr Ser His Pro Thr Ser Tyr
            340                 345                 350

Gly Pro Pro Pro Thr Leu Glu Pro Asn Leu Asp Asn Ser Gln Gly Thr
        355                 360                 365

Pro Ser Ser Asn Gly Gly Ser Pro His Met Ala Asn Val Gly Trp Gln
        370                 375                 380

Ser Pro Ser His Met Ala Ser Pro Ser Gln Asn Asn Ala Ser Tyr Val
385                 390                 395                 400

Tyr Pro Asp Pro Ala Asp Ala Tyr Pro Thr Asn Asn Ala Met Asn Gln
                405                 410                 415

Met Tyr Tyr Gly Ala Ala Thr His Met Arg Arg Pro Gln Ser Ala Glu
            420                 425                 430

Pro Gly Leu Val His Met Ala
        435

<210> SEQ ID NO 131
<211> LENGTH: 468
<212> TYPE: PRT
<213> ORGANISM: Artificial Sequence
<220> FEATURE:
<223> OTHER INFORMATION: synthesized

<400> SEQUENCE: 131

Met Asp Ile Leu Glu Leu Ile Asp Asp Arg Glu Gln Thr Val Ala Glu
1               5                   10                  15

Ser Ser Pro Arg Pro Phe Cys Cys Pro Glu Gln Ser Cys Asn Lys Ser
            20                  25                  30

Phe Asn Arg Lys Ser Asp Leu Gln Arg His His Arg Ile His Thr Asn
        35                  40                  45

Glu Arg Pro Tyr Ser Cys Thr Phe Pro Asn Cys Gly Lys Ser Phe Ile
    50                  55                  60

Gln Arg Ser Ala Leu Thr Val His Thr Arg Thr His Thr Gly Glu Lys
65                  70                  75                  80

Pro His Ser Cys Glu Tyr Ile Gly Cys Gly Lys Cys Phe Ser Asp Ser
                85                  90                  95

```
Ser Ser Leu Ala Arg His Arg Arg Ile His Thr Gly Lys Arg Pro Tyr
            100                 105                 110

Ser Cys Pro Ile Asp Lys Cys Gly Lys Ser Phe Cys Arg Lys Thr Thr
            115                 120                 125

Leu Thr Lys His Ala Arg Lys Asn His Gln Leu Arg Ala Glu Asn Asp
        130                 135                 140

Val Ser Asp Asp Val Glu Glu Ser Asp Asp Asp Leu Ser Pro
145                 150                 155                 160

Lys Ala Ser Gly Lys Ala Gly Ser Arg Ala Gln Ser Lys Arg Leu Thr
                165                 170                 175

Lys Ala Ser Ala Arg Arg Ala Ala Pro Pro Ser Ala Pro Ser Arg Pro
            180                 185                 190

Ser Val Leu Arg Thr Ser Ser Phe Ala Glu Pro Leu Thr Pro His Ser
            195                 200                 205

Pro Gln Ser Thr Val Arg Ser Gly His Ser Ser Arg Asn Thr Ser Phe
        210                 215                 220

Ser Ala Ala Ser Asp Ser Tyr Arg His Ser Met Pro Met Ala Met Thr
225                 230                 235                 240

His Ser Val His Gln His Gln Pro Pro Thr Pro Gln Ser Pro Tyr Tyr
                245                 250                 255

Thr Glu Glu Asp Val Gly Asp Gly Arg Glu Ile Ser Pro Asn Ala Ile
            260                 265                 270

Ile His Arg Asp Asp Glu Tyr Gly Thr Thr Pro Thr Gly Pro Pro Pro
        275                 280                 285

Pro Leu Gln Gly Asn Arg Ser Phe Asp Thr Leu Ser Ile Val Cys Ser
        290                 295                 300

Thr Pro Thr Thr His Gln Leu Leu Ala Ala Gln Gln Thr Leu Gln Ser
305                 310                 315                 320

Ser Pro Gly Ser Leu Ser Ser Cys Ser Ser Ala Thr Thr Ala Ser Cys
                325                 330                 335

Gly Ser Asp Tyr Phe Tyr Arg Ala Pro Gln Pro Thr Ser Ser Gly His
            340                 345                 350

Tyr Gln Asn Met Gly Gln Ala Ile Ser Pro Gly Gly Ile Pro Pro Tyr
        355                 360                 365

Pro Ala Gln Met Pro Val His Thr Gly Pro Ser Gln His Pro Ile Val
        370                 375                 380

Met Tyr Ser Gln Asn Gly His Gln Ser Asn Gly Ile Leu Ser Pro
385                 390                 395                 400

His Ser Gln Ala Gln Ala Gln Gln Gln Gln Gln Pro Val Trp
                405                 410                 415

Tyr Asp Tyr Pro Ala Tyr Gln Gln Gln Ile Leu Ala Ala Gln Thr Gln
            420                 425                 430

Pro Pro Gln His Arg Ile Tyr Tyr Thr Gly Val Pro Val Gln Asp Pro
        435                 440                 445

Asn Phe Ile Lys Thr Glu Gln Glu Gln Asn Leu Leu Pro Thr Pro Arg
        450                 455                 460

Gly Ser Phe Cys
465
```

<210> SEQ ID NO 132
<211> LENGTH: 470
<212> TYPE: PRT
<213> ORGANISM: Artificial Sequence
<220> FEATURE:
<223> OTHER INFORMATION: synthesized

<400> SEQUENCE: 132

```
Met Glu Leu Gly Asn Ile Leu Asn Thr Lys Phe Pro Ala Ala Ala Val
1               5                   10                  15

Leu Ala Ser Pro Phe Asn Met Gln His Ala Met Gln His Glu Leu Gln
            20                  25                  30

Gln Gln His Phe Ala Pro Thr Tyr Leu Asn Gly Arg Ile Lys Ser Glu
        35                  40                  45

Thr Gly Ser Asp Arg Gly Val Ser Pro His Pro Ser Asp Ser Ser Arg
    50                  55                  60

Tyr Ser Ser Gln Ala Pro Gln Pro Leu Gln Ser Tyr Pro Pro Pro Met
65                  70                  75                  80

Ser Asn Asn Met Asn Gly Met Arg Tyr Pro Ser Pro Ser Gln Met Gln
                85                  90                  95

Thr Pro Met Pro Leu Leu Asn Asn Asn Tyr Ile Pro Asn Pro Pro
            100                 105                 110

Glu His Thr Tyr Pro Gln Gln Pro Thr Pro Asp Pro Gln Gln Gln Met
            115                 120                 125

Gly Gly Arg Pro Ala Ser Asp Thr Gly Pro Pro Lys Ala Phe Ala Cys
130                 135                 140

Ser Thr Cys Ser Lys Gly Phe Ala Arg Arg Ser Asp Leu Ala Arg His
145                 150                 155                 160

Glu Arg Ile His Ser Gly Ile Arg Pro His Val Cys Asp His Pro Gly
                165                 170                 175

Cys Gly Lys Gln Phe Ile Gln Arg Ser Ala Leu Thr Val His Gln Arg
            180                 185                 190

Val His Thr Gly Glu Lys Pro His Met Cys Glu Arg Cys Gly Lys Pro
        195                 200                 205

Phe Ser Asp Ser Ser Leu Ala Arg His Arg Ile His Ser Gly
210                 215                 220

Lys Arg Pro Tyr Lys Cys Pro Tyr Ala Asp Cys Gln Lys Thr Phe Thr
225                 230                 235                 240

Arg Arg Thr Thr Leu Thr Arg His Gln Asn His His Thr Gly Thr Val
                245                 250                 255

Glu Glu Ala Ala Ala Ala Thr Ala Ala Ala Leu Ala Ser Arg Ala Ala
            260                 265                 270

Asn Pro Asn Arg Ser Ala Arg Ser Glu Ala Asp Glu Phe Ser Glu Thr
        275                 280                 285

Ala Ser Pro Leu Gly Thr Pro Ser Pro Asn Glu Arg Pro Leu Ser Leu
    290                 295                 300

Ser Pro Ala Ala Gly Met Pro Val Val Pro Asn Met His Arg Gln Ala
305                 310                 315                 320

Ser Asp Tyr Ala Tyr Leu Gly Asn Met Asn Val Pro Pro His Leu Arg
                325                 330                 335

Asn Glu Ile Pro Gln Pro Ser Arg Ser Ser Pro Ser Leu Thr Ala
            340                 345                 350

Gln Ser Tyr Asn Ser Ala Val Ser Asn Gly Arg Pro Ala Ile Thr Ser
        355                 360                 365

His Pro Ser Gly Tyr Gly Pro Ser Ile Leu Glu Pro Pro Ala Ser
    370                 375                 380

Ala Thr His Asn Gln Pro Gly Ser Ala Asn Gly Ser Pro His Met Gly
385                 390                 395                 400

Thr Met Gly Trp Gln Ser Pro Ser Gln Gln Ala Met Pro Ser Pro Gly
```

-continued

```
                405                 410                 415

Ala Gly Asp Ser Tyr Val Tyr Pro Glu Pro His Tyr Gln Ser Asn Gly
            420                 425                 430

Gly Asn Met Tyr Tyr Gln Asn Ala Gly Ile Gln Arg Pro Asn Ser Thr
        435                 440                 445

Glu Pro Asp Arg Tyr Asn Pro Gln Gln Gln Arg Met Thr Asn Glu Met
    450                 455                 460

Trp Ala Pro Ala Val Gln
465                 470

<210> SEQ ID NO 133
<211> LENGTH: 491
<212> TYPE: PRT
<213> ORGANISM: Artificial Sequence
<220> FEATURE:
<223> OTHER INFORMATION: synthesized

<400> SEQUENCE: 133

Met Ala Leu Pro Glu Gln Thr Ala Ala Pro Gln Ala Trp Gly Arg Trp
1               5                   10                  15

Gln Gln Gln Pro Ala Gly His Asp Tyr Gly Met Met Asp Asn Ser Thr
            20                  25                  30

Phe Val Gln Tyr Asp Ser Arg Ala Ala Thr Ser Ala Pro Met Asn Gly
        35                  40                  45

Ala Ile Met Ala Pro Gln Tyr Met Val Ala Pro Gln Tyr Asn Met Thr
    50                  55                  60

Gln Met Pro Ala Met Gly His Gln Cys Pro Thr Gln Asn His Phe Ala
65                  70                  75                  80

Tyr Thr Gln Tyr Asp Ser Ser Pro Thr Asn Met Asn Met Pro Phe Arg
                85                  90                  95

Leu Pro Pro Gln Pro Glu Arg Pro Val Met Pro Val Ala Ala Ser Glu
            100                 105                 110

His Asp Ile Pro Arg Ala Ser Ser Tyr Pro Gln Glu Ser Pro Ser Val
        115                 120                 125

Lys Asn Asp Arg His Arg Ser Pro Ser Ser Arg Ser Glu Thr Lys Met
    130                 135                 140

Ser Asn Pro Lys Thr Pro His Pro Leu Asn Thr Lys Glu Ile Lys Tyr
145                 150                 155                 160

Asn Lys Pro Thr Ser Ala Asp Pro Val Asn Phe Thr Thr Ala Ile Asp
                165                 170                 175

Thr Leu Met Lys Ala Ile Gln Lys Arg Asn Asp Ser Glu Asp Ile Val
            180                 185                 190

Lys Gly Val Pro Glu Ile Glu Gln Val Val Lys Pro Glu Arg Met Leu
        195                 200                 205

Ser Leu Glu Pro Glu Ala Gly Ser Ile Ala Pro Val Gln Ala Pro Ala
    210                 215                 220

Pro Ile Ala Thr Glu Ser Thr Asp Ala Pro Lys Pro Lys Arg Tyr Ile
225                 230                 235                 240

Cys Asp Val Glu Gly Cys Gly Lys Ser Phe Tyr Gln Ser Thr His Leu
                245                 250                 255

Asp Thr His Arg Arg Ala His Thr Gly Glu Lys Pro Tyr Gln Cys Asn
            260                 265                 270

Trp Pro Arg Cys Gly Arg Thr Phe Ser Gln Pro Gly Asn Leu Lys Thr
        275                 280                 285

His Met Arg Arg His Thr Gly Glu Lys Pro Phe Arg Cys Glu Gln Cys
```

```
                290                 295                 300
Ser Lys Val Phe Ala Gln Arg Gly Asn Leu Gln Thr His Met Ala Thr
305                 310                 315                 320

His Thr Asn Ala Lys Pro Phe Val Cys Lys Leu Asp Asp Cys Asn Lys
                325                 330                 335

Met Phe Thr Gln Arg Gly Asn Leu Lys Asn His Gln Asn Lys Tyr His
                340                 345                 350

Glu Lys Thr Leu Met Glu Met Thr Asp Trp Ile Val Ser Ile Ser Asp
            355                 360                 365

Ile Asp Ala Leu Ser Asp Asp Gln Arg Glu Met Tyr Trp Tyr Phe Ala
        370                 375                 380

Asn Leu Tyr Lys Asn Ser Asn Lys Gly Ile Lys Gly Arg Gly Lys Asp
385                 390                 395                 400

Arg Arg Val Ser Asn Arg Gly Ala Lys Ser Arg Thr Ala Pro Ser Ser
                405                 410                 415

Tyr Pro Val Lys Arg Val Pro Gly Pro Ala Ser Leu Ala Ala Tyr Ser
                420                 425                 430

Ser Lys Arg Leu Pro Pro Glu Gln Tyr Met Gln Gln Gln Gln His
            435                 440                 445

His Gln His Gly Tyr Glu Val Tyr Asp Thr Asp Met Asp Gln Ser Ser
        450                 455                 460

Ser Ala Ser Ser Pro Arg Tyr Asp Gly Leu Pro Ala Thr Tyr Arg Asp
465                 470                 475                 480

Arg Met Tyr Gln Gln Ser Thr His Ala Met Tyr
                485                 490

<210> SEQ ID NO 134
<211> LENGTH: 397
<212> TYPE: PRT
<213> ORGANISM: Artificial Sequence
<220> FEATURE:
<223> OTHER INFORMATION: synthesized

<400> SEQUENCE: 134

Met Arg Leu Ser Glu Ala Asp Ala Pro Leu Glu Val Lys Ala Ala Arg
1               5                   10                  15

Pro Phe Ala Cys Thr Tyr Asp Ala Cys Gln Lys Ser Phe Ser Arg Arg
                20                  25                  30

Ser Asp Leu Val Arg His Val Arg Ile His Thr Asn Glu Arg Pro Phe
            35                  40                  45

Lys Cys Asp Phe Leu Ser Cys Gly Lys Cys Phe Ile Gln Arg Ser Ala
        50                  55                  60

Leu Thr Val His Met Arg Thr His Thr Gly Glu Arg Pro His Val Cys
65                  70                  75                  80

Glu Leu Cys Gly Arg Ala Phe Ser Asp Ser Ser Ser Leu Ala Arg His
                85                  90                  95

Arg Arg Val His Thr Gly Lys Arg Pro Tyr Arg Cys Pro Phe Asn Gly
                100                 105                 110

Cys Asp Lys Thr Phe Cys Arg Lys Thr Thr Leu Ile Lys His His Lys
            115                 120                 125

Gly His Thr Glu Asp Gly Leu Leu Leu Asn Ser Pro Asp Tyr Ser Ser
        130                 135                 140

Lys Ser Ser Pro Thr Gly Asp Ser Thr Ser Ala Ser Ser Ser Ser Thr
145                 150                 155                 160

Met Thr Pro Leu Ser Thr Asn Phe Ser Phe Ala Thr Tyr Ser Ser His
```

165                 170                 175
Pro Glu Gln Ile Tyr Ser Ala Pro Ala Ser Ser Gln Tyr Phe Asn Ile
            180                 185                 190

Pro Ala Leu His His Ser Gln Asp Ser Asn Phe Ser Trp Gly Asn Pro
            195                 200                 205

Ser Asn Gln Phe Ser Pro Ser Pro Ser Phe Pro Arg Pro Asn Asn Thr
            210                 215                 220

Thr Ser Gly Trp Ser Ser Arg Ala Pro Leu Ser Glu Phe Pro Met Thr
225                 230                 235                 240

Ser Ile Ser Pro Glu Tyr Asn Arg Phe Pro Arg Glu Thr Ala Phe Asn
            245                 250                 255

Asn Pro Pro His Ser Thr Asp Ala Thr Ser Ser Ser Arg Ser Phe Ser
            260                 265                 270

Val Ser Gln Gly Tyr Gly Ser Asn Pro Gln Asp Asn Ile Leu Pro Asp
            275                 280                 285

Ile Lys Pro Ser Phe Pro Phe Pro Pro Thr Thr Leu His Gln Ser Ala
            290                 295                 300

Pro Thr Val Tyr His Asp Thr Asn Pro Tyr Thr Ser Ser Phe Ala Asn
305                 310                 315                 320

Thr Val Val Lys Glu Val Pro Asn Glu Pro Ser Tyr Ser Ser Gly Thr
            325                 330                 335

His Met Leu Asp Val Gly Arg His Thr Asn Val Ala Asp Phe Asn Asn
            340                 345                 350

Arg Glu Met Leu Pro Pro Leu Gly Asn Ile Pro Ile Gln Pro Leu Ser
            355                 360                 365

Leu Pro Arg Met Ser Asn Ile Asp Leu Ser Ser Ser Lys Leu Asn Gly
            370                 375                 380

Ile Gly Ser Tyr Trp Lys Ser Glu Ser Thr Trp Glu Gly
385                 390                 395

<210> SEQ ID NO 135
<211> LENGTH: 468
<212> TYPE: PRT
<213> ORGANISM: Artificial Sequence
<220> FEATURE:
<223> OTHER INFORMATION: synthesized

<400> SEQUENCE: 135

Met Ala Ala Val Val Ala His Gln Gln Ala Ala Leu Trp His Arg Arg
1               5                   10                  15

Leu Asp His Phe His Ile Pro Asp Val His Phe Thr Gly Met Met Pro
            20                  25                  30

Gln Tyr Glu Asn Gln Arg Thr Gly Gly Ser Ala Pro Thr Ser Arg Ser
            35                  40                  45

Phe Leu Pro Ala Thr Thr Gln Met Asp Leu Ser Leu Pro Leu Phe Ser
50                  55                  60

Ala Asn Gly Leu Pro Thr Ser Val Pro Tyr Gln Ser Ser Gly Thr Phe
65                  70                  75                  80

Ala Tyr Gly Ser Ser Val Asp Pro Tyr Asn Met Gln Gln Ser Asn Met
            85                  90                  95

Gln His Ser Tyr Ser Met Asn Tyr Thr Ser Asn Leu Ser Pro Ala Val
            100                 105                 110

Ser Tyr Ala Asp Arg Thr Glu His Gln Ser Leu Ala Asn Val His Glu
            115                 120                 125

Ala Arg His Ala Phe Ala Leu Asp Asn Ala His Leu Val Lys Ala Glu

```
                    130                 135                 140
Ser Ala Ser Pro Ala Gln Ser Pro Val Tyr Asn Asn Thr Ser Tyr
145                 150                 155                 160

Thr Ser Glu Cys Lys Arg Ser Ser Glu Pro Met Asp Pro Ser Asn
                165                 170                 175

Ile Asn Phe Ala Thr Asp Val Asp Thr Leu Met Lys Ala Ile Gln Ala
                    180                 185                 190

Lys Gln Thr Thr Ser Thr Gln Gln Gln Glu Ala Pro Pro Lys Arg Glu
                195                 200                 205

Glu Pro Lys Val Ser Gln Lys Pro Arg Lys Arg Tyr Gln Cys His Met
210                 215                 220

Pro Asp Cys Asn Lys Ser Phe Phe Gln Lys Thr His Leu Glu Ile His
225                 230                 235                 240

Ile Arg Ala His Thr Gly Ala Lys Pro Phe Glu Cys Lys Ala Pro Gly
                    245                 250                 255

Cys Gly Gln Arg Phe Ser Gln Leu Gly Asn Leu Lys Thr His Glu Arg
                260                 265                 270

Arg His Thr Gly Glu Arg Pro Tyr Ser Cys Asp Ile Cys Gly Lys Thr
                275                 280                 285

Phe Ala Gln Arg Gly Asn Val Arg Ala His Lys Ile Val His Gln Gln
290                 295                 300

Ile Lys Pro Phe Thr Cys Arg Leu Asp Asp Cys Gly Lys Gln Phe Thr
305                 310                 315                 320

Gln Leu Gly Asn Leu Lys Ser His Gln Asn Lys Phe His Ala Ser Thr
                    325                 330                 335

Leu Lys Tyr Leu Thr Gln Lys Phe Ala Thr Ile Thr Pro Gly Asp Tyr
                340                 345                 350

Val Ser His Ala Asp Lys Glu Leu Trp Glu Tyr Phe Ala Ser Leu Tyr
                355                 360                 365

Lys Asn Ser Asn Lys Gly Ile Lys Gly Arg Gly Lys Asp Arg Arg Ile
370                 375                 380

Ser Ala Met Ser Ser Ser Ala Ser Val His Pro Leu Ser Tyr Ser Thr
385                 390                 395                 400

Met Pro Thr Ser Asn Asn Arg Ser Tyr Pro Gly Leu Tyr Asn His Asn
                    405                 410                 415

Gly Ser Asp Arg Ser Ser Arg Ser Ser Ala Cys Thr Asp Leu Ser
                420                 425                 430

Asn Gln Arg Pro Glu Pro Asn Tyr Asp Phe Asn Ala Pro Met Gln Ala
                435                 440                 445

Gly Tyr Pro Thr Gln Gly Thr Gly Tyr Asp Asp Met Val Phe Pro Glu
                450                 455                 460

Arg Lys Met Tyr
465

<210> SEQ ID NO 136
<211> LENGTH: 452
<212> TYPE: PRT
<213> ORGANISM: Artificial Sequence
<220> FEATURE:
<223> OTHER INFORMATION: synthesized

<400> SEQUENCE: 136

Met Glu Ala Ala Glu Pro Val Ser Tyr Glu Phe Pro Gly His Ala Ile
1               5                   10                  15

Gly Ala Val Ala Pro Arg Arg Met Met Asn Thr Gly Leu Gly His Thr
```

```
               20                  25                  30
Leu Pro Phe Tyr Pro Gly Pro Thr Ala Ser Phe Pro Leu Ser Phe His
                35                  40                  45

Gln Gln Ser Ser Ala Ser Tyr Gly Phe Gly His Pro Met Asn Gln His
        50                  55                  60

His His His Pro Gln Gln His His His Gln Thr Ser Tyr Gln His
 65              70                  75                  80

Tyr Phe Val Pro Gly Gln Gln Pro Leu Asn Ser Gln Pro Val Arg Leu
                85                  90                  95

Leu Ser Glu Pro Pro Ser Ile Gln Pro Ile Pro Glu Ile Arg Pro Ala
               100                 105                 110

Lys Asn Ala Val Ser Arg Met Met Lys Asp Ala Ser Ala Ser Ile Gly
           115                 120                 125

His Lys Ser Ser Val Gln Gln Pro Leu Gly Gln His Pro Thr Ser Gly
           130                 135                 140

Gly Pro Thr Gln Gly Arg Ser Pro Cys Pro Asn Glu Ile Glu Phe Ser
145                 150                 155                 160

Thr Glu Val Asp Ile Leu Met Lys Ala Ile Gln Ser Lys Ala Ser Thr
                165                 170                 175

Gln Ser Ala Ile Val Gln Ser Leu Pro Pro Leu Gln Gln Met Thr His
            180                 185                 190

Gly Val Asn Pro Ser Thr Phe Ala Pro Gln Tyr Ser Ile Gln Ala Ala
            195                 200                 205

Thr Asn Pro Arg Cys Thr Val Ile Val Glu Asp Gln Pro Leu Leu Ser
        210                 215                 220

Ala Lys Lys Arg Lys Tyr Ala Cys Thr Leu Pro His Cys Gly Lys Ser
225                 230                 235                 240

Phe Ala Gln Lys Thr His Leu Asp Ile His Met Arg Ala His Thr Gly
                245                 250                 255

Asp Lys Pro Phe Val Cys Lys Glu Pro Leu Cys Gly Gln Arg Phe Ser
            260                 265                 270

Gln Leu Gly Asn Leu Lys Thr His Gln Arg Arg His Thr Gly Glu Lys
        275                 280                 285

Pro Phe Ser Cys Glu Ile Cys His Lys Arg Phe Ala Gln Arg Gly Asn
    290                 295                 300

Val Arg Ala His Lys Ile Thr His Gln His Ala Lys Pro Phe Thr Cys
305                 310                 315                 320

Leu Leu Asp Asp Cys Gly Lys Gln Phe Thr Gln Leu Gly Asn Leu Lys
                325                 330                 335

Ser His Gln Asn Lys Phe His Ala Ala Thr Leu Lys Ile Leu Thr Leu
            340                 345                 350

Lys Phe Ser Gln Val Thr Asp Ala Asp Asn Met Ser Ser Gln Asp Gln
            355                 360                 365

Lys Leu Trp Glu Tyr Phe Ala Thr Leu Tyr Lys Asn Ser Asn Lys Gly
        370                 375                 380

Ile Lys Gly Arg Gly Lys Asp Arg Arg Ile Ser Pro Thr Ala Arg Ser
385                 390                 395                 400

Glu Thr Arg Pro Asp Thr Arg Arg Leu Gln Ser Leu Thr Asn Ser
                405                 410                 415

Asp Gly Lys Gly Arg Arg Ala Ser Tyr Gly Glu Met Ser Thr Cys Asn
            420                 425                 430

Gly Ala Ser Ser Ser Asp Glu Glu Asp Ile Gly Pro Tyr Phe Leu Asp
            435                 440                 445
```

Arg Gln Gly His
    450

<210> SEQ ID NO 137
<211> LENGTH: 479
<212> TYPE: PRT
<213> ORGANISM: Artificial Sequence
<220> FEATURE:
<223> OTHER INFORMATION: synthesized

<400> SEQUENCE: 137

Met Gln Tyr Glu Val Pro Met Pro Ile Thr Met Ser His Asp Met Ser
1               5                   10                  15

Thr Ala Thr Gly His Tyr Ala His Gln Asn Leu Tyr Val Pro Asn Asn
            20                  25                  30

Asn Ala Asn Arg Ile Lys Ser Glu Thr Gly Ser Glu Arg Gly Val Ser
        35                  40                  45

Pro His Ser Asn Ser Asp His Ser Arg Tyr Ser Gln Thr Pro His
    50                  55                  60

Asn Asn Ser Val Ala Tyr Gln Gln Ile Ala Ala Gln Leu Gln Asn Gly
65              70                  75                  80

Met Arg Tyr Pro Ser Pro Asn Gly Leu Gln Gln Asn Gly Met Ser
            85                  90                  95

Met Leu Gln His Asn Tyr Gln Pro Ser Ala Thr Pro Gly Gln Pro Phe
            100                 105                 110

Gln Gln Gln Gln Ser Ala Ser Met Gly Ala Val Gln Gln Ala Val Ser
        115                 120                 125

Gln Pro Gln Gln Glu Gln Ser Pro Met Glu Gly Gly Arg Ala Ser Thr
    130                 135                 140

Gly Ser Thr Gly Leu Pro Lys Ala Phe Ala Cys Ser Thr Cys Gln Lys
145                 150                 155                 160

Gly Phe Ala Arg Arg Ser Asp Leu Ala Arg His Glu Arg Ile His Ser
                165                 170                 175

Gly Val Arg Pro His Val Cys Asp His Pro Gly Cys Gly Lys Gln Phe
            180                 185                 190

Ile Gln Arg Ser Ala Leu Thr Val His Ser Arg Val His Thr Gly Glu
        195                 200                 205

Lys Pro His Met Cys Glu Arg Cys Gly Lys Pro Phe Ser Asp Ser Ser
    210                 215                 220

Ser Leu Ala Arg His Arg Arg Ile His Ser Gly Lys Arg Pro Tyr Lys
225                 230                 235                 240

Cys Pro Tyr Ala Asp Cys Gln Lys Thr Phe Thr Arg Arg Thr Thr Leu
                245                 250                 255

Thr Arg His Gln Asn His His Thr Gly Thr Ile Glu Glu Ser Glu Ala
            260                 265                 270

Ala Thr Ala Ala Ala Leu Ala Ser Arg Val Ser Leu Gln Asn Ser Arg
        275                 280                 285

Ser Arg Gly Ser Asp Glu Glu Asn Asp Tyr Ser Asp Gly Lys Ser Pro
    290                 295                 300

Met Pro Asn Ala Ser Glu Arg Thr Ala Thr Pro Val Asn Gly Asn Gln
305                 310                 315                 320

Asn Leu Gln Arg Gln Ala Ser Asp Tyr Tyr Met Asn Ala Met Gln Gly
                325                 330                 335

Gly Met Ala Ala Val Pro Thr His Ile Arg Ala Glu Met Pro Asn Gly
            340                 345                 350

```
Val Pro Ser Arg Ala Ala Ser Pro Ala Gln Tyr Pro Met Pro Ala Val
        355                 360                 365

Asn Gly Gln Gln Gln Arg Pro Pro Leu Thr Ser Asn Pro Ser Ser Gly
        370                 375                 380

Tyr Asn Pro Pro Gln Ile Met Glu Pro Ser Val Gly Asn Gly Gln Gln
385                 390                 395                 400

Thr Gly Ser Gly Thr Asn Ser Pro His Met Gln Gly Trp Gln Ser Pro
                405                 410                 415

His Thr Gly Val Gln Ala Gln Pro Asn Asp Tyr Ser Tyr Thr Asp Ala
                420                 425                 430

Asn Asn Asn Tyr Asn Gly Thr Asn Val Asn Val Leu Gln Gln Tyr Tyr
                435                 440                 445

Thr Thr Pro Asp Val Gln Arg Pro His Ser Thr Gly Pro Val Gly Tyr
                450                 455                 460

His Asn Gln Met Arg Gly Gln Glu Met Trp Ala Gln His Gln Gln
465                 470                 475

<210> SEQ ID NO 138
<211> LENGTH: 468
<212> TYPE: PRT
<213> ORGANISM: Artificial Sequence
<220> FEATURE:
<223> OTHER INFORMATION: synthesized

<400> SEQUENCE: 138

Met Asp Leu Thr Asn Ile Leu Asn Thr Lys Asp Ala Ala Ala Ala Ala
1               5                   10                  15

Ala Gly Ala Ala Pro Pro Leu Thr Leu Ser Leu Glu Met Gln Lys Asn
                20                  25                  30

Pro Tyr Leu Ala Asn Pro Gly His Pro His Ser Pro Ala Ala Ala Ser
            35                  40                  45

Asp Phe Ile Ser Asp Arg Glu Gly Ser Pro His Ser Thr Ser Pro
        50                  55                  60

Ser Ala Ser Glu His Ser Pro Ser Ala Tyr Pro Leu Pro Ser Asn Ala
65                  70                  75                  80

Leu Val Ser Ala Asn Gly Ser Tyr Ser Gly Val Pro Ser Gly Ala Val
                85                  90                  95

Asn Thr Val Pro Arg Gly Pro Gly Arg Pro Ser Ser Gly Asp Pro Tyr
            100                 105                 110

Ser Lys Ala Phe Pro Cys Ser Val Cys Ser Lys Gly Phe Ala Arg Arg
        115                 120                 125

Ser Asp Leu Ala Arg His Glu Arg Ile His Thr Gly Val Arg Pro His
    130                 135                 140

Val Cys Asp Tyr Pro Gly Cys Asp Lys Gln Phe Ile Gln Arg Ser Ala
145                 150                 155                 160

Leu Thr Val His Ala Arg Val His Thr Gly Glu Lys Pro His Met Cys
                165                 170                 175

Asp Thr Cys Gly Lys Pro Phe Ser Asp Ser Ser Ser Leu Ala Arg His
            180                 185                 190

Arg Arg Ile His Ser Gly Lys Arg Pro Tyr Lys Cys Pro Tyr Ala Asp
        195                 200                 205

Cys Gln Lys Thr Phe Thr Arg Arg Thr Thr Leu Thr Arg His Gln Asn
    210                 215                 220

His His Thr Gly Thr Ile Ser Glu Ala Ala Ala Ala Thr Ala Ala Ala
225                 230                 235                 240
```

```
Leu Ala Ala Arg Pro Thr Leu Pro Lys Pro Gly Arg Pro Pro Arg Ser
                245                 250                 255

Pro Asn Ala Arg Pro Leu Gly Arg Pro Pro Asn Asp Ser Asn Pro Ser
            260                 265                 270

Ser Ala His Ser Thr Pro Ser Pro Gly Gln Arg His Ala Ser Leu Ser
        275                 280                 285

Pro Ser Thr Glu Leu Pro Pro Pro Phe Ser Ala His Arg Gln Gly Gly
    290                 295                 300

Asp Tyr His Tyr Arg Gln Ser Asn Ile Thr Ser His Pro Ser Thr Ser
305                 310                 315                 320

Leu Met Asn Glu Leu Gln Pro Leu Thr Pro Arg Pro Thr Pro Thr Thr
                325                 330                 335

Thr Pro Thr Ile Ser Ser Gly Met Val Pro Ala Gly Pro Arg Gln Pro
            340                 345                 350

Pro Thr Ser Asn Pro Thr Phe Met Ser Ser Leu Pro Pro Ile Leu Glu
        355                 360                 365

Pro Pro Pro Lys Pro Asp Ala Gln Arg Gln Gly Ser Pro His Leu Ser
    370                 375                 380

Gly Ser Pro His Met Ser Ala Ala Gly Ser Pro His Met Ser His Pro
385                 390                 395                 400

Ser Pro Leu Phe Ser Pro Gly Tyr Arg Ser Pro Ser Cys His Ser Thr
                405                 410                 415

Val Ser Glu Asp Thr Val Phe Phe Pro Pro His Asn Ser Phe Gln Ser
            420                 425                 430

Pro Val Leu Gly Ser His Tyr Gly Ser Asp His Leu Arg Arg Pro His
        435                 440                 445

Ser Ser Asp Ser Leu His Ser Tyr Glu Gln Arg Glu Val Arg Leu Pro
    450                 455                 460

Gly Val Tyr Pro
465

<210> SEQ ID NO 139
<211> LENGTH: 492
<212> TYPE: PRT
<213> ORGANISM: Artificial Sequence
<220> FEATURE:
<223> OTHER INFORMATION: synthesized

<400> SEQUENCE: 139

Met Ala Leu Thr Glu Gln Thr Ala Thr Pro Gln Ala Trp Gly Arg Trp
1               5                   10                  15

Gln Gln Gln Pro Thr Gly His Gly Tyr Ala Met Met Asp Asn Ser Thr
            20                  25                  30

Phe Val Pro Tyr Glu Ser Arg Ala Ala Thr Ser Ala Pro Met Asn Gly
        35                  40                  45

Ala Ile Met Ala Pro Gln Tyr Met Val Ala Pro Gln Tyr Asn Met Thr
    50                  55                  60

Pro Met Pro Ala Met Gly His Cys Thr Ser Gln Asn His Phe Ala Tyr
65                  70                  75                  80

Ala Gln Tyr Asp Ser Pro Pro Thr Asn Met Asn Met Pro Phe Arg Leu
                85                  90                  95

Pro Ala His Gln Glu Arg Pro Val Met Pro Val Ala Ala Pro Glu His
            100                 105                 110

Asp Ile Pro Arg Ala Ser Ser Tyr Pro Gln Glu Ser Pro Ser Ser Gln
        115                 120                 125
```

```
Asn Asp Arg His Ser Ser Pro Ser Thr Arg Ser Glu Thr Lys Met Ser
130                 135                 140

Asn Pro Lys Thr Pro His Pro Leu Asn Thr Lys Asp Ile Lys Phe Asn
145                 150                 155                 160

Lys Pro Thr Ser Ala Glu Pro Val Asn Phe Thr Thr Ala Ile Asp Thr
                165                 170                 175

Leu Met Lys Ala Ile Gln Lys Arg Arg Asp Ser Glu Asp Ile Val Lys
            180                 185                 190

Gly Val Pro Glu Ile Glu Gln Leu Val Lys Pro Glu Pro Arg Ser Pro
        195                 200                 205

Lys Pro Glu Ala Gly Pro Val Thr Ser Val Pro Thr Pro Ala Pro Ala
210                 215                 220

Ala Thr Glu Ser Thr Asp Thr Pro Lys Pro Lys Arg Tyr Val Cys Thr
225                 230                 235                 240

Ile Asp Gly Cys Gly Lys Ser Phe Tyr Gln Ser Thr His Leu Asp Thr
                245                 250                 255

His Arg Arg Ala His Thr Gly Glu Lys Pro Tyr Gln Cys Asn Trp Pro
            260                 265                 270

Arg Cys Gly Arg Thr Phe Ser Gln Pro Gly Asn Leu Lys Thr His Met
        275                 280                 285

Arg Arg His Thr Gly Glu Lys Pro Phe Arg Cys Glu Gln Cys Ser Lys
290                 295                 300

Val Phe Ala Gln Arg Gly Asn Leu Gln Thr His Met Ala Thr His Thr
305                 310                 315                 320

Asn Ala Lys Pro Phe Val Cys Lys Leu Asp Asp Cys Asn Lys Met Phe
                325                 330                 335

Thr Gln Arg Gly Asn Leu Lys Asn His Gln Asn Lys Tyr His Glu Lys
            340                 345                 350

Thr Leu Met Glu Met Thr Asp Trp Ile Val Ser Ile Ser Asp Ile Asp
        355                 360                 365

Ala Leu Ser Asp Asp Gln Arg Glu Met Tyr Trp Tyr Phe Ala Asn Leu
370                 375                 380

Tyr Lys Asn Ser Asn Lys Gly Ile Lys Gly Arg Gly Lys Asp Arg Arg
385                 390                 395                 400

Val Ser Asn Arg Gly Ser Lys Ser Arg Thr Ala Pro Ser Ser Tyr Pro
                405                 410                 415

Val Lys Arg Val Pro Gly Pro Ser Ser Leu Ala Ala Tyr Ser Ser Lys
            420                 425                 430

Arg Leu Pro Pro Glu Gln Tyr Met Gln Gln Gln Gln Gln Gln Gln Gln
        435                 440                 445

His His Gln Gln Ser Tyr Glu Val Tyr Asp Thr Asp Met Asp Gln Ser
450                 455                 460

Ser Ser Ala Ser Ser Pro Arg Tyr Asp Gly Ile Pro Val Ala Tyr Arg
465                 470                 475                 480

Asp Arg Met Tyr Gln Gln Ser Thr His Ala Met Tyr
                485                 490

<210> SEQ ID NO 140
<211> LENGTH: 453
<212> TYPE: PRT
<213> ORGANISM: Artificial Sequence
<220> FEATURE:
<223> OTHER INFORMATION: synthesized

<400> SEQUENCE: 140
```

```
Arg Ser Asn Ala Val Met Ser Ala Ser Pro Glu Val Met Asp Ile
1               5                   10                  15

Thr Asn Met Leu Asn Asn Lys Gly Gly Ala Met Thr His Gly Leu Gly
                20                  25                  30

Gly Gly Met His Asp His His Gln His Gln His His His Leu Gly Leu
        35                  40                  45

Val Lys His Glu Pro Thr Met Asp Arg Ser Gly Ser Pro His Met Ser
    50                  55                  60

Glu His Ser Ser Tyr Ser Ala His Ser Met Ser Arg Ala Tyr Pro Ser
65              70                  75                  80

Pro Thr Ala Met Gln Ala Pro Met Gln Ile Pro Asn Ser Met His Asn
                85                  90                  95

Ala Met Gln Met Gly Gly Phe Ala Asp Met Ser Gly Met Gly Gly Val
                100                 105                 110

Pro Ser Met Ala Met His His Ile Pro Gln His Pro Gln Gln Gln
        115                 120                 125

Gln Gln Gln Gln Gln Gln Pro Gln Gln Pro Gln Ala Pro Val Lys
130                 135                 140

Ala Tyr Pro Cys Ser Thr Cys Gly Lys Gly Phe Ala Arg Arg Ser Asp
145                 150                 155                 160

Leu Ala Arg His Glu Arg Ile His Thr Gly Val Arg Pro His Val Cys
                165                 170                 175

Asp Tyr Pro Lys Cys Asn Lys Gln Phe Ile Gln Arg Ser Ala Leu Thr
            180                 185                 190

Val His Gln Arg Val His Thr Gly Glu Lys Pro His His Cys Glu Thr
        195                 200                 205

Cys Ala Lys Pro Phe Ser Asp Ser Ser Ser Leu Ala Arg His Arg Arg
210                 215                 220

Thr His Ser Gly Lys Arg Pro Tyr Lys Cys Pro Tyr Ala Asp Cys Gln
225                 230                 235                 240

Lys Thr Phe Thr Arg Arg Thr Thr Leu Thr Arg His Gln Asn His His
                245                 250                 255

Thr Gly Thr Ile Glu Glu Ala Ala Ala Thr Ala Ala Ala Leu Ala
            260                 265                 270

Ala Ser Arg Ala Lys Asn Gly Ser Gln Ala Arg Ser Asp Gly Asp His
    275                 280                 285

Met Ser Ser His Gly Ser Pro Leu Ser Thr Pro Ser Pro Ser Gln His
    290                 295                 300

Gly Met Met Ser Pro Ala Leu Asp Leu Ser Gly Ser Asn Gly Ile Pro
305                 310                 315                 320

Arg His Ala Ala Asp Phe Gln Gln Tyr Ile Thr Gln Ser Gly Gly Leu
                325                 330                 335

Pro Pro His Leu Arg Val Gly Ser Pro Thr Ser Thr Thr Ser Ala Ala
            340                 345                 350

Ser Tyr Asn Thr Gly Ile Arg Pro Thr Ser His Pro Thr Gly Tyr Gly
    355                 360                 365

Pro Pro Pro Thr Leu Glu Pro Asn Leu Glu Gln His Pro Ala Gly Ser
370                 375                 380

Gly Ser Ala Gly Gly Ser Pro His Met Ser Gln Val Ser Trp Gln Ser
385                 390                 395                 400

Pro Gln Thr His Ser Pro Ser His Asn Gly Gly Ser Tyr Ile Tyr Pro
                405                 410                 415
```

Asp Pro Asp Gly Gly Tyr Pro Pro Asn Pro Ala Met Ser Gln Met Tyr
            420                 425                 430

Tyr Gly Ala Pro Gln Gln Met Arg Arg Pro Gln Ser Ala Glu Pro Gly
            435                 440                 445

Leu Val His Met Ala
        450

<210> SEQ ID NO 141
<211> LENGTH: 1437
<212> TYPE: PRT
<213> ORGANISM: Artificial Sequence
<220> FEATURE:
<223> OTHER INFORMATION: promoter region of the glyceraldehyde-3-
      phosphate dehydrogenase gene (GPDp) of T. reesei

<400> SEQUENCE: 141

Gly Ala Cys Gly Cys Ala Gly Ala Ala Gly Ala Ala Gly Gly Ala Ala
1               5                   10                  15

Ala Thr Cys Gly Cys Cys Cys Gly Cys Cys Gly Gly Thr Thr Cys
            20                  25                  30

Cys Gly Thr Ala Ala Ala Ala Ala Ala Ala Thr Ala Thr Gly Ala
        35                  40                  45

Gly Cys Gly Cys Ala Gly Gly Ala Cys Ala Ala Gly Cys Ala Cys
        50                  55                  60

Ala Gly Cys Cys Thr Thr Gly Cys Cys Thr Gly Gly Gly Cys
65                  70                  75                  80

Cys Thr Ala Gly Cys Cys Thr Thr Gly Cys Gly Cys Thr Gly
                85                  90                  95

Thr Thr Thr Gly Ala Thr Gly Cys Ala Ala Thr Cys Gly Gly Cys Gly
                100                 105                 110

Ala Cys Ala Thr Gly Thr Cys Gly Ala Ala Thr Gly Cys Thr Gly Thr
            115                 120                 125

Ala Ala Thr Thr Thr Thr Thr Thr Thr Gly Thr Thr Thr Ala Gly
        130                 135                 140

Gly Thr Thr Cys Cys Cys Thr Thr Thr Thr Cys Cys Thr Thr
145                 150                 155                 160

Thr Gly Thr Gly Thr Thr Ala Ala Thr Ala Ala Thr Ala Thr
                165                 170                 175

Cys Thr Cys Gly Ala Ala Gly Gly Cys Gly Thr Gly Ala Thr
                180                 185                 190

Thr Thr Thr Gly Ala Ala Ala Thr Thr Thr Gly Thr Cys Gly Gly Thr
                195                 200                 205

Gly Ala Gly Ala Gly Cys Cys Ala Ala Ala Cys Gly Gly Ala Thr Ala
            210                 215                 220

Thr Ala Cys Ala Gly Gly Cys Gly Cys Gly Gly Cys Thr Gly Ala Thr
225                 230                 235                 240

Gly Ala Ala Thr Ala Ala Thr Gly Ala Thr Gly Ala Ala Thr Cys Gly
                245                 250                 255

Ala Gly Cys Thr Gly Ala Cys Thr Thr Gly Ala Thr Gly Cys Thr Gly
                260                 265                 270

Thr Ala Thr Gly Thr Ala Cys Ala Ala Thr Ala Thr Gly Ala Cys
            275                 280                 285

Thr Gly Cys Gly Ala Gly Gly Ala Cys Cys Ala Thr Cys Ala Gly Gly
        290                 295                 300

Thr Gly Thr Thr Gly Thr Ala Thr Gly Gly Ala Thr Gly Gly Ala Ala
305                 310                 315                 320

-continued

```
Thr Cys Ala Thr Thr Cys Thr Gly Thr Ala Ala Cys Cys Ala Cys Cys
                325                 330                 335

Ala Ala Gly Gly Thr Gly Cys Ala Thr Gly Cys Ala Thr Cys Ala Thr
            340                 345                 350

Ala Ala Gly Gly Thr Ala Thr Thr Cys Thr Cys Cys Thr Cys Ala Gly
        355                 360                 365

Cys Thr Cys Ala Cys Cys Ala Ala Cys Ala Ala Cys Gly Ala Ala Cys
    370                 375                 380

Gly Ala Thr Gly Gly Cys Cys Ala Thr Gly Thr Thr Ala Gly Thr Ala
385                 390                 395                 400

Ala Ala Gly Gly Cys Ala Cys Cys Gly Thr Gly Ala Thr Gly Gly Cys
                405                 410                 415

Ala Ala Gly Ala Thr Ala Gly Ala Ala Cys Cys Ala Cys Thr Ala Thr
            420                 425                 430

Thr Gly Cys Ala Thr Cys Thr Gly Cys Gly Cys Thr Thr Cys Cys Cys
        435                 440                 445

Ala Cys Gly Cys Ala Cys Ala Gly Thr Ala Cys Gly Thr Cys Ala Ala
    450                 455                 460

Thr Gly Thr Ala Ala Cys Gly Thr Cys Ala Ala Ala Gly Cys Cys Gly
465                 470                 475                 480

Cys Cys Cys Thr Cys Cys Cys Gly Thr Ala Ala Cys Cys Thr Cys Gly
                485                 490                 495

Cys Cys Cys Gly Thr Thr Gly Thr Thr Gly Cys Thr Cys Cys Cys Cys
            500                 505                 510

Cys Cys Gly Ala Thr Thr Gly Cys Cys Thr Cys Ala Ala Thr Cys Ala
        515                 520                 525

Cys Ala Thr Ala Gly Thr Ala Cys Cys Thr Ala Cys Cys Thr Ala Thr
    530                 535                 540

Gly Cys Ala Thr Thr Ala Thr Gly Gly Cys Gly Cys Cys Thr Cys Ala
545                 550                 555                 560

Ala Cys Cys Cys Ala Cys Cys Cys Cys Cys Cys Cys Ala Gly Ala Thr
                565                 570                 575

Thr Gly Ala Gly Ala Gly Cys Thr Ala Cys Cys Thr Thr Ala Cys Ala
            580                 585                 590

Thr Cys Ala Ala Thr Ala Thr Gly Gly Cys Cys Ala Gly Cys Ala Cys
        595                 600                 605

Cys Thr Cys Thr Thr Cys Gly Gly Cys Gly Ala Thr Ala Cys Ala Thr
    610                 615                 620

Ala Cys Thr Cys Gly Cys Cys Ala Cys Cys Cys Cys Ala Gly Cys Cys
625                 630                 635                 640

Gly Gly Gly Gly Cys Gly Ala Thr Thr Gly Thr Gly Thr Gly Thr Ala
                645                 650                 655

Cys Thr Ala Gly Gly Thr Ala Gly Gly Cys Thr Cys Gly Thr Ala Cys
            660                 665                 670

Thr Ala Thr Ala Cys Cys Ala Gly Cys Ala Gly Gly Ala Gly Ala Gly
        675                 680                 685

Gly Thr Gly Cys Thr Gly Cys Thr Thr Gly Gly Cys Ala Ala Thr Cys
    690                 695                 700

Gly Thr Gly Cys Thr Cys Ala Gly Cys Thr Gly Thr Thr Ala Gly Gly
705                 710                 715                 720

Thr Thr Gly Thr Ala Cys Thr Thr Gly Thr Ala Thr Gly Gly Thr Ala
                725                 730                 735
```

```
Cys Thr Thr Gly Thr Ala Ala Gly Gly Thr Cys Ala Thr
            740                 745             750

Gly Cys Ala Gly Thr Thr Gly Cys Thr Ala Gly Gly Thr Ala Cys
        755                 760             765

Cys Thr Ala Gly Gly Ala Gly Gly Ala Thr Thr Cys Ala Ala
        770             775                 780

Cys Gly Ala Gly Cys Cys Thr Gly Cys Thr Thr Cys Ala Ala
785             790             795             800

Thr Gly Thr Cys Cys Ala Thr Cys Thr Gly Ala Thr Ala Gly Gly
            805             810                 815

Ala Thr Gly Gly Cys Gly Gly Cys Thr Gly Gly Cys Gly Gly Gly
            820             825                 830

Cys Cys Gly Ala Ala Gly Cys Thr Gly Gly Ala Ala Cys Thr Cys
            835             840                 845

Gly Cys Cys Ala Ala Cys Ala Gly Thr Cys Ala Thr Ala Thr Gly Thr
            850             855             860

Ala Ala Thr Ala Gly Cys Thr Cys Ala Ala Gly Thr Thr Gly Ala Thr
865             870             875                 880

Gly Ala Thr Ala Cys Cys Gly Thr Thr Thr Thr Gly Cys Cys Ala Gly
                885                 890             895

Gly Ala Thr Thr Ala Gly Gly Ala Thr Gly Cys Gly Ala Gly Ala Ala
                900             905             910

Gly Cys Ala Gly Cys Ala Thr Gly Ala Ala Thr Gly Thr Cys Gly Cys
            915             920                 925

Thr Cys Ala Thr Cys Cys Gly Ala Thr Gly Cys Cys Gly Cys Ala Thr
            930                 935                 940

Cys Ala Cys Cys Gly Thr Thr Gly Thr Gly Thr Cys Ala Gly Ala Ala
945                 950             955             960

Ala Cys Gly Ala Cys Cys Ala Ala Gly Cys Thr Ala Ala Gly Cys Ala
                965             970             975

Ala Cys Thr Ala Ala Gly Gly Thr Ala Cys Cys Thr Ala Cys Cys
            980             985                 990

Gly Thr Cys Cys Ala Cys Thr Ala Thr Cys Thr Cys Ala Gly Gly Thr
            995                 1000                1005

Ala Ala Cys Cys Ala Gly Gly Thr Ala Cys Thr Ala Cys Cys Ala
1010                1015                1020

Gly Cys Thr Ala Cys Cys Cys Thr Ala Cys Cys Thr Gly Cys Cys
            1025                1030                1035

Gly Thr Gly Cys Cys Thr Ala Cys Cys Thr Gly Cys Thr Thr Thr
            1040                1045                1050

Ala Gly Thr Ala Thr Thr Ala Ala Thr Cys Thr Thr Cys Cys
1055                1060                1065

Ala Cys Cys Thr Cys Cys Cys Thr Cys Cys Thr Cys Ala Ala Thr
1070                1075                1080

Cys Thr Thr Cys Thr Thr Thr Thr Cys Cys Thr Cys Cys Thr
            1085                1090                1095

Cys Thr Cys Cys Thr Cys Thr Thr Thr Thr Thr Thr Thr Thr
            1100                1105                1110

Thr Cys Thr Thr Cys Thr Cys Cys Thr Cys Thr Thr Cys Thr
            1115                1120                1125

Thr Cys Thr Cys Cys Ala Thr Ala Ala Cys Cys Ala Thr Thr Cys
            1130                1135                1140

Cys Thr Ala Ala Cys Ala Ala Cys Ala Thr Cys Gly Ala Cys Ala
```

```
    1145                1150                1155

Thr Thr  Cys Thr Cys Thr Cys  Cys Thr Ala Ala Thr  Cys Ala Cys
    1160                1165                1170

Cys Ala  Gly Cys Cys Thr Cys  Gly Cys Ala Ala Ala  Thr Cys Cys
    1175                1180                1185

Thr Cys  Ala Gly Gly Thr Thr  Ala Gly Thr Ala Thr  Thr Ala Cys
    1190                1195                1200

Thr Ala  Cys Thr Ala Cys Thr  Ala Cys Ala Ala Thr  Cys Ala Thr
    1205                1210                1215

Cys Ala  Cys Cys Ala Cys Gly  Ala Thr Gly Cys Thr  Cys Cys Gly
    1220                1225                1230

Cys Cys  Cys Gly Ala Cys Gly  Ala Thr Gly Cys Gly  Gly Cys Thr
    1235                1240                1245

Thr Cys  Thr Gly Thr Thr Cys  Gly Cys Cys Thr Gly  Cys Cys Cys
    1250                1255                1260

Cys Thr  Cys Cys Thr Cys Thr  Cys Ala Cys Thr Cys  Gly Thr Gly
    1265                1270                1275

Cys Cys  Cys Thr Thr Gly Ala  Cys Gly Ala Gly Cys  Thr Ala Cys
    1280                1285                1290

Cys Cys  Cys Gly Cys Cys Ala  Gly Ala Cys Thr Cys  Thr Cys Cys
    1295                1300                1305

Thr Gly  Cys Gly Thr Cys Ala  Cys Cys Ala Ala Thr  Thr Thr Thr
    1310                1315                1320

Thr Thr  Thr Cys Cys Cys Thr  Ala Thr Thr Thr Ala  Cys Cys Cys
    1325                1330                1335

Cys Thr  Cys Cys Thr Cys Cys  Cys Thr Cys Thr Cys  Thr Cys Cys
    1340                1345                1350

Cys Thr  Cys Thr Cys Gly Thr  Thr Thr Cys Thr Thr  Cys Cys Thr
    1355                1360                1365

Ala Ala  Cys Ala Ala Ala Cys  Ala Ala Cys Cys Ala  Cys Cys Ala
    1370                1375                1380

Cys Cys  Ala Ala Ala Ala Thr  Cys Thr Cys Thr Thr  Thr Gly Gly
    1385                1390                1395

Ala Ala  Gly Cys Thr Cys Ala  Cys Gly Ala Cys Thr  Cys Ala Cys
    1400                1405                1410

Gly Cys  Ala Ala Gly Cys Thr  Cys Ala Ala Thr Thr  Cys Gly Cys
    1415                1420                1425

Ala Gly  Ala Thr Ala Cys Ala  Ala Ala
    1430                1435

<210> SEQ ID NO 142
<211> LENGTH: 909
<212> TYPE: PRT
<213> ORGANISM: Artificial Sequence
<220> FEATURE:
<223> OTHER INFORMATION: terminator region of the glyceraldehyde-3-
      phosphate dehydrogenase gene (GPDt) of T. reesei

<400> SEQUENCE: 142

Gly Thr Gly Cys Thr Gly Thr Gly Thr Thr Cys Cys Thr Cys Ala Gly
1               5                   10                  15

Ala Ala Thr Gly Gly Gly Cys Cys Cys Cys Ala Gly Ala Ala Gly Gly
            20                  25                  30

Gly Cys Gly Thr Cys Gly Ala Gly Cys Ala Thr Thr Gly Thr Cys Thr
        35                  40                  45
```

-continued

Ala Thr Gly Ala Ala Thr Gly Cys Ala Ala Ala Cys Ala Ala Ala Ala
50 55 60

Ala Thr Ala Gly Thr Ala Ala Ala Thr Ala Ala Ala Thr Ala Gly Thr
65 70 75 80

Ala Ala Thr Thr Cys Thr Gly Gly Cys Cys Ala Thr Gly Ala Cys Gly
85 90 95

Ala Ala Thr Ala Gly Ala Gly Cys Cys Ala Ala Thr Cys Thr Gly Cys
100 105 110

Thr Cys Cys Ala Cys Thr Thr Gly Ala Cys Thr Ala Thr Cys Cys Thr
115 120 125

Thr Gly Thr Gly Ala Cys Thr Gly Thr Ala Thr Cys Gly Thr Ala Thr
130 135 140

Gly Thr Cys Gly Ala Ala Cys Cys Cys Thr Thr Gly Ala Cys Thr Gly
145 150 155 160

Cys Cys Cys Ala Thr Thr Cys Ala Ala Ala Cys Ala Ala Thr Thr Gly
165 170 175

Thr Ala Ala Ala Gly Gly Ala Ala Thr Ala Thr Gly Ala Gly Cys Thr
180 185 190

Ala Cys Ala Ala Gly Thr Thr Ala Thr Gly Thr Cys Thr Cys Ala Cys
195 200 205

Gly Thr Thr Thr Gly Cys Gly Thr Gly Cys Gly Ala Gly Cys Cys Cys
210 215 220

Gly Thr Thr Thr Gly Thr Ala Cys Gly Thr Thr Ala Thr Thr Thr Thr
225 230 235 240

Gly Ala Gly Ala Ala Ala Gly Cys Gly Thr Thr Gly Cys Cys Ala Thr
245 250 255

Cys Ala Cys Ala Thr Gly Cys Thr Cys Ala Cys Ala Gly Thr Cys Ala
260 265 270

Cys Thr Thr Gly Gly Cys Thr Thr Ala Cys Gly Ala Thr Cys Ala Thr
275 280 285

Gly Thr Thr Thr Gly Cys Gly Ala Thr Cys Thr Thr Thr Cys Gly Gly
290 295 300

Thr Ala Ala Gly Ala Ala Thr Ala Cys Ala Cys Ala Gly Ala Gly Thr
305 310 315 320

Ala Ala Cys Gly Ala Thr Thr Ala Thr Ala Cys Ala Thr Cys Cys Ala
325 330 335

Thr Cys Gly Cys Thr Thr Thr Cys Thr Ala Thr Gly Ala Thr Thr Ala
340 345 350

Gly Gly Thr Ala Cys Thr Cys Ala Gly Ala Cys Ala Ala Cys Ala Cys
355 360 365

Ala Thr Gly Gly Gly Ala Ala Ala Cys Ala Ala Gly Ala Thr Ala Ala
370 375 380

Cys Cys Ala Thr Cys Gly Cys Ala Thr Gly Cys Ala Ala Gly Gly Thr
385 390 395 400

Cys Gly Ala Thr Thr Cys Cys Ala Ala Thr Cys Ala Thr Gly Ala Thr
405 410 415

Cys Thr Gly Gly Ala Cys Thr Gly Gly Gly Gly Thr Ala Thr Thr Cys
420 425 430

Cys Ala Thr Cys Thr Ala Ala Gly Cys Cys Ala Thr Ala Gly Thr Ala
435 440 445

Cys Cys Cys Thr Cys Gly Ala Gly Ala Gly Ala Ala Gly Gly Ala Ala
450 455 460

Thr Gly Gly Thr Ala Gly Gly Ala Cys Cys Thr Cys Thr Cys Ala Gly

-continued

```
            465                 470                 475                 480
Gly Cys Gly Thr Cys Cys Ala Cys Cys Ala Thr Cys Thr Gly Thr Gly
                        485                 490                 495
Cys Thr Gly Cys Ala Ala Thr Cys Cys Ala Ala Gly Ala Ala Ala
                500                 505                 510
Cys Cys Cys Cys Cys Ala Ala Ala Gly Cys Ala Cys Cys Thr
            515                 520                 525
Ala Cys Cys Thr Ala Thr Cys Thr Ala Cys Thr Ala Gly Ala Gly
        530                 535                 540
Thr Ala Ala Thr Cys Thr Gly Cys Ala Cys Gly Ala Gly Ala Ala Ala
545                 550                 555                 560
Ala Gly Ala Ala Ala Gly Gly Ala Gly Cys Ala Gly Ala Ala Gly
                565                 570                 575
Ala Ala Gly Ala Ala Thr Gly Ala Thr Cys Thr Cys Ala Ala Gly Ala
                580                 585                 590
Gly Gly Cys Cys Gly Thr Gly Ala Ala Cys Gly Cys Ala Gly Ala Ala
            595                 600                 605
Ala Cys Ala Cys Ala Cys Thr Cys Cys Thr Cys Cys Cys Ala Ala Cys
        610                 615                 620
Thr Thr Thr Thr Cys Ala Ala Gly Thr Thr Thr Thr Gly Ala Ala Cys
625                 630                 635                 640
Ala Ala Ala Ala Ala Ala Ala Gly Ala Ala Ala Gly Ala Thr Gly Ala
                645                 650                 655
Gly Gly Ala Cys Thr Ala Gly Ala Ala Gly Ala Thr Gly Gly Ala Gly
                660                 665                 670
Thr Ala Thr Thr Thr Cys Cys Thr Thr Cys Thr Thr Ala Gly Ala Gly
            675                 680                 685
Ala Gly Cys Thr Cys Thr Cys Gly Gly Thr Gly Ala Gly Gly Thr Gly
        690                 695                 700
Ala Cys Cys Thr Gly Thr Cys Ala Gly Gly Gly Thr Thr Thr Ala Cys
705                 710                 715                 720
Cys Thr Cys Ala Ala Ala Cys Cys Gly Thr Cys Thr Gly Thr Gly Gly
                725                 730                 735
Thr Thr Cys Thr Ala Thr Cys Cys Ala Ala Thr Thr Ala Ala Thr Cys
                740                 745                 750
Ala Ala Gly Thr Cys Cys Thr Cys Thr Cys Thr Cys Thr Cys
            755                 760                 765
Cys Thr Cys Thr Thr Cys Thr Cys Thr Cys Cys Thr Gly Thr Cys Cys
        770                 775                 780
Thr Thr Thr Cys Ala Thr Ala Gly Ala Ala Thr Cys Cys Thr Thr
785                 790                 795                 800
Thr Thr Cys Cys Thr Thr Gly Thr Thr Gly Cys Thr Thr Gly Ala Thr
                805                 810                 815
Cys Gly Ala Ala Gly Cys Gly Gly Gly Thr Thr Ala Thr Cys Gly Ala
                820                 825                 830
Cys Gly Cys Cys Ala Cys Cys Ala Ala Ala Gly Thr Ala Thr Thr Gly
            835                 840                 845
Thr Cys Thr Thr Gly Gly Thr Gly Ala Cys Thr Thr Ala Thr Cys Ala
        850                 855                 860
Ala Ala Thr Cys Cys Cys Thr Thr Gly Gly Thr Gly Ala Thr Cys
865                 870                 875                 880
Ala Ala Ala Cys Ala Gly Cys Cys Cys Cys Gly Ala Gly Thr Gly
                885                 890                 895
```

```
Ala Thr Cys Ala Gly Ala Thr Cys Cys Gly Thr Ala Ala
            900                 905

<210> SEQ ID NO 143
<211> LENGTH: 2603
<212> TYPE: PRT
<213> ORGANISM: Artificial Sequence
<220> FEATURE:
<223> OTHER INFORMATION: HygroR cassette

<400> SEQUENCE: 143

Cys Ala Ala Gly Thr Gly Thr Ala Cys Cys Gly Thr Gly Cys Ala
1               5                   10                  15

Thr Thr Cys Thr Gly Gly Thr Ala Ala Cys Gly Ala Cys Thr
                20                  25                  30

Cys Ala Thr Ala Gly Gly Ala Gly Ala Gly Thr Thr Gly Thr Ala Ala
                35                  40                  45

Ala Ala Ala Ala Gly Thr Thr Thr Cys Gly Gly Cys Cys Gly Gly Cys
            50                  55                  60

Gly Thr Ala Thr Thr Gly Gly Gly Thr Gly Thr Ala Cys Gly Gly
65                  70                  75                  80

Ala Gly Cys Ala Thr Thr Cys Ala Cys Thr Ala Gly Gly Cys Ala Ala
                85                  90                  95

Cys Cys Ala Thr Gly Cys Ala Thr Cys Cys Thr Thr Ala Cys Thr Ala
                100                 105                 110

Thr Thr Gly Thr Ala Thr Ala Cys Cys Ala Cys Thr Thr Ala Gly
                115                 120                 125

Thr Ala Gly Gly Ala Ala Thr Gly Ala Thr Thr Thr Cys Gly Ala Gly
            130                 135                 140

Gly Thr Thr Thr Ala Thr Ala Cys Cys Thr Ala Cys Gly Ala Thr Gly
145                 150                 155                 160

Ala Ala Thr Gly Thr Gly Thr Gly Thr Cys Cys Thr Gly Thr Ala Gly
                165                 170                 175

Gly Cys Thr Thr Gly Ala Gly Ala Gly Thr Thr Cys Ala Ala Gly Gly
                180                 185                 190

Ala Ala Gly Ala Ala Ala Cys Ala Thr Gly Cys Ala Ala Thr Thr Ala
            195                 200                 205

Thr Cys Thr Thr Thr Gly Cys Gly Ala Ala Cys Cys Ala Gly Gly
                210                 215                 220

Gly Cys Thr Gly Gly Thr Gly Ala Cys Gly Gly Ala Ala Thr Thr Thr
225                 230                 235                 240

Thr Cys Ala Thr Ala Gly Thr Cys Ala Ala Gly Cys Ala Thr Cys
                245                 250                 255

Ala Gly Ala Gly Thr Ala Ala Gly Ala Ala Gly Ala Gly Gly Ala
                260                 265                 270

Gly Cys Ala Thr Gly Thr Cys Ala Ala Ala Gly Thr Ala Cys Ala Ala
                275                 280                 285

Thr Thr Ala Gly Ala Gly Ala Cys Ala Ala Ala Thr Ala Thr Ala Thr
            290                 295                 300

Ala Gly Thr Cys Gly Cys Gly Thr Gly Gly Ala Gly Cys Cys Ala Ala
305                 310                 315                 320

Gly Ala Gly Cys Gly Gly Ala Thr Thr Cys Cys Thr Cys Ala Gly Thr
                325                 330                 335

Cys Thr Cys Gly Thr Ala Gly Gly Thr Cys Thr Cys Thr Thr Gly Ala
                340                 345                 350
```

Cys Gly Ala Cys Cys Gly Thr Thr Gly Ala Thr Cys Thr Gly Cys Thr
        355                 360                 365

Thr Gly Ala Thr Cys Thr Cys Gly Thr Cys Thr Cys Cys Cys Gly Ala
    370                 375                 380

Ala Ala Ala Thr Gly Ala Ala Ala Ala Thr Ala Gly Cys Thr Cys Thr
385                 390                 395                 400

Gly Cys Thr Ala Ala Gly Cys Thr Ala Thr Thr Cys Thr Thr Cys Thr
                405                 410                 415
Cys Thr Thr Cys Gly Cys Cys Gly Gly Ala Gly Cys Cys Thr Gly Ala
            420                 425                 430
Ala Gly Gly Cys Gly Thr Thr Ala Cys Thr Ala Gly Gly Thr Thr Gly
        435                 440                 445

Cys Ala Gly Thr Cys Ala Ala Thr Gly Cys Ala Thr Thr Ala Ala Thr
    450                 455                 460

Gly Cys Ala Thr Thr Gly Cys Ala Gly Ala Thr Gly Ala Gly Cys Thr
465                 470                 475                 480
Gly Thr Ala Thr Cys Thr Gly Gly Ala Ala Gly Ala Gly Gly Thr Ala
                485                 490                 495

Ala Ala Cys Cys Cys Gly Ala Ala Ala Ala Cys Gly Cys Gly Thr Thr
            500                 505                 510

Thr Thr Ala Thr Thr Cys Thr Thr Gly Thr Thr Gly Ala Cys Ala Thr
        515                 520                 525

Gly Gly Ala Gly Cys Thr Ala Thr Thr Ala Ala Ala Thr Cys Ala Cys
    530                 535                 540

Thr Ala Gly Ala Ala Gly Gly Cys Ala Cys Thr Cys Thr Thr Thr Gly
545                 550                 555                 560
Cys Thr Gly Cys Thr Thr Gly Gly Ala Cys Ala Ala Ala Thr Gly Ala
                565                 570                 575
Ala Cys Gly Thr Ala Thr Cys Thr Thr Ala Thr Cys Gly Ala Gly Ala
            580                 585                 590
Thr Cys Cys Thr Gly Ala Ala Cys Ala Cys Cys Ala Thr Thr Thr Gly
        595                 600                 605

Thr Cys Thr Cys Ala Ala Cys Thr Cys Cys Gly Gly Cys Thr Ala Gly
    610                 615                 620
Cys Gly Ala Ala Thr Thr Cys Thr Cys Gly Ala Cys Thr Cys Ala Thr
625                 630                 635                 640

Thr Cys Cys Thr Thr Thr Gly Cys Cys Cys Thr Cys Gly Gly Ala Cys
                645                 650                 655

Gly Ala Gly Thr Gly Cys Thr Gly Gly Gly Gly Cys Gly Thr Cys Gly
            660                 665                 670

Gly Thr Thr Thr Cys Cys Ala Cys Thr Ala Thr Cys Gly Gly Cys Gly
        675                 680                 685

Ala Gly Thr Ala Cys Thr Thr Cys Thr Ala Cys Ala Cys Ala Gly Cys
    690                 695                 700

Cys Ala Thr Cys Gly Gly Thr Cys Cys Ala Gly Ala Cys Gly Gly Cys
705                 710                 715                 720

Cys Gly Cys Gly Cys Thr Thr Cys Thr Gly Cys Gly Gly Gly Cys Gly
                725                 730                 735

Ala Thr Thr Thr Gly Thr Gly Thr Ala Cys Gly Cys Cys Cys Gly Ala
            740                 745                 750

Cys Ala Gly Thr Cys Cys Cys Gly Gly Cys Thr Cys Cys Gly Gly Ala
        755                 760                 765

-continued

```
Thr Cys Gly Gly Ala Cys Gly Ala Thr Thr Gly Cys Gly Thr Cys Gly
770                 775                 780
Cys Ala Thr Cys Gly Ala Cys Cys Thr Gly Cys Gly Cys Cys
785                 790                 795                 800
Ala Ala Gly Cys Thr Gly Cys Ala Thr Cys Ala Thr Cys Gly Ala Ala
                805                 810                 815
Ala Thr Thr Gly Cys Cys Gly Thr Cys Ala Ala Cys Ala Ala Gly
                820                 825                 830
Cys Thr Cys Thr Gly Ala Thr Ala Gly Ala Gly Thr Thr Gly Gly Thr
                835                 840                 845
Cys Ala Ala Gly Ala Cys Cys Ala Ala Thr Gly Cys Gly Gly Ala Gly
                850                 855                 860
Cys Ala Thr Ala Thr Ala Cys Gly Cys Cys Gly Gly Ala Gly Thr
865                 870                 875                 880
Cys Gly Thr Gly Gly Cys Gly Ala Thr Cys Cys Thr Gly Cys Ala Ala
                885                 890                 895
Gly Cys Thr Cys Cys Gly Gly Ala Thr Gly Cys Cys Thr Cys Cys Gly
                900                 905                 910
Cys Thr Cys Gly Ala Ala Gly Thr Ala Gly Cys Gly Gly Cys Gly Thr Cys
                915                 920                 925
Thr Gly Cys Thr Gly Cys Thr Cys Cys Ala Thr Ala Cys Ala Ala Gly
                930                 935                 940
Cys Cys Ala Ala Cys Cys Ala Cys Gly Gly Cys Cys Thr Cys Cys Ala
945                 950                 955                 960
Gly Ala Ala Gly Ala Ala Gly Ala Thr Gly Thr Thr Gly Gly Cys Gly
                965                 970                 975
Ala Cys Cys Thr Cys Gly Thr Ala Thr Thr Gly Gly Gly Ala Ala Thr
                980                 985                 990
Cys Cys Cys Cys Gly Ala Ala Cys  Ala Thr Cys Gly Cys  Cys Thr Cys
                995            1000                1005
Gly Cys  Thr Cys Cys Ala Gly  Thr Cys Ala Ala Thr  Gly Ala Cys
    1010                1015                1020
Cys Gly Cys Thr Gly Thr Thr  Ala Thr Gly Cys Gly  Gly Cys Cys
    1025                1030                1035
Ala Thr  Thr Gly Thr Cys Cys  Gly Thr Cys Ala Gly  Gly Ala Cys
    1040                1045                1050
Ala Thr  Thr Gly Thr Thr Gly  Gly Ala Gly Cys Cys  Gly Ala Ala
    1055                1060                1065
Ala Thr  Cys Cys Gly Cys Gly  Thr Gly Cys Ala Cys  Gly Ala Gly
    1070                1075                1080
Gly Thr  Gly Cys Cys Gly Gly  Ala Cys Thr Thr Cys  Gly Gly Gly
    1085                1090                1095
Gly Cys  Ala Gly Thr Cys Cys  Thr Cys Gly Gly Cys  Cys Cys Ala
    1100                1105                1110
Ala Ala  Gly Cys Ala Thr Cys  Ala Gly Cys Gly Thr  Ala Thr Cys
    1115                1120                1125
Gly Ala  Gly Ala Gly Cys Cys  Thr Gly Cys Gly Cys  Gly Ala Cys
    1130                1135                1140
Gly Gly  Ala Cys Gly Cys Ala  Cys Thr Gly Ala Cys  Gly Gly Thr
    1145                1150                1155
Gly Thr  Cys Gly Thr Cys Cys  Ala Thr Cys Ala Cys  Ala Gly Thr
    1160                1165                1170
Thr Thr  Gly Cys Cys Ala Gly  Thr Gly Ala Thr Ala  Cys Ala Cys
```

-continued

|     |     |     |     |     |     |     |     |     |     |
|-----|-----|-----|-----|-----|-----|-----|-----|-----|-----|
|     | 1175 |     |     | 1180 |     |     | 1185 |     |     |
| Ala | Thr | Gly | Gly | Gly | Ala | Thr | Cys | Ala | Gly |
|     | 1190 |     |     | 1195 |     |     |     | 1200 |     |

Ala Thr Gly Gly Gly Ala Thr Cys Ala Gly Cys Ala Ala Thr
        1190           1195           1200

Cys Gly Cys Gly Cys Ala Thr Ala Thr Gly Ala Ala Ala Thr Cys
        1205           1210           1215

Ala Cys Gly Cys Cys Ala Thr Gly Thr Ala Gly Thr Gly Thr Ala
        1220           1225           1230

Thr Thr Gly Ala Cys Cys Gly Ala Thr Cys Cys Thr Thr Gly
        1235           1240           1245

Cys Gly Gly Thr Cys Gly Ala Ala Thr Gly Gly Cys Cys
        1250           1255           1260

Gly Ala Ala Cys Cys Gly Cys Thr Gly Thr Cys Thr Gly
        1265           1270           1275

Gly Cys Thr Ala Ala Gly Ala Thr Cys Gly Gly Cys Cys Gly Cys
        1280           1285           1290

Ala Gly Cys Gly Ala Thr Cys Gly Cys Ala Thr Cys Cys Ala Thr
        1295           1300           1305

Ala Gly Cys Cys Thr Cys Cys Gly Cys Gly Ala Cys Cys Gly Gly
        1310           1315           1320

Thr Thr Gly Thr Ala Gly Ala Ala Cys Ala Gly Cys Gly Gly Gly
        1325           1330           1335

Cys Ala Gly Thr Thr Cys Gly Gly Thr Thr Cys Ala Gly Gly
        1340           1345           1350

Cys Ala Gly Gly Thr Cys Thr Gly Cys Ala Ala Cys Gly Thr
        1355           1360           1365

Gly Ala Cys Ala Cys Cys Thr Gly Thr Gly Cys Ala Cys Gly
        1370           1375           1380

Gly Cys Gly Gly Gly Ala Gly Ala Thr Gly Cys Ala Ala Thr Ala
        1385           1390           1395

Gly Gly Thr Cys Ala Gly Gly Cys Thr Cys Thr Cys Gly Cys Thr
        1400           1405           1410

Ala Ala Ala Cys Thr Cys Cys Cys Ala Ala Thr Gly Thr Cys
        1415           1420           1425

Ala Ala Gly Cys Ala Cys Thr Thr Cys Cys Gly Gly Ala Ala Thr
        1430           1435           1440

Cys Gly Gly Gly Ala Gly Cys Gly Cys Gly Gly Cys Cys Gly Ala
        1445           1450           1455

Thr Gly Cys Ala Ala Ala Gly Thr Gly Cys Cys Gly Ala Thr Ala
        1460           1465           1470

Ala Ala Cys Ala Thr Ala Ala Cys Gly Ala Thr Cys Thr Thr Thr
        1475           1480           1485

Gly Thr Ala Gly Ala Ala Ala Cys Cys Ala Thr Cys Gly Gly Cys
        1490           1495           1500

Gly Cys Ala Gly Cys Thr Ala Thr Thr Ala Cys Cys Cys Gly
        1505           1510           1515

Cys Ala Gly Gly Ala Cys Ala Thr Ala Thr Cys Cys Ala Cys Gly
        1520           1525           1530

Cys Cys Cys Thr Cys Cys Thr Ala Cys Ala Thr Cys Gly Ala Ala
        1535           1540           1545

Gly Cys Thr Gly Ala Ala Ala Gly Cys Ala Cys Gly Ala Gly Ala
        1550           1555           1560

Thr Thr Cys Thr Thr Cys Gly Cys Cys Cys Thr Cys Cys Gly Ala
        1565           1570           1575

-continued

Gly Ala Gly Cys Thr Gly Cys Ala Thr Cys Ala Gly Gly Thr Cys
1580                1585                1590

Gly Gly Ala Gly Ala Cys Gly Cys Thr Gly Thr Cys Gly Ala Ala
1595                1600                1605

Cys Thr Thr Thr Thr Cys Gly Ala Thr Cys Ala Gly Ala Ala Ala
1610                1615                1620

Cys Thr Thr Cys Thr Cys Gly Ala Cys Ala Gly Ala Cys Gly Thr
1625                1630                1635

Cys Gly Cys Gly Gly Thr Gly Ala Gly Thr Thr Cys Ala Gly Gly
1640                1645                1650

Cys Thr Thr Thr Thr Thr Cys Ala Thr Gly Ala Thr Gly Gly Cys
1655                1660                1665

Cys Cys Thr Cys Cys Thr Ala Cys Cys Gly Gly Thr Gly Ala Thr
1670                1675                1680

Cys Thr Cys Ala Gly Cys Thr Gly Thr Ala Gly Gly Ala Ala Ala
1685                1690                1695

Gly Ala Gly Ala Ala Gly Ala Ala Gly Gly Thr Thr Ala Gly Thr
1700                1705                1710

Ala Gly Thr Cys Gly Ala Cys Ala Thr Gly Thr Gly Gly Cys
1715                1720                1725

Cys Cys Thr Cys Cys Thr Ala Thr Ala Gly Thr Gly Ala Gly Thr
1730                1735                1740

Cys Gly Thr Ala Thr Thr Ala Thr Ala Cys Thr Ala Thr Gly Cys
1745                1750                1755

Cys Gly Ala Thr Ala Thr Ala Cys Thr Ala Thr Gly Cys Cys Gly
1760                1765                1770

Ala Thr Gly Ala Thr Ala Ala Thr Thr Gly Thr Cys Ala Ala
1775                1780                1785

Cys Ala Cys Thr Ala Gly Gly Cys Gly Cys Cys Gly Gly Thr Cys
1790                1795                1800

Ala Cys Ala Ala Cys Thr Ala Gly Thr Ala Gly Ala Thr Ala Thr
1805                1810                1815

Cys Ala Cys Thr Thr Ala Cys Gly Thr Gly Thr Thr Gly Ala Gly
1820                1825                1830

Ala Gly Gly Cys Gly Gly Cys Ala Thr Gly Cys Gly Ala Thr Ala
1835                1840                1845

Ala Gly Ala Gly Gly Thr Gly Thr Ala Ala Thr Thr Ala Cys Cys
1850                1855                1860

Thr Gly Ala Gly Ala Ala Cys Ala Thr Cys Thr Thr Gly Thr Thr
1865                1870                1875

Gly Cys Cys Cys Thr Gly Cys Thr Thr Cys Cys Gly Thr Gly
1880                1885                1890

Cys Gly Ala Ala Ala Thr Ala Cys Thr Ala Cys Cys Gly Gly Thr
1895                1900                1905

Ala Cys Thr Thr Thr Thr Gly Gly Gly Ala Ala Ala Cys Ala Ala
1910                1915                1920

Gly Gly Gly Ala Ala Cys Ala Gly Gly Ala Gly Gly Cys Gly
1925                1930                1935

Cys Thr Gly Cys Thr Gly Thr Gly Cys Gly Cys Gly Gly Thr Thr
1940                1945                1950

Cys Thr Gly Ala Gly Thr Gly Thr Thr Cys Ala Gly Gly Ala Thr
1955                1960                1965

```
Thr Gly Ala Ala Gly Cys Thr Gly Ala Ala Gly Ala  Ala Gly Gly
    1970            1975            1980

Thr Gly Cys Thr Gly Ala Gly Gly Ala Ala Gly Cys  Gly Thr Ala
    1985            1990            1995

Gly Ala Ala Cys Thr Gly Thr Thr Gly Cys Gly Gly  Ala Cys Gly
    2000            2005            2010

Cys Gly Ala Gly Thr Thr Cys Thr Gly Ala Gly Ala  Ala Gly Ala
    2015            2020            2025

Gly Cys Thr Gly Thr Ala Cys Cys Gly Ala Thr Thr  Gly Gly Thr
    2030            2035            2040

Gly Ala Ala Ala Gly Cys Cys Gly Ala Ala Gly Ala  Ala Gly Thr
    2045            2050            2055

Gly Ala Gly Thr Thr Gly Gly Thr Gly Cys Cys Cys  Thr Gly Thr
    2060            2065            2070

Thr Gly Cys Cys Thr Gly Gly Ala Thr Ala Ala Thr  Gly Thr Thr
    2075            2080            2085

Thr Gly Cys Ala Ala Cys Thr Cys Gly Cys Thr Gly  Gly Thr Thr
    2090            2095            2100

Cys Thr Gly Cys Ala Gly Ala Gly Ala Cys Gly Gly  Ala Gly Ala
    2105            2110            2115

Cys Ala Ala Ala Thr Gly Cys Thr Gly Gly Cys Thr  Ala Cys Gly
    2120            2125            2130

Ala Thr Gly Thr Thr Gly Cys Thr Gly Ala Thr Thr  Cys Ala Gly
    2135            2140            2145

Gly Thr Thr Gly Ala Thr Ala Cys Cys Thr Cys Gly  Gly Thr Cys
    2150            2155            2160

Gly Ala Gly Ala Cys Ala Cys Thr Gly Thr Thr Thr  Thr Gly Gly
    2165            2170            2175

Thr Thr Thr Gly Ala Thr Ala Gly Gly Gly Thr Gly  Gly Ala Thr
    2180            2185            2190

Thr Thr Gly Gly Thr Thr Gly Cys Ala Gly Ala Gly  Ala Ala Gly
    2195            2200            2205

Ala Gly Ala Ala Ala Gly Gly Ala Ala Gly Gly Thr  Cys Ala Ala
    2210            2215            2220

Ala Gly Ala Gly Gly Gly Ala Ala Ala Cys Thr Gly  Gly Gly
    2225            2230            2235

Cys Gly Gly Ala Gly Gly Gly Ala Ala Gly Gly Ala  Thr Thr Thr
    2240            2245            2250

Thr Gly Thr Ala Thr Cys Ala Gly Gly Cys Ala Gly  Cys Ala Ala
    2255            2260            2265

Ala Cys Thr Gly Cys Cys Ala Cys Thr Gly Cys Ala  Gly Thr Gly
    2270            2275            2280

Gly Cys Cys Cys Thr Gly Gly Cys Ala Gly Thr Gly  Cys Cys Gly
    2285            2290            2295

Gly Gly Cys Gly Ala Gly Gly Cys Ala Cys Cys Cys  Ala Cys Gly
    2300            2305            2310

Cys Ala Cys Gly Gly Cys Cys Gly Cys Gly Cys Ala  Ala Cys Cys
    2315            2320            2325

Gly Gly Thr Thr Gly Gly Thr Cys Cys Thr Gly Cys  Cys Cys
    2330            2335            2340

Ala Cys Cys Ala Cys Gly Ala Ala Ala Cys Cys Cys  Thr Thr Cys
    2345            2350            2355

Thr Gly Ala Ala Ala Gly Gly  Thr Cys Ala Gly Ala  Thr Gly Gly
```

```
                    2360                2365                2370

Ala  Ala  Gly  Thr  Gly  Thr  Gly  Cys  Gly  Ala  Cys  Ala  Gly  Thr  Gly
               2375                2380                2385

Cys  Gly  Cys  Gly  Thr  Cys  Cys  Cys  Ala  Ala  Gly  Cys  Cys  Ala
               2390                2395                2400

Ala  Thr  Gly  Cys  Ala  Gly  Gly  Cys  Gly  Cys  Cys  Ala  Thr  Gly  Cys
     2405                2410                2415

Ala  Cys  Thr  Cys  Cys  Cys  Ala  Cys  Cys  Cys  Gly  Cys  Ala  Ala
     2420                2425                2430

Gly  Ala  Thr  Thr  Cys  Ala  Cys  Thr  Gly  Thr  Gly  Cys  Gly  Thr  Thr
     2435                2440                2445

Cys  Thr  Thr  Ala  Thr  Thr  Gly  Gly  Thr  Gly  Cys  Cys  Gly  Cys
     2450                2455                2460

Ala  Ala  Gly  Gly  Cys  Cys  Ala  Gly  Cys  Cys  Ala  Ala  Ala  Gly  Gly
     2465                2470                2475

Gly  Gly  Gly  Ala  Ala  Gly  Thr  Ala  Thr  Gly  Ala  Gly  Thr  Cys  Ala
     2480                2485                2490

Cys  Ala  Gly  Cys  Ala  Cys  Cys  Gly  Ala  Thr  Ala  Cys  Ala  Ala  Gly
     2495                2500                2505

Ala  Ala  Ala  Ala  Thr  Thr  Gly  Cys  Ala  Gly  Ala  Ala  Cys  Thr  Ala
     2510                2515                2520

Ala  Cys  Ala  Thr  Ala  Thr  Gly  Gly  Ala  Thr  Gly  Cys  Gly  Cys  Gly
     2525                2530                2535

Cys  Gly  Cys  Thr  Ala  Thr  Thr  Cys  Thr  Gly  Thr  Ala  Gly  Ala  Gly
     2540                2545                2550

Cys  Thr  Cys  Thr  Gly  Gly  Gly  Cys  Ala  Ala  Ala  Gly  Cys  Ala  Cys
     2555                2560                2565

Cys  Ala  Ala  Thr  Cys  Cys  Thr  Gly  Cys  Gly  Gly  Gly  Thr  Cys  Gly
     2570                2575                2580

Gly  Thr  Ala  Cys  Ala  Cys  Ala  Cys  Ala  Cys  Thr  Ala  Gly  Cys  Ala
     2585                2590                2595

Cys  Thr  Gly  Cys  Cys
     2600

<210> SEQ ID NO 144
<211> LENGTH: 40
<212> TYPE: DNA
<213> ORGANISM: Artificial Sequence
<220> FEATURE:
<223> OTHER INFORMATION: forward primer

<400> SEQUENCE: 144
attgggtacc gggccccccc gacgcagaag aaggaaatcg                              40

<210> SEQ ID NO 145
<211> LENGTH: 30
<212> TYPE: DNA
<213> ORGANISM: Artificial Sequence
<220> FEATURE:
<223> OTHER INFORMATION: reverse primer

<400> SEQUENCE: 145
cgagggccat tttgtatctg cgaattgagc                                        30

<210> SEQ ID NO 146
<211> LENGTH: 30
<212> TYPE: DNA
<213> ORGANISM: Artificial Sequence
```

```
<220> FEATURE:
<223> OTHER INFORMATION: forward primer

<400> SEQUENCE: 146
cagatacaaa atggccctcg cagctcaaca                                               30

<210> SEQ ID NO 147
<211> LENGTH: 32
<212> TYPE: DNA
<213> ORGANISM: Artificial Sequence
<220> FEATURE:
<223> OTHER INFORMATION: reverse primer

<400> SEQUENCE: 147
aacacagcac tcaggatagg tggctcgcaa tg                                            32

<210> SEQ ID NO 148
<211> LENGTH: 30
<212> TYPE: DNA
<213> ORGANISM: Artificial Sequence
<220> FEATURE:
<223> OTHER INFORMATION: forward primer

<400> SEQUENCE: 148
cctatcctga gtgctgtgtt cctcagaatg                                               30

<210> SEQ ID NO 149
<211> LENGTH: 30
<212> TYPE: PRT
<213> ORGANISM: Artificial Sequence
<220> FEATURE:
<223> OTHER INFORMATION: reverse primer

<400> SEQUENCE: 149

Gly Gly Thr Ala Cys Ala Cys Thr Thr Gly Thr Thr Ala Cys Gly Gly
1               5                   10                  15

Ala Thr Cys Thr Gly Ala Thr Cys Ala Cys Thr Cys Gly Gly
            20                  25                  30

<210> SEQ ID NO 150
<211> LENGTH: 31
<212> TYPE: DNA
<213> ORGANISM: Artificial Sequence
<220> FEATURE:
<223> OTHER INFORMATION: forward primer

<400> SEQUENCE: 150
agatccgtaa caagtgtacc tgtgcattct g                                             31

<210> SEQ ID NO 151
<211> LENGTH: 40
<212> TYPE: DNA
<213> ORGANISM: Artificial Sequence
<220> FEATURE:
<223> OTHER INFORMATION: reverse primer

<400> SEQUENCE: 151
tggatccccc gggctgcagg ggcagtgcta gtgtgtgtac                                    40

<210> SEQ ID NO 152
<211> LENGTH: 20
<212> TYPE: DNA
<213> ORGANISM: Artificial Sequence
<220> FEATURE:
<223> OTHER INFORMATION: forward primer
```

```
<400> SEQUENCE: 152
gacgcagaag aaggaaatcg                                               20

<210> SEQ ID NO 153
<211> LENGTH: 21
<212> TYPE: DNA
<213> ORGANISM: Artificial Sequence
<220> FEATURE:
<223> OTHER INFORMATION: reverse primer

<400> SEQUENCE: 153
ggtacacaca ctagcactgc c                                             21

<210> SEQ ID NO 154
<211> LENGTH: 6384
<212> TYPE: DNA
<213> ORGANISM: Artificial Sequence
<220> FEATURE:
<223> OTHER INFORMATION: sequence of example 2

<400> SEQUENCE: 154
gacgcagaag aaggaaatcg ccccgccggt tccgtaaaaa aaatatgagc gcagggacaa    60
gcacagcctt ggccctgggc ctagccttgc gccttgtttg atgcaatcgg cgacatgtcg   120
aatgctgtaa ttttttttgt ttaggttccc cttttccttt tgtgttaata ataattctcg   180
aagggcgctg attttgaaat ttgtcggtga gagccaaacg gatatacagg cgcggctgat   240
gaataatgat gaatcgagct gacttgatgc tgtatgtaca atattgactg cgaggaccat   300
caggtgttgt atggatggaa tcattctgta accaccaagg tgcatgcatc ataaggtatt   360
ctcctcagct caccaacaac gaacgatggc catgttagta aaggcaccgt gatggcaaga   420
tagaaccact attgcatctg cgcttcccac gcacagtacg tcaatgtaac gtcaaagccg   480
ccctcccgta acctcgcccg ttgttgctcc ccccgattgc ctcaatcaca tagtacctac   540
ctatgcatta tggcgcctca acccaccccc ccagattgag agctacctta catcaatatg   600
gccagcacct cttcggcgat acatactcgc caccccagcc ggggcgattg tgtgtactag   660
gtaggctcgt actataccag caggagaggt gctgcttggc aatcgtgctc agctgttagg   720
ttgtacttgt atggtacttg taaggtggtc atgcagttgc taaggtacct agggagggat   780
tcaacgagcc ctgcttccaa tgtccatctg gataggatgg cggctggcgg ggccgaagct   840
gggaactcgc caacagtcat atgtaatagc tcaagttgat gataccgttt tgccaggatt   900
aggatgcgag aagcagcatg aatgtcgctc atccgatgcc gcatcaccgt tgtgtcagaa   960
acgaccaagc taagcaacta aggtaccttc ccgtccacta tctcaggtaa ccaggtacta  1020
ccagctaccc tacctgccgt gcctacctgc tttagtatta atctttccac ctccctcctc  1080
aatcttcttt tccctcctct cctctttttt ttttcttcct cctcttcttc tccataacca  1140
ttcctaacaa catcgacatt ctctcctaat caccagcctc gcaaatcctc aggttagtat  1200
tactactact acaatcatca ccacgatgct ccgcccgacg atgcggcttc tgttcgcctg  1260
cccctcctct cactcgtgcc cttgacgagc taccccgcca gactctcctg cgtcaccaat  1320
ttttttccct atttacccct cctccctctc tccctctcgt ttcttcctaa caaacaacca  1380
ccaccaaaat ctctttggaa gctcacgact cacgcaagct caattcgcag atacaaaatg  1440
gccctcgcag ctcaacagca tactcaggcc gattggggcc gctggtctca ccagattcca  1500
cagagttttc ccatgatggg ctctccagga ttcatgtcat acgatccgag agctcaggac  1560
ggcagtcaga tgcagcgtca ggtgtctgct cagtacctgg tgaactcgaa ctacaaccag  1620
```

-continued

```
cccccgatgc ccactgcttc gtctccccag tatcaacacg cagggccatt ttcctatgtg   1680
ccttaccaca gcccgccgcc gtccactcct cttggttccc cattcaagag cgaatttccc   1740
gagcaccctc ttacgcgcat gacacactct acggtcgatc gacaccattc tcaggccatg   1800
agggactacc aaccttattc tcctgtatcg aggaggggat cgatttcttc agtcgccacc   1860
aagccctcag cagctcccgt cacaccaggt ccaactactc ctggctcttt cacttcaagt   1920
tccgacgccc agagccccag cactccaaac ccccagactg cgtctcagcc tgtcagctcc   1980
aagactctca cttacaatga gaccgttcat ccgggcgata ggatcagctt cagaaccgat   2040
gttgatgaac tcatgaaggc catccagaag acacagacga ccgacgagtg tcagcaaaca   2100
ctcacacctg cgcgaacacc aaagaactgt accacaagta ctcccgtact cgtacacaa    2160
agcgggaagc cgagaaaaca gtgggtttgc gatggcccca actgcggcaa ggcctttgtc   2220
cagaagacgc atcgcgacat tcaccgacgc actcacaccg gccatcgacc atacgtacgc   2280
gcccagctcc tcttcactgc aacgccggct aattaaatgt tgataggtct gcaccatgga   2340
aaattgcggt cttacgttct cgcagcgagg aaacctcaag gtaagcttca gctgctaaga   2400
atctcctttg agaatgcgta tactgaccag atggtgtgtg gacagactca catacgacgc   2460
cacacaggtg aaaagccgtt ctcttgcgct gcttgtggca agtgcttcgc tcagcgtggg   2520
aatcttcgat cccacgagga gacacacaaa ggcctgaagc ccttcgtctg ccggctcgat   2580
gattgcaaca gtcgtttttc tcagctgggc aatatgaagg tatgcaacat ctagcacatg   2640
aaagcagtat gagaacgctc taacgctgag ggaactgcag actcatcaga caaactttca   2700
caaagaaacg ctccagaaac tcacacacat gtttgtgcaa ttctcggaga acggcgaggt   2760
gcccagagac tatcaggatc ttttcgaata cttccagaag cactacaaga atagcaacaa   2820
gggagtcaag ggccgaggaa agactcgcgc tgtggcagct cgtgggcctc aagattccgc   2880
gtttcggcag gctgcctccc cagtgccgcg gttactgaag acgccggcta cgactcattt   2940
gccccagatg acaatgccag cccatgatcc ccatggcaga atctcaccat acgccatgac   3000
ccagggagct gcgaacactc tgagcaatgt cctgcgcaac cccaacccct cttacggcct   3060
ttatggaccc acgtttgccc cgggccctgt acgagatggc gtcttcaca tgggcattgc    3120
gagccaccta tcctgatcta gaaagaagga ttacctctaa acaagtgtac ctgtgcattc   3180
tgggtaaacg actcatagga gagttgtaaa aagtttcgg ccggcgtatt gggtgttacg    3240
gagcattcac taggcaacca tgcatcctta ctattgtata ccatcttagt aggaatgatt   3300
tcgaggttta tacctacgat gaatgtgtgt cctgtaggct tgagagttca aggaagaaac   3360
atgcaattat ctttgcgaac ccagggctgg tgacggaatt ttcatagtca agctatcaga   3420
gtaaagaaga ggagcatgtc aaagtacaat tagagacaaa tatatagtcg cgtggagcca   3480
agagcggatt cctcagtctc gtaggtctct tgacgaccgt tgatctgctt gatctcgtct   3540
cccgaaaatg aaaatagctc tgctaagcta ttcttctctt cgccggagcc tgaaggcgtt   3600
actaggttgc agtcaatgca ttaatgcatt gcagatgagc tgtatctgga agaggtaaac   3660
ccgaaaacgc gtttattct tgttgacatg gagctattaa atcactagaa ggcactcttt    3720
gctgcttgga caaatgaacg tatcttatcg agatcctgaa caccatttgt ctcaactccg   3780
gcaagtgtac ctgtgcattc tgggtaaacg actcatagga gagttgtaaa aagtttcgg    3840
ccggcgtatt gggtgttacg gagcattcac taggcaacca tgcatcctta ctattgtata   3900
ccatcttagt aggaatgatt tcgaggttta tacctacgat gaatgtgtgt cctgtaggct   3960
```

```
tgagagttca aggaagaaac atgcaattat ctttgcgaac ccagggctgg tgacggaatt    4020
ttcatagtca agctatcaga gtaaagaaga ggagcatgtc aaagtacaat tagagacaaa    4080
tatatagtcg cgtggagcca agagcggatt cctcagtctc gtaggtctct tgacgaccgt    4140
tgatctgctt gatctcgtct cccgaaaatg aaaatagctc tgctaagcta ttcttctctt    4200
cgccggagcc tgaaggcgtt actaggttgc agtcaatgca ttaatgcatt gcagatgagc    4260
tgtatctgga agaggtaaac ccgaaaacgc gttttattct tgttgacatg gagctattaa    4320
atcactagaa ggcactcttt gctgcttgga caaatgaacg tatcttatcg agatcctgaa    4380
caccatttgt ctcaactccg gctagcgaat tctcgactca ttcctttgcc ctcggacgag    4440
tgctggggcg tcggttttca ctatcggcga gtacttctac acagccatcg gtccagacgg    4500
ccgcgcttct gcgggcgatt tgtgtacgcc cgacagtccc ggctccggat cggacgattg    4560
cgtcgcatcg accctgcgcc caagctgcat catcgaaatt gccgtcaacc aagctctgat    4620
agagttggtc aagaccaatg cggagcatat acgcccggag tcgtggcgat cctgcaagct    4680
ccggatgcct ccgctcgaag tagcgcgtct gctgctccat acaagccaac cacggcctcc    4740
agaagaagat gttggcgacc tcgtattggg aatccccgaa catcgcctcg ctccagtcaa    4800
tgaccgctgt tatgcggcca ttgtccgtca ggacattgtt ggagccgaaa tccgcgtgca    4860
cgaggtgccg gacttcgggg cagtcctcgg cccaaagcat cagctcatcg agagcctgcg    4920
cgacggacgc actgacggtg tcgtccatca cagtttgcca gtgatacaca tggggatcag    4980
caatcgcgca tatgaaatca cgccatgtag tgtattgacc gattccttgc ggtccgaatg    5040
ggccgaaccc gctcgtctgg ctaagatcgg ccgcagcgat cgcatccata gcctccgcga    5100
ccggttgtag aacagcgggc agttcggttt caggcaggtc ttgcaacgtg acaccctgtg    5160
cacggcggga gatgcaatag gtcaggctct cgctaaactc cccaatgtca agcacttccg    5220
gaatcgggag cgcggccgat gcaaagtgcc gataaacata acgatctttg tagaaaccat    5280
cggcgcagct atttacccgc aggacatatc cacgccctcc tacatcgaag ctgaaagcac    5340
gagattcttc gccctccgag agctgcatca ggtcggagac gctgtcgaac ttttcgatca    5400
gaaacttctc gacagacgtc gcggtgagtt caggcttttt catgatggcc ctcctaccgg    5460
tgatctcagc tgtaggaaag agaagaaggt tagtagtcga catggtggcc ctcctatagt    5520
gagtcgtatt atactatgcc gatatactat gccgatgatt aattgtcaac actaggcgcc    5580
ggtcacaact agtagatatc acttacgtgt tgagaggcgg catgcgataa gaggtgtaat    5640
tacctgagaa catcttgttg ccctgctttc cgtgcgaaat actaccggta cttttgggaa    5700
acaagggaac aggagggcgc tgctgtgcgc ggttctgagt gttcaggatt gaagctgaag    5760
aaggtgctga ggaagcgtag aactgttgcg gacgcgagtt ctgagaagag ctgtaccgat    5820
tggtgaaagc cgaagaagtg agttggtgcc ctgttgcctg gataatgttt gcaactcgct    5880
ggttctgcag agacggagac aaatgctggc tacgatgttg ctgattcagg ttgataccct    5940
ggtcgagaca ctgttttggt ttgatagggt ggatttggtt gcagagaaga gaaaggaagg    6000
tcaaagaggg aaaactgggc ggagggaagg attttgtatc aggcagcaaa ctgccactgc    6060
agtggccctg gcagtgccgg gcgaggcacc cacgcacggc cgcgcaaccg gttggtcctt    6120
gcccaccacg aaacccttct gaaaggtcag atggaagtgt gcgacagtgc gcgtccccaa    6180
gccaatgcag gcgccatgca ctcccccaccc gcaagattca ctgtgcgttc ttattggttg    6240
ccgcaaggcc agccaagggg ggaagtatga gtcacagcac cgatacaaga aaattgcaga    6300
actaacatat ggatgcgcgc gctattctgt agagctctgg gcaaagcacc aatcctgcgg    6360
```

-continued gtcggtacac acactagcac tgcc                                                6384

<210> SEQ ID NO 155
<211> LENGTH: 21
<212> TYPE: DNA
<213> ORGANISM: Artificial Sequence
<220> FEATURE:
<223> OTHER INFORMATION: forward primer

<400> SEQUENCE: 155
gtcagaaacg accaagctaa g                                                   21

<210> SEQ ID NO 156
<211> LENGTH: 20
<212> TYPE: DNA
<213> ORGANISM: Artificial Sequence
<220> FEATURE:
<223> OTHER INFORMATION: reverse primer

<400> SEQUENCE: 156
gcctgagaat ggtgtcgatc                                                     20

<210> SEQ ID NO 157
<211> LENGTH: 18
<212> TYPE: DNA
<213> ORGANISM: Artificial Sequence
<220> FEATURE:
<223> OTHER INFORMATION: forward primer

<400> SEQUENCE: 157
tcgtgggcct caagattc                                                       18

<210> SEQ ID NO 158
<211> LENGTH: 18
<212> TYPE: DNA
<213> ORGANISM: Artificial Sequence
<220> FEATURE:
<223> OTHER INFORMATION: reverse primer

<400> SEQUENCE: 158
gacgcctgag aggtccta                                                       18

<210> SEQ ID NO 159
<211> LENGTH: 20
<212> TYPE: DNA
<213> ORGANISM: Artificial Sequence
<220> FEATURE:
<223> OTHER INFORMATION: forward primer

<400> SEQUENCE: 159
ccttcttaga gagctctcgg                                                     20

<210> SEQ ID NO 160
<211> LENGTH: 20
<212> TYPE: DNA
<213> ORGANISM: Artificial Sequence
<220> FEATURE:
<223> OTHER INFORMATION: reverse primer

<400> SEQUENCE: 160
cgggtttacc tcttccagat                                                     20